United States Patent
Hearn et al.

(10) Patent No.: US 8,748,582 B2
(45) Date of Patent: Jun. 10, 2014

(54) AFFINITY LIGANDS AND METHODS FOR PROTEIN PURIFICATION

(75) Inventors: Milton T W Hearn, Balwyn (AU); Anjali Makarand Bhagwat, Wantirna South (AU); William Roy Jackson, Camberwell (AU); Simon John Mountford, Beaconsfield (AU)

(73) Assignee: Monash University, Victoria (AU)

( * ) Notice: Subject to any disclaimer, the term of this patent is extended or adjusted under 35 U.S.C. 154(b) by 0 days.

(21) Appl. No.: 13/502,103

(22) PCT Filed: Oct. 15, 2010

(86) PCT No.: PCT/AU2010/001368
§ 371 (c)(1),
(2), (4) Date: Jun. 21, 2012

(87) PCT Pub. No.: WO2011/044637
PCT Pub. Date: Apr. 21, 2011

(65) Prior Publication Data
US 2012/0259094 A1 Oct. 11, 2012

(30) Foreign Application Priority Data
Oct. 15, 2009 (AU) .............................. 2009905049

(51) Int. Cl.
| | | |
|---|---|---|
| C07K 1/22 | (2006.01) | |
| C07D 213/70 | (2006.01) | |
| C07D 213/76 | (2006.01) | |
| C07D 215/36 | (2006.01) | |
| C07D 217/22 | (2006.01) | |
| C07D 401/12 | (2006.01) | |
| C07D 401/14 | (2006.01) | |
| C08B 37/00 | (2006.01) | |

(52) U.S. Cl.
USPC .................... 530/387.1; 530/413; 536/123.1; 546/141; 546/153; 546/157; 546/257; 546/277.1; 546/296; 546/297; 546/300

(58) Field of Classification Search
None
See application file for complete search history.

(56) References Cited

U.S. PATENT DOCUMENTS

| | | | | |
|---|---|---|---|---|
| 3,535,328 | A * | 10/1970 | Zielinski | 546/268.1 |
| 3,876,647 | A * | 4/1975 | Durant et al. | 546/300 |
| 4,216,318 | A * | 8/1980 | Brown et al. | 544/310 |
| 8,273,752 | B2 | 9/2012 | Siegel et al. | |
| 2004/0192712 | A1 | 9/2004 | Beckmann et al. | |
| 2006/0173022 | A1 | 8/2006 | Schaper | |

FOREIGN PATENT DOCUMENTS

| | | |
|---|---|---|
| EP | 0522606 | 4/1996 |
| WO | WO 95/33557 | 12/1995 |
| WO | WO 2007/142578 | 12/2007 |

OTHER PUBLICATIONS

Buschauer et al., Synthesis & Histamine H2-receptor Activity of Heterocyclic Impromidine Analogs, 47(2) Pharmazie 86-91 (1992).*
Scholz G H et al., "Salt-independent binding of antibodies from human serum to thiophilic heterocyclic ligands," Journal of Chromatography B, 709 (1998) 189-196.

* cited by examiner

Primary Examiner — Janet L Andres
Assistant Examiner — Timothy R Rozof

(57) ABSTRACT

The present invention relates generally to affinity ligands and chemical affinity ligand-matrix conjugates for use as chromatographic adsorbents and methods which utilize the adsorbents in the purification of proteins by affinity chromatography. The affinity ligand-matrix conjugates of the present invention comprise ligands of general formula (I): wherein m represents an integer from 0-2, n represents an integer from 0-6, p represents an integer from 0-4, $R^1$ represents H or $C_{1-3}$ alkyl, $R^2$ is an optional substituent, and X is the position at which the ligand is immobilized, optionally via a linker.

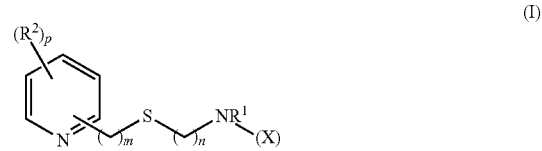

(I)

15 Claims, 42 Drawing Sheets

Code to abbreviations (named by Standard IUPAC nomenclature)

2-PSEA refers to 2-(pyridin-2'-ylsulfanyl)ethanamine

6-Me-2-PSEA refers to 2-(6'-methylpyridin-2'-ylsulfanyl)ethanamine

6-OMe-2-PSEA (1mL)
75 mL Injection of a 2 mg/mL mAb sample (13.8mg/mL orig.),
Curve Compare for 5CV Wash, 20CV and 30CV (unbound mAb Wash))

(a)

TerPSEA (1mL)
75 mL Injection of a 2 mg/mL mAb sample (13.8mg/mL orig.),
5CV Wash and 30CV (unbound mAb Wash) Curve Compare (13/07/07)

(b)

(c)

(d)

(a)

(b)

(a)

(b)

(c)

(d)

(a)

(b)

AFFINITY LIGANDS AND METHODS FOR PROTEIN PURIFICATION

Cross-Reference to Related Applications

This application is a national stage application under 35 U.S.C. §371 of International Application No. PCT/AU2010/001368, filed Oct. 15, 2010, which in turn claims priority Australian Patent Application No. 2009905049, filed Oct. 15, 2009, the entire contents of each of which are each hereby incorporated by reference into the present disclosure.

FIELD OF THE INVENTION

The present invention relates generally to affinity ligands and chemical affinity ligand-matrix conjugates for use as chromatographic adsorbents and methods which utilise the adsorbents in the purification of proteins by affinity chromatography.

BACKGROUND OF THE INVENTION

Approximately one-third to one-half of all human pharmaceutical products currently under development and in clinical trials are derived from humanised monoclonal antibodies (mAbs). Monoclonal antibodies are ideal therapeutic candidates as they mimic natural processes of the body and are, in principle, devoid of the intrinsic toxicity often present with the use of small-molecule drugs. The global shortfall of available biomanufacturing capacity is becoming a critical limitation in mAb commercialisation. Improvements are required in all areas of the pharmaceutical supply chain, particularly downstream processing, to manage these manufacturing challenges.

Antibodies are glycoprotein molecules and belong to a class of biomolecules known as the immunoglobulins, of which there are five major classes, IgG, IgA, IgM, IgD and IgE. They are separated into these classes according to their heavy chain components and each have characteristic biological and structural properties. Antibodies are a significant part of the immune system and are produced by B lymphocytes in response to a foreign molecule (antigen). Each B lymphocyte cell will only produce a single antibody molecule specific for one binding site (epitope) on the antigen. Polyclonal antibodies are produced from more than one B lymphocyte cell clone and collectively bind to several sites on a single antigen. Each monoclonal antibody is produced by a single clone of plasma cell and are specific for a single site on the antigen.

The G class of immunoglobulins (IgG) are the most common in serum and have a molecular mass of ca. 150 kDa. Furthermore, they can be divided into four subclasses (G1-4) in humans. IgG is composed of four polypeptide chains (2 identical heavy chains and 2 identical light chains) joined by disulfide bridges to form a Y shape structure. Immunoglobulin G can be divided into two regions. The 'tail' of the antibody is referred to as Fc (fragment crystallisable) while the other region contains two identical fragments termed Fab (fragment antigen binding). Furthermore, each of the 4 polypeptide chains contains a constant region ($C_H$ or $C_L$) and variable region ($V_H$ or $V_L$). Formation of two identical antigen binding sites occurs when the variable regions of the heavy and light chains combine.

Monoclonal antibodies are currently being utilised and trialed as therapeutic and diagnostic agents. Diagnostically, they can be tagged with fluorescent or radioactive labels to test for aberrant biological phenomena associated, for example, with pregnancy, blood clots, cancers, heart disease, and viruses (e.g. AIDS). Therapeutically, they can be used for treatment in transplant rejection, various forms of cancer, auto-immune diseases (e.g. multiple sclerosis, rheumatoid arthritis) and infectious diseases (respiratory syncytial virus, cytomegalovirus, septicaemia). Furthermore, they can also be used in protein structure analysis, affinity purification of biomolecules and drugs.

The sources from which antibodies can be isolated include natural sources (body fluids of immunised animals or humans) and recombinant sources (supernatents of lysates from engineered cells derived from hybridoma or bacterial cells). The number of expression systems for antibody production has recently expanded and now includes mammalian cells, insect cells, yeasts, bacteria, transgenic animals and transgenic plants, all of which have their advantages and disadvantages. The therapeutic monoclonal antibodies available on the market today are derived from animal cell culture.

Antibodies need to be extracted and purified whether they are derived from natural sources or recombinant cells. Although generic purification schemes have been suggested, they only serve as a guide with each purification method examined on a case-by-case basis, where it may be necessary to optimise certain steps. Differences in amino acid composition and sequence of the variable domains of monoclonal antibodies, the level and type of glycosylation, and the nature of any other post-translational or chemical modification (e.g. pegylation) have a profound effect on the chemical, physical and biological properties of the antibody. Antibodies vary in their isoelectric point, solubility and resistance to extremes of pH which complicates the use of a generic purification system.

Since polyclonal antibodies have heterogeneous specificity due to diversity in their antigen binding site, a method is required that facilitates purification of the total antibody population from a mixture. Although homogeneous in terms of specificity, monoclonal antibodies similarly require robust separation methods for their purification from feedstock mixtures. In both cases, the highly conserved regions (Fc) of antibodies can be exploited for their capture and subsequent purification from complex feedstocks. As well as the host cells and cell debris, contaminants may include host cell proteins, viruses and bacterial pathogens or their breakdown products (e.g. endotoxins) and media additives (protein growth promoters and stabilizers or serum supplements). Furthermore, impurities may also consist of the expressed antibody which is miss-folded or proteolytically degraded, as well as aggregates of the desired antibody.

Because of the current dosage regimes (i.e. several hundred milligrams to a gram per dose), a large production capacity is required for the manufacture of therapeutic mAbs with hundreds of kilograms to more than one metric ton of product needed per year. The conditions and diseases to be treated often require repeat doses on a gram scale unlike small-molecule pharmaceuticals where dosing is often only in the milligram range. This is due to the large size of the mAb molecules, their mode of action and the nature of the therapies used.

The high doses of therapeutic antibodies required, has two implications:
  i) they must meet stringent requirements such as proof of identity, purity, stability, potency and safety; and
  ii) production cost per dose must be kept to a minimum.

To achieve these goals, effective purification strategies and processes need to be developed and employed. A general purification scheme for mAb production can be divided into three parts: the capture step, the intermediate fractionation step and the final purification and final polishing steps. No single generic downstream process is currently available that attains all of these features. With new production methods under accelerated development, cell culture and fermentation capabilities are being increased significantly with respect to expression levels. However, the growing demand for mAbs over the coming years is expected to exceed the current worldwide production capacity. The aim of downstream processing (extraction, separation and purification) is to implement the most direct route from starting material to the desired final product. Due to the rate limiting upstream production requirements, downstream processing must be made as fast and efficient as possible. Yields need to be maximized while retaining the original biological activity of the antibody. Furthermore, when developing monoclonal antibody therapeutics, it is vital to consider the downstream processing costs as they can account for up to 80% of the overall cost of production.

Downstream processing commonly involves a range of membrane filtration steps and chromatographic unit operations. The general guidelines for these operations ensure that:
- the most abundant impurities are removed early in the process;
- the easiest separations are run early in the process;
- the difficult and/or expensive separations are performed towards the end of the process;
- separations are chosen to take advantages of differences in the properties of the antibody and contaminating impurities;
- the operations are structured in an orthogonal manner to exploit different separation mechanisms.

After cell culture or fermentation, an initial clarification step, which is required to remove whole cells and large cell debris particles, can be achieved by centrifugation or microfiltration. A second clarification step helps to clear colloidal particulate material destructive towards finer filters downstream. Bacteria and other bioburden are then eliminated by using sterilizing filters before the first chromatographic unit operation.

Chromatographic techniques for the purification of monoclonal antibodies, include hydrophobic interaction chromatography (HIC), ion exchange chromatography (IEC), hydroxyapatite chromatography (HAC), immobilised metal affinity chromatography (IMAC) or even size exclusion chromatography (SEC) and affinity chromatographic procedures.

Affinity chromatography involves the separation of the target protein from a complex mixture based on a highly specific, reversible adsorption of the desired protein onto a chromatographic matrix. The interaction occurs between certain proteins in the mixture and a bio-specific ligand that is immobilised on the solid phase, most often a polymeric solid support material such as a polymeric gel in the form of a bead. Affinity chromatography is best suited for a capture or intermediate purification step within a purification process as it possesses high selectivity and high capacity, which enables high recovery of concentrated sample with up to several thousand fold increase in purity.

Affinity adsorbents need to be reusable and the stability of the ligand and matrix with respect to the cleaning conditions used will determine the number of cycles possible. For sanitisation, a treatment with 1M sodium hydroxide is often employed to remove impurities that remain bound after the elution step and provide a column ready for further purification cycles. Alternative regeneration methods will need to be determined and optimised if the ligand or adsorbent is not resistant to caustic treatment since this will have a material bearing on critical infrastructure protection requirements.

Affinity chromatography using immobilised Protein A is currently a commonly used method for purification of antibodies. The production and isolation of Protein A involves a complex and labour intensive procedure, making the final product very expensive. Particular care is therefore needed to preserve the column for multiple uses. Protein A is limited in its selectivity towards different classes of immunoglobulins. It will mainly bind IgG, although not all subtypes, and has no affinity towards IgE and IgY. Its binding is variable towards IgA and IgM. Antibodies are commonly eluted from Protein A affinity columns under low pH (pH 2-3) conditions, however such conditions can alter their conformation and ultimately may cause a loss in their biological activity. The Protein A—IgG interaction, occurring at the Fc fragment, can affect the antibody's local structure to a certain extent, causing destabilisation and an altered susceptibility to proteolytic attack or aggregation.

Two of the most serious issues that limit the use of Protein A are its cost and leakage into the purified antibody preparations. This can be due to its degradation by proteases in the feedstock itself, the immobilisation method used or the stability of the backbone chromatographic support material. Time consuming analytical methods are therefore needed to detect contaminants in the purified product before it can be approved for therapeutic use. Furthermore, a reduction in binding capacity of the column occurs as a result of Protein A leakage. Because the immobilised Protein A also has a low resistance when cleaning the column with caustic solutions (unlike chemical ligands), this makes its use less practical in terms of sanitisation and longevity, although Protein A structural variants which have been genetically engineered for greater pH stability are now available.

Another bacterial Fc receptor, Protein G, has specificity for different antibody classes, subclasses and species. However, the cost of this reagent is much greater than Protein A itself and this constraint has limited its commercial use, even though purification conditions are less harsh compared to those for Protein A.

Bio-specific affinity chromatography involves separation based on antibody-antibody affinity recognition, antigen-antibody affinity interaction, or bacterial Fc receptor-antibody adsorption. Monoclonal and polyclonal antibodies can be selectively purified by immobilising specific antibodies (anti-immunoglobulins) as affinity ligands on a chromatographic matrix. Due to the extreme specificity of the antibody ligand, a new adsorbent must be designed every time a new antibody requires separation. This approach involves production of the antibody's ligand, and its purification and immobilisation. All of these processes increase costs, hence this approach is currently restricted to laboratory scale applications. Because antibodies possess recognition sites for specific antigens, immobilisation of these antigens as affinity ligands is commonly used. The restrictions of this method are the availability of the antigen and difficulties to achieve elution of the antibody in high yield due to the high affinity.

In an attempt to overcome some of the drawbacks of Protein A as mentioned previously, a range of triazine-dye related mimetic compounds have been generated via combinatorial library screening or computer modelling. Lowe and co-workers synthesised Protein A mimetic ligands based around phenylalanine, tyrosine and isoleucine residues attached to a trichlorotriazine ring. The resulting ligands had millimolar affinities ($K_A$'s) for IgG, $10^2$-$10^4$ M$^{-1}$.[1] Lowe et al. also attached 4-amino-1-naphthol and 3-aminophenol to the triazine core (Ligand 22/8) and the resulting adsorbent again had suboptimal (millimolar) affinity ($1.4 \times 10^5$ M$^{-1}$) with binding capacity of 51.9 mg IgG/g moist weight gel.[2,3] Other chemical or peptidic ligands have also been investigated. Thus, Fassina et al. have reported a synthetic peptide ligand, TG19318: (Arg-Thr-Tyr)-4-(Lys)-3-Gly, which is able to mimic Protein A in recognition of the Fc region of antibodies.[4] Moreover, the ligand had a broader specificity than Protein A, interacting with IgG, IgA, IgM, IgE and IgY from different sources.

In 1985, Porath and co-workers described an adsorption process for the fractionation of certain proteins, i.e. immunoglobulins and α2-macroglobulins, from serum, which they termed "thiophilic adsorption".[5] This adsorption was particularly affected by the presence of high concentrations of neutral salts, using resins that were divinylsulphone (DVS)-activated and blocked with β-mercaptoethanol. A series of ligands related to β-mercaptoethanol were also screened for their protein binding ability. The general structure for a thiophilic adsorbent (T-Gel) could be represented by the structure depicted below:

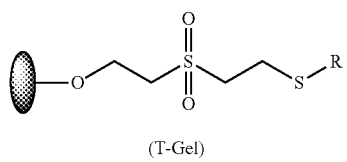

(T-Gel)

Porath and Oscarsson later described a similar protein binding behaviour to that of the thiophilic adsorbent (T-Gel) when 2-mercaptopyridine was coupled to epichlorohydrin activated gels. Protein adsorption was achieved in a salt promoted manner[6].

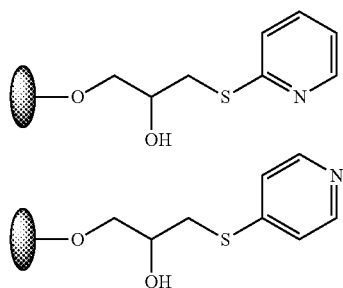

2- and 4-Mercaptopyridine attached to epichlorohydrin activated gel

Knudsen and co-workers prepared adsorbents based on hetero-aromatic ligands immobilised on divinylsulfone-activated gel which gave them a thiophilic character. Isolation of IgG from human serum in the presence of lyotropic salts using ligands including 2-, 3-, or 4-hydroxypyridine, 2-aminopyridine, 4-aminobenzoic acid, 4-methoxyphenol and imidazole was achieved.[7] Although a high binding capacity was observed, the eluted samples were still contaminated with other serum proteins.

Schwarz et al. immobilised 2-mercaptopyridine, 2-mercaptopyrimidine and mercaptothiazoline onto both epoxy-activated agarose and silica.[8] The latter two ligands were chosen on the basis of their higher hydrophilicity and electron density compared to 2-mercaptopyridine. Adsorption of antibodies was achieved in the presence of sodium sulfate with dissociation constants ($K_D$) in the mid $10^{-7}$ M range. Binding capacities were also found to be higher for the silica based adsorbents. Schwarz later prepared several adsorbents using five-membered heterocyclic rings, containing at least two heteroatoms, as ligands (see below).[9] The presence of at least one double bond within the ring was required for antibody adsorption, and only a slight increase in capacity at comparable densities was achieved with two double bonds, as found in the mercaptothiazole structure.

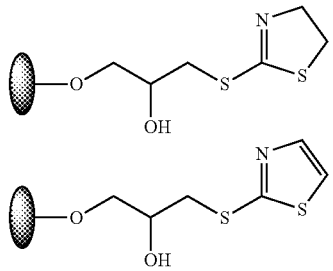

Mercaptothiazoline and mercaptothiazole immobilised on Epoxy-HyperD beads

Scholz and co-workers coupled 2-mercaptopyridine, 2-mercaptopyrimidine and 2-mercaptonicotinic acid to DVS- and epichlorohydrin-activated Sepharose.[10] The adsorbents prepared by DVS-activation gave a higher recovery than the corresponding epichlorohydrin-activated adsorbents under salt-promoted conditions. The DVS-activated adsorbents immobilised with 2-mercaptopyridine and 2-mercaptonicotinic acid (see below) were additionally shown to bind immunoglobulins in a salt-independent manner and consequently desorbed with 10 mM NaOH.

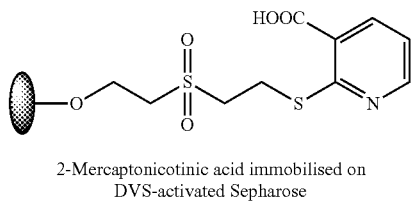 [SMILES: COCCS(=O)(=O)CCSc1ncccc1C(=O)O]

2-Mercaptonicotinic acid immobilised on DVS-activated Sepharose

Scholz et al. also immobilised MECH, 3-(2-mercaptoethyl)quinazoline-2,4(1H,3H)dione, an immunostimulatory substance described by Drössler[11] to DVS-activated agarose.[12] The derivatised gel was able to bind antibodies (ca. 18 mg/mL gel) from human or animal serum under low-salt conditions at pH 7.4 and elution was achieved by raising the pH with dilute alkali.

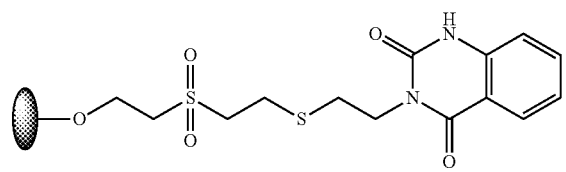

MECH immobilised on DVS-activated agarose

In contrast to Protein A and Protein G affinity chromatography, thiophilic chromatography has the following potential advantages:
   low adsorbent cost,
   broad specificity for antibodies (type and subclass) from various sources, high binding capacity,
mild elution conditions,
greater chemical stability of the affinity ligands,
lack of ligand leakage,
ability to separate and purify (recombinant) antibody fragments lacking the Fc receptor.

The binding of antibodies to the prior art adsorbents is, however, less specific than the binding to Protein A or G bacterial Fc receptors.

With an increasing number of therapeutic monoclonal antibodies being developed, and the lack of reliable and cost effective purification protocols currently available, there is a need for procedures that can guarantee consistency in the quality of the product. Considerable effort has thus been made towards the synthesis of low-molecular weight molecules which are able to:

i) bind antibodies with similar or enhanced affinity as found with Protein A, and/or
ii) possess improved chemical and physical properties within a process context.

The synthetic affinity ligands used in the aforementioned thiophilic chromatographic adsorbents are also preferably endowed with characteristics that result in increased chemical and biological resistance to degradation, reduced toxicity and leakage, high antibody binding capacity and broader selectivity. Overall, improvements in these characteristics will achieve a significant reduction in antibody production costs. The present invention seeks to address one or more of these existing shortcomings.

SUMMARY OF THE INVENTION

In a first aspect the present invention provides affinity ligand-matrix conjugates comprising a ligand of general formula (I):

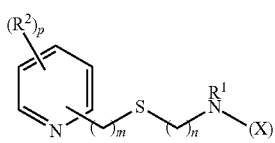

wherein:
m represents an integer from 0-2;
n represents an integer from 0-6;
p represents an integer from 0-4;
$R^1$ represents hydrogen or $C_{1-3}$ alkyl; and
each $R^2$, when present, may be selected independently from carboxyl, cyano, halogen, hydroxy, nitro, phosphono, phosphorylamino, phosphinyl, sulfo, trihalomethanethio, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, and optionally substituted thioacylamino, or any two adjacent $R^2$ may together form an optionally substituted aryl, optionally substituted heteroaryl, or optionally substituted heterocyclyl and said ligand is immobilised unto a support matrix in position (X), optionally through a linker group (L) interposed between the matrix and ligand.

In a further aspect the invention provides the use of an affinity ligand-matrix conjugate as described above in the separation or purification of proteins.

In still a further aspect the invention provides a process for the separation or purification of proteins by affinity chromatography using the affinity ligand-matrix conjugate as described above.

DETAILED DESCRIPTION OF THE INVENTION

Figure 1:
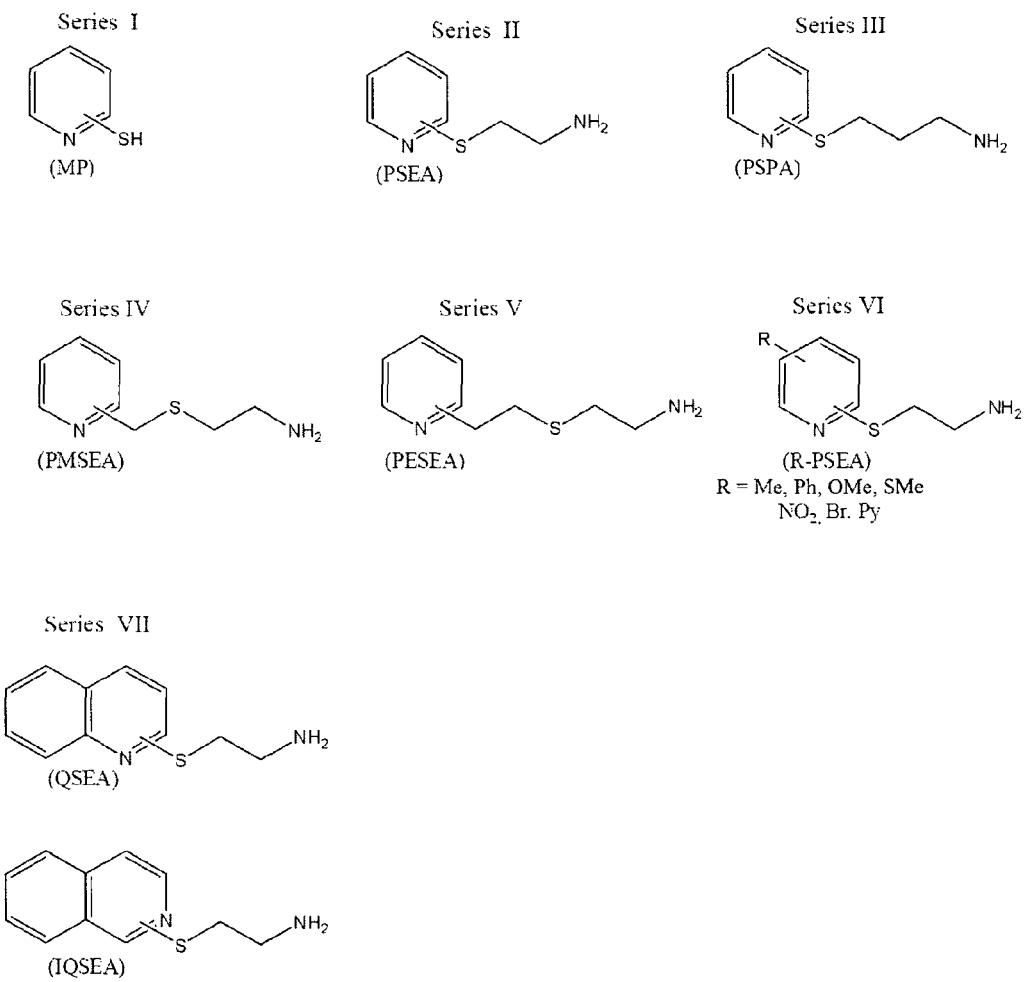
FIG. 1: Depiction of adsorbent series I-VII.
Figure 1:
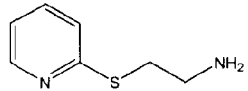
Figure 1:
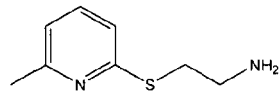

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention is based on the discovery that affinity ligand-matrix conjugates comprising a ligand of formula (I) as described in the above Summary of the Invention, display high selectivity and specificity for proteinaceous materials and therefore possess utility as chromatographic adsorbents in the purification of protein, and in particular antibodies.

The affinity ligands disclosed herein bear a unique aminoalkylene-S-arrangement which is thought to provide benefits in not only selectivity and specificity with respect to protein binding affinity but also provides benefits in relation to the preparation of the corresponding affinity ligand-matrix conjugates. For instance the amino group provides a nucleophilic moiety to enable efficient tethering (immobilisation) unto a support matrix.

Chemical Definitions

"Alkyl" refers to monovalent alkyl groups which may be straight chained or branched and preferably have from 1 to 10 carbon atoms or more preferably 1 to 6 carbon atoms. Examples of such alkyl groups include methyl, ethyl, n-propyl, iso-propyl, n-butyl, iso-butyl, n-hexyl, and the like.

"Alkylene" refers to divalent alkyl groups preferably having from 1 to 10 carbon atoms and more preferably 1 to 6 carbon atoms. Examples of such alkylene groups include methylene (—$CH_2$—), ethylene (—$CH_2CH_2$—), and the propylene isomers (e.g., —$CH_2CH_2CH_2$— and —$CH(CH_3)CH_2$—), and the like.

"Aryl" refers to an unsaturated aromatic carbocyclic group having a single ring (eg. phenyl) or multiple condensed rings (eg. naphthyl or anthryl), preferably having from 6 to 14 carbon atoms. Examples of aryl groups include phenyl, naphthyl and the like.

"Arylene" refers to a divalent aryl group wherein the aryl group is as described above.

"Aryloxy" refers to the group aryl-O— wherein the aryl group is as described above.

"Arylalkyl" refers to -alkylene-aryl groups preferably having from 1 to 10 carbon atoms in the alkylene moiety and from 6 to 10 carbon atoms in the aryl moiety. Such arylalkyl groups are exemplified by benzyl, phenethyl and the like.

"Arylalkoxy" refers to the group arylalkyl-O— wherein the arylalkyl group are as described above. Such arylalkoxy groups are exemplified by benzyloxy and the like.

"Alkoxy" refers to the group alkyl-O— where the alkyl group is as described above. Examples include, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkenyl" refers to a monovalent alkenyl group which may be straight chained or branched and preferably have from 2 to 10 carbon atoms and more preferably 2 to 6 carbon atoms and have at least 1 and preferably from 1-2, carbon to carbon, double bonds. Examples include ethenyl (—CH=CH$_2$), n-propenyl (—CH$_2$CH=CH$_2$), iso-propenyl (—C(CH$_3$)=CH$_2$), but-2-enyl (—CH$_2$CH=CHCH$_3$), and the like.

"Alkenyloxy" refers to the group alkenyl-O— wherein the alkenyl group is as described above.

"Alkenylene" refers to divalent alkenyl groups preferably having from 2 to 8 carbon atoms and more preferably 2 to 6 carbon atoms. Examples include ethenylene (—CH=CH—), and the propenylene isomers (e.g., —CH$_2$CH=CH— and —C(CH$_3$)=CH—), and the like.

"Alkynyl" refers to alkynyl groups preferably having from 2 to 10 carbon atoms and more preferably 2 to 6 carbon atoms and having at least 1, and preferably from 1-2, carbon to carbon, triple bonds. Examples of alkynyl groups include ethynyl (—C≡CH), propargyl (—CH$_2$C≡CH), pent-2-ynyl (—CH$_2$C≡CCH$_2$—CH$_3$), and the like.

"Alkynyloxy" refers to the group alkynyl-O— wherein the alkynyl groups is as described above.

"Alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

"Acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are as described herein.

"Oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

"Amino" refers to the group —NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Aminoacyl" refers to the group —C(O)NR"R" where each R" is independently hydrogen, alkyl, cycloalkyl, aryl, heteroaryl, and heterocyclyl and where each of alkyl, cycloalkyl, aryl, heteroaryl and heterocyclyl is as described herein.

"Acylamino" refers to the group —NR"C(O)R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyloxy" refers to the groups —OC(O)-alkyl, —OC(O)-aryl, —C(O)O-heteroaryl, and —C(O)O-heterocyclyl where alkyl, aryl, heteroaryl and heterocyclyl are as described herein.

"Aminoacyloxy" refers to the groups —OC(O)NR"-alkyl, —OC(O)NR"-aryl, —OC(O)NR"-heteroaryl, and —OC(O)NR"-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacylamino" refers to the groups —NR"C(O)O-alkyl, —NR"C(O)O-aryl, —NR"C(O)O-heteroaryl, and NR"C(O)O-heterocyclyl where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxyacyloxy" refers to the groups —OC(O)O-alkyl, —O—C(O)O-aryl, —OC(O)O-heteroaryl, and —OC(O)O-heterocyclyl where alkyl, cycloalkyl, aryl, heteroaryl, and heterocyclyl are as described herein.

"Acylimino" refers to the groups —C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Acyliminoxy" refers to the groups —O—C(NR")—R" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Oxyacylimino" refers to the groups —C(NR")—OR" where each R" is independently hydrogen, alkyl, cycloalkyl, aryl, heteroaryl and heterocyclyl and where each of alkyl, cycloalkyl, aryl, heteroaryl, and heterocyclyl are as described herein.

"Cycloalkyl" refers to cyclic alkyl groups having a single cyclic ring or multiple condensed rings, preferably incorporating 3 to 11 carbon atoms. Such cycloalkyl groups include, by way of example, single ring structures such as cyclopropyl, cyclobutyl, cyclopentyl, cyclohexyl, cyclooctyl, and the like, or multiple ring structures such as adamantanyl, indanyl, 1,2,3,4-tetrahydronapthalenyl and the like.

"Cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

"Halo" or "halogen" refers to fluoro, chloro, bromo and iodo.

"Heteroaryl" refers to a monovalent aromatic heterocyclic group which fulfils the Mickel criteria for aromaticity (ie. contains $4n+2\pi$ electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl). It will be understood that where, for instance, $R_2$ or $R'$ is an optionally substituted heteroaryl which has one or more ring heteroatoms, the heteroaryl group can be connected to the core molecule of the compounds of the present invention, through a C—C or C-heteroatom bond, in particular a C—N bond.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen. It will be understood that where, for instance, $R_2$ or R' is an optionally substituted heterocyclyl which has one or more ring heteroatoms, the heterocyclyl group can be connected to the core molecule of the compounds of the present invention, through a C—C or C-heteroatom bond, in particular a C—N bond.

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Heteroarylene" refers to a divalent heteroaryl group wherein the heteroaryl group is as described above.

"Heterocyclylene" refers to a divalent heterocyclyl group wherein the heterocyclyl group is as described above.

"Thio" refers to groups H—S—, alkyl-S—, cycloalkyl-S—, aryl-S—, heteroaryl-S—, and heterocyclyl-S—, where alkyl, cycloalkyl, aryl, heteroaryl and heterocyclyl are as described herein.

"Thioacyl" refers to groups H—C(S)—, alkyl-C(S)—, cycloalkyl-C(S)—, aryl-C(S)—, heteroaryl-C(S)—, and heterocyclyl-C(S)—, where alkyl, cycloalkyl, aryl, heteroaryl and heterocyclyl are as described herein.

"Oxythioacyl" refers to groups HO—C(S)—, alkylO—C(S)—, cycloalkylO—C(S)—, arylO—C(S)—, heteroarylO—C(S)—, and heterocyclylO—C(S)—, where alkyl, cycloalkyl, aryl, heteroaryl and heterocyclyl are as described herein.

"Oxythioacyloxy" refers to groups HO—C(S)—O—, alkylO—C(S)—O—, cycloalkylO—C(S)—O—, arylO—C(S)—O—, heteroarylO—C(S)—O—, and heterocyclylO—C(S)—O—, where alkyl, cycloalkyl, aryl, heteroaryl and heterocyclyl are as described herein.

"Phosphorylamino" refers to the groups —NR"—P(O)(R''')(OR'''') where R" represents H, alkyl, cycloalkyl, alkenyl, or aryl, R''' represents OR'''' or is hydroxy or amino and R'''' is alkyl, cycloalkyl, aryl or arylalkyl, where alkyl, amino, alkenyl, aryl, cycloalkyl, and arylalkyl are as described herein.

"Thioacyloxy" refers to groups H—C(S)—O—, alkyl-C(S)—O—, cycloalkyl-C(S)—O—, aryl-C(S)—O—, heteroaryl-C(S)—O—, and heterocyclyl-C(S)—O—, where alkyl, cycloalkyl, aryl, heteroaryl, and heterocyclyl are as described herein.

"Sulfinyl" refers to groups H—S(O)—, alkyl-S(O)—, cycloalkyl-S(O)—, aryl-S(O)—, heteroaryl-S(O)—, and heterocyclyl-S(O)—, where alkyl, cycloalkyl, aryl, heteroaryl and heterocyclyl are as described herein.

"Sulfonyl" refers to groups H—S(O)$_2$—, alkyl-S(O)$_2$—, cycloalkyl-S(O)$_2$—, aryl-S(O)$_2$—, heteroaryl-S(O)$_2$—, and heterocyclyl-S(O)$_2$—, where alkyl, cycloalkyl, aryl, heteroaryl and heterocyclyl are as described herein.

"Sulfinylamino" refers to groups H—S(O)—NR"—, alkyl-S(O)—NR"—, cycloalkyl-S(O)—NR"—, aryl-S(O)—NR"—, heteroaryl-S(O)—NR"—, and heterocyclyl-S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Sulfonylamino" refers to groups H—S(O)$_2$—NR"—, alkyl-S(O)$_2$—NR"—, cycloalkyl-S(O)$_2$—NR"—, aryl-S(O)$_2$—NR"—, heteroaryl-S(O)$_2$—NR"—, and heterocyclyl-S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfinylamino" refers to groups HO—S(O)—NR"—, alkylO—S(O)—NR"—, cycloalkylO—S(O)—NR"—, arylO—S(O)—NR"—, heteroarylO—S(O)—NR"—, and heterocyclylO—S(O)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Oxysulfonylamino" refers to groups HO—S(O)$_2$—NR"—, alkylO—S(O)$_2$—NR"—, cycloalkylO—S(O)$_2$—NR"—, arylO—S(O)$_2$—NR"—, heteroarylO—S(O)$_2$—NR"—, and heterocyclylO—S(O)$_2$—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminothioacyl" refers to groups R"R"N—C(S)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Thioacylamino" refers to groups H—C(S)—NR"—, alkyl-C(S)—NR"—, cycloalkyl-C(S)—NR"—, aryl-C(S)—NR"—, heteroaryl-C(S)—NR"—, and heterocyclyl-C(S)—NR"—, where R" is independently hydrogen, alkyl, cycloalkyl, aryl, heteroaryl, and heterocyclyl and where each of alkyl, cycloalkyl, aryl, heteroaryl and heterocyclyl is as described herein.

"Aminosulfinyl" refers to groups R"R"N—S(O)—, where each R" is independently hydrogen, alkyl, cycloalkyl, aryl, heteroaryl, and heterocyclic and where each of alkyl, cycloalkyl, aryl, heteroaryl and heterocyclyl is as described herein.

"Aminosulfonyl" refers to groups R"R"N—S(O)$_2$—, where each R" is independently hydrogen, alkyl, cycloalkyl, aryl, heteroaryl, and heterocyclic and where each of alkyl, cycloalkyl, aryl, heteroaryl and heterocyclyl is as described herein.

In this specification "optionally substituted" is taken to mean that a group may or may not be further substituted or fused (so as to form a condensed polycyclic group) with one or more groups selected from hydroxyl, acyl, alkyl, alkoxy, alkenyl, alkenyloxy, alkynyl, alkynyloxy, amino, aminoacyl, thio, arylalkyl, arylalkoxy, aryl, aryloxy, carboxyl, acylamino, cyano, halogen, nitro, phosphono, sulfo, phosphorylamino, phosphinyl, heteroaryl, heteroaryloxy, heterocyclyl, heterocyclyloxy, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like.

In the case of the divalent linker group alkylene, the term "optionally substituted" also indicates that one or more saturated carbon atoms may be substituted for a heteroatom or heterogroup, such as O, S, NH, C(O), SO$_2$ and the like. For example an optionally substituted alkylene group could be represented by a group such as —CH$_2$CH$_2$OCH$_2$—, —CH$_2$CH$_2$NH—CH$_2$—, —CH$_2$NHCH$_2$—, —CH$_2$OCH$_2$—, —CH$_2$—C(O)—CH$_2$—, —CH$_2$CH$_2$OCH$_2$CH$_2$OCH$_2$CH$_2$—, —CH$_2$CH$_2$SO$_2$CH$_2$—CH$_2$—, —CH$_2$—NH—C(O)—CH$_2$— and the like. The term also denotes that the substituent may also be pendant to the alkylene chain such as —CH$_2$—CH(OH)—CH$_2$—, —CH$_2$—CH(CF$_3$)—CH$_2$— and the like.

In some embodiments of the invention, and with reference to the ligand of general formula (I), one or more of the following preferred definitions may apply:

(a) R$^1$ is H;

(b) m is 0 or 1;

(c) n is 2 or 3;

(d) p is 0, 1, or 2;

In an even more preferred embodiment m is 0, R$^1$ is H, n is 2 or 3, and p is 0, 1, or 2.

In some embodiments of the invention, together (a)-(d) above, one or more of the further following preferred definitions may apply:

(e) p is 0; or p is 1 and R$^2$ is selected from halogen, nitro, thio, optionally substituted C$_{1-3}$ alkyl, optionally substituted C$_{1-3}$ alkoxy, optionally substituted heteroaryl, optionally substituted heterocyclyl, optionally substituted aryl; or p is 2 and each R$^2$ is independently selected from halogen, optionally substituted C$_{1-3}$ alkyl, optionally substituted C$_{1-3}$ alkoxy, thio, optionally substituted heteroaryl, optionally substituted heterocyclyl, optionally substituted aryl; or the R$^2$ groups are adjacent and represent an optionally substituted aryl, optionally substituted heteroaryl or optionally substituted heterocyclyl group.

Examples of suitable

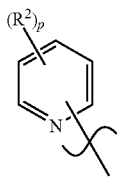

groups include the following:

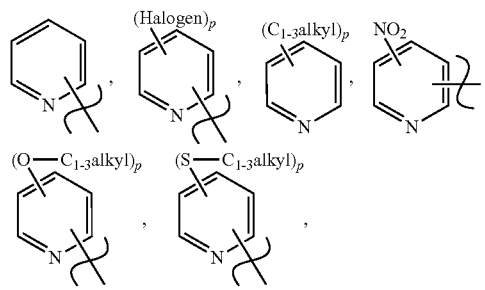

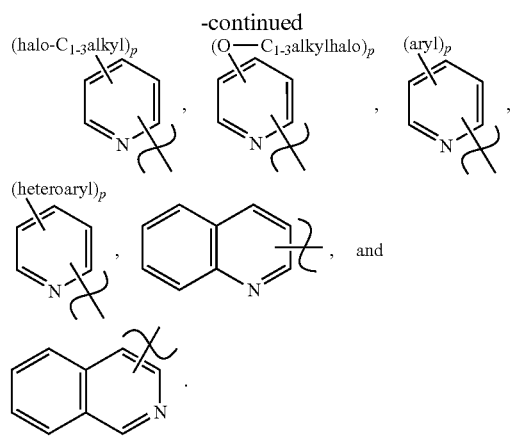

(where p is 1 or 2, and preferably p is 1).

More preferred

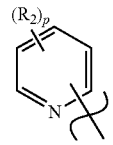

groups include the following:

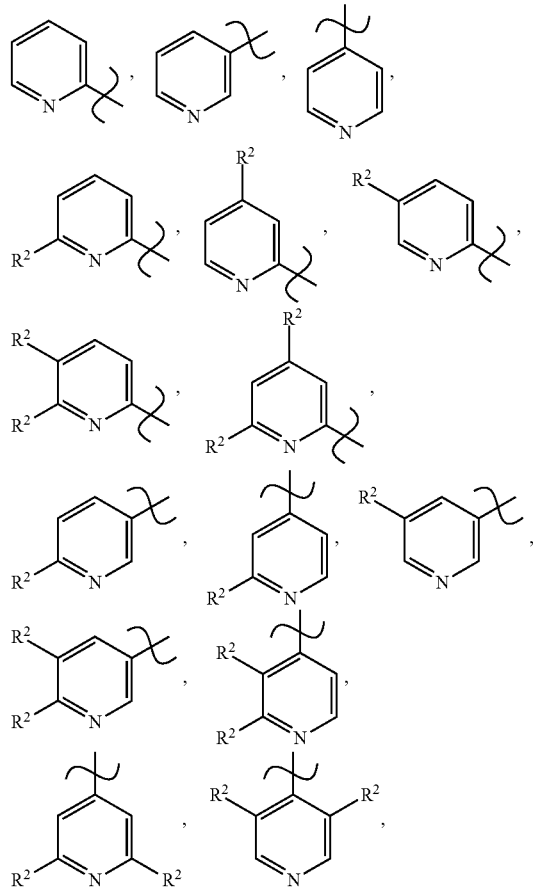

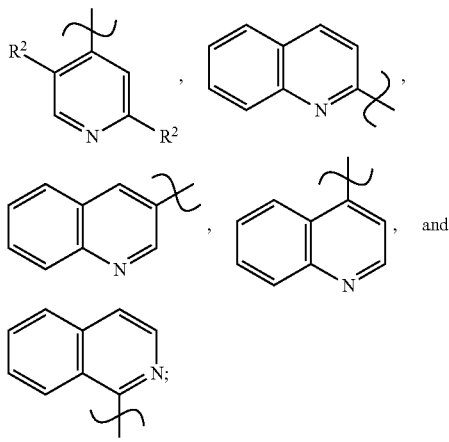

wherein each R², when present, independently represents halogen (preferably Br or Cl), nitro, thio, $C_{1-3}$alkyl, halo-$C_{1-3}$alkyl, $C_{1-3}$alkoxy, halo-$C_{1-3}$alkoxy, optionally substituted heteroaryl, optionally substituted heterocyclyl, and optionally substituted aryl.

In respect to the halo-$C_{1-3}$ alkyl and halo-$C_{1-3}$ alkoxy groups preferred groups include mono-, di-, and tri-halo-$C_{1-3}$ alkyl such as trifluoromethyl, difluoromethyl, pentafluoroethyl, and the like, mono- di-, and tri-halo-$C_{1-3}$ alkoxy such as trifluoromethoxy, difluoromethoxy, pentafluoroethoxy and the like.

Even more preferred

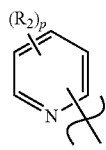

groups include the following:

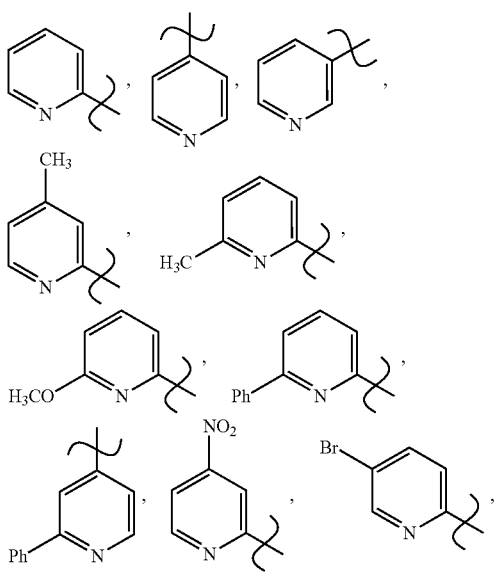

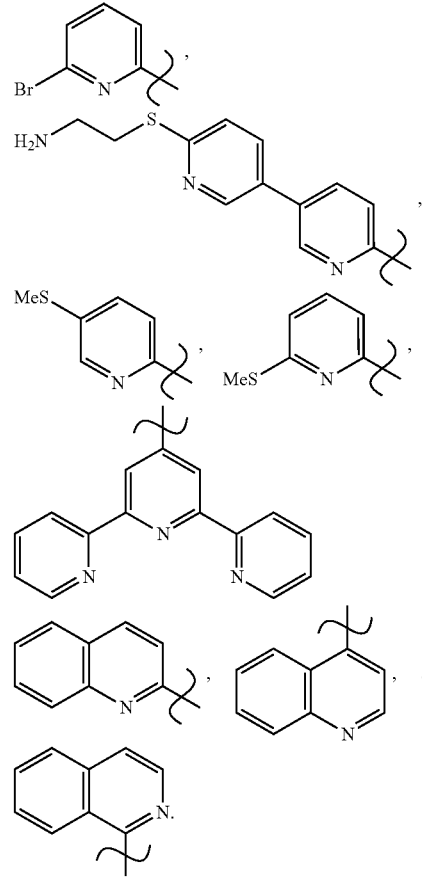

In some other embodiments of the invention, together with (a)-(e) above, the further following definition may apply:
(f) the ligand is immobilised unto a solid support matrix in position (X) (see formula (I)) through a linker group (L) interposed between the matrix and ligand, where L is the divalent group of formula (II)

$$-(Y-V)-\quad\quad(II)$$

wherein Y represents a bond, O, S, NR³ (where R³ represents hydrogen or $C_{1-3}$ alkyl), C(O), C(O)O, OC(O), NR³C(O) (where R³ represents hydrogen or $C_{1-3}$ alkyl), or C(O)NR³ (where R³ represents hydrogen or $C_{1-3}$ alkyl), and V represents a bond, optionally substituted heterocyclylene, optionally substituted arylene, optionally substituted heteroarylene, or optionally substituted $C_{1-20}$ alkylene.

Examples of suitable linker groups include:

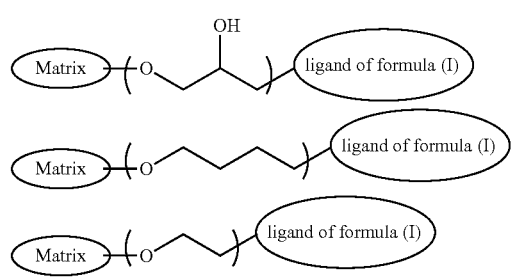

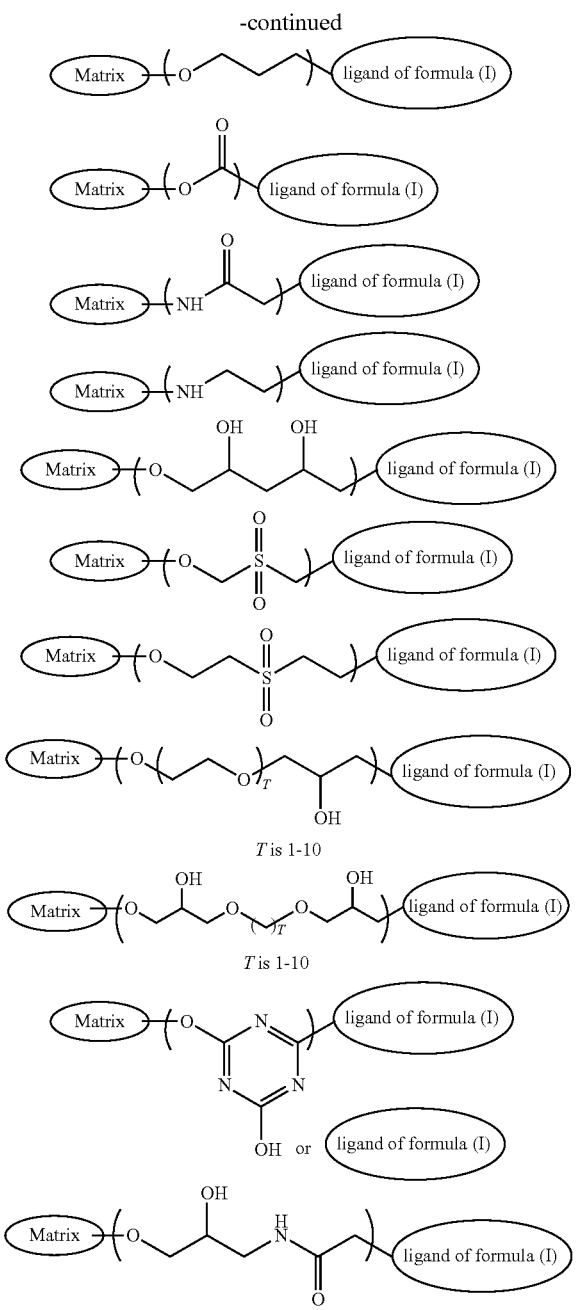

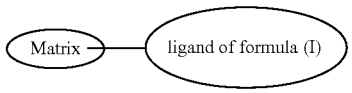

In an embodiment, Y represents O, S or NR³ (where R³ represents hydrogen or $C_{1-3}$ alkyl), and V represents an optionally substituted $C_{1-20}$ alkylene.

Preferably the linker group L is an optionally substituted $C_{1-20}$ alkylene group, and more preferably a hydroxy substituted $C_{1-20}$ alkylene group.

Even more preferably, the linker group L is

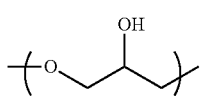

In another embodiment both Y and V are a bond the resultant conjugate of which may be represented by:

Suitable matrix materials for the affinity ligand-matrix conjugates of the present invention include any which are known in the field of affinity chromatography such as polymer based matrix materials.

Useful polymer substrates in the context of the invention include both water-soluble polymers and substantially water-insoluble polymers, and may be selected from a very wide range of polymeric materials. Examples thereof include the following:

Polysaccharides and derivatives thereof, including agaroses, dextrans, celluloses, hemicelluloses, starches, xylans and the like, and derivatives of these polysaccharides. Suitable polysaccharide derivatives will, in general, include derivatives in which some proportion of the hydroxy groups of the polysaccharide in question is derivatized to form ethers (e.g. lower alkyl ethers, such as methyl ethers) or esters (e.g. lower carboxylic acid esters, such as acetate, propionate and the like), as well as materials in which the starting polysaccharide or a derivative thereof has been cross-linked by treatment with an appropriate cross-linking reagent.

Generally speaking, functionalized polymer substrates based on substantially water-insoluble polymers are, for example, well suited for packing into chromatography columns, for direct introduction into a medium (batchwise use) and the like, and polysaccharides that are particularly well suited for this type of application in the context of the invention include agaroses, dextrans and derivatives thereof, a variety of suitable types of which are readily commercially available. Thus, for example, a variety of agarose products are available from GE Healthcare, and marketed under the name Sepharose™; available grades include Sepharose™ 2B, 4B and 6B. Cross-linked derivatives of these various grades of agarose (prepared by cross linking of Sepharose™ with 2,3-dibromopropanol) are also available from the same company, and are marketed as Sepharose™ CL-2B, CL-4B and CL-6B, Sepharose™ 4 and 6 Fast Flow, Sepharose™ 6MB, and Superose™ 6 and 12, respectively.

A number of dextran-based or dextran-agarose composite materials suitable for use in the context of the present invention are also available from GE Healthcare under the names Sephadex™, Superdex™ (e.g. Superdex™ 30, 75 and 200) and Sephacryl™. Products in the Sephadex™ range are prepared by cross-linking dextran with epichlorohydrin and are available in the following grades: Sephadex™ G-10, G-15, G-25, G-50, G-75, G-100, G-150 and G-200, the degree of cross-linking decreasing with increasing G number. Products in the Sephacryl™ range are prepared by cross-linking allyl-dextran with N,N'-methylene-bisacrylamide, and include Sephacryl™ S-100, S-200, S-300, S-400, S-500 and S-1000; the latter six products differ with respect to their range of pore size and particle size distribution. Products in the Superdex™ range are prepared by cross-linking allyl-dextran with agarose derivatives of various compositions.

Polyalkylene glycols and derivatives thereof, including, in particular, polyethylene glycols (PEG), i.e. condensation polymers of ethylene glycol having the general formula $HOCH_2(CH_2OCH_2)_nCH_2OH$ or $H(OCH_2CH_2)_nOH$ and typically having average molecular weights in the range from 200 to 6000. A number of PEG's (including PEG's of average molecular weight 400, 600, 1500, 4000 and 6000, respectively) are available under various names (e.g. Macrogol™, PEG™, Carbowax™, Nycoline™, Pluracol E™, Poly-G™, Polyglycol E™, Solbase™) from a variety of commercial sources. PEG's are generally soluble in or miscible with water, as well as in ethanol and a number of other organic solvents, including aromatic hydrocarbons. The analogous polypropylene glycols [having the general formula $H(OC_3H_6)_nOH$], the lower molecular weight members of which are soluble in water, are also of relevance in the context of the invention. Relevant derivatives of such polyalkylene glycols include partially etherified derivatives, e.g. derivatives in which one of the terminal hydroxy groups has been converted to a lower alkyl ether group, such as a methyl ether group.

Such polymers can also be readily immobilized into support matrix materials, thereby producing substrates that can subsequently be activated and then functionalized or derivatized.

Polyvinyl polymers, including polyvinyl alcohols—i.e. hydroxylic polymers normally produced by hydrolysis ("alcoholysis") of various molecular weight fractions of polyvinyl acetate, typically by base or acid hydrolysis—and derivatives thereof. The degree of "alcoholysis" may be varied by either allowing the hydrolysis of acetate ester groups in polyvinyl acetate to proceed to substantial completion, or by stopping it at a desired degree of alcoholysis. Polyvinyl alcohols are normally commercially available in four molecular weight ranges, viz. ca. 250,000-300,000 (termed super-high viscosity), ca. 170,000-ca. 220,000 (termed high-viscosity), ca. 120,000-150,000 (termed medium-viscosity) and ca. 25,000-ca. 35,000 (termed low-viscosity). In general, the lower the molecular weight of polyvinyl alcohols, the higher is their water sensitivity or ease of water solubility; however, the degree of alcoholysis also plays a role with regard to the water-solubility and other properties of polyvinyl alcohols. Polyvinyl alcohols within all of the above-outlined categories are or relevance in the context of the present invention, as are, for example, ether derivatives thereof, such as methyl ether derivatives.

Other polyvinyl polymer materials of interest include materials such as the Toyopearl™ HW range of porous, semi-rigid spherical gel particles designed for medium- and low-pressure liquid chromatography. Such materials, after activation and functionalization/derivatization, provide another option for the preparation of IMAC sorbents of relevance in the context of the invention. Toyopearl™ HW gels (obtainable from Tosoh Corp, Yamaguchi, Japan, and other suppliers) are synthesized from hydrophilic vinyl polymer containing exclusively C, H and O atoms. Available grades (differing with respect to particle and pore sizes) include Toyopearl™ HW-40, HW-40C, HW-40F, HW-40S, HW-50, HW-50F, HW-505, HW-55, HW-55F, HW-555, HW-65F, HW-65S and HW-75F.

Polyacrylamides and derivatives thereof, including composite materials based on polyacrylamide and agarose, such as Ultrogel™ AcA gels (composite polyacrylamide-agarose gel in bead form, available from, e.g., GE Healthcare). The Ultrogel™ AcA gel range includes AcA 22, AcA 34, AcA 44 and AcA 54, where the number refers to the percentage of acrylamide and agarose, i.e., AcA 22 contains 2% acrylamide and 2% agarose. Activation of hydroxylic groups of these support materials provides an avenue to the preparation of IMAC sorbents.

Surface-modified silicas, including glycidylpropoxy-modified porous silica, such as LiChroSpher™ Diol (E. Merck, Darmstadt, Germany), Toyosoda™ TSKSW3000 (Tosoh Corp., Yamaguchi, Japan); amino-propyl-modified silica, prepared by reaction (in the presence of a suitable catalyst) of aminopropyldiethoxysilane with silicas of appropriate pore size and appropriate average diameter; and mercaptopropylsilicas, prepared by reaction (in the presence of a suitable catalyst) of mercaptopropyldiethoxysilane with silicas of appropriate pore sizes and appropriate average diameters. Alternatively, dextran modified or butadiene-vinyl copolymer modified silicas of appropriate pore sizes and appropriate average diameters can be employed as the chromatographic support materials. "Naked" porous silicas suitable for such derivatization and subsequent modification to generate the respective novel IMAC sorbents can readily be obtained from a variety of suppliers, including E. Merck, (Darmstadt, Germany), Tosoh Corporation, Yamaguchi, Japan), Eka-Nobel AB (Goteborg, Sweden) and Grace Davison GmbH (Worms, Germany).

Surface-modified metal oxides, including glycidylpropoxy-modified porous zirconias, titanias or aluminas, as well as modifications/variants thereof based on the respective metal oxide "doped" with a second metal oxide; amino-propyl-modified zirconia, titania or alumina, prepared by reaction (in the presence of a suitable catalyst) of aminopropyldiethoxysilane with the zirconia, titania or alumina of appropriate pore size and appropriate average diameter; and mercaptopropyl-modified zirconia, titania or alumina, prepared by reaction (in the presence of a suitable catalyst) of mercaptopropyldiethoxysilane with the zirconia, titania or alumina of appropriate pore size and appropriate average diameter. Alternatively, dextran modified or butadiene-vinyl copolymer modified zirconia, titania or alumina of appropriate pore sizes and average diameters can be employed as the chromatographic support materials. "Naked" porous zirconia, titania or alumina suitable for such derivatization and subsequent modification to generate the respective novel IMAC sorbents can readily be obtained from a variety of suppliers, including YMC Co. Ltd. (Kyoto, Japan), Grace GmbH (Worms, Germany) and BioSepra Corp. (Paris, France).

Well suited polymer substrates in the context of the matrix support material of the invention include agaroses, dextrans and derivatives thereof, e.g. materials selected among those outlined above.

Preferably the matrix support material is selected from a hydrophilic polymer. Preferably, the matrix material is sepharose including Sepharose 4B, Sepharose 6B, Sepharose CL-2B, Sepharose CL-4B, Sepharose CL-6B, etc. More preferably the Sepharose is Sepharose 6 Fast Flow® which is available from GE Healthcare.

More preferably the matrix support material is Sepharose (more preferably Sepharose 6Fast Flow®) and the linking group L is

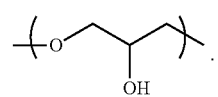

The aforementioned matrix and linker compounds are known in the art. Since the invention described herein lies in the nature of the ligand and not in the mode of attachment (immobilisation) to the matrix support, the preparation of the present matrix-ligand conjugates may be prepared with the use of known condensation methodologies with known condensation agents. Suitable said condensation agents, include but are not limited to, epichlorohydrin, butanediol diglycidyl ether, bisepoxisane, divinylsulfone, sulfonyl chloride, cyanuric chloride, dicyclohexyl carbodiimide, 1-ethyl-3-(3-dimethylaminopropyl)-carbodiimide and 1,1'-carbonyldiimidazole (CDI), etc.

In a preferred embodiment the invention provides an affinity ligand-supporting matrix conjugate as represented by formula (III):

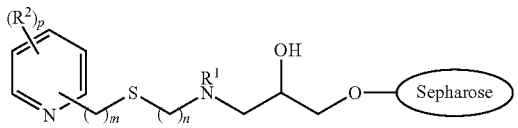
(III)

where variables $R^1$, $R^2$, m, n and p have the meanings hereinbefore specified.

In a further embodiment the invention provides novel compounds for use as affinity ligands as described herein, said novel compounds are represented by formula (IV):

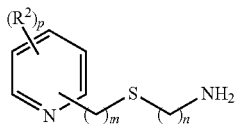
(IV)

or amino protected forms thereof, wherein m represents an integer from 0-2;

n represents an integer from 1-6;

p represents an integer from 0-4; and each $R^2$, when present, may be selected from halogen, nitro, thio, optionally substituted $C_{1-3}$ alkyl, optionally substituted $C_{1-3}$ alkoxy, optionally substituted heteroaryl, optionally substituted aryl, or any two adjacent $R^2$ groups represent an optionally substituted aryl group.

Preferably, m is 0. Accordingly, in another aspect the invention provides affinity ligands

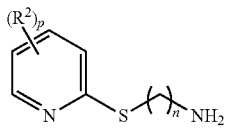
(IVa)

or amino protected forms thereof, wherein n represents an integer from 1-6;

p represents an integer from 0-4; and each $R^2$, when present, may be selected from halogen, nitro, optionally substituted $C_{1-3}$ alkyl, optionally substituted $C_{1-3}$ alkoxy, thio, optionally substituted heteroaryl, optionally substituted aryl, or any two adjacent $R^2$ groups represent an optionally substituted aryl group.

In a preferred aspect the invention provides affinity ligands of formula (IVb):

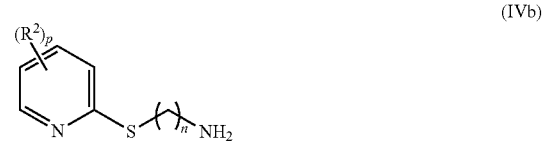
(IVb)

or amino protected forms thereof, wherein n represents an integer from 1-6;

p represents an integer from 0-4; and each $R^2$, when present, may be selected from halogen, nitro, thio, $C_{1-3}$ alkyl, $C_{1-3}$ alkoxy, optionally substituted heteroaryl, optionally substituted aryl, or any two adjacent $R^2$ groups represent an optionally substituted aryl group.

In relation to formulae (IV), (IVa), and (IVb) compounds, preferably n is 2 or 3.

As would be appreciated the novel affinity ligands of the present invention are based on pyridine. Accordingly the preparation of the ligands may be achieved by substitution of a pyridine ring or from the cyclisation of appropriately substituted starting materials such as in the well known Bohlmann-Rahtz or Hantzsch dihydropyridine-pyridine synthesis.

Substituted pyridines and quinolines may also be prepared based on the following methodologies:

1. Addition of Grignard reagents to pyridine N-oxides in THF at room temperature and subsequent treatment with acetic anhydride at 120° C. afforded 2-substituted pyridines in good yields. By exchanging acetic anhydride for DMF in the second step, 2-substituted pyridine N-oxides can be obtained, enabling the synthesis of 2,6-disubstituted pyridines (see H. Andersson, F. Almqvist, R. Olsson, *Org. Lett.*, 2007, 9, 1335-1337).

2. A cascade reaction comprising a novel Cu-catalyzed cross-coupling of alkenylboronic acids with α,β-unsaturated ketoxime O-pentafluorobenzoates, electrocyclization of the resulting 3-azatriene, and air oxidation affords highly substituted pyridines (see S. Liu, L. S. Liebeskind, *J. Am. Chem. Soc.*, 2008, 130, 6918-6919).

3. Amide activation with trifluoromethanesulfonic anhydride in the presence of 2-chloropyridine followed by π-nucleophile addition to the activated intermediate and annulation affords substituted pyridines and quinolines (see M. Movassaghi, M. D. Hill, O. K. Ahmad, *J. Am. Chem. Soc.*, 2007, 129, 10096-10097).

4. A range of highly functionalised pyridines may be prepared from enamino and alkynones in a single synthetic step by the use of acetic acid or amberlyst 15 ion exchange resin at 50° C. (see M. C. Bagley, J. W. Dale, J. Bower, *Synlett*, 2001, 1149-1151).

5. Polysubstituted pyridines may be prepared with total regiocontrol by the one-pot reaction of an alkynone, 1,3-dicarbonyl compound and ammonium acetate in alcoholic solvents. This three-component heteroannulation reaction proceeds under mild conditions in the absence of an additional acid catalyst (see X. Xiong, M. C. Bagley, K. Chapaneri, *Tetrahedron Lett.*, 2004, 45, 6121-6124).

6. Tri- or tetrasubstituted pyridines may be prepared by microwave irradiation of ethyl β-aminocrotonate and various alkynones in a single synthetic step and with total control of regiochemistry. (see M. C. Bagley, R. Lunn, X. Xiong, *Tetrahedron Lett.*, 2002, 43, 8331-8334).

7. The direct conversion of amides, including sensitive N-vinyl amides, to the corresponding trimethylsilyl alkynyl imines followed by a ruthenium-catalyzed protodesilylation and cycloisomerization gives various substituted pyridines and quinolines (see M. Movassaghi, M. D. Hill, *J. Am. Chem. Soc.*, 2006, 128, 4592-4593).
8. A rhodium-catalyzed chelation-assisted C—H activation of 4-unsaturated ketoximes and the reaction with alkynes affords highly substituted pyridine derivatives (see K. Parthasararathy, M. Jeganmohan, C.-H. Cheng, *Org. Lett.*, 2008, 10, 325-328).
9. Cationic rhodium(I)/modified-BINAP complexes catalyze a chemo- and regioselective [2+2+2] cycloaddition of a wide variety of alkynes and nitriles leading to highly functionalized pyridines under mild reaction conditions (see K. Tanaka, N. Suzuki, G. Nishida, *Eur. J. Org. Chem.*, 2006, 3917-3922).
10. Conversion of unsaturated ketones and aldehydes derived from the cycloisomerization of primary and secondary propargyl diynols in the presence of [CpRu(CH$_3$CN)$_3$]PF$_6$ to 1-azatrienes and a subsequent electrocyclization-dehydration provides pyridines with excellent regiocontrol (see B. M. Trost, A. C. Gutierrez, *Org. Lett.*, 2007, 9, 1473-1476).
11. Coupling of acetylene, nitrile, and a titanium reagent generated new azatitanacyclopentadienes in a highly regioselective manner. The subsequent reaction with sulfonylacetylene and electrophiles may afford substituted pyridines (see D. Suzuki, Y. Nobe, R. Tanaka, Y. Takayama, F. Sato, H. Urabe, *J. Am. Chem. Soc.*, 2005, 127, 7474-7479).
12. A mild, efficient, and general aromatization of Hantzsch 1,4-dihydropyridines with oxygen may be achieved at room temperature with 5 mol % of 9-phenyl-10-methylacridinium perchlorate as photocatalyst (see X. Fang, Y.-C. Liu, C. Li, *J. Org. Chem.*, 2007, 72, 8608-8610).
13. In the presence of activated carbon, Hantzsch 1,4-dihydropyridines and 1,3,5-trisubstituted pyrazolines were aromatized with molecular oxygen to the corresponding pyridines and pyrazoles (see N. Nakamichi, Y. Kawashita, M. Hayashi, *Synthesis*, 2004, 1015-1020).
14. 4-Substituted-1,4-dihydropyridines are readily and efficiently aromatized using commercial manganese dioxide in the absence of an inorganic support at 100° C. under microwave irradiation (see M. C. Bagley, M. C. Lubinu, *Synthesis*, 2006, 1283-1288).
15. Hantzsch 1,4-dihydropyridines undergo smooth aromatization catalyzed by iodoxybenzoic acid (IBX) to afford the corresponding pyridine derivatives (see J. S. Yadav, B. V. S. Reddy, A. K. Basak, G. Baishya, A. V. Narsaiah, *Synthesis*, 2006, 451-454).
16. [bmim]OH, a basic ionic liquid, efficiently promotes a one-pot condensation of aldehydes, malononitrile, and thiophenols to produce highly substituted pyridines (see B. C. Ranu, R. Jana, S. Sowmiah, *J. Org. Chem.*, 2007, 72, 3152-3154).

Direct substitution of pyridine can be achieved by standard electrophilic and nucleophilic substitution chemistry.

Other substitution patterns can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. Second Edition, 1999.

Examples of functional group inter-conversions are: —C(O)NR*R** from —CO$_2$—CH$_3$ by heating with or without catalytic metal cyanide, e.g. NaCN, and HNR*R** in CH$_3$OH; —OC(O)R from —OH with e.g., ClC(O)R in pyridine; —NC(S)NR*R** from —NHR with an alkylisothiocyanate or thiocyanic acid; —NRC(O)OR* from —NHR with alkyl chloroformate; —NRC(O)NR*R** from —NHR by treatment with an isocyanate, e.g. HN═C═O or RN═C═O; —NRC(O)R* from —NHR by treatment with ClC(O)R* in pyridine; —C(═NR)NR*R** from —C(NR*R**)SR with H$_3$NR$^+$OAc$^-$ by heating in alcohol; —C(NR*R**)SR from —C(S)NR*R** with R—I in an inert solvent, e.g. acetone; —C(S)NR*R** (where R* or R** is not hydrogen) from —C(S)NH$_2$ with HNR*R**; —C(═NCN)—NR*R** from —C(═NR*R**)—SR with NH$_2$CN by heating in anhydrous alcohol, alternatively from —C(═NH)—NR*R** by treatment with BrCN and NaOEt in EtOH; —NR—C(═NCN)SR from —NHR* by treatment with (RS)$_2$C═NCN; —NR**SO$_2$R from —NHR* by treatment with ClSO$_2$R by heating in pyridine; —NR*C(S)R from —NR*C(O)R by treatment with Lawesson's reagent [2,4-bis(4-methoxyphenyl)-1,3,2,4-dithiadiphosphetane-2,4-disulfide]; —NRSO$_2$CF$_3$ from —NHR with triflic anhydride and base, —CH(NH$_2$)CHO from —CH(NH$_2$)C(O)OR* with Na(Hg) and HCl/EtOH; —CH$_2$C(O)OH from —C(O)OH by treatment with SOCl$_2$ then CH$_2$N$_2$ then H$_2$O/Ag$_2$O; —C(O)OH from —CH$_2$C(O)OCH$_3$ by treatment with PhMgX/HX then acetic anhydride then CrO$_3$; R—OC(O)R* from RC(O)R* by R**CO$_3$H; —CCH$_2$OH from —C(O)OR* with Na/R*OH; —CHCH$_2$ from —CH$_2$CH$_2$OH by the Chugaev reaction; —NH$_2$ from —C(O)OH by the Curtius reaction; —NH$_2$ from —C(O)NHOH with TsCl/base then H$_2$O; —CHC(O)CHR from —CHCHOHCHR by using the Dess-Martin Periodinane regent or CrO$_3$/aqH$_2$SO$_4$/acetone; —C$_6$H$_5$CHO from —C$_6$H$_5$CH$_3$ with CrO$_2$Cl$_2$; —CHO from —CN with SnCl$_2$/HCl; —CN from —C(O)NHR with PCl$_5$; —CH$_2$R from —C(O)R with N$_2$H$_4$/KOH.

During the reactions described above a number of the moieties may need to be protected. Suitable protecting groups are well known in industry and have been described in many references such as Protecting Groups in Organic Synthesis, Greene T W. And Wutz, P.G.M. Wiley-Interscience, New York, Third Edition, 1999.

In a further aspect the invention provides a method for separating or purifying a desired protein from a mixture of proteins said method comprising the steps of:
(i) contacting a mixture of proteins comprising said desired protein with an affinity ligand-matrix conjugate according to the present invention for a time and under conditions sufficient to enable binding between a portion of said desired protein and the affinity ligand-matrix conjugate, and
(ii) separating the unbound proteins from the desired protein bound to the affinity ligand-matrix conjugate.

The above method may include additional purification steps known in the art and referred to hereinbefore.

In a preferred embodiment, the method is directed to the separation or purification of antibodies (immunoglobins). Preferred classes of antibodies include IgG, IgA and IgM or structural fragments thereof.

In a further preferred embodiment, the method is directed to the separation or purification of IgGs of subclass 1 or 2, or structural fragments thereof.

In another further preferred embodiment, the method is directed to the separation or purification of humanised monoclonal antibodies (immunoglobins), including those preferred classes of antibodies IgG, IgA and IgM or structural fragments thereof.

In another preferred embodiment, the method is directed to the separation or purification of recombinant or recombinant chimeric fusion proteins or structural fragments thereof.

In another preferred embodiment, the method is directed to the separation or purification of transferrin related proteins or other plasma proteins or structural fragments thereof.

The present inventors have found that the favourable dissociation constant values and the high binding capacity of the present affinity ligand-matrix conjugates (which are exhibited towards monoclonal antibodies) make them very attractive as adsorbents for the separation of mAbs from crude extracts. Purification of monoclonal antibodies from complex biological mixtures rarely occurs in a single step and two or three orthogonal chromatographic steps are usually required. The intended use of present conjugates as adsorbents could be at the stages of capture or alternatively at the polishing stages depending on the application. Thus, the choice is conditional on the need to selectively bind mAbs from crude feedstock or partially purified feedstocks, thus acting as a capture or intermediate purification step respectively. The eluted mAbs could then undergo further purification by complementary methods. Such applications could be used for monoclonal IgGs of different isotype or genetically/chemically engineered structure or alternatively with immunoglobulins of other classes such as IgMs.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

References

1. Li, R.; Dowd, V.; Stewart, D. J.; Burton, S. J.; Lowe, C. R. *Nat. Biotechnol.* 1998, 16, 190-195.
2. Teng, S. F.; Sproule, K.; Hussain, A.; Lowe, C. R. *J. Mol. Recognit.* 1999, 12, 67-75.
3. Teng, S. F.; Sproule, K.; Hussain, A.; Lowe, C. R. *J. Chromatogr. B* 2000, 740, 1-15.
4. Fassina, G.; Verdoliva, A.; Palombo, G.; Ruvo, M.; Cassani, G. *J. Mol. Recognit.* 1998, 11, 128-33.
5. Porath, J.; Maisano, F.; Belew, M. *FEBS Lett.* 1985, 185, 306-310.
6. Porath, J., Oscarsson, S. *Makromol. Chem., Macromol. Symp.* 1988, 17, 359-371.
7. Knudsen, K. L.; Hansen, M. B.; Henriksen, L. R.; Andersen, B. K.; Lihme, A. *Anal. Biochem.* 1992, 201, 170-177.
8. Schwarz, A.; Kohen, F.; Wilchek, M. *J. Chromatogr. B* 1995, 664, 83-88.
9. Schwarz, A. *J. Mol. Recognit.* 1996, 9, 672-674.
10. Scholz, G. H.; Wippich, P.; Leistner, S.; Huse, K. *J. Chromatogr. B* 1998, 709, 189-196.
11. Drössler, K.; Leistner, S. *Immunobiology* 1993, 189, 232.
12. Scholz, G. H., Vieweg, S., Leistner, S., Seissler, J., Scherbaum, W. A., Huse, K. *J. Immunol. Methods* 1998, 219, 109-118.
13. Constable, E. C.; Morris, D.; Can, S, *New J. Chem.* 1998, 22, 287-294.
14. Blackburn, T. P.; Cox, B.; Guildford, A. J.; LeCount, D. J.; Middlemiss, D. N.; Pearce, R. J.; Thornber, C. W. *J. Med. Chem.* 1987, 30, 2252-2259.
15. Boschelli, D. H.; Connor, D. T.; Lesch, M. E.; Schrier, D. J. *Bioorg. Med. Chem.* 1996, 4, 557-562.
16. Sohda, T.; Yamazaki, I.; Kawamura, N.; Taketomi, S. Eur. Pat. Appl. 1992, EP 464509; *Chem. Abstr.* 1992, 140, 77261.
17. Takatani, M.; Saijo, T.; Tomimatsu, K. Can. Pat. Appl. 1992, CA 2068255; Chem. Abstr., 1992, 121, 35336.
18. Zaragoza, F. *Tetrahedron* 2001, 57, 5451-5454.
19. Buschauer, A. *Archiv der Pharmazie* 1988, 321, 415-418.
20. Fel'dman, I. Kh.; Voropaeva, A. V. Trudy Leningradskogo Khimiko-Farmatsevticheskogo Instituta 1962, 21-24.
21. Tilley, J. W.; Levitan, P.; Lind, J.; Welton, A. F.; Crowley, H. J.; Tobias, L. D.; O'Donnell, M. *J. Med. Chem.* 1987, 30, 185-193.
22. Sekine, Y.; Nishimura, M.; Emoto, Y.; Yamaura, T.; Kojima, H.; Higashide, K. Jpn. Kokai Tokkyo Koho 1992, JP 04059754; Chem. Abstr., 1992, 117, 48117.
23. Carson, M.; Le Mahieu, R. A.; Nason, W. C.; Tilley, J. W. U.S. Pat. Appl. 1986, U.S. Pat. No. 521,308; Chem. Abstr. 1986, 105, 226620.
24. Kaasjager, V. E.; Puglisi, L.; Bouwman, E.; Driessen, W. L.; Reedijk, *J. Inorg. Chim. Acta* 2000, 310, 183-190.
25. Zhang, C. X.; Liang, H.-C.; Kim, E.; Shearer, J.; Helton, M. E.; Kim, E.; Kaderli, S.; Incarvito, C. D.; Zuberbuehler, A. D.; Rheingold, A. L.; Karlin, K. D. *J. Am. Chem. Soc.* 2003, 125, 634-635.
26. Tolstikov, G. A.; Emileev, U. M.; Yur'ev, V. P.; Gershanov, F. B.; Rafikov, S. R. *Tetrahedron Lett.* 1971, 2807-2808.
27. Malkov, A. V.; Hand, J. B.; Kocovsky, P. *Chem. Commun.* 2003, 1948-1949.
28. Shiotani, S.; Taniguchi, K. *J. Heterocycl. Chem.* 1997, 34, 925-929.
29. Gros, P.; Fort, Y. *J. Org. Chem.* 2003, 68, 2028-2029.
30. Gilman, H.; Edward, J. T. *Can. J. Biochem.* 1953, 31, 457-468.
31. Hamana, M.; Kumadaki, S. *Yakugaku Zasshi* 1968, 6, 672-677, Chem. Abstr. 1968, 69, 106503.
32. Inhoff, O; Richards, J. M.; Briet, J. W.; Lowe, G.; Krauth-Siegel, R. L. *J. Med. Chem.* 2002, 45, 4524-4530.
33. Constable, E. C; Ward, M. D. *J. Chem. Soc. Dalton Trans.* 1990, 1405-1409.
34. Testaferri, L. T.; Tiecco, M.; Tingol, M.; Bartoli, D.; Massoli, A. *Tetrahedron* 1985, 41, 1373-1340.
35. Porath, J.; Janson, J. C.; Laas, T. *J. Chromatogr.* 1971, 60, 167-177.
36. Wirth, H. J.; Unger, K. K.; Hearn, M. T. W. *Anal. Biochem.* 1993, 208, 16-25.
37. Hearn, M. T. *Physiochemical factors in polypeptide and protein purification and analysis by High-Performance Liquid Chromatographic techniques: Current status and challenges for the future*; In Handbook of Bioseparations, Vol. 2; Ahuja, S., Ed.; Academic Press: San Diego, 2000, 72-237.
38. Anspach, F. B.; Johnston, A.; Wirth, H. J.; Unger, K. K.; Hearn, M. T. *J. Chromatogr.* 1990, 499, 103-124.
39. Wirth, H. J.; Unger, K. K.; Hearn, M. T. W. *J. Chromatogr.* 1990, 550, 383-395.
40. Laemmli, U. K. *Nature* 1970, 227, 680-685.
41. Sambrook, J.; Fritsch, E. F.; Maniatis, T. Molecular Cloning: A Laboratory Manual; 2nd ed.; Ford, N., Nolan, C., Ferguson, M., Ed.; Cold Spring Harbor Laboratory Press: New York, 1989, 18.55.
42. Swain, M.; Ross, N. W. *Electrophoresis* 1995, 16, 948-951.

43. Porath, J. *General methods and coupling procedures*; In Methods in Enzymology: Affinity Techniques; Jakoby, W. B., Wilchek, M., Eds.; Elsevier Inc.: Amsterdam, 1974, 34, 13-30.
44. Harris, E. L. V. *Concentration of the Extract*; In Protein Purifications Methods: A Practical Approach; Harris, E. L. V., Angal, S., Eds.; IRL Press at Oxford University Press: 1989, 125-161.
45. Pall Corporation Product Note, MEP HyperCel® Hydrophobic Charge Induction Chromatography (HCIC) Sorbent, http://www.pall.com/datasheet_biopharm_35677.asp (accessed February 2006).
46. Richter, A.; Jostameling, M.; Müller, K.; Hellmann, A.; Pitschke, M. *Quality control of antibodies for human use*; In Antibodies, Vol. 1: Production and purification; Subramanian, G., Ed.; Kluwer Academic/Plenum Publishers: New York, 2004, 169-187.
47. Aris, J. P., "In-Gel" Trypsin Digestion Protocol for Proteins in SDS-PAGE Gel Slices, Department of Anatomy and Cell Biology, University of Florida, Gainesville, plaza.ufl.edu/johnaris/Protocols/Protein/ProteinInGel-Trypsin.pdf (accessed April 2006).
48. UniProt Knowledgebase, ExPASy Swiss-Prot and TrEMBL, http://ca.expasy.org/sprot/ (accessed October 2003).

Certain embodiments of the invention will now be described with reference to the following examples which are intended for the purpose of illustration only and are not intended to limit the scope of the generality hereinbefore described.

EXAMPLES

EXPERIMENTAL (i) Synthetic Procedures for the Affinity Ligands

1. General

Melting points were determined using a Gallenkamp or a Buchi B-545 melting point apparatus with a digital thermometer and are uncorrected. Boiling points as quoted for distillations using Kugelrohr apparatus refer to oven temperatures and serve only as a guide to boiling points.

Infrared spectra were recorded on a Bruker Equinox 55 or a Perkin Elmer 1600 series Fourier Transform infrared spectrometer as paraffin (Nujol) mulls of solids between sodium chloride plates, KBr disks of solids or thin films of liquid (neat) between sodium chloride plates. The infrared data were recorded in wavenumbers (cm$^{-1}$) with the intensity of the absorption ($v_{max}$) specified as either s (strong), m (medium), w (weak) and prefixed b (broad) where appropriate.

Proton nuclear magnetic resonance ($^1$H n.m.r.) spectra were recorded at 200 MHz on a Bruker AC-200 spectrometer, 300 MHz with a Bruker DPX-300 spectrometer or at 400 MHz with a Bruker DRX-400 spectrometer. The $^1$H n.m.r. spectra refer to solutions in deuterated solvents as indicated. The residual solvent peaks have been used as an internal reference, except CDCl$_3$ where tetramethylsilane (TMS) was used as the internal standard ($\delta$ 0.00 ppm). Solutions of basic compounds were run in base-washed (Na$_2$CO$_3$) CDCl$_3$. Each resonance was assigned according to the following convention: chemical shift ($\delta$) measured in parts per million (ppm) relative to the residual solvent peak (or TMS), multiplicity, coupling constants (J Hz), number of protons and assignment. Multiplicities are denoted as (s) singlet, (d) doublet, (dd) doublet of doublets, (ddd) doublet of doublet of doublets, (t) triplet, (dt) doublet of triplets, (td) triplet of doublets, (q) quartet, or (m) multiplet and prefixed (b) broad where appropriate.

Carbon nuclear magnetic resonance ($^{13}$C n.m.r.) spectra were recorded at 50 MHz on a Bruker AC-200 spectrometer, at 75 MHz on a Bruker DPX-300 spectrometer or at 100 MHz on a Bruker DRX-400 spectrometer with the spectra referring to deuterated solutions in solvents indicated. Each resonance was assigned according to the following convention: chemical shift ($\delta$) in (ppm), measured relative to the residual solvent peak (or TMS). Assignments were determined from J-modulated Spin Echo experiments for X-nuclei coupled to $^1$H in order to determine the number of attached protons. Correlation spectroscopy (COSY) was used to correlate the chemical shifts of $^1$H that were J-coupled to one another. Heteronuclear Multiple Quantum Correlation (HMQC) was used to determine which $^1$H were attached to the corresponding $^{13}$C. Heteronuclear Multiple Bond Correlation (HMBC) was used to determine long range ($^2$J or $^3$J) $^{13}$C-$^1$H connectivity. Two dimensional experiments were carried out using either the Bruker DPX-300 or the Bruker DRX-400 spectrometer.

Low resolution electrospray ionisation mass spectra (ESI) were recorded on a Micromass Platform II API QMS Electrospray mass spectrometer with cone voltage generally at 25 V as solutions in MeOH unless otherwise indicated. Analyses were conducted in positive (ESI$^+$) mode. Principle ion peaks (m/z) are reported with their intensities expressed as percentages of the base peak in brackets. High-resolution electrospray mass spectra (HRMS) were recorded on a Brucker BioApex 47e Fourier Transform mass spectrometer as specified solutions. M denotes the molecular ion. High resolution laser desportion time of flight mass spectroscopy (MALDI-TOF MS) was carried out using an ABI 880 instrument calibrated to have a mass accuracy of 1 amu in 100,000 amu.

Analytical thin layer chromatography (t.l.c.) was performed on Merck plastic or aluminium sheets coated in silica gel 60 F$_{254}$. The components were visualised by fluorescence under 254 nm ultraviolet irradiation or by exposure to iodine vapour when necessary. Preparative thin layer chromatography (t.l.c.) was performed on a glass plate coated in Merck silica gel 60 PF$_{254}$. The components were visualised by fluorescence under 254 nm ultraviolet irradiation.

Flash chromatography was performed using Merck silica gel 60, 0.040-0.063 mm, (230-400 mesh). Eluent mixtures are expressed as volume percentages using solvents described below in Section 1.1. Microanalyses were performed by The Campbell Microanalytical Laboratory, Department of Chemistry, University of Otago, Dunedin, New Zealand.

Microwave synthesis was carried out using a Biotage-Initiator 8.

1.1. Solvents and Reagents

Tetrahydrofuran (THF) was distilled from lithium aluminium hydride, stored over sodium wire and distilled from sodium and benzophenone prior to use. Dichloromethane (DCM) was dried over CaCl$_2$, distilled from fresh CaCl$_2$ and stored over 4 Å molecular sieves. Hexane (refers to light petroleum, b.p. 60-80° C.) was stirred over anhydrous CaCl$_2$, distilled from NaOH pellets and stored over 4 Å molecular sieves. Ethyl acetate (EtOAc) was washed with 5% aqueous Na$_2$CO$_3$ solution and then with saturated NaCl solution, dried over K$_2$CO$_3$ and distilled from fresh K$_2$CO$_3$. Diethyl ether (ether) was dried over KOH and distilled from fresh KOH or from Na and benzophenone before use. Methanol (MeOH) was distilled from magnesium methoxide and stored over 4 Å molecular sieves. Ethanol (EtOH) was distilled from magnesium ethoxide and stored over 4 Å molecular sieves. Acetone was heated to reflux over KMnO$_4$, distilled, stirred over $K_2CO_3$ and redistilled. Chloroform ($CHCl_3$) was stirred over $CaCl_2$, distilled from $CaCl_2$ and EtOH (superdry) 1% was added. Hexamethylphosphoramide (HMPA) was distilled under vacuum at 60° C. from $CaH_2$. Dimethylformamide (DMF) was dried over 4 Å molecular sieves. N,N,N',N'-Tetramethylethylenediamine (TMEDA) was partially dried with 4 Å molecular sieves and distilled in vacuo from n-butyllithium. Diisopropylamine was distilled from Na wire. 1,2 Dimethoxyethane was purchased from Aldrich and used as obtained. n-Butyllithium was obtained from Aldrich as a 1.6 M solution in hexanes. Distilled water was used for aqueous manipulations. Saturated aqueous solutions of reagents were written, for example, as sat. $NaHCO_3$.

Common reagents and compounds were purchased from Sigma-Aldrich, Castle Hill, NSW, Australia. Deuterated solvents were purchased from Merck, Kilsyth, Victoria, Australia.

2. General Method A

General method for the preparation of sulfanylethanamine-substituted pyridines by modification of the method of Constable et al.[13] as described below (Scheme 1).

Sodium metal (2.0-4.3 eq.) was dissolved in freshly distilled EtOH (20-40 mL) in an ice-cold water bath under an atmosphere of nitrogen. 2-Aminoethanethiol hydrochloride (1.5 eq.) was added to the solution which was then stirred magnetically for 10 min at ambient temperature to give a white suspension. Bromo- or chloro-substituted pyridine (1 eq., 10.5 mmol) was added and the resulting suspension was heated at reflux under nitrogen with continuous stirring for 24 h.

Scheme 1: Synthesis of PSEA

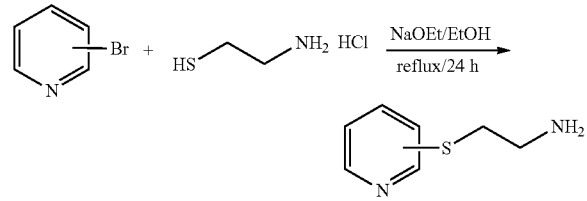

2.1. General Workup

The mixture was cooled to ambient temperature, water added and the EtOH was evaporated under reduced pressure. The solution was extracted with DCM (3×30 mL), washed with sat. NaCl, dried using anhydrous $MgSO_4$ and filtered. The solvent was removed under reduced pressure to give the crude product as yellow oil. The crude oil (~1 g) was dissolved in dry $Et_2O$ (10 mL), then dry HCl in $Et_2O$ (3 mL) was added to the solution. The solid that precipitated was washed with DCM:$Et_2O$ (1:1 v/v: 5 mL) and dried under reduced pressure to give the hydrochloride salt. Alternatively, the crude oil (0.5 g) was dissolved in dry $Et_2O$ (5 mL), then 2 M $H_2SO_4$ (1.65 mL) was slowly added to the solution. Ether was removed under reduced pressure. White crystals of product as the sulfate salt were formed after cooling and drying under vacuum.

3. Synthesis of Sulfanylethanamine-Substituted Pyridines by Microwave Technique The synthetic route for production of PSEA compounds using microwave synthesis is shown in Scheme 2.

Scheme 2: General scheme for microwave synthesis of PSEA

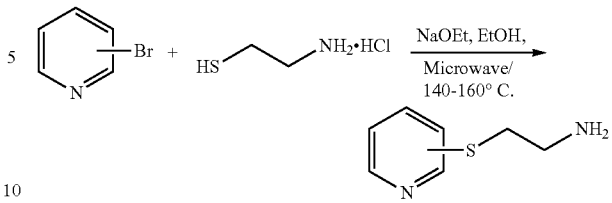

3.1. General Method B—Microwave Technique

Sodium metal (2 eq.-4.3 eq.) was dissolved in freshly distilled EtOH (2-4 mL or 18 mL) in an ice-cold water bath under a nitrogen atmosphere in a 5 mL or 20 mL microwave vial. 2-Aminoethanethiol hydrochloride (1.5 eq.) was added to the solution, which was stirred magnetically for 10 min under a nitrogen atmosphere at ambient temperature to give a white suspension. Bromo- or chloro-substituted pyridine (1 eq.) was added into the suspension. The microwave vial was sealed and the resulting suspension was heated under microwave irradiation in the range of 140° C. to 160° C. for 21 min to 1 h. The general method described in Section 2.1 was followed to workup the reaction. The crude product was then purified and stored as the hydrochloride salt.

4. General Method C for Reaction of 2-Aminoethanethiol-.HCl with Halogenated Heterocycles The method described by Blackburn et al.[14] was modified as follows: 2-Aminoethanethiol hydrochloride (1.1-1.2 eq.) was suspended in THF (15 mL) under a nitrogen atmosphere and HMPA (5 mL) was added. NaH (dry, 95%) (2.4-2.6 eq.) was added portion-wise over 10-20 min while the mixture was cooled in an ice-cold water bath under a nitrogen atmosphere. The mixture stirred for 10 min at ambient temperature before portion-wise addition of the halogenated heterocycle (1.22-17.5 mmol) over 10-20 min. and the reaction mixture stirred at ambient temperature for 2 h-2 d. Water (30 mL) was added slowly to quench the reaction and the THF was removed under reduced pressure. The aqueous solution was extracted with EtOAc or DCM (3×20 mL), dried ($MgSO_4$), filtered and solvent removed in vacuo to give the crude product. Purification of the resulting product is described in the relevant sections.

4.1. Preparation of 2-[2'-(pyridin-2"-sulfanyl)ethyl]-1H-isoindole-1,3(2H)-dione

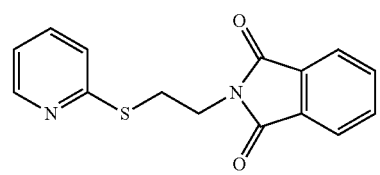 [SMILES: O=C1c2ccccc2C(=O)N1CCSc1ccccn1]

The phthalimide was prepared by modifying the procedure outlined by Boschelli et al.[15] using N-(2-bromoethyl)phthalimide (6.86 g, 27.0 mmol), $K_2CO_3$ (6.84 g, 49.5 mmol) and 2-mercaptopyridine (2.50 g, 22.5 mmol) in dry acetone (75 mL). The title compound was obtained as a white solid (4.10 g, 64%), m.p. 94-96° C. (lit.[16] m.p. 98-99° C.). $^1$H n.m.r. (200 MHz, $CDCl_3$): δ 3.52 (t, J 6.6 Hz, 2H); 4.06 (t, J 6.6 Hz, 2H); 6.93 (ddd, J 7.3, 4.9, 1.1 Hz, 1H); 7.17 (apparent dt, J 8.1, 1.0 Hz, 1H); 7.44 (ddd, J 8.0, 7.4, 1.9 Hz, 1H); 7.67-7.85 (m, 4H); 8.36 (ddd, J 4.9, 1.8, 0.9 Hz, 1H). $^{13}$C n.m.r. (50 MHz, CDCl$_3$): δ 28.6; 37.9; 119.9; 122.7; 123.6; 132.5; 134.2; 136.3; 149.8; 158.0; 168.5. The $^1$H n.m.r. data were consistent with literature data.[17]

Preparation of 2-[2'-(pyridin-4''-sulfanyl)ethyl]-1H-isoindole-1,3(2H)-dione

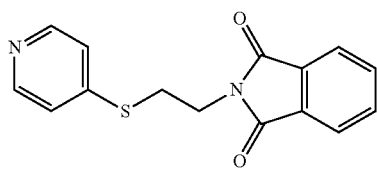 [SMILES: O=C1c2ccccc2C(=O)N1CCSc1ccncc1]

The phthalimide was prepared by modifying the procedure outlined by Boschelli et al.[15] using N-(2-bromoethyl)phthalimide (6.86 g, 27.0 mmol), K$_2$CO$_3$ (6.84 g, 49.5 mmol) and 4-mercaptopyridine (2.50 g, 22.5 mmol) in dry acetone (125 mL). The title compound was obtained as a light brown solid (2.78 g, 43%), m.p. 143-145° C. (lit.[16] m.p. 147-148° C.). $^1$H n.m.r. (300 MHz, CDCl$_3$): δ 3.29 (t, J 7.3 Hz, 2H); 3.99 (t, J 7.4 Hz, 2H); 7.25 (d, J 5.9 Hz, 2H); 7.72-7.87 (m, 4H); 8.41 (d, J 6.0 Hz, 2H). $^{13}$C n.m.r. (75 MHz, CDCl$_3$): δ 28.8; 37.0; 121.2; 123.7; 132.1; 134.5; 147.6; 149.8; 168.2. The $^1$H n.m.r. were consistent with literature data.[18]

4.3. Preparation of 2-(pyridin-2'-ylsulfanyl)ethanamine (2-PSEA)

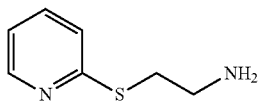

2PSEA was prepared by modifying the method described by Boschelli et al.[15] using 2-[2'-(pyridin-2''-sulfanyl)ethyl]-1H-isoindole-1,3(2H)-dione (1.50 g, 5.27 mmol) and hydrazine hydrate (0.33 mL, 6.86 mmol) in dry EtOH (30 mL) to yield the title compound as a yellow oil (0.48 g, 58%). n.m.r. (400 MHz, CDCl$_3$): δ 1.60 (bs, 2H); 3.00 (t, J 6.2 Hz, 2H); 3.29 (t, J 6.4 Hz, 2H); 6.97 (ddd, J 7.4, 4.9, 1.1 Hz, 1H); 7.19 (apparent dt, J 8.1, 1.0 Hz, 1H); 7.46 (ddd, J 8.1, 7.4, 1.9 Hz, 1H); 8.40 (ddd, J 4.9, 1.9, 1.0 Hz, 1H). $^{13}$C n.m.r. (75 MHz, CDCl$_3$): δ 34.1; 41.9; 119.5; 122.6; 136.0; 149.5; 158.7. The spectral data were consistent with literature data.[13]

Preparation of 2PSEA via General Method C (Blackburn et al.[14]) The general procedure in Section 4. was followed using 2-bromopyridine (2.00 g, 12.7 mmol), 2-aminoethanethiol hydrochloride (2.16 g, 19.0 mmol) and NaH (dry, 95%) (1.14 g, 47.5 mmol) in THF (15 mL) and HMPA (5 mL) under a nitrogen atmosphere. Workup as described in the general method gave a brown oil (1.54 g). Column chromatography (SiO$_2$, DCM:MeOH:NH$_4$OH, 9:1:0.1) gave 2PSEA as a yellow oil (0.95 g, 49%). The spectral data were consistent with those given above.

Preparation of 2PSEA via General Method A (Constable et al.[13]) The general procedure in Section 2. was followed using 2-bromopyridine (1 mL, 10.5 mmol), 2-aminoethanethiol hydrochloride (1.81 g, 15.75 mmol, 1.5 eq.) and sodium (0.80 g, 34.05 mmol, 3.3 eq.) in EtOH (40 mL). The reaction was worked up as described in Section 2.1 and the title compound was isolated as pale yellow oil. Yield 1.48 g, 85%.

Preparation of Sulfate Salt: Yield 0.7 g, 89%; (ESI$^+$): m/z 137.9 (M+H−NH$_3$)$^+$: $^1$H n.m.r. (300 MHz, D$_2$O): δ 3.32 (t, J 6.8 Hz, 2H); 3.6 (t, J 6.8 Hz, 2H); 7.70 (ddd, J 7.6, 1.3, 0.8 Hz, 1H); 7.90 (d, J 1.4 Hz, 1H); 8.33 (ddd, J 7.6, 1.3, 0.8 Hz, 1H); 8.51 (dd, J 4.6, 1.3 Hz, 1H).

Preparation of HCl Salt: Yield 0.83 g, 85%. m.p. 178° C.-180° C. (lit.[19] m.p. 194° C.-196° C.); Mass spectrum (ESI$^+$): m/z 154.9 (M+H)$^+$ (100%). $^1$H n.m.r. (300 MHz, D$_2$O): δ 3.44 (t, J 6.4 Hz, 2H); 3.64 (t, J 6.4 Hz, 2H); 7.63 (ddd, J 7.6, 5.6, 1 Hz, 1H); 7.84 (dd, J 8.3, 1.0 Hz, 1H); 8.20 (ddd, J 8.3, 7.6, 1.8 Hz, 1H); 8.61 (ddd, J 5.6, 1.8, 0.8 Hz, 1H). $^{13}$C n.m.r. (75 MHz, CDCl$_3$): δ 27.57; 37.49; 121.63; 123.99; 141.47; 144.5; 158.5. IR: 2497s, 1602s, 1531m, 1458w, 1444s, 1431w, 1386m, 1256s, 1130m, 1075m, 1045s, 1000w, 948m, 923m, 769s, 714m, 621m cm$^1$.

Preparation of 2PSEA via General Method B (microwave): The general procedure in Section 3.1. was followed using 2-bromopyridine (0.1 mL, 1.05 mmol, 1 eq.), 2-aminoethanethiol hydrochloride (0.18 g, 1.575 mmol, 1.5 eq) and sodium (0.08 g, 3.4 mmol, 3.3 eq) in EtOH (2 mL). The reaction was carried out at 140° C. for 21 min using the Biotage-Initiator 8. The reaction was worked up as described in Section 2.1. to yield the compound as pale yellow oil. $^1$H n.m.r. spectroscopy showed 100% conversion.

The above reaction was repeated using 2-bromopyridine (1 mL, 10.5 mmol, 1 eq.), 2-aminoethanethiol chloride (1.81 g, 15.75 mmol, 1.5 eq.) and sodium (0.80 g, 34.05 mmol, 3.3 eq.) with EtOH (18 mL) as solvent in 20 mL microwave vial. The reaction was worked up as described above to yield the compound as pale yellow oil (1.62 g, ~100% conversion by $^1$H n.m.r. spectroscopy). $^1$H n.m.r. spectral data were identical to those described above.

4.4. Preparation of 2-(pyridin-4'-ylsulfanyl)ethanamine (4-PSEA)

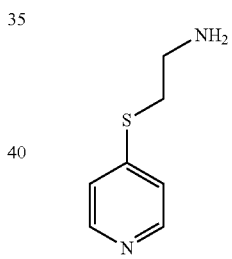

4PSEA was prepared by modifying the method described by Boschelli et al.[15] using 2-[2'-(pyridin-4''-sulfanyl)ethyl]-1H-isoindole-1,3(2H)-dione (2.20 g, 7.74 mmol) and hydrazine hydrate (0.49 mL, 10.1 mmol) in dry EtOH (35 mL) to give the title compound as an orange oil (0.99 g, 83%). HRMS (ESI$^+$, MeOH): Found: m/z 155.0640 (M+H)$^+$, C$_7$H$_{11}$N$_2$S requires m/z 155.0643. n.m.r. (300 MHz, CDCl$_3$): δ 1.60 (bs, 2H); 3.02-3.12 (m, 4H); 7.14 (d, J 6.7 Hz, 2H); 8.39 (d, J 6.3 Hz, 2H). $^{13}$C n.m.r. (75 MHz, CDCl$_3$): δ 35.0; 40.8; 121.2; 148.7; 149.5. Mass Spectrum (ESI): m/z 154.7 (M+H)$^+$ (100%). The $^1$H n.m.r. data were consistent with literature data.[16]

Preparation of 4PSEA via General Method C (Blackburn et al.[14]) The general procedure in Section 4. was followed using 4-chloropyridine hydrochloride (1.94 g, 12.9 mmol), 2-aminoethanethiol hydrochloride (2.70 g, 23.8, mmol) and NaH (dry, 95%) (1.58 g, 65.8 mmol) in THF (10 mL) and HMPA (5 mL) under a nitrogen atmosphere. The mixture was allowed to warm to ambient temperature and stirred for a further 2 d during which time the THF evaporated. Water (30 mL) was added slowly and the aqueous solution was extracted with CH$_2$Cl$_2$ (3×20 mL). Workup as described in the general method gave a brown oil which was purified by chromatography (SiO$_2$, CH$_2$Cl$_2$:MeOH:NH$_4$OH, 9:1:0.1) to afford the title compound as a light brown oil (1.73 g, 87%). The spectral data for the title compound were consistent with those given above.

In previous attempts described in the literature for the above reaction, removal of HMPA via distillation caused decomposition of the title compound. The above reaction conditions circumvented this limitation.

Preparation of 4PSEA via General Method A (Constable et al.[13]) The general procedure described in Section 2. was followed using 4-bromopyridine hydrochloride (1 g, 6.24 mmol, 1 eq.), 2-aminoethanethiol chloride (1.08 g, 9.49 mmol, 1.5 eq) and sodium (0.63 g, 27.21 mmol, 4.3 eq) in EtOH (40 mL). The reaction was worked up as described in Section 2.1. to yield the compound as pale yellow oil. (0.98 g, 99%).

Preparation of HCl Salt: Yield 0.78 g, (80%). m.p. 194° C. (lit.[20] m.p. 236° C.); Mass spectrum (ESI): m/z 154.9 (M+H)$^+$. $^1$H n.m.r. (300 MHz, D$_2$O): δ 3.33 (t, J 7.7 Hz, 2H); 3.49 (t, J 7.7 Hz, 2H); 7.63 (dd, J 5.4, 1.5, Hz, 1H); 8.37 (ddd, J 6.8, 5.2. 1.5 Hz, 1H). $^{13}$C n.m.r. (75 MHz, D$_2$O): δ 29.0; 39.1; 123.7; 144.5. IR: 2868s, 1621s, 1582s, 1490w, 1473s, 1461w, 1372m, 1208w, 1146m, 1109m, 1090s, 1014w, 945m, 802m, 775m, 708w, 641w cm$^{-1}$.

Preparation of 4PSEA via General Method B (microwave): General procedure in Section 3.1. was followed using 4-bromopyridine hydrochloride salt (0.1 g, 1 eq.), 2-aminoethanethiol chloride (0.11 g, 1.5 eq.) and sodium (0.063 g, 4.3 eq.) in EtOH (4 mL). The reaction was carried out at 140° C. for 21 min. The reaction was worked up as described in Section 2.1. to yield the compound as pale yellow oil. $^1$H n.m.r. spectroscopy showed 100% conversion.

4.5. Preparation of 2-(pyridin-3'-ylsulfanyl)ethanamine (3-PSEA)

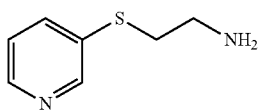

Preparation of 3PSEA via General Method C (Blackburn et al.[14]) The general procedure in Section 4. was followed using 3-bromopyridine (1.50 g, 9.49 mmol), 2-aminoethanethiol hydrochloride (0.67 g, 5.88 mmol) and NaH (dry, 95%) (0.35 g, 13.9 mmol) in THF (15 mL) and HMPA (3 mL) under a nitrogen atmosphere. The mixture was stirred for 2 d at ambient temperature. Workup as described in the general method gave brown oil. The $^1$H n.m.r. spectrum indicated a 58% conversion to the desired product. Column chromatography (SiO$_2$, DCM:MeOH:NH$_3$ in MeOH, 9:0.8:0.2) gave 3PSEA as an orange-brown oil (0.73 g, 50%). HRMS (ESI$^+$, MeOH): Found: m/z 155.0642 (M+H)$^+$, C$_7$H$_{11}$N$_2$S requires m/z 155.0643 (M+H)$^+$. $v_{max}$ (Neat): 3362m, 3288m, 3034w, 2923m, 2861w, 1595w, 1568m, 1468s, 1404s, 1322w, 1274w, 1229w, 1189w, 1109m, 1071w, 1019s, 862m, 796s, 706s cm$^{-1}$. $^1$H n.m.r. (300 MHz, CDCl$_3$): δ 1.91 (bs, 2H); 2.92 (m, 2H); 3.03 (m, 2H); 7.22 (ddd, J 8.0, 4.8, 0.9 Hz, 1H); 7.69 (ddd, J 8.0, 2.4, 1.6 Hz, 1H); 8.43 (dd, J 4.8, 1.6 Hz, 1H); 8.60 (dd, J 2.4, 0.8 Hz, 1H). $^{13}$C n.m.r. (75 MHz, CDCl$_3$): δ 38.1; 40.9; 123.8; 133.2; 137.7; 147.5; 150.8. Mass Spectrum (ESI): m/z 154.9 (M+H)$^+$ (100%).

Preparation of 3PSEA via General Method A (Constable et al.[13]) The general procedure in Section 2. was followed using 3-bromopyridine (1 mL, 10.5 mmol, 1 eq.), 2-aminoethanethiol chloride (1.81 g, 15.75 mmol, 1.5 eq.) and sodium (0.80 g, 34.05 mmol, 3.3 eq.) in EtOH (40 mL). The resulting suspension was refluxed for 5 days. The reaction was worked up as described in Section 2.1. to yield a pale yellow oil (1.19 g). $^1$H n.m.r. spectroscopy showed a mixture of the product (3PSEA) and starting material (3-bromopyridine) in a ratio of 1:10 (yield ~10%).

Preparation of 3PSEA via General Method B (microwave): The general procedure in Section 3.1. was followed using 3-bromopyridine (0.1 mL, 1.05 mmol, 1 eq.), 2-aminoethanethiol chloride (0.18 g, 1.575 mmol, 1.5 eq.) and sodium (0.088 g, 3.405 mmol, 3.3 eq.) in EtOH (4 mL). The reaction was carried out at 140° C. for 21 min and worked up as described in Section 2.1. to yield a pale yellow oil. $^1$H n.m.r. spectroscopy showed a mixture of the product (3PSEA) and starting material (3-bromopyridine) in a ratio of 1:10 (yield ~10%). The same reaction was carried out under various conditions: 140° C. for 42 min; 150° C. for 21 min, 42 min & 1 h; 160° C. for 21 min & 38 min; 170° C. for 21 min. Yields were 20%, 18%, 55%, 67%, 63%, 95% and 86%, respectively, as determined from $^1$H n.m.r. spectroscopy.

The reaction was also carried out on a larger scale using 3-bromopyridine (1 mL, 10.5 mmol, 1 eq.), 2-aminoethanethiol chloride (1.81 g, 15.75 mmol, 1.5 eq.) and sodium (0.80 g, 34.05 mmol, 3.3 eq.) in EtOH (18 mL) in a 20 mL microwave vial at 160° C. for 38 min. The reaction was worked up as described in section 2.1. to yield a pale yellow oil. (Yield 1.0 g, 95%).

Preparation of HCl Salt: Yield 94%. 217.7° C. (14.[19] m.p. 215° C.); Mass spectrum (ESI$^+$): m/z 155 (M+H)$^+$ (100%). $^1$H n.m.r. (300 MHz, D$_2$O): δ 3.31 (t, J 6.5 Hz, 2H); 3.4 (t, J 6.5 Hz, 2H); 7.8 (dd, J 8.1, 2.8 Hz, 1H); 8.34 (dd, J 8.2, 4.5 Hz, 1H); 8.63 (dd, J 5.2, 1.0 Hz, 1H); 8.77 (d, J 2.9 Hz, 1H). $^{13}$C n.m.r. (75 MHz, D$_2$O): δ 29.4; 37.0; 124.9; 135.9; 141.6; 142.9; 145.05

4.6. Preparation of 2-[3'-(pyridin-2"-ylsulfanyl)propyl]-1H-isoindole-1,3(2H)-dione

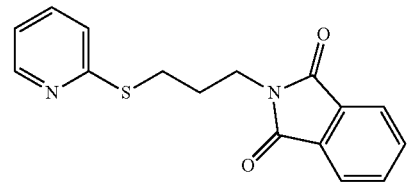 [SMILES: O=C1c2ccccc2C(=O)N1CCCSc1ccccn1]

The phthalimide was prepared by following the method described by Boschelli et al.[15] using N-(3-bromopropyl)phthalimide (6.63 g, 24.7 mmol), K$_2$CO$_3$ (6.84 g, 49.5 mmol) and 2-mercaptopyridine (3.03 g, 27.2 mmol) in dry acetone (75 mL) to give the title compound as a light yellow solid (6.94 g, 94%), m.p. 100-101° C. (lit.[16] m.p. 103-104° C.). $^1$H n.m.r. (300 MHz, CDCl$_3$): δ 2.11 (m, 2H); 3.21 (t, J 7.3 Hz, 2H); 3.84 (t, J 6.9 Hz, 2H); 6.92 (ddd, J 7.3, 4.9, 1.1 Hz, 1H); 7.14 (dt, J 8.1, 1.0 Hz, 1H); 7.43 (ddd, J 8.1, 7.3, 1.9 Hz, 1H); 7.71 (m, 2H); 7.83 (m, 2H); 8.30 (ddd, J 4.9, 1.9, 1.0 Hz, 1H). $^{13}$C n.m.r. (75 MHz, CDCl$_3$): δ 27.3; 28.9; 37.3; 119.5; 122.5; 123.3; 132.3; 134.0; 135.9; 149.5; 158.7; 168.5.

4.7. Preparation of 2-[3'-(pyridin-4"-ylsulfanyl)propyl]-1H-isoindole-1,3(2H)-dione

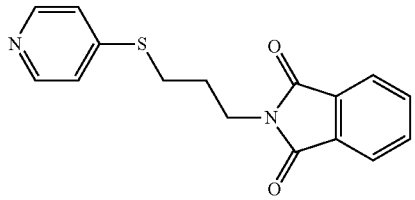 [SMILES: O=C1c2ccccc2C(=O)N1CCCSc1ccncc1]

The phthalimide was prepared according to the procedure outlined by Sodha et al.[16] using N-(3-bromopropyl)phthalimide (6.63 g, 24.74 mmol), K$_2$CO$_3$ (6.84 g, 49.47 mmol) and 4-mercaptopyridine (2.75 g, 24.7 mmol) in DMF (50 mL). The mixture stirred at ambient temperature for 3.5 h and workup gave, after recrystallisation from EtOAc, the product as pale pink crystals (3.57 g, 48%), m.p. 128-129° C. (lit.[15] m.p. 128-130° C.). $^1$H n.m.r. (300 MHz, CDCl$_3$): δ 2.06 (m, 2H); 3.02 (t, J 7.4 Hz, 2H); 3.86 (t, J 6.8 Hz, 2H); 7.09 (dd, J 4.6, 1.6 Hz, 2H); 7.74 (m, 2H); 7.85 (m, 2H); 8.38 (dd, J 4.6, 1.6 Hz, 2H). $^{13}$C n.m.r. (75 MHz, CDCl$_3$): δ 27.9; 28.4; 37.1; 121.0; 123.6; 132.2; 134.3; 148.7; 149.6; 168.5.

4.8. Preparation of 3-(pyridin-2'-ylsulfanyl)propanamine (2-PSPA)

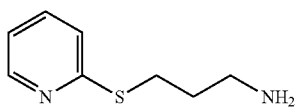 [SMILES: NCCCSc1ccccn1]

The title compound was prepared by following a procedure outlined by Boschelli et al.[15] using 2-[3'-(pyridin-2"-ylsulfanyl)propyl]-1H-isoindole-1,3(2H)-dione (3.00 g, 10.1 mmol) and hydrazine hydrate (1.01 g, 20.1 mmol) in dry EtOH (40 mL) to give the title compound as a yellow oil (1.63 g, 96%). $^1$H n.m.r. (300 MHz, CDCl$_3$): δ 1.53 (bs, 2H); 1.85 (m, 2H); 2.83 (t, J 6.7 Hz, 2H); 3.24 (t, J 7.1 Hz, 2H); 6.95 (ddd, J 7.3, 4.9, 1.1 Hz, 1H); 7.16 (dt, J 8.1, 1.0 Hz, 1H); 7.45 (ddd, J 8.1, 7.3, 1.9 Hz, 1H); 8.41 (ddd, J 4.9, 1.9, 1.0 Hz, 1H). $^{13}$C n.m.r. (75 MHz, CDCl$_3$): δ 27.3; 33.4; 40.9; 119.3; 122.3; 135.9; 149.4; 159.2. Mass Spectrum (ESI): m/z 169.0 (M+H)$^+$ (100%). The $^1$H n.m.r. data were consistent with literature values.[16]

4.9. Preparation of 3-(pyridin-4'-ylsulfanyl)propanamine (4-PSPA)

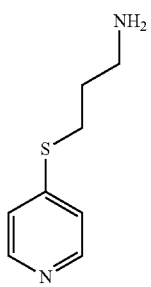 [SMILES: NCCCSc1ccncc1]

The title compound was prepared by following the procedure outlined by Boschelli et al.[15] using 2-[3'-(pyridin-4"-ylsulfanyl)propyl]-1H-isoindole-1,3(2H)-dione (2.50 g, 8.38 mmol) and hydrazine hydrate (0.84 g, 16.8 mmol) in dry EtOH (50 mL). Workup gave an orange oil (1.63 g) which was loaded onto a plug of silica, washed (DCM:MeOH, 10:1) and the title compound eluted (DCM:MeOH:NH$_3$ in MeOH, 10:1:0.2) as a yellow oil (0.96 g, 68%). $^1$H n.m.r. (300 MHz, CDCl$_3$): δ 1.62 (bs, 2H); 1.85 (m, 2H); 2.86 (t, J 6.8 Hz, 2H); 3.05 (t, J 7.2 Hz, 2H); 7.12 (dd, J 4.7, 1.6 Hz, 2H); 8.37 (dd, J 4.7, 1.6 Hz, 2H). $^{13}$C n.m.r. (75 MHz, CDCl$_3$): δ 28.2; 32.1; 41.0; 120.8; 149.3; 149.3. The $^1$H n.m.r. data were consistent with literature values.[16]

4.10. Preparation of 2-(pyridin-2'-ylmethylsulfanyl)ethanamine (2-PMSEA)

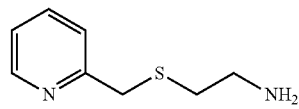 [SMILES: NCCSCc1ccccn1]

2-PMSEA was prepared by the method of Tilley et al.[21] 2-Aminoethanethiol hydrochloride (1.39 g, 12.2 mmol) and 2-(chloromethyl)pyridine hydrochloride (1.00 g, 6.10 mmol) were added to a solution of NaOH (0.98 g, 24.4 mmol) in EtOH (20 mL) with ice bath cooling. The reaction mixture was stirred for 30 min before the ice bath was removed and the mixture stirred at ambient temperature for 2.5 h. The EtOH was removed under reduced pressure and water (25 mL) was added to the resulting residue. The aqueous solution was extracted with DCM (3×25 mL) and the combined organic layer was washed with brine (10 mL), dried (K$_2$CO$_3$), filtered, and solvent removed in vacuo to afford a crude yellow oil (1.18 g). Column chromatography (SiO$_2$, DCM:MeOH:NH$_4$OH, 9:2:0.2) gave the title compound as a yellow oil (0.92 g, 89%). $^1$H n.m.r. (300 MHz, CDCl$_3$): δ 1.75 (bs, 2H); 2.61 (t, J 6.3 Hz, 2H); 2.85 (t, J 6.3 Hz, 2H); 3.84 (s, 2H); 7.17 (ddd, J 7.5, 4.9, 1.2 Hz, 1H); 7.38 (apparent dt, J 7.8, 1.0 Hz, 1H); 7.66 (apparent td, J 7.7, 1.9, Hz, 1H); 8.52 (ddd, J 4.9, 1.8, 0.9 Hz, 1H). $^{13}$C n.m.r. (75 MHz, CDCl$_3$): δ 34.7; 36.8; 39.9; 121.0; 122.1; 135.8; 148.2; 157.9. Mass Spectrum (ESI): m/z 168.8 (M+H)$^+$ (100%). The $^1$H n.m.r. data were consistent with literature data.[22]

4.11. Preparation of 2-(pyridin-3'-ylmethylsulfanyl)ethanamine (3-PMSEA)

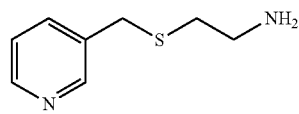 [SMILES: NCCSCc1cccnc1]

2-(Pyridin-3'-ylmethylsulfanyl)ethanamine was prepared according to the method described by Tilley et al.[21] Reaction of 2-aminoethanethiol hydrochloride (1.39 g, 12.2 mmol) and 3-(chloromethyl)pyridine hydrochloride (1.00 g, 6.10 mmol) in a solution of NaOH (0.98 g, 24.4 mmol) in EtOH (20 mL) as described above in Section 4.10. gave a crude orange oil (1.08 g). Column chromatography (SiO$_2$, DCM:MeOH:NH$_4$OH, 9:2:0.2) afforded the title compound as a yellow oil (0.77 g, 75%). HRMS (ESI$^+$, MeOH): Found: m/z 169.0795 (M+H)$^+$, C$_8$H$_{13}$N$_2$S requires m/z 169.0799. ν$_{max}$ (Neat): 3356bs, 2918s, 1591s, 1576s, 1478s, 1423s, 1253w, 1192m, 1100m, 1027s, 874m, 713s cm$^{-1}$. $^1$H n.m.r. (300 MHz, CDCl$_3$): δ 1.64 (bs, 2H); 2.54 (t, J 6.3 Hz, 2H); 2.85 (bt, J ca 5.9 Hz, 2H); 3.70 (s, 2H); 7.26 (ddd, J 7.9, 4.8, 0.8 Hz, 1H); 7.69 (m, 1H); 8.50 (apparent dd, J 4.8, 1.6 Hz, 1H); 8.53 (bd, J 2.3 Hz, 1H). $^{13}$C n.m.r. (75 MHz, CDCl$_3$): δ 33.3; 35.6; 40.9; 123.7; 134.3; 136.5; 148.7; 150.1. Mass Spectrum (ESI): m/z 168.8 (M+H)$^+$ (100%).

4.12. Preparation of 2-(pyridin-4'-ylmethylsulfanyl)ethanamine (4-PMSEA)

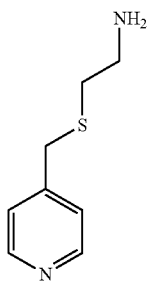 [SMILES: NCCSCc1ccncc1]

2-(Pyridin-4'-ylmethylsulfanyl)ethanamine was prepared by the method described by Carson et al.[23] Reaction of 2-aminoethanethiol hydrochloride (2.77 g, 24.4 mmol) and 4-(chloromethyl)-pyridine hydrochloride (2.00 g, 12.2 mmol) in a solution of NaOH (1.95 g, 48.8 mmol) in ethanol (40 mL) as described above Section 4.10 gave a brown oil (2.12 g). Column chromatography (SiO$_2$, DCM:MeOH: NH$_4$OH, 9:2:0.2) afforded the title compound as a yellow oil (1.93 g, 94%). HRMS (ESI$^+$, MeOH): Found: m/z 169.0796 (M+H)$^+$, C$_8$H$_{13}$N$_2$S requires m/z 169.0799. $v_{max}$ (Neat): 3356bs, 2919s, 1601s, 1560m, 1495w, 1415s, 1219w, 1068m, 994m, 882m, 819m cm$^{-1}$. $^1$H n.m.r. (300 MHz, CDCl$_3$): δ 1.75 (bs, 2H); 2.53 (t, J 6.3 Hz, 2H); 2.84 (t, J 6.3 Hz, 2H); 3.67 (s, 2H); 7.26 (d with fine splitting, J 6.0 Hz, 2H); 8.54 (d with fine splitting, J 6.0 Hz, 2H). $^{13}$C n.m.r. (75 MHz, CDCl$_3$): δ 35.1; 35.8; 40.9; 124.0; 147.7; 150.1. Mass Spectrum (ESI): m/z 168.7 (M+H)$^+$ (100%).

4.13. Preparation of 2-(2'-pyridin-2"-ylethylsulfanyl)ethanamine (2-PESEA)

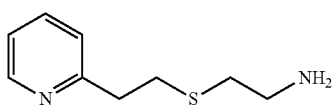 [SMILES: NCCSCCc1ccccn1]

2-(2'-Pyridin-2"-ylethylsulfanyl)ethanamine was synthesised according to the method described by Kaasjager et al.[24] 2-Aminoethanethiol hydrochloride (2.16 g, 19.0 mmol) was added to a solution of 2-vinylpyridine (2.00 g, 19.0 mmol) in dry EtOH (50 mL). The mixture was stirred at reflux for 2 h before addition of 1 M NaOH in EtOH (20 mL) and reflux continued for a further 30 min. The cloudy solution was filtered to remove NaCl and the filtrate was concentrated in vacuo to give a brown oil (3.66 g). The residue was dissolved in water (20 mL) and the aqueous solution was extracted with DCM (3×20 mL). The combined organic extract was dried (MgSO$_4$), filtered and the solvent removed under reduced pressure to give the title compound as a brown oil (3.30 g, 95%). n.m.r. (300 MHz, CDCl$_3$): δ 1.41 (bs, 2H); 2.62 (t, J 6.5 Hz, 2H); 2.87 (t, J 6.4 Hz, 2H); 2.94 (m, 2H); 3.07 (m, 2H); 7.13 (ddd, J 7.5, 4.9, 1.2 Hz, 1H); 7.18 (apparent dt, J 7.8, 1.0 Hz, 1H); 7.60 (apparent td, J 7.7, 1.9 Hz, 1H); 8.54 (ddd, J 4.9, 1.8, 0.9 Hz, 1H). $^{13}$C n.m.r. (75 MHz, CDCl$_3$): δ 31.5; 36.7; 38.7; 41.3; 121.6; 123.3; 136.5; 149.5; 160.1. Mass Spectrum (ESI): m/z 182.8 (M+H)$^+$ (100%). The spectral data were consistent with literature data.[24]

4.14. Preparation of 2-(2'-pyridin-4"-ylethylsulfanyl)ethanamine (4-PESEA)

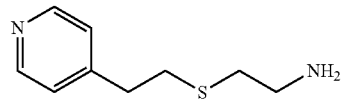 [SMILES: NCCSCCc1ccncc1]

Reaction of 2-aminoethanethiol hydrochloride (2.16 g, 19.0 mmol) and 4-vinylpyridine (2.00 g, 19.0 mmol) in dry EtOH (50 mL) as described above in Section 4.13. gave a crude yellow oil (3.18 g). The crude product was purified to remove remaining 4-vinylpyridine using a plug of silica (EtOAc:hexane, 3:1, containing 10% EtOH). Elution (EtOAc:hexane, 3:1, containing 10% NH$_3$ in MeOH) gave the desired compound as a yellow oil (2.86 g, 82%). HRMS (ESI$^+$, MeOH): Found: m/z 183.0944 (M+H)$^+$, C$_9$H$_{15}$N$_2$S requires m/z 183.0956. $v_{max}$ (Neat): 3359bs, 3070m, 2920s, 2858m, 1602s, 1559m, 1416s, 1321w, 1275w, 1222m, 1070w, 994m, 805s cm$^{-1}$. n.m.r. (200 MHz, CDCl$_3$): δ 1.47 (bs, 2H); 2.60-2.94 (m, 8H); 7.13 (d with fine splitting, J 6.0 Hz, 2H); 8.52 (d with fine splitting, J 6.0 Hz, 2H). $^{13}$C n.m.r. (75 MHz, CDCl$_3$): δ 32.0; 35.5; 36.4; 41.3; 123.8; 149.1; 149.7. Mass Spectrum (ESI): m/z 182.9 (M+H)$^+$ (100%).

4.15. Preparation of 2-(4'-methylpyridin-2'-ylsulfanyl)ethanamine (4-Me-2-PSEA)

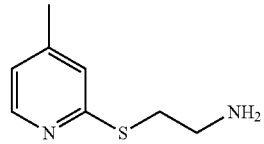

Preparation of 4-Me-2-PSEA via General Method C (Blackburn et al.[14]) The general procedure in Section 4. was followed using 4-chloropyridine hydrochloride (1.94 g, 12.9 mmol), 2-aminoethanethiol hydrochloride (1.50 g, 13.2 mmol) and NaH (dry, 95%) (0.79 g, 32.9 mmol) in THF (15 mL) and HMPA (10 mL) under a nitrogen atmosphere. The mixture was allowed to warm to ambient temperature and stirred for a further 2 d. Water (30 mL) was added slowly and the THF removed under reduced pressure and the aqueous solution was extracted with CH$_2$Cl$_2$ (3×20 mL). Workup as described in the general method gave a brown oil (2.54 g) which was purified by chromatography (SiO$_2$, DCM:MeOH: NH$_4$OH, 9:1:0.1) to give the title compound as a light brown oil (0.70 g, 38%). HRMS (ESI$^+$, MeOH): Found: m/z 169.0794 (M+H)$^+$, C$_8$H$_{13}$N$_2$S requires m/z 169.0799. $v_{max}$ (Neat): 3362m, 3287m, 3048w, 2922s, 2863m, 1594s, 1547s, 1467s, 1372s, 1284m, 1224m, 1122s, 1094s, 1070w, 1015w, 986m, 870s, 816s, 716m cm$^{-1}$. $^1$H n.m.r. (300 MHz, CDCl$_3$): δ 1.52 (bs, 2H); 2.27 (s, 3H); 2.99 (t, J 6.4 Hz, 2H); 3.28 (t, J 6.3 Hz, 2H); 6.80 (d with fine splitting, J 5.1 Hz, 1H); 7.03 (s with fine splitting, 1H); 8.26 (d, J=5.1 Hz, 1H). $^{13}$C n.m.r. (75 MHz, CDCl$_3$): δ 20.7; 33.0; 41.4; 120.9; 122.9; 147.1; 148.9; 158.0. Mass Spectrum (ESI): m/z 168.8 (M+H)$^+$ (100%).

Preparation of 4-methyl-2PSEA via General Method B (microwave): The general procedure in Section 3.1. was followed using sodium (0.41 g, 17.4 mmol, 3 eq.), 2-aminoethanethiol hydrochloride (1 g, 8.7 mmol, 1.5 eq.) and 2-bromo-4-methylpyridine (1 g, 5.8 mmol, 1 eq.) in EtOH (18 mL) in a 20 mL microwave vial. The resulting suspension was heated under microwave irradiation at 140° C. for 1 h. The cooled mixture was analysed by t.l.c. which indicated presence of some starting material (10% by $^1$H n.m.r. spectroscopy). The reaction was then repeated at 160° C. for 21 min and 160° C. for 38 min. The $^1$H n.m.r. spectrum of the last reaction showed 100% conversion. The mixture was cooled to room temperature and the reaction was worked up as described in Section 2.1. to yield the compound as a yellow oil. Yield 0.92 g, (90%).

Preparation of HCl Salt: Yield 0.85 g, (83%). m.p. 73.4° C.; Mass spectrum (ESI): m/z 169 (M+H)$^+$; 152 (M+H−NH$_3$)$^+$. $^1$H n.m.r. (300 MHz, D$_2$O): δ 2.54 (bs, 3H); 3.43 (t, J 6.6 Hz, 2H); 3.62 (t, J 6.6 Hz, 2H); 7.46 (dd, J 5.8, 0.7 Hz, 1H); 8.41 (d, J 5.8 Hz, 1H); 7.66 (s, 1H). $^{13}$C n.m.r. (75 MHz, D$_2$O): δ 20.1; 27.7; 37.5; 122.9; 124.4; 143.4; 152.0; 156.5. (Found: C, 40.94, 40.70; H, 5.93, 6.11; Cl, 25.56; N, 11.85, 11.70%. C$_8$H$_{14}$Cl$_2$N$_2$S requires C, 39.84; H, 5.85; Cl, 29.40; N, 11.62%).

4.16. Preparation of 2-(6'-methylpyridin-2'-ylsulfanyl)ethanamine (6-Me-2-PSEA)

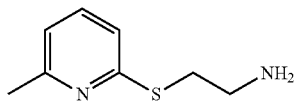

Preparation of 6-Me-2-PSEA via General Method C (Blackburn et al.[14]) The general procedure in Section 4. was followed using HMPA (3 mL), NaH (dry, 95%) (1.35 g, 56.3 mmol), 2-aminoethanethiol hydrochloride (2.00 g, 17.6 mmol) and 2-chloro-6-methylpyridine (1.50 g, 11.76 mmol). The mixture was stirred at ambient temperature for 22 h and workup as described in the general method gave a brown oil which was loaded onto a plug of silica, washed (100% EtOH) and eluted (DCM:NH$_3$, 7N in MeOH, 9:1) to afford the title compound as a brown oil (1.25 g, 63%). HRMS (ESI$^+$, MeOH): Found: m/z 169.0794 (M+H)$^+$, C$_8$H$_{13}$N$_2$S requires m/z 169.0799. $\nu_{max}$ (Neat): 3363m, 3286m, 3056w, 2924s, 2864m, 1566s, 1436s, 1373m, 1256w, 1161s, 1087m, 1035m, 1001m, 975m, 869s, 776s, 729m, 677m cm$^{-1}$. $^1$H n.m.r. (300 MHz, CDCl$_3$): δ 1.47 (bs, 2H); 2.48 (s, 3H); 2.99 (t, J 6.3 Hz, 2H); 3.28 (t, J 6.4 Hz, 2H); 6.82 (d with fine splitting, J 7.5 Hz, 1H); 7.00 (d with fine splitting, J 7.7 Hz, 1H); 7.36 (apparent t, J 7.7 Hz, 1H). $^{13}$C n.m.r. (75 MHz, CDCl$_3$): δ 24.6; 34.3; 42.0; 119.0; 119.4; 136.4; 157.6; 158.6. Mass Spectrum (ESI) m/z 168.9 (M+H)$^+$ (100%).

4.17. Preparation of 2-phenylpyridine N-oxide

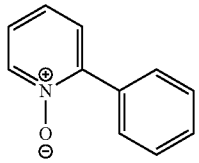 [SMILES: [O-][n+]1ccccc1-c1ccccc1]

The N-oxide was prepared by modifying the method outlined by Zhang et al.[25] using 2-phenylpyridine (5.00 g, 32.2 mmol) and 30% H$_2$O$_2$ in glacial acetic acid to yield the title compound as a light yellow solid (4.00 g, 72%), m.p. 154-157° C. (lit.[26] m.p. 155-155.5° C.). The spectral data were consistent with literature data.[27]

4.18. Preparation of 2-chloro-6-phenylpyridine and 4-chloro-2-phenylpyridine

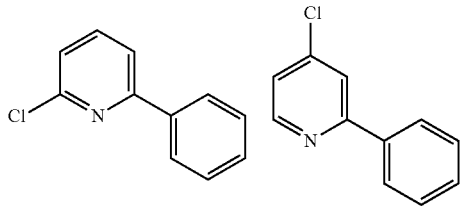

The compounds above were prepared by modifying the method described by Shiotani and Taniguchi.[28] using phosphorus oxychloride (28.66 g, 186.9 mmol) and 2-phenylpyridine N-oxide (4.00 g, 23.36 mmol) in CHCl$_3$ (10 mL) to give a mixture of isomers (4.08 g) which were separated by column chromatography (SiO$_2$, DCM). 2-Chloro-6-phenylpyridine was isolated as a pink solid (2.30 g, 52%), m.p. 33-35° C. $^1$H n.m.r. (300 MHz, CDCl$_3$): δ 7.25 (dd, J 7.4, 1.2 Hz, 1H); 7.42-7.50 (m, 3H); 7.64 (dd, J 7.8, 1.2 Hz, 1H); 7.70 (t, J 7.6 Hz, 1H); 7.99 (m, 2H). $^{13}$C n.m.r. (50 MHz, CDCl$_3$): δ 118.8; 122.7; 127.2; 129.0; 129.8; 138.0; 139.4; 151.6; 158.3. The spectral data were consistent with literature data.[29]

Further elution gave 4-chloro-2-phenylpyridine as a yellow oil (1.08 g, 24%). $^1$H n.m.r. (300 MHz, CDCl$_3$): δ 7.24 (dd, J 5.3, 1.9 Hz, 1H); 7.43-7.51 (m, 3H); 7.73 (dd, J 1.9, 0.6 Hz, 1H); 7.97 (m, 2H); 8.58 (dd, J 5.3, 0.6 Hz, 1H). $^{13}$C n.m.r. (50 MHz, CDCl$_3$): δ 121.1; 122.5; 127.2; 129.1; 129.8; 138.4; 145.0; 150.7; 159.3. Mass Spectrum (ESI): m/z 192.1 (M($^{37}$Cl)+H)$^+$ (32%), 190.1 (M($^{35}$Cl)+H)$^+$ (100). The spectral data were consistent with literature data.[30]

5. General Procedure for Reaction of 2-Aminoethanethiol.HCl with Chlorine-Substituted N-Heterocycles See General Method C for reaction of 2-aminoethanethiol.HCl with halogenated heterocycles (Section 4.). The method described by Blackburn et al.[14] was modified as follows:

2-Aminoethanethiol hydrochloride was suspended in dry HMPA. NaH (dry, 95%) was added portion-wise over 5-30 min while the reaction mixture was cooled in an ice-cold water bath under a nitrogen atmosphere. The mixture was stirred for 10-20 min at ambient temperature before portion-wise addition of the desired chloro-N-heterocycle over 5-20 min. The reaction mixture was stirred at ambient temperature for 2 h-2 d. Water was added slowly to quench the reaction then the aqueous layer was extracted with DCM, dried (MgSO$_4$), filtered, and solvent removed in vacuo to give the crude product in HMPA. Purification of the resulting product is described in the relevant sections.

TABLE A

Reagents used for preparation of various derivatives

| Entry | Section | Starting Material | Amount of S.M. | 2-Amino-ethanethiol•HCl | NaH | Solvent HMPA | Time |
|---|---|---|---|---|---|---|---|
| A | 5.1. | 2-chloro-6-phenylpyridine | 1.80 g<br>9.49 mmol | 1.29 g<br>11.35 mmol | 0.58 g<br>24.0 mmol | 4 mL | 27 h |

TABLE A-continued

Reagents used for preparation of various derivatives

| Entry | Section | Starting Material | Amount of S.M. | | 2-Amino-ethanethiol•HCl | | NaH | | Solvent HMPA | Time |
|-------|---------|-------------------|--------|------|--------|------|--------|------|------|------|
| B | 5.2. | 4-chloro-2-phenylpyridine | 0.90 | g | 0.65 | g | 0.30 | g | 3 mL | 3 h |
|   |      |                           | 4.75 | mmol | 5.70 | mmol | 12.5 | mmol |      |     |
| C | 5.3. | 2-chloro-6-methoxypyridine | 1.50 | g | 1.42 | g | 0.69 | g | 2 mL | 2 d |
|   |      |                            | 10.5 | mmol | 12.5 | mmol | 28.8 | mmol |      |     |
| D | 5.4. | 2-chloro-4-nitropyridine | 0.20 | g | 0.17 | g | 0.08 | g | 1 mL | 3 h |
|   |      |                          | 1.26 | mmol | 1.51 | mmol | 3.48 | mmol |      |     |
| E | 5.6. | 2-chloro-quinoline | 2.00 | g | 1.67 | g | 0.81 | g | 2 mL | 2 h |
|   |      |                    | 12.2 | mmol | 14.7 | mmol | 33.7 | mmol |      |     |
| F | 5.7. | 1-chloro-isoquinoline | 2.00 | g | 1.67 | g | 0.81 | g | 3 mL | 2.5 h |
|   |      |                       | 12.2 | mmol | 14.7 | mmol | 33.7 | mmol |      |     |

5.1. Preparation of 2-(6'-phenylpyridin-2'-ylsulfanyl)ethanamine (6-Ph-2-PSEA)

The title compound was prepared by the method described in the general procedure Section 5., (Entry A, Table A). The crude brown liquid obtained was loaded onto a plug of silica, washed (hexane:Et$_2$O:EtOH, 3:2:1) to remove HMPA and the title compound eluted (DCM:MeOH:NH$_3$ 7N in MeOH, 85:10:5) as a yellow oil (1.79 g, 82%). HRMS (ESI$^+$, MeOH): Found: m/z 231.0953 (M+H)$^+$, C$_{13}$H$_{15}$N$_2$S requires m/z 231.0956. $v_{max}$ (Neat): 3363bs, 3062s, 2926s, 2868m, 1959w, 1558s, 1496m, 1430s, 1387m, 1312m, 1239w, 1184m, 1159s, 1142s, 1089w, 1063m, 1025m, 982m, 907m, 803s, 758s, 694s cm$^{-1}$. $^1$H n.m.r. (400 MHz, CDCl$_3$): δ 1.50 (bs, 2H); 3.08 (t, J 6.3 Hz, 2H); 3.41 (t, J 6.3 Hz, 2H); 7.13 (dd, J 7.8, 0.8 Hz, 1H); 7.40-7.48 (m, 4H); 7.53 (apparent t, J 7.8 Hz, 1H); 8.01 (m, 2H). $^{13}$C n.m.r. (75 MHz, CDCl$_3$): δ 34.2; 42.0; 116.0; 121.0; 126.9; 128.9; 129.2; 136.8; 139.2; 156.9; 158.3. Mass Spectrum (ESI): m/z 231.3 (M+H)$^+$ (100%).

5.2. Preparation of 2-(2'-phenylpyridin-4'-ylsulfanyl)ethanamine (2-Ph-4-PSEA)

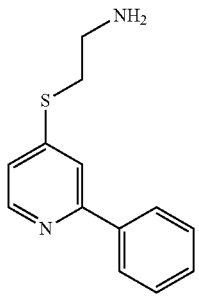 [SMILES: NCCSc1ccnc(-c2ccccc2)c1]

The title compound was prepared by the method described in the general procedure Section 5., (Entry B, Table A). The crude orange-brown liquid obtained was loaded onto a plug of silica, washed (hexane:EtOAc:EtOH, 3:2:1) and the title compound eluted (DCM:MeOH:NH$_3$ 7N in MeOH, 85:10:5) as a yellow oil (0.90 g, 82%). HRMS (ESI$^+$, MeOH): Found: m/z 231.0961 (M+H)$^+$, C$_{13}$H$_{15}$N$_2$S requires m/z 231.0956. $v_{max}$ (Neat): 3372bw, 3037w, 2924w, 1712w, 1663s, 1572s, 1535s, 1498w, 1464m, 1444m, 1381m, 1280w, 1244w, 1221w, 1179w, 1111m, 1074w, 986w, 804m, 774s, 733m, 695s cm$^{-1}$. $^1$H n.m.r. (400 MHz, CDCl$_3$): δ 1.42 (bs, 2H); 3.05 (m, 2H); 3.14 (m, 2H); 7.09 (dd, J 5.3, 1.8 Hz, 1H); 7.39-7.48 (m, 3H); 7.57 (dd, J 1.8, 0.7 Hz, 1H); 7.94 (m, 2H); 8.48 (dd, J 5.3, 0.7 Hz, 1H). $^{13}$C n.m.r. (100 MHz, CDCl$_3$): δ 35.2; 41.0; 118.3; 119.5; 127.2; 128.9; 129.3; 139.3; 149.3; 149.5; 157.6. Mass Spectrum (ESI): m/z 231.1 (M+H)$^+$ (100%).

5.3. Preparation of 2-(6'-methoxypyridin-2'-ylsulfanyl)ethanamine (6-OMe-2-PSEA)

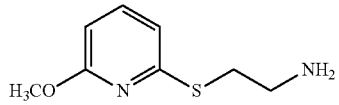 [SMILES: COc1cccc(SCCN)n1]

The title compound was prepared by the method described in the general procedure Section 5., (Entry C, Table A). The $^1$H n.m.r. spectra of the crude product indicated that no starting materials were present, only the desired product and HMPA. The crude brown liquid obtained was dissolved in dry Et$_2$O (3 mL) and dry MeOH (3 mL) and a saturated solution of HCl in Et$_2$O (3 mL) was added. The resulting precipitate was collected by filtration, washed with dry Et$_2$O and obtained as a beige solid (1.05 g). The solid was dissolved in water, basified (pH 8-9) with a sat. K$_2$CO$_3$ solution and extracted with DCM (3×15 mL). The combined organic extract was dried (MgSO$_4$), filtered and solvent removed in vacuo to give the title compound as a brown oil (0.58 g, 30%). HRMS (ESI$^+$, MeOH): Found: m/z 185.0741 (M+H)$^+$, C$_8$H$_{13}$N$_2$OS requires m/z 185.0749. $v_{max}$ (Neat): 3372m, 2946m, 2862m, 1568s, 1462s, 1405s, 1347w, 1288s, 1260s, 1190m, 1147s, 1074m, 1025s, 984m, 884s, 785s, 729m cm$^{-1}$. $^1$H n.m.r. (300 MHz, CDCl$_3$): δ 1.45 (bs, 2H, 3.02 (t, J 6.3 Hz, 2H); 3.27 (t, J 6.3 Hz, 2H); 3.93 (s, 3H); 6.42 (dd, J 8.1, 0.7 Hz, 1H); 6.79 (dd, J 7.5, 0.7 Hz, 1H); 7.38 (dd, J 8.1, 7.5 Hz, 1H). $^{13}$C n.m.r. (75 MHz, CDCl$_3$): δ 34.2; 41.8; 53.3; 105.8; 114.6; 138.7; 155.7; 163.7. Mass Spectrum (ESI): m/z 185.0 (M+H)$^+$ (100%).

5.4. Preparation of 2-(4'-nitropyridin-2'-ylsulfanyl)ethanamine (4-NO₂-2-PSEA)

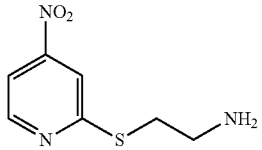 [SMILES: NCCSc1cc([N+](=O)[O-])ccn1]

tert-Butyl (2-sulfanylethyl)carbamate (1.38 g, 7.81 mmol) was dissolved in dry THF (20 mL) under a nitrogen atmosphere. NaH (dry, 95%) (0.24 g, 10.2 mmol) was added portion-wise over 45 min and the mixture was then cooled to −78° C. 2-Chloro-4-nitropyridine N-oxide (1.50 g, 8.59 mmol) was dissolved in dry THF (40 mL) and added drop-wise over 45 min to the cold carbamate solution. The mixture was allowed to warm to ambient temperature over 2 h and stirred for a further 2 h. The THF was removed under reduced pressure. The residue was treated with CHCl₃ (50 mL) followed by drop-wise addition of PCl₃ (3 mL). The reaction mixture was stirred at ambient temperature for 16 h and then poured into water (50 mL) slowly. The organic layer was separated and the aqueous layer washed with CHCl₃ (4×15 mL). The aqueous layer was basified (pH 8.5-10) with 2 M NaOH solution and extracted several times with CH₂Cl₂. The combined organic extract was dried (MgSO₄), filtered, and solvent removed in vacuo to give a red-brown oil (ca. 95% pure) (1.06 g, ca. 68%). Preparative t.l.c. (SiO₂, DCM: MeOH:NH₃ in MeOH, 9:0.8:0.2) using a sample of the red-brown oil gave the pure title compound as a yellow oil. HRMS (ESI⁺, MeOH): Found: m/z 200.0494 (M+H)⁺, $C_7H_{10}N_3O_2S$ requires m/z 200.0494. $\nu_{max}$ (Neat): 3372m, 3083m, 2927m, 2870m, 1600m, 1560s, 1531s, 1453m, 1427w, 1355s, 1234m, 1153s, 1100m, 1073w, 1015w, 982w, 910m, 881m, 838m, 761s, 734s, 679m cm⁻¹. ¹H n.m.r. (300 MHz, CDCl₃): δ 1.52 (bs, 2H); 3.03 (t, J 6.4 Hz, 2H); 3.35 (t, J 6.4 Hz, 2H); 7.66 (dd, J 5.4, 2.0 Hz, 1H); 7.89 (dd, J 2.0, 0.7 Hz, 1H); 8.66 (dd, J 5.4, 0.7 Hz, 1H). ¹³C n.m.r. (50 MHz, CDCl₃): δ 34.5; 41.6; 111.8; 115.1; 151.5; 153.9; 162.9. Mass Spectrum (ESI): m/z 200.0 (M+H)⁺ (30%), 183.0 (100).

The preparation of 4-NO₂-2-PSEA was previously attempted by following the method described in the general procedure Section 5., (Entry D, Table A). The crude yellow liquid obtained was dissolved in dry ether (3 mL) and dry MeOH (3 mL) to which a saturated solution of HCl in Et₂O (2 mL) was added. The resulting precipitate was filtered, washed with ice-cold dry Et₂O and collected as a yellow solid (132 mg). The yellow solid was dissolved in water (5 mL), basified (pH 8-9) with sat. K₂CO₃ solution and extracted with DCM (3×5 mL). The combined organic extract was dried (MgSO₄), filtered and solvent removed in vacuo to yield 2-(2'-chloro-pyridin-4'-yl-sulfanyl)ethanamine as the only product, as a brown oil (85 mg, 36%). HRMS (ESI⁺, MeOH): Found: m/z 189.0245 (M+H)⁺, $C_7H_{10}ClN_2S$ requires m/z 189.0253. $\nu_{max}$ (Neat): 3362bs, 2927s, 2868m, 2457w, 1569s, 1523s, 1456s, 1428m, 1371s, 1284m, 1230m, 1151s, 1111m, 1082s, 986s, 795s, 750m cm⁻¹. ¹H n.m.r. (400 MHz, CDCl₃): δ 1.38 (bs, 2H); 3.02-3.11 (m, 4H, H1); 7.05 (dd, J 5.4, 1.7 Hz, 1H); 7.15 (dd, J 1.7, 0.4 Hz, 1H); 8.15 (dd, J 5.4, 0.4 Hz, 1H). ¹³C n.m.r. (100 MHz, CDCl₃): δ 35.0; 40.7; 119.6; 120.5; 149.0; 151.9; 152.3. Mass Spectrum (ESI): m/z 190.8 (M (³⁷Cl)+H)⁺ (36%), 188.8 (M (³⁵Cl)+H)⁺ (100).

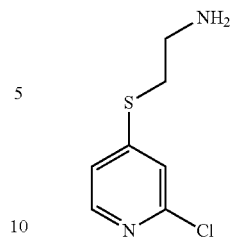

5.5. Preparation of 2-(quinolin-4'-ylsulfanyl)ethanamine (4-QSEA)

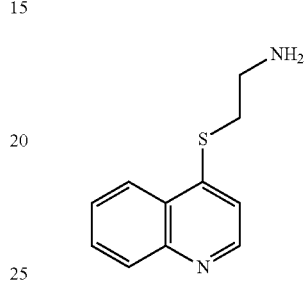

Preparation of 4-QSEA via General Method C (Blackburn et al.¹⁴) The general procedure in Section 4. was followed using HMPA (3 mL), NaH (dry, 95%) (0.30 g, 12.5 mmol) and 2-aminoethanethiol hydrochloride (0.61 g, 5.37 mmol). The suspension was stirred for 10 min at ambient temperature before being re-immersed in an ice bath. 4-Chloroquinoline (0.80 g, 4.89 mmol) was added and the mixture stirred at ambient temperature for 18 h. Workup as described previously gave a yellow solution (4.21 g). The ¹H n.m.r. spectrum showed the presence of HMPA and the desired product and no further purification was carried out. Integration of relevant peaks in the ¹H n.m.r. spectrum showed that the title compound was obtained in an 88% yield. (0.88 g in HMPA). HRMS (ESI⁺, MeOH): Found: m/z 205.0794 (M+H)⁺, $C_{11}H_{13}N_2S$ requires m/z 205.0799. $\nu_{max}$ (Neat): 1563m, 1376w, 933m, 822w, 810w, 667w, 643m, 630m cm⁻¹. ¹H n.m.r. (300 MHz, CDCl₃): δ 1.97 (bs, 2H); 3.12 (m, 2H); 3.24 (m, 2H); 7.24 (d, J 4.8 Hz, 1H); 7.56 (apparent ddd, J 8.4, 6.9, 1.4 Hz, 1H); 7.72 (apparent ddd, J 8.4, 6.9, 1.5 Hz, 1H); 8.07 (ddd, J 8.5, 1.3, 0.6 Hz, 1H); 8.17 (ddd, J 8.4, 1.4, 0.6 Hz, 1H); 8.72 (d, J 4.8 Hz, 1H). ¹³C n.m.r. (75 MHz, CDCl₃): δ 35.4; 40.7; 116.5; 123.8; 126.5; 129.9; 130.2; 127.0; 147.1; 147.7; 149.4. Mass Spectrum (ESI): m/z 205.0 (M+H)⁺ (15%), 179.8 (HMPA+H)⁺ (100).

The above reaction was repeated using 4-chloroquinoline (0.20 g, 1.22 mmol) and the brown oil obtained was dissolved in dry Et₂O (3 mL) and dry MeOH (3 mL) and treated with HCl in ether in order to precipitate the amine salt. The salt was collected by filtration and washed with dry Et₂O to give 4QSEA.2HCl as a white solid (240 mg, 71%), m.p. 221-224° C., (lit.³¹ m.p. 222-226° C.). The solid was dissolved in water, basified with K₂CO₃, extracted with DCM (3×10 mL), dried (MgSO₄), filtered and solvent removed in vacuo to give 4QSEA as a brown oil (130 mg, 52%).

The CHCl₃ solution recovered from the trituration step was concentrated and passed through an alumina column. Analysis of the eluent (¹H n.m.r. spectroscopy) again showed significant decomposition.

5.6. Preparation of 2-(quinolin-2'-ylsulfanyl)ethanamine (2-QSEA)

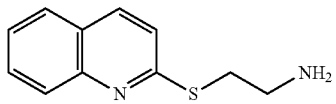 [SMILES: NCCSc1ccc2ccccc2n1]

The title compound was prepared by the method described in the general procedure Section 5., (Entry E, Table A). The organic extract obtained was extracted with 2 M HCl (2×15 mL). The aqueous layer was washed with DCM (7×10 mL) to remove HMPA. The aqueous layer was basified (pH 10) with 5 M NaOH and extracted with DCM (3×15 mL). The combined organic extract was dried ($MgSO_4$), filtered and solvent removed in vacuo to give a brown oil (2.93 g). The $^1$H n.m.r. spectrum showed ca. 20% HMPA was still present. Dry $Et_2O$ (5 mL) was added to the brown oil followed by a saturated solution of HCl in $Et_2O$ (3 mL). The resulting precipitate was collected by filtration and washed with ice-cold dry $Et_2O$ to give the 2HCl salt of 2QSEA as a yellow solid (2.82 g), m.p. 210-211° C. (Found: C, 47.4; H, 5.2; N, 10.0%. $C_{11}H_{12}N_2S.2HCl$ requires C, 47.7; H, 5.1; N, 10.1%). The solid was dissolved in water, basified (pH 8-9) with a sat. $K_2CO_3$ solution and extracted with $CH_2Cl_2$ (3×15 mL). The organic extract was dried ($MgSO_4$), filtered and solvent removed in vacuo to give the title compound as a green-brown oil (2.10 g, 84%). HRMS (ESI$^+$, MeOH): Found: m/z 205.0802 (M+H)$^+$, $C_{11}H_{13}N_2S$ requires m/z 205.0799. $v_{max}$ (Neat): 3358m, 3281m, 3055m, 2925m, 2862m, 1614s, 1593s, 1555s, 1497s, 1452m, 1420s, 1376w, 1294s, 1138s, 1089s, 1017w, 942m, 861m, 817s, 780m, 750s cm$^{-1}$. n.m.r. (300 MHz, CDCl$_3$): δ 1.67 (bs, 2H); 3.08 (bt, J 6.1 Hz, 2H); 3.45 (t, J=6.3 Hz, 2H); 7.20 (d, J 8.6 Hz, 1H); 7.40 (apparent ddd, J 8.1, 6.9, 1.2 Hz, 1H); 7.61 (apparent ddd, J 8.4, 7.0, 1.5 Hz, 1H); 7.68 (apparent dd, J 8.1, 1.5 Hz, 1H); 7.84 (dd, J 8.7, 0.6 Hz, 1H); 7.91 (apparent dd, J 8.4, 1.2 Hz, 1H). $^{13}$C n.m.r. (75 MHz, CDCl$_3$): δ 33.8; 41.9; 121.2; 125.4; 126.1; 127.7; 128.1; 129.7; 135.5; 148.4; 158.9. Mass Spectrum (ESI): m/z 205.1 (M+H)$^+$ (100%).

5.7. Preparation of 2-(isoquinolin-1'-ylsulfanyl)ethanamine (1-IQSEA)

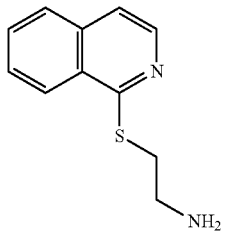 [SMILES: NCCSc1nccc2ccccc12]

The title compound was prepared by the method described in the general procedure Section 5., (Entry F, Table A). The crude yellow liquid obtained was dissolved in dry $Et_2O$ (6 mL) and dry MeOH (3 mL). A saturated solution of HCl in $Et_2O$ (3 mL) was added and the resulting precipitate was collected by filtration, washed with ice-cold dry $Et_2O$ and dried under vacuum to yield the 2HCl salt of the title compound as a white solid (3.12 g, 92%), m.p. dec. >120° C. (Found: C, 44.2; H, 5.7; N, 9.3%. $C_{11}H_{12}N_2S.2HCl.1.2H_2O$ requires C, 44.2; H, 5.5; N, 9.4%).

The white solid (1.50 g) was dissolved in water, basified (pH 8-9) with sat. $K_2CO_3$ solution and extracted with DCM (3×15 mL). The combined organic extract was dried ($MgSO_4$), filtered and solvent removed in vacuo to yield the title compound as a yellow oil (1.09 g, 99%). HRMS (ESI$^+$, MeOH): Found: m/z 204.0714 M$^+$, $C_{11}H_{12}N_2S$ requires m/z 204.0721. $v_{max}$ (Neat): 3366m, 3293m, 3051m, 2926m, 2870m, 2806w, 1766w, 1619s, 1589s, 1551s, 1494s, 1450m, 1402m, 1373m, 1337s, 1301s, 1261s, 1226m, 1201m, 1184m, 1150s, 1066m, 1025m, 989s, 909m, 866m, 816s, 745s, 675s, 648s cm$^{-1}$. $^1$H n.m.r. (400 MHz, CDCl$_3$): δ 1.43 (bs, 2H); 3.05 (t, J 6.4 Hz, 2H); 3.47 (t, J 6.4 Hz, 2H); 7.29 (dd, J 5.7, 0.6 Hz, 1H); 7.51 (apparent ddd, J 8.4, 6.9, 1.4 Hz, 1H); 7.61 (apparent ddd, J 8.2, 6.9, 1.2 Hz, 1H); 7.70 (bd, J 8.2 Hz, 1H); 8.20 (bd, J 8.4 Hz, 1H); 8.27 (d, J 5.7 Hz, 1H). $^{13}$C n.m.r. (100 MHz, CDCl$_3$): δ 33.7; 41.8; 117.3; 124.6; 127.0; 127.1; 127.2; 130.3; 135.5; 141.8; 159.0. Mass Spectrum (ESI): m/z 205.2 (M+H)$^+$ (100%), 188.2 (100).

5.8. 4'-(2-Aminoethanesulfanyl)-2,2':6',2''-terpyridine (4-TerPSEA)

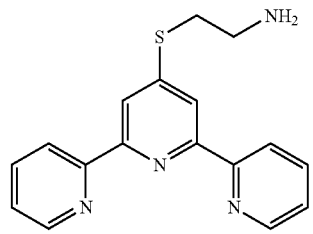 [SMILES: NCCSc1cc(-c2ccccn2)nc(-c2ccccn2)c1]

4-TerPSEA[32] was prepared via the method outlined in Section 5. using DMF as the solvent and obtained in a 95% yield with no purification required. The starting 4'-chloro-2,2':6',2''-terpyridine derivative was prepared as described by Constable and Ward[33] in an overall yield of 52% from ethyl pyridine-2-carboxylate. The spectral data for 4-TerPSEA were consistent with data reported by Inhoff et al.[32]

5.9. 5-Bromo-2PSEA

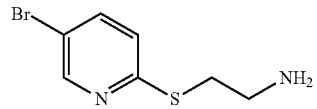 [SMILES: NCCSc1ccc(Br)cn1]

Preparation of 5-Br-2PSEA via General Method B (microwave): The general procedure in section 3.1. was followed using sodium metal (0.3 g, 13 mmol, 3 eq.), 2-aminoethanethiol hydrochloride (0.072 g, 0.63 mmol, 1.5 eq.) and 2,5-dibromopyridine (1 g, 4.2 mmol, 1 eq.) in EtOH (18 mL) in a 20 mL microwave vial. The vial was sealed and the resulting suspension was heated under microwave irradiation at 140° C. for 21 min. The mixture was cooled to room temperature; the reaction was worked up as described in section 2.1 to yield the compound as a white solid. (0.91 g, 89%). Mass spectrum (ESI): m/z 234.7/232.7 (M+H)$^+$; 217.7/215.7 (M+H−NH$_3$)$^+$. ($^1$H n.m.r. spectroscopy showed 100% conversion). $^1$H n.m.r. (300 MHz, CDCl$_3$): δ 1.39 (bs, 2H); 2.98 (t, J 6.4 Hz, 2H); 3.26 (t, J 6.4 Hz, 2H); 7.08 (dd, J 8.5, 0.7 Hz, 1H); 7.56 (dd, J 8.5, 2.4 Hz, 1H); 8.45 (dd, J 2.4, 0.6 Hz, 1H). $^{13}$C n.m.r. (75 MHz, CDCl$_3$): δ 34.4; 41.8; 116.2; 123.7; 138.6; 150.4; 157.5.

Preparation of HCl Salt: m.p. 180.5° C. Mass spectrum (ESI): m/z 235/233 (M+H)$^+$; 217.9/215.9 (M+H−NH$_3$)$^+$. $^1$H n.m.r. (400 MHz, CDCl₃): δ); 3.29 (t, J 6.5 Hz, 2H); 3.44 (t, J 6.5 Hz, 2H); 7.4 (d, J 8.7 Hz, 1H); 8.0 (dd, J 8.7, 2.3 Hz, 1H); 8.5 (d, J 2.8 Hz, 1H). $^{13}$C n.m.r. (75 MHz, CDCl₃): δ 28.6; 39.0; 117.7; 125.5; 143.3; 148.2; 154.9. (Found: C, 26.21, 26.23; H, 3.58, 3.48; Cl, 21.33, 21.22, N, 8.98, 9.09; %. C₇H₁₁BrCl₂N₂S requires C, 27.47; H, 3.62; Cl, 23.17; N, 9.15%). (Cl analysed by a total halogen method and calculated as 1Bn2Cl).

5.10. 6-Bromo-2PSEA

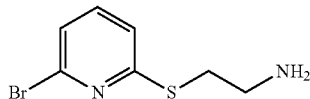 [SMILES: NCCSc1cccc(Br)n1]

Preparation of 6-Br-2PSEA via General Method B (microwave): The general procedure in section 3.1. was followed. Sodium metal (0.19 g, 8.4 mmol, 2 eq.) was dissolved in EtOH (18 mL) in a 20 mL microwave vial. 2-Aminoethanethiol hydrochloride (0.48 g, 4.2 mmol, 1 eq.) was added to the solution which was stirred magnetically for 10 min under a nitrogen atmosphere at ambient temperature to give a white suspension. Half of the suspension was added to a fresh 20 mL microwave vial. 2,6-Dibromopyridine (1 g, 4.2 mmol, 1 eq.) was added into each suspension and the microwave vials were sealed. The resulting suspensions were heated under microwave irradiation at 100° C. for 21 min and 140° C. for 21 min respectively. The mixtures were cooled to room temperature and the reactions were worked up as described in section 2.1. The reaction at 140° C. gave the title compound as a white solid (0.67 g, 72%), $^1$H n.m.r. (300 MHz, CDCl₃): δ 1.78 (bs, 2H); 2.99 (t, J 6.3 Hz, 2H); 3.25 (t, J 6.3 Hz, 2H); 7.11 (dd, J 2.4, 0.7 Hz, 1H); 7.14 (d, J 2.3, 0.6 Hz, 1H); 7.29 (dd, J 5.3, 2.4 Hz, 1H).

Preparation of HCl Salt: Yield 0.56 g, (60%). m.p. 189.5° C. Mass spectrum (ESI): m/z 235/233 (M+H)⁺. $^1$H n.m.r. (300 MHz, D₂O): δ 3.43 (t, J 6.4 Hz, 2H); 3.52 (t, J 6.4 Hz, 2H); 7.43-7.48 (m, 2H); 7.64 (apparent t, J 7.8 Hz, 1H). $^{13}$C n.m.r. (75 MHz, D₂O): δ 28.1; 39.5; 122.2; 125.2; 140.2; 141.2; 158.0.

5.11. 6,6'-Di(2-aminoethylsulfanyl)-3,3'-bipyridine (3BPSEA)

a) Preparation of 5-Bromo-2-ethoxypyridine

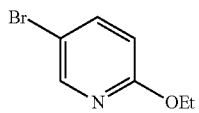

The title compound was prepared as described by Constable et al.[13] from sodium (1.2 g, 52.2 mmol, 3 eq.) and 2,5-dibromopyridine (17.4 mmol, 1 eq.) in EtOH (60 mL) to yield 5-bromo-2-ethoxypyridine which was used further without purification in subsequent reactions. (3.13 g, 90%).

Preparation of 5-Br-2-ethoxy pyridine via General Method B (microwave): The general procedure in section 3.1. was followed using sodium metal (0.3 g, 1.3 mmol, 3 eq.) and 2,5-dibromopyridine (0.1 g, 4.22 mmol, 1 eq.) in ethanol (2 mL). The mixture was heated under microwave irradiation at 140° C. for 21 min. Workup as above gave 5-bromo-2-ethoxypyridine (0.80 gm, 93%). Spectral data were identical to those reported above.

b) Preparation of 6,6'-diethoxy-3,3'-bipyridine

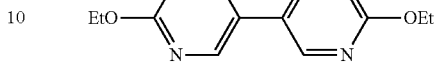

The title compound was prepared as described by Constable et al.[13] using NiCl₂(PPh₃)₂ (327 mg, 0.5 mmol, 0.3 eq.), acid washed Zn powder (164 mg, 1.5 eq.) and Et₄NI (435 mg, 1.7 mmol, 1 eq.) in. distilled THF (10 mL). with a solution of 5 bromo-2 ethoxypyridine (344 mg, 1.7 mmol, 1 eq.) in THF (5 mL) at 50° C. for 24 h. Workup gave a white crystalline solid (237 mg; 80%). The reaction was also carried out on a larger scale (1.0 g or 1.7 g of starting material) giving yields of 85% and 90% respectively. The spectral data were consistent with literature data[13].

c) Preparation of 6,6'-dichloro-3,3'-bipyridine

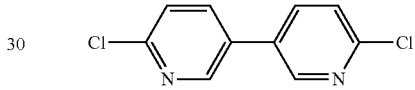

The title compound was prepared as described by Constable et al.[13] using phosphorus oxychloride (5.53 mL, 35 mmol, 8.1 eq.) and 6,6'-diethoxy-3,3'-bipyridine (1 g, 4.44 mmol, 1 eq.) in dry DMF (15 mL) to give the product which was recrystallised from ethanol and dried to give beige crystals of 6,6'-dichloro-3,3'-bipyridine (0.61 g 86%). The spectral data were consistent with literature data[13].

d) Preparation of 6,6'-di(2-aminoethylsulfanyl)-3,3'-bipyridine

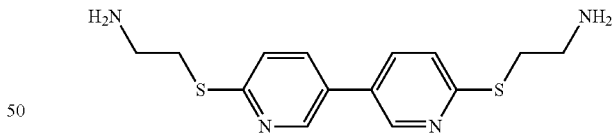

Preparation of 6,6'-di(2-aminoethylsulfanyl)-3,3'-bipyridine via General Method B (microwave): The general procedure in section 3.1. was followed using sodium metal (0.25 g, 10.9 mmol, 16 eq.) 2-aminoethanethiol hydrochloride (0.64 g, 5.63 mmol, 8.2 eq.) and 6,6'-dichloro-3,3'-bipyridine (0.154 g, 0.684 mmol, 1 eq.) in EtOH (18 mL). The mixture was heated under microwave irradiation at 150° C. for 21 min. Workup gave a pale brown solid (0.18 g). $^1$H n.m.r. spectroscopy showed the presence of target molecule and the monosubstituted derivative (30%) which were isolated by column chromatography.

The title compound was prepared as described by Constable et al.[13] The same reaction was repeated using 6,6'-dichloro-3,3'-bipyridine (0.154 g, 0.684 mmol) in EtOH (150 mL) under reflux for 24 h to give a yellow oil. The crude product showed the presence of cysteamine ($^1$H n.m.r.) and washing with water gave a clean product (1.3 g, 75%). Mass spectrum (ESI): m/z 153.9 [½ (M+2H)$^{2+}$]; 307.2 (M+H)$^+$. $^1$H n.m.r. (300 MHz, CDCl$_3$): δ 1.5 (bs, 4H); 3.02 (t, J 6.4 Hz, 4H); 3.32 (t, J 6.4 Hz, 4H); 7.26 (dd, J 8.4, 0.6 Hz, 2H); 7.63 (dd, J 8.4, 2.4 Hz, 2H); 8.60 (d, J 2.4 Hz, 2H). $^{13}$C n.m.r. (75 MHz, CDCl$_3$): δ 34.4; 42.1; 122.8; 129.4; 134.3; 147.7; 156.1. Spectra were consistent with literature data[13].

Preparation of HCl Salt: m.p. 256.6° C. Mass spectrum (ESI): m/z 307.1 (M+H)$^+$; 154 [½ (M+2H)$^{2+}$]. $^1$H n.m.r. (300 MHz, CDCl$_3$): δ 3.38 (t, J 6.5 Hz, 4H); 3.55 (t, J=6.8 Hz, 4H); 7.69 (dd, J 8.5, 0.7 Hz, 4H); 8.17 (dd, J 8.5, 2.4 Hz, 4H); 8.77 (dd, J 2.4, 0.6 Hz, 4H). $^{13}$C n.m.r. (75 MHz, CDCl$_3$): δ 28.7; 38.7; 125.1; 129.8; 140.2; 143.8; 156.1. (Found: C, 36.44; 36.35; H, 5.11, 5.31; Cl, 29.94, 29.48; N, 11.76, 11.84%. C$_{14}$H$_{22}$Cl$_4$H$_4$S$_2$ requires C, 37.18; H, 4.90; Cl, 31.35; N, 12.39%).

5.12  5-Thiomethoxy-2-(pyridine-2'-ylsulfanyl)ethanamine (5-SMe-2PSEA)

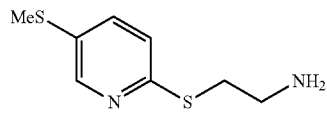 [SMILES: CSc1ccc(SCCN)nc1]

5-Bromo-2-(pyridine-2'-ylsulfanyl)ethanamine was prepared by modifying the procedure outlined by Testaferri et al.[34]

5-Bromo-2-(pyridine-2'-ylsulfanyl)ethanamine (1.00 g, 4.2 mmol, 1 eq) was dissolved in anhydrous DMF (20 mL) under a nitrogen atmosphere to give clear suspension. Sodium thiomethoxide (0.45 g, 6.4 mmol, 1.5 eq) was added to the solution and stirred magnetically at 80° C. overnight. The mixture was cooled to room temperature, poured onto water and extracted with ether. The organic layer was washed with sat. NaCl, dried over MgSO$_4$ and evaporated. The crude product (1.38 g) was purified by column chromatography (SiO$_2$, DCM:MeOH:NH$_4$OH, 92:7:1) to give the title compound as a white crystalline solid (0.5 g, 58%). m.p. 75.5° C. Mass spectrum (ESI): m/z 201.2 (M+H)$^+$; 184.2 (M+H–NH$_3$)$^+$. $^1$H n.m.r. (300 MHz, CDCl$_3$): δ 1.43 (bs, 2H); 2.46 (s, 3H); 2.98 (t, J 6.4 Hz, 2H); 3.26 (t, J 6.4 Hz, 2H); 7.12 (dd, J 8.4, 0.8 Hz, 1H); 7.42 (dd, J 8.4, 2.4 Hz, 1H); 8.35 (dd, J 2.4, 0.8 Hz, 1H). $^{13}$C n.m.r. (75 MHz, CDCl$_3$): δ 16.6; 33.9; 41.4; 122.1; 130.2; 136.0; 148.1; 155.4. IR: 3330s, 2916m, 2581m, 2172m, 1636w, 1566s, 1426m, 1327m, 1130s998m, 1009m, 817m, 807m, 730m, 630m, 489 cm$^{-1}$.

The amine was converted to its hydrochloride salt. $^1$H n.m.r. (300 MHz, D$_2$O): δ 2.51 (s, 3H); 3.30 (t, J 6.3 Hz, 2H); 3.42 (t, J 6.4 Hz, 2H); 7.47 (dd, J 8.4, 0.8 Hz, 1H); 7.75 (dd, J 8.4, 2.4 Hz, 1H); 8.32 (dd, J 2.4, 0.8 Hz, 1H). $^{13}$C NMR (75 MHz, D$_2$O): δ 15.1; 28.9; 39.2; 124.8; 134.5; 138.2; 145.4; 151.7. (Found: C, 35.03; 35.41; H, 5.69; 5.65; N, 10.19; 10.28%; C$_8$H$_{14}$Cl$_2$N$_2$S$_2$ requires C, 35.16; H, 5.61; N, 10.25%).

5.13  2-Bromo-6-thiomethoxypyridine (2-Br-6-MeS-pyridine)

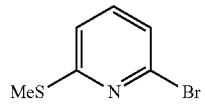

2-Bromo-6-thiomethoxypyridine was prepared according to the method described by Testaferri et al[34] from 2,6-dibromopyridine (1.00 g, 4.2 mmol, 1 eq) and sodium thiomethoxide (0.295 g, 4.2 mmol, 1 eq) in anhydrous DMF (20 mL) under a nitrogen atmosphere. The mixture was stirred at ambient temperature for 2.5 h and workup as described above gave the product as a clear oil (0.78 g, 92%). $^1$H n.m.r. (300 MHz, CDCl$_3$): δ 2.56 (s, 3H); 7.09-7.48 (m, 3H). The spectral data were consistent with literature data[34].

5.14  6-Thiomethoxy-2-(pyridine-2'-ylsulfanyl)ethanamine (6-SMe-2PSEA)

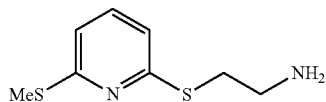 [SMILES: CSc1cccc(SCCN)n1]

Preparation of 6-SMe-2PSEA from 2Br-6MeS-pyridine: The general procedure in section 3.1. was followed. Sodium metal (0.23 g, 4.9 mmol, 2 eq) was dissolved in EtOH (18 mL) in a 20 mL microwave vial. 2-Aminoethanethiol hydrochloride (0.67 g, 5.88 mmol, 1.2 eq) was added to the solution which was stirred magnetically for 10 min under a nitrogen atmosphere at ambient temperature to give a white suspension. 2-Br-6-MeS-pyridine (1.00 g, 4.89 mmol, 1 eq) was added and the resulting suspension was heated under microwave irradiation at 140° C. for 21 min. The mixture was cooled to room temperature and worked up as described in section 2.1. to give the title compound as a yellow oil (0.95 g, 96%). $^1$H n.m.r. (300 MHz, CDCl$_3$): δ 1.40 (bs, 2H). 2.56 (s, 3H); 3.01 (t, J 6.2 Hz, 2H); 3.33 (t, J 6.2 Hz, 2H); 7.24 (apparent t, J 7.9, 2H); 8.34 (t, J 8.0 Hz, 1H).

Preparation of 6-SMe-2PSEA from 6-Br-2PSEA: 6-Bromo-2PSEA (1.00 g, 4.2 mmol, 1 eq) was dissolved in anhydrous DMF (20 mL) under a nitrogen atmosphere to give a clear suspension. Sodium thiomethoxide (0.451 g, 6.4 mmol, 1.5 eq) was added and the mixture stirred at 80° C. overnight. The mixture was cooled to room temperature, poured onto water and extracted with ether. The organic layer was washed with sat. NaCl, dried over MgSO$_4$ and evaporated to give the product as a yellow oil (1.07 g, 91.3%). The spectral data were consistent with those given above.

The amine was converted to its hydrochloride salt. Yield: 2.59 g (85%). m.p. 211.4° C. Mass spectrum (ESI): m/z 201.2 (M+H)$^+$; 184.2 (M+H–NH$_3$)$^+$. $^1$H n.m.r. (300 MHz, D$_2$O): δ 2.64 (s, 3H). 3.43 (t, J 6.2 Hz, 2H); 3.56 (t, J 6.2 Hz, 2H); 7.28 (d, J 8.0 Hz, 1H); 7.30 (d, J 8.0 Hz, 1H); 7.74 (t, J 8.0, 1H). $^{13}$C NMR (75 MHz, D$_2$O): δ 13.7; 28.3; 39.05; 118.6; 119.3; 140.0; 155.7; 161.1. (Found: C, 34.53; 34.43; H, 5.30; 5.25; N, 10.24; 10.26; S, 22.90; 23.01%; C$_8$H$_{14}$Cl$_2$N$_2$S$_2$ requires C, 35.16; H, 5.16; N, 10.25; S, 23.47%). The reaction was scaled up 4 times and gave the similar results.

(ii) Biologics and Absorbent Preparation

6. Materials

A purified monoclonal antibody (IgG of subclass IgG2) was stored at 4° C. in 25 mM sodium acetate, 220 mM sodium chloride buffer (pH 5) at concentrations of 7.7, 8.5 and 12 mg/mL. Further samples of purified monoclonal (IgG of subclass IgG2) of various concentrations such as 7.7 mg/mL; 11 mg/mL, 12 mg/mL (mAb) and 6.7 mg/mL) in 25 mM sodium acetate, 220 mM sodium chloride buffer (pH 5) were stored at 4° C.

A crude monoclonal antibody supernatent (IgG of subclass IgG2) as a NSO$^†$ cell culture supernatant (pH 6.6) was stored at 4° C. at concentrations of 1.0 mg/mL, 1.08 mg/mL and 2.3 g/L of the mAb.

† NSO: murine myeloma cell line (plasmacytoma)

A crude immunoglobulin M antibody (IgM) in DMEM†† media (10% fetal calf serum) was stored at 4° C.

†† DMEM: Dulbecco's Modified Eagle Media

Purified recombinant chimeric fusion protein-A, recombinant chimeric fusion protein-B, recombinant chimeric fusion protein-C, recombinant chimeric fusion protein-D and recombinant chimeric fusion protein-E were stored at 4° C. A recombinant human transferrin chimeric fusion protein-F (37.9 mg/mL) and a holo bovine transferrin sample were stored at −20° C. and 0° C. respectively.

Bicinchoninic acid (BCA) Protein Assay Reagent, Pierce, Rockford, Ill., USA.

Bio-Rad Protein Assay Reagent, Bio-Rad Laboratories Pty Ltd, NSW, Australia.

Sepharose 6 Fast Flow®, stored in 20% aqueous ethanol at 4° C., Amersham Pharmacia Biotechnology, Uppsala, Sweden.

Centrifugations were performed using a Biofuge Pico Microcentrifuge, Heraeus, Kendro Laboratory Products, Australia.

BCA assays were processed using a Bio-Rad micro plate reader, Model 3550.

UV-Visible absorption analysis was carried out using a Bio-Rad Smart Spec Plus spectrometer.

Fast Protein Liquid Chromatography (FPLC) experiments were performed using a Bio-Rad BioLogic Duo Flow Chromatographic System and a GE-Box-900, Akta Purifier (GE Healthcare). The Unicorn 5.11 programme was used to analyze FPLC results. Size exclusion chromatography was performed on a HiLoad 16/60 Superdex® 200 column, Amersham Pharmacia Biotechnology, Upssala, Sweden SDS-PAGE was performed using a Hoefer miniVE vertical electrophoresis system, Amersham Biosciences connected to a Bio-Rad PowerPC Basic. PAGE and NuPAGE 4-12% Bis-Tris precasting gradient gels (10 well and 15 well) were used. The running buffers were Tris, MES and MOPS SDS. LDS (lithium dodecyl sulfate) is used in the 4× NuPAGE sample (instead of SDS) because the amount of SDS needed in 4× sample buffer tends to precipitate and makes the solution too thick to pipette. (LDS has higher solubility). Coomassie-stained SDS-PAGE were analysed (band density) with a Bio-Rad ChemiDoc.

Samples were evaluated for pH using a standard pH meter, pH M210 from Radiometer Analytical; Pacific Lab Products.

Mixing of Sepharose 6 Fast Flow with epichlorohydrin and ligand immobilization was performed on a shaking platform, Microdigital control, Axyos Tech. Orbital Shaker, Quantum Scientific, at 175 r.p.m. in a controlled temperature room at 23° C. or 28° C. Samples less than 50 mL were mixed on a Ratek suspension mixer (rotating wheel).

6.1. Epichlorohydrin Activated Sepharose

Epichlorohydrin activated Sepharose 6 Fast Flow® was prepared by modifying the method described by Porath.[35]

Sepharose 6 Fast Flow® (500 g) was filtered and washed extensively with distilled water (5× volume of wet gel, 2.5 L). The gel was suction dried and transferred to a round bottom flask. A 2 M NaOH solution (500 mL) containing $NaBH_4$ (0.937 g) (1.875 mg/mL) was added and the resulting suspension mixed vigorously for 2 h at ambient temperature using a Buchi rotary evaporator (no vacuum). Epichlorohydrin (300 mL) was added and the gel slurry was mixed for a further 6 days. The epoxy-activated resin was collected by vacuum filtration and washed with distilled water (2.5 L). The activated resin was stored in a 20% (v/v) EtOH solution at 4° C. until required for ligand immobilization.

Alternatively, Sepharose 6 Fast Flow® (250 g) was filtered and washed with distilled water (5×250 mL). The gel was suction-dried and transferred to a Schott bottle. A 2M NaOH solution (250 mL) containing $NaBH_4$ (0.47 g) was added and the resulting suspension mixed on a shaking platform for 2 h at 23° C. or 28° C. at 175 r.p.m. Epichlorohydrin (150 mL) was then added and the gel mixed for a further 21 h or 5.5 days at 23° C. or 28° C. The epoxy-activated gel was collected by vacuum filtration and washed with distilled water (5×250 mL) and stored as described above.

6.2. Immobilisation of Ligands

The synthesised ligands were attached to the activated Sepharose by modifying the methods described by Hearn[36-39]. A solution of the ligand (0.2 M) was prepared by dissolving the desired heterocycle in an appropriate solvent (e.g. 25% or 50% (v/v) MeOH/$H_2O$). The ligand free base, its HCl salt or the free base with added NaCl were used. When the HCl salt was used, it was dissolved in required amount of 2M NaOH to neutralize (to ca pH 9), then MeOH and water added to give the required percentage of MeOH solution.). Suction dried epichlorohydrin-activated resin was added to the ligand solution and the suspension was mixed thoroughly on a rotating wheel (or shaking platform for larger volumes) for ca. 21 h or 5.5 days at 23° C. or 28° C. The resulting adsorbent was collected by vacuum filtration, washed with the appropriate solvent (ca. 10 bed volumes) followed by distilled water (ca. 10 bed volumes). The adsorbent was stored in 20% (v/v) aqueous EtOH at 4° C. Table B summarises the masses and volumes used for immobilisation of ligands at ambient temperature.

6.3. Analysis of Immobilised Ligand Density

The extent of ligand immobilisation onto the epichlorohydrin activated Sepharose 6 Fast Flow® was determined from the nitrogen or sulfur elemental content. The adsorbent (2 to 10 g wet weight) was collected by filtration, washed with 25% aqueous acetone followed by 50%, then 75%, and finally 100% acetone, (ca. 2 bed volumes) and dried in vacuo to a constant weight freeze-dried for 2 to 3 days. The dried resin was accurately weighed and then analysed for total nitrogen, and for some sample, sulfur content. The analyses were conducted by Dairy Technical Services Ltd., Melbourne, Australia and/or by Campbell Microanalytical Laboratory, Chemistry Department, University of Otago, Dunedin, New Zealand. The amount of immobilised ligand per gram of dry resin was determined from the analysis result. The results presented are associated with an uncertainty of ±14 or ±25 mmol/g dry gel for nitrogen and sulfur analysis respectively.

TABLE B

Immobilisation conditions for ligand attachment to activated Sepharose

| Entry | Ligand | Mass (g) | Conc (M) | Solvent |
|---|---|---|---|---|
| 1 | 2-MP | 0.33 | 0.2 | 50% MeOH, 15 mL |
| 2 |  | 0.33 | 0.2 | 50% MeOH, 15 mL (pH 8, with NaOH) |
| 3 |  | 0.33 | 0.2 | 66% MeOH, 15 mL |
| 4 |  | 0.44 | 0.2 | 0.2M $Na_2CO_3$/ $NaHCO_3$ (pH 9)* |
| 5 |  | 0.44 | 0.2 | 0.1M $Na_2HPO_4$/ $NaH_2PO_4$ (pH 7.5)* |
| 6 | 4-MP | 0.33 | 0.17 | 50% MeOH, 17.5 mL |
| 7 | 2-PSEA | 0.50 | 0.16 | 25% MeOH, 20 mL |

TABLE B-continued

Immobilisation conditions for ligand attachment to activated Sepharose

| Entry | Ligand | Mass (g) | Conc (M) | Solvent |
|---|---|---|---|---|
| 8 | | 0.25 | 0.16 | 66% MeOH, 10 mL (pH 10 with NaOH) |
| 9 | 2-PSEA | 0.22 | 0.2 | 25% MeOH, 7 mL (pH 10 with NaOH) |
| 10 | | 0.22 | 0.2 | 25% MeOH, 7 mL |
| 11 | 2-PSEA•2•HCl | 0.32 | 0.2 | 25% MeOH, 7 mL (pH 10 with NaOH) |
| 12 | 3-PSEA | 0.62 | 0.2 | 50% MeOH, 20 mL |
| 13 | 4-PSEA | 0.50 | 0.16 | 25% MeOH, 20 mL |
| 14 | | 0.62 | 0.2 | 50% MeOH, 20 mL |
| 15 | 2-PSPA | 0.67 | 0.2 | 50% MeOH, 20 mL |
| 16 | 4-PSPA | 0.67 | 0.2 | 60% MeOH, 20 mL |
| 17 | 2-PMSEA | 0.34 | 0.1 | 25% MeOH, 20 mL |
| 18 | 3-PMSEA | 0.34 | 0.1 | 25% MeOH, 20 mL |
| 19 | 4-PMSEA | 0.67 | 0.2 | 25% MeOH, 20 mL |
| 20 | | 0.34 | 0.2 | 25% MeOH, 10 mL |
| 21 | 2-PESEA | 0.73 | 0.2 | 25% MeOH, 20 mL |
| 22 | 4-PESEA | 0.73 | 0.2 | 25% MeOH, 20 mL |
| 23 | 4-Me-2-PSEA | 0.50 | 0.15 | 50% MeOH, 20 mL |
| 24 | 6-Me-2-PSEA | 0.67 | 0.2 | 50% MeOH, 20 mL |
| 25 | 6-Ph-2-PSEA | 0.92 | 0.2 | 90% EtOH, 20 mL |
| 26 | 2-Ph-4-PSEA | 0.69 | 0.15 | 100% EtOH, 20 mL |
| 27 | 6-OMe-2-PSEA | 0.58 | 0.16 | 80% MeOH, 20 mL |
| 28 | 3-NO$_2$-2-PSEA | 0.23 | 0.12 | 100% DMSO, 10 mL |
| 29 | 4-NO$_2$-2-PSEA | 0.60 | 0.2 | 66% MeOH, 15 mL |
| 30 | | 0.40 | 0.2 | 50% MeOH, 10 mL |
| 31 | 2-QSEA | 0.82 | 0.2 | 80% MeOH, 20 mL |
| 32 | 2-QSEA•2HCl | 1.11 | 0.2 | 50% MeOH, 20 mL (inc. 4 mL 2M NaOH)* |
| 33 | | 0.56 | 0.2 | 50% MeOH, 10 mL (inc. 2 mL 2M NaOH)* |
| 34 | 4-QSEA | 0.82 in 3.9 HMPA | 0.2 | 25% MeOH, made to 20 mL |
| 35 | 4-QSEA•2HCl | 1.11 | 0.2 | 50% MeOH, 20 mL (inc. 4 mL 2M NaOH)* |
| 36 | 1-IQSEA | 0.82 | 0.2 | 80% MeOH, 20 mL |
| 37 | 1-IQSEA•2HCl | 0.55 | 0.2 | 50% MeOH, 10 mL (inc. 2 mL 2M NaOH) |

*Indicates reaction time of ca. 21 h.

The adsorbents listed in Table C were similarly prepared.

TABLE C

Adsorbents evaluated during relative binding studies.

| Entry | Ligand | Mass (g) | Conc (M) | Solvent |
|---|---|---|---|---|
| 1 | 2PSEA | 0.31 | 0.2 | 25% MeOH, 10 mL |
| 2 | | 0.62 | 0.2 | 25% MeOH, 20 mL |
| 3 | | 0.31 | 0.2 | 25% MeOH, 10 mL (incl. 2eq NaCl) |
| 4 | | 0.31 | 0.2 | 25% MeOH, 10 mL |
| 5 | | 0.31 | 0.2 | 50% MeOH, 10 mL |
| 6 | 2PSEA•2HCL | 0.46 | 0.2 | 25% MeOH, 10 mL (incl. 2 mL NaOH) |
| 7 | | 0.91 | 0.2 | 25% MeOH, 20 mL (incl. 4 mL NaOH) |
| 8 | | 0.46 | 0.2 | 50% MeOH, 10 mL (incl. 2 mL NaOH) |
| 9 | | 0.91 | 0.2 | 50% MeOH, 20 mL (incl. 4 mL NaOH) |
| 10 | 2PSEA•sulfate | 0.46 | 0.2 | 25% MeOH, 10 mL (incl. 2 mL NaOH) |
| 11 | | 0.46 | 0.2 | 50% MeOH, 10 mL (incl. 2 mL NaOH) |
| 12 | 3PSEA | 0.62 | 0.2 | 25% MeOH, 20 mL |
| 13 | 3PSEA•2HCl | 0.46 | 0.2 | 25% MeOH, 10 mL (incl. 2 mL NaOH) |
| 14 | 4PSEA | 0.31 | 0.2 | 25% MeOH, 10 mL |
| 15 | 4PSEA•2HCl | 0.69 | 0.2 | 25% MeOH, 15 mL (incl. 3 mL NaOH) |
| 16 | 5-Br-2PSEA•2HCl | 1.215 | 0.2 | 25% MeOH, 20 mL (incl. 4 mL NaOH) |
| 17 | 6-Br-2PSEA•2HCl | 1.215 | 0.2 | 25% MeOH, 20 mL (incl. 4 mL NaOH) |
| 18 | 4-Me-2PSEA•2HCl | 0.96 | 0.2 | 25% MeOH, 20 mL (incl. 4 mL NaOH) |
| 19 | BPSEA• | 0.7 | 0.2 | 50% MeOH, 10 mL |
| 20 | TerPSEA | 1.54 | 0.2 | 50% MeOH, 25 mL (incl. 5 mL NaOH) |

6.4. Characterisation of Starting Material

The monoclonal antibody mAb, recombinant chimeric fusion proteins A-E and the transferrin samples were characterised by measuring the pH of their buffered solutions and performing both MALDI-TOF mass spectroscopy and SDS-PAGE. Concentrations of mAb samples were determined after plotting a standard concentration curve using a known sample concentration, i.e. mAb sample (IgG, 7.7 mg/mL). Absorbance was measured on a UV Spectrometer. Concentrations of both mAb A and mAb B were found to be slightly different to the labeled values shown in Table D.

TABLE D

Characterisation of antibody samples.

| Abs (Labelled conc) | pH | Actual conc mg/mL | Mol wt (kDa) |
|---|---|---|---|
| 8.5 mg/mL | 4.99 | 8.5 | 152 |
| mAb A (11 mg/mL) | 5.37 | 13.8 | 148 |
| mAb B (11 mg/mL) | 5.37 | 12 | 150 |
| 12 mg/mL | 5.19 | 12 | 148 |
| mAb B 6.7 mg/mL (new sample) | | 6.7 | 150 |

The molecular weight of the transferrin-related proteins and the recombinant chimeric fusion proteins A-E are approximately 98 kDa and 33-38 kDa respectively: similar values were obtained based on their mobility on SDS-PAGE and MALDI-TOF mass spectroscopy.

6.5. Static Batch Binding Studies 6.5.1. Effect of Buffers

A range of stock buffer solutions (incubation buffers) were prepared in order to ascertain the optimal pH for maximum protein binding, namely:
 a) 250 mM sodium acetate (NaAc) buffer, adjusted to pH 3.75 with acetic acid.
 b) 250 mM NaAc buffer, adjusted to pH 5.0 with acetic acid.

c) 250 mM Hepes† buffer, adjusted to pH 7.0 with 5 M NaOH solution.

† Hepes: N-(2-hydroxyethyl)piperazine-N'-(2-ethanesulfonic acid)

d) 250 mM Tris†† buffer, adjusted to pH 9.0 with 10 M HCl solution.

†† Tris: 2-amino-2-(hydroxymethyl)-1,3-propanediol

These stock solutions were diluted to a final concentration of 25 mM for all the binding reactions.

The pure mAb solution (7.7 mg/mL) (55 µL) was then added to each tube to give a final total volume of 550 µL. Alternatively the incubation buffer (55 µL) and $Na_2SO_4$ solution (390 µL of 0, 300, 500, 600 mM) were added into Eppendorf tubes. The gel slurry was vortexed and 50 µL immediately pipetted to the appropriate labeled tube. Finally, the protein solution (55 µL) was added to each tube to give a final total volume of 550 µL.

TABLE E

Volumes of sodium sulfate solution and water required in assay

| | Final conc. 0 mM | | Final conc. 100 mM | | Final conc. 300 mM | | Final conc. 600 mM | |
| --- | --- | --- | --- | --- | --- | --- | --- | --- |
| pH | 1M $Na_2SO_4$ (µL) | $H_2O$ (µL) | 1M $Na_2SO_4$ (µL) | $H_2O$ (µL) | 1M $Na_2SO_4$ (µL) | $H_2O$ (µL) | 1M $Na_2SO_4$ (µL) | $H_2O$ (µL) |
| 3.75 | 0 | 390 | 55 | 335 | 165 | 225 | 330 | 60 |
| 5.0 | 0 | 390 | 55 | 335 | 165 | 225 | 330 | 60 |
| 7.0 | 0 | 390 | 55 | 335 | 165 | 225 | 330 | 60 |
| 9.0 | 0 | 390 | 55 | 335 | 165 | 225 | 330 | 60 |

The pure mAb solution (7.7 mg/mL) was diluted (1 part in 10) in the subsequent investigations to allow the effect of the composition of the mAb buffer solution on the pH of the incubation buffer to be tested. A series of solutions (11 mL) were prepared by mixing the desired incubation buffer (1.1 mL), the mAb buffer solution (25 mM sodium acetate, 220 mM NaCl, pH 5) (1.1 mL) and water (8.8 mL), and the pH measured. The pH values of these solutions were found to be 3.78, 4.96, 6.7 and 8.8 compared to the initial values of the incubation buffers described above, i.e. pH 3.75, 5.0, 7.0 and 9.0.

All other antibody samples were diluted to 7.7 mg/mL with either water or antibody dilution buffer (25 mM sodium acetate, 220 mM sodium chloride, pH 5.0) for batch binding assays in order to compare the binding results with the results obtained for the pure mAb solution (7.7 mg/mL).

6.5.2. Batch Adsorption Assay

The binding capacity of the immobilised ligands was investigated by varying pH (3.75, 5.0, 7.0, 8.0, 9.0) and $Na_2SO_4$ concentration (0, 100, 300, 600 mM) to provide a matrix of 20 possible separate binding conditions. A selection of these ligands was also tested for their binding capacity with recombinant chimeric fusion proteins and the transferrin samples by varying pH (5.0, 7.0, 8.0 and 9.0) and $Na_2SO_4$ concentrations (0, 300 and 600 mM) to provide 12 different conditions. The following description is illustrative of the methodology employed for small scale screening studies employing 50 µL of gels in a conventional 96-tube (well) format. This approach formed the basis to then linearly scale the evaluations through 500 µL, 5 mL and finally 50 mL gel columns.

Thus, for the small scale investigations the ligand-immobilised gel was washed with distilled water (5 bed volumes) and suspended 1:1 in distilled water as a slurry (5 mL of suspended gel in 10 mL total volume). This resin slurry was vortexed and 50 µL immediately pipetted into Eppendorf tubes (i.e. equivalent to 25 µL wet gel). The incubation buffer (55 µL), $H_2O$ and a 1 M $Na_2SO_4$ stock solution were added to give the final salt concentrations of (0, 100, 300, 600 mM) in the total reaction volume as per Table E, in different tubes.

The tubes were incubated for 30 min to 1 h at ambient temperature with continuous end-over-end mixing on a rotating wheel. The tubes were centrifuged (13,000 r.p.m., 30 seconds to 1 min) to sediment the adsorbent, and the supernatant removed and tested for remaining unbound protein content (the test value) by either UV-Visible (UV-Vis) spectrometry or BCA protein assay.

A negative control was also prepared by adding unactivated Sepharose 6 Fast Flow® in place of the ligand immobilised adsorbents. All incubation conditions were tested in duplicate or triplicate. The amount of protein bound to the immobilised ligand was then determined by subtracting the standard protein value (no gel) from the test value; 100% bound indicates that there was no protein detected in the supernatant after incubation with the adsorbent. When a blank sample containing no protein (i.e. BCA assay reagent and buffers only) was measured by the BCA assay, the resultant value for this blank experiment corresponded to a notional 83% bound instead of the actual 100% bound (i.e. the blank solution gave a background reading equivalent to a free protein concentration of 17% of the total).

6.5.3. Effect of Increasing the Sodium Sulfate Concentration

The conditions showing favourable binding of the mAb with the immobilised ligands from the original batch adsorption studied were then investigated in more detail with a narrower range of incubation conditions. The sodium sulfate content was varied from 300 mM to 600 mM in 50 mM increments at pH 9.0. The method was carried out in a manner identical to that given in Section 6.5.21

TABLE F

Volumes of sodium sulfate solution and water required in assay

| Final Conc (mM) | 1M $Na_2SO_4$ (µL) | $H_2O$ (µL) |
| --- | --- | --- |
| 300 | 165.0 | 225.0 |
| 350 | 192.5 | 197.5 |
| 400 | 220.0 | 170.0 |
| 450 | 247.5 | 142.5 |
| 500 | 275.0 | 115.0 |
| 550 | 302.5 | 87.5 |
| 600 | 330.0 | 60.0 |

6.5.4. Effect of Varying the Salt Type

Further evaluation of the binding capacity of mAbs with the immobilised ligands was also investigated with the small scale screening procedures by varying the types of salt, with KCl (Table G) and $(NH_4)_2SO_4$ (Table H) also examined, at final concentrations of 0.3 M, 0.6 M, 1.0 M and 2.0 M. Assays were carried out as described above, however the mAb solution (55 µL) was diluted (1:1) in $H_2O$ and the mAb content of the final supernatant was determined by either BCA assay (KCl) or Bio-Rad protein assay ($(NH_4)_2SO_4$).

($Na_2SO_4$ salt concentration and pH) for binding of bovine holo-transferrin and recombinant human transferrin chimeric fusion protein-F. Conditions tested were:

25 mM NaOAc pH 5.0 with 0, 300, 600 mM $Na_2SO_4$
25 mM Hepes pH 7.0 with 0, 300, 600 mM $Na_2SO_4$
25 mM Tris pH 8.0 with 0, 300, 600 mM $Na_2SO_4$
25 mM Tris pH 9.0 with 0, 300, 600 mM $Na_2SO_4$

TABLE G

Volumes of potassium chloride solution and water required in assay

| | Final conc. 0.3M | | Final conc. 0.6M | | Final conc. 1.0M | | Final conc. 2.0M | |
|---|---|---|---|---|---|---|---|---|
| pH | 3.5M KCl (µL) | $H_2O$ (µL) | 3.5M KCl (µL) | $H_2O$ (µL) | 3.5M KCl (µL) | $H_2O$ (µL) | 3.5M KCl (µL) | $H_2O$ (µL) |
| 7.0 | 47 | 343 | 94 | 296 | 157 | 233 | 314 | 76 |
| 9.0 | 47 | 343 | 94 | 296 | 157 | 233 | 314 | 76 |

TABLE H

Volumes of ammonium sulfate solution and water required in assay

| | Final conc. 0.3M | | Final conc. 0.6M | | Final conc. 1.0M | | Final conc. 2.0M | |
|---|---|---|---|---|---|---|---|---|
| pH | 4.0M $(NH_4)_2SO_4$ (µL) | $H_2O$ (µL) | 4.0M $(NH_4)_2SO_4$ (µL) | $H_2O$ (µL) | 4.0M $(NH_4)_2SO_4$ (µL) | $H_2O$ (µL) | 4.0M $(NH_4)_2SO_4$ (µL) | $H_2O$ (µL) |
| 9.0 | 41 | 349 | 82 | 308 | 137 | 253 | 275 | 115 |

6.5.5. UV-Vis Spectrometry

Using a Bio-Rad SmartSpec spectrometer, a sample of the incubation supernatant (100 µL) was placed in a Bio-Rad disposable micro-cuvette and the absorbance read at 280 nm. A comparison was made between the standard samples (contained no gel, 0% bound) and those that contained the immobilised ligand. The values obtained allowed for calculation of the percentage of mAb bound.

6.5.6. BCA Assay

The protein concentrations were also be determined by a BCA protein assay according to the manufacturer's specifications. Briefly, an aliquot of the supernatant from the sample or standard experiments (20 µL) were placed in the wells of a 96-well microplate in duplicate (or triplicate). A mixture of reagent A (50 parts) and reagent B (1 part) was prepared and 200 µL of this resulting solution was added to each well. The plate was shaken on a BioRad Microplate Reader Model 3550 for 15 sec then incubated at 37° C. for 10-40 min to allow the color to develop. The absorbance was read on the same Bio-Rad Microplate Reader at 595 nm. The percentage of protein bound was then determined by comparing the values of the experiments without gel to those in the presence of gel.

The extent of protein binding (mAb, transferrin-related proteins or recombinant chimeric fusion proteins) to an adsorbent was calculated from the concentrations of $Protein_{Total} - Protein_{Free/unbound}$ and expressed either as a percentage or as mg/mL.

6.5.7. Bio-Rad Protein Assay

A Bio-Rad protein assay was also used in order to determine mAb concentration for batch adsorption assays containing $(NH_4)_2SO_4$. Using the Bio-Rad Reagent (1 part) and water (4 parts) the assay was carried out as described for the BCA assay in Section 6.5.6.

6.5.8. Transferrin-Related Protein Static Binding Studies

Batch binding assays were carried out with the holo-transferrin and the recombinant human transferrin chimeric fusion protein-F to evaluate the static binding capacities of a selection of immobilised ligands under a range of conditions The amount of the transferrin related protein present in the supernatant was calculated using the BCA assay technique as described above (see Section 6.5.6.).

6.5.9. Recombinant Chimeric Fusion Protein Batch Binding Studies

Binding assays were carried out to evaluate the static binding capacities of selected immobilized ligands under a range of conditions ($Na_2SO_4$ salt concentration and pH) for the recombinant chimeric fusion protein-A, recombinant chimeric fusion protein-B and recombinant chimeric fusion protein-C and recombinant chimeric fusion protein-E. Conditions tested were:

25 mM NaOAc pH 5
25 mM Hepes pH 7 with 0, 300, 600 mM $Na_2SO_4$
25 mM Tris pH 8 with 600 mM $Na_2SO_4$
25 mM Tris pH 9 with 0, 300, 600 mM $Na_2SO_4$ The amount of the recombinant chimeric fusion proteins in the supernatant was calculated using the BCA assay technique as described above (see Section 6.5.6.).

6.6. Adsorbent Binding Properties

6.6.1. Adsorption Isotherms Using Static Binding Experiments

A series of experiments with different mAb concentrations were carried out in order to determine the equilibrium binding constants for the mAb with the adsorbent. A batch adsorption assay was carried out in which the adsorbent was incubated with different mAb concentrations under a defined buffer condition (pH 9, 600 mM $Na_2SO_4$). For the small scale screening experiments, each incubation (550 µL) contained Tris buffer (55 µL), mAb stock solution (110 µL), adsorbent slurry (20 µL), 1 M $Na_2SO_4$ (330 µL) and $H_2O$ (35 µL). These conditions were then adjusted linearly by a factor of 10-fold for the larger scale studies. The mAb stock solution was prepared as follows in Table I.

TABLE I

Volumes, amounts and monoclonal antibody concentrations used in the small scale screening studies

| mAb Stock Solution | | Vol. stock | Final mAb conc. |
|---|---|---|---|
| mAb (7.7 mg/ml) (μL) | mAb Buffer (μL) | in reaction (μL) | in reaction (μg/mL) |
| 1400 | 0 | 110 | 1540 |
| 1200 | 200 | | 1320 |
| 1050 | 350 | | 1155 |
| 850 | 550 | | 935 |
| 700 | 700 | | 770 |
| 500 | 900 | | 550 |
| 300 | 1100 | | 330 |
| 100 | 1300 | | 110 | mAb Buffer (25 mM sodium acetate pH 5, 220 mM sodium chloride buffer).

The assay was performed by the method described for the batch adsorption assay (Section 6.5.2) (in triplicate) and the mAb concentration in the supernatant measured by either BCA protein assay (in triplicate) or UV-Vis spectrometry. The values for the amount of bound mAb at different concentrations of free mAb were presented as adsorption isotherm, Scatchard, semi-reciprocal and double-reciprocal plots. Analysis of these plots by non-linear or linear regression (Graph Pad Prism) allowed for the calculation of the equilibrium dissociation constant ($K_D$) and the theoretical total binding capacity of the adsorbents.

6.7. Dynamic Binding Capacity (FPLC)

A solution of pure mAb (8.5 mg/mL) was diluted in the optimal binding buffer (600 mM $Na_2SO_4$, 25 mM Tris pH 9) to give solutions of various concentrations (5 mg/30 mL, 10 mg/30 mL, 15 mg/30 mL, 20 mg/30 mL, 30 mg/30 mL, 50 mg/50 mL, 100 mg/100 mL). The adsorbent to be tested was packed into a glass Econo-Columns (1.0 mL, 5 mL and 50 mL) and connected to a Bio-Rad BioLogic Duo Flow Chromatographic System and the following protocol executed at flow rates between 1 mL/min and 10 mL/min. In the case of the small column studies, the following conditions, which were appropriately adapted for the studies with the larger columns, were used:

The column was equilibrated with Buffer A (600 mM $Na_2SO_4$, 25 mM Tris pH 9.0) (5 mL), The pure mAb sample (in 30, 50 or 100 mL) was injected onto the column at a flow rate from 0.33 mL/min through to 1 mL/min, The column was washed with Buffer A (15 mL), Bound mAb was eluted with Buffer B (10 mL) (25 mM Hepes pH 7.0), The column was regenerated with a 0.5 M NaOH wash (5 mL), The column was washed with Buffer B (5 mL).

The collected fractions were analysed at 280 nm using UV-Vis spectrometry. A standard curve was prepared by recording the absorbance of pure mAb at concentrations of 0.25, 0.50, 0.75, 1.0, 1.5 mg/mL. The amount in the elution fractions and the total recovery was then determined.

6.7.1. FPLC Protocol for Transferrin-Related Protein Separation

Procedure used to evaluate the binding behaviour of the recombinant human transferrin chimeric fusion protein-F and holo-transferrin used a flow rate of 1 mL/min:

Equilibrate Column 5 CV: Binding buffer, 25 mM HEPES pH 7,

Inject Sample: 5 mL (~1 mg/mL Tf in Binding buffer),

Wash out unbound sample 5 CV: Binding buffer, 25 mM HEPES pH 7,

Elute 10 CV: i) 25 mM NaAc pH 5.0 or
   ii) 25 mM HEPES pH 7.0 Gradient 0-300 mM $Na_2SO_4$, Regenerate 5 CV: 0.5 M NaOH, Wash 5 CV: 25 mM NaOAc pH 5.

The collected fractions were analysed at 280 nm and 230 nm using UV-Vis spectrometry and SDS-PAGE. The amount of protein obtained in the elution fractions was calculated by measuring their UV absorbance. The total recovery was also calculated from the UV results.

6.7.2. FPLC Protocol for Recombinant Chimeric Fusion Protein Binding

Equilibrate Column 5 CV: Binding buffer, 25 mM HEPES pH 7,

Inject Sample: 5 ml (~1 mg/mL Tf in Binding buffer),

Wash out unbound sample 5 CV: Binding buffer, 25 mM HEPES pH 7,

Elute 10 CV: i Elute i) 25 mM NaAc pH 5.0 (5 mL) or
   ii) 25 mM Hepes pH 7.0 Gradient 0-1 M NaCl or
   iii) 25 mM Hepes pH 7.0 Gradient 0-600 mM $Na_2SO_4$, Regenerate 5 CV: 0.5 M NaOH, Wash 5 CV: 25 mM NaOAc pH 5, Flow rate: 1 mL/min.

The collected fractions were analysed at 280 nm using UV-Vis spectrometry. The amount of protein obtained in the elution fractions was calculated by measuring their UV absorbance. The total recovery was also calculated from the UV results.

6.8. SDS-PAGE

SDS-PAGE analyses were performed as described by Laemmli[40] using Hoefer miniVE Vertical Electrophoresis systems. Gels were 1 mm thick, and prepared in a multicaster as gradient (7.5-15%) acrylamide gels with a 4% stacker. The resolving gel and stacker were prepared according to Sambrook[41] with the volumes described in Table J (volumes for 4 gels):

TABLE J

Formulation of resolving gel and stacker

| | Resolving Gel | | |
|---|---|---|---|
| | 7.5% | 15% | Stacker |
| Acrylamide Solution | 7.5 mL | 15 mL | 1.76 mL |
| 1.5M Tris-Cl pH 8.8 | 7.5 mL | 7.5 mL | — |
| 0.5M Tris-Cl pH 6.8 | — | — | 3.32 mL |
| 10% (w/v) SDS | 0.3 mL | 0.3 mL | 132 μL |
| $H_2O$ | 14.55 mL | 7.05 mL | 8.10 mL |
| 10% (w/v) APS | 150 μL | 150 μL | 67 μL |
| TEMED | 20 μL | 20 μL | 13 μL |

Abbreviations
Acrylamide/Bis-acrylamide 30%/0.8% (w/v)
SDS: sodium dodecyl sulfate
APS: ammonium persulfate
TEMED: N,N,N',N'-tetramethylethylenediamine Gels containing only 5% or 10% acrylamide were also prepared and the corresponding samples also evaluated with these two different types of "constant" porosity gels. PAGE and NuPAGE 4-12% Bis-Tris precasting gradient gels (10 well or 15 well) were used.

6.8.1 Sample Buffer

Protein samples (20 μL) were loaded using either a 5× reducing buffer or 5× non-reducing buffer as prepared in Table K.

TABLE K

Formulation of 5 x sample buffer

| | |
|---|---|
| 1.0M Tris-Cl pH 6.8 | 1.5 mL |
| Glycerol | 2.5 mL |
| SDS | 0.5 g |
| Bromophenol blue | 2 mg |
| β-Mercaptoethanol (reducing buffer only) | 1.0 mL |
| Water | to final vol. 5.0 mL |

Protein samples were also prepared as shown below:

TABLE L

Preparation of standard protein ladder and antibody/transferrin-related proteins/recombinant chimeric fusion protein samples.

| Sample loaded | Protein ladder | Dist Water | 4 × LDS | Ab sample 1 in 10 diluted | Total volume |
|---|---|---|---|---|---|
| Std sample | 5 µl | 10 µl | 5 µl | | 20 µl |
| Ab sample | | | 5 µl | 15 µl | 20 µl |

The sample (10 or 15 µL) was loaded on the precast NuPAGE or PAGE 4-12 Tris gels (10 or 15 µL well).

6.8.2. Tank Running Buffer/Running Conditions

Once the samples were loaded, electrophoresis was carried out on the gels in the tank running buffer, at a constant current of 20 mA per gel using a Pharmacia Biotechnology Electropower Supply EPS 3500 XL, until the dye front reached the bottom of the resolving gel.

Tank Running Buffer: 0.025 M Tris, 0.192 M Glycine, 0.1% SDS, pH 8.3.

Running buffers used with PAGE and NuPAGE 4-12% Bis-Tris precasting gradient gels:

MES SDS Running Buffer, pH 7.3
MOPS SDS Running Buffer, pH 7.7

6.8.3. Silver Staining/Coomassie Staining

Silver staining was carried out by following the method described by Swain and Ross.[42]

For Coomassie staining[41], gels were soaked overnight in the following solution:

0.25% Coomassie Brilliant Blue in 45% MeOH, 45% $H_2O$, 10% Acetic acid.

Destaining was achieved via a rapid destain solution containing: 30% MeOH, 60% $H_2O$, 10% Acetic acid followed by drying on cellophane overnight.

6.9. Open-Column Purifications 6.9.1. Starting Materials

The pure and crude mAb samples obtained were run on a gradient (7.5-15%) SDS-PAGE gel under reducing and non-reducing conditions. The gels were Coomassie-stained as described above. A 1 in 35 dilution of pure mAb (7.7 mg/mL) was prepared and a 1 in 5 dilution of the crude mAb (1.0 mg/mL) was prepared for this SDS-PAGE analysis.

6.9.2. Trial Conditions

Determination of practical purification conditions, i.e. useful binding and elution for the monoclonal antibodies, were obtained from trial purification studies using pure mAb. Generally, the suction-dried adsorbents to be tested were washed with water (at least 5× the gel volume) to remove any residual ethanol. The adsorbent was equilibrated with binding buffer (25 mM Tris pH 9.0, 600 mM $Na_2SO_4$) in a 10 mL Econo-Column (Bio-Rad). The pure mAb (7.7 mg/mL) was diluted (1 in 10) into the binding buffer. This solution (10 mL) was loaded onto the column and the flow through collected. The column was washed with the binding buffer (4×3 mL). Elution of bound mAb was then achieved by washing the column with elution buffer i) (25 mM NaAc pH 5.0, 600 mM $Na_2SO_4$), (2×0.9 mL) and elution buffer ii) (25 mM NaAc pH 5.0), (3×0.9 mL).

An aliquot of the starting material (SM), flow through (FT), washes (W1 and W4), and all elutions (E1-5) were analysed on a 10% SDS-PAGE gel using Coomassie staining as described in Section 6.8.3. A 1 M $Na_2SO_4$ solution was added to the elution fraction sample to achieve the same concentration as the wash and flow through fractions. Samples were then analysed by a BCA assay to estimate the amount of mAb recovered in each elution fraction using the pure mAb starting material as a reference.

6.9.3. Purification of Crude mAb

Purification of the crude mAb (IgG) was performed under similar conditions to those utilised for the trial experiments described above. The adsorbent was equilibrated with binding buffer (25 mM Tris pH 9.0, 600 mM $Na_2SO_4$) in a 10 mL Econo-Column (Bio-Rad). The crude mAb (1.0 mg/mL) was diluted (1 in 4) into the binding buffer. This solution (20 mL) was loaded onto the column and the flow through collected. The column was washed with binding buffer (5×30 mL). Elution of bound mAb was then achieved by washing the column with elution buffer (25 mM NaAc pH 5.0), (3×8 mL). A sample of the flow through (FT), washes (W1 and W5), and elutions (E1-3) were analysed on a gradient (7.5-15%) SDS-PAGE gel using silver staining.[42] Again, samples were adjusted to achieve a constant concentration of $Na_2SO_4$.

6.9.4. Loading Conditions Experiment

The adsorbents to be tested were washed with water (10 mL) and a 1:1 slurry was prepared. The crude mAb stock solution (1.08 mg/mL) was diluted into the required binding buffer (25 mM Tris pH 9, 600 mM $Na_2SO_4$) as detailed in Table M.

TABLE M

Preparation of crude mAb sample

| | For 2.16 mg in 50 mL | For 20.52 mg in 50 |
|---|---|---|
| Crude mAb (1.08 mg/mL) | 2 mL | 19 mL |
| 250 mM Tris pH 9.0 | 5 mL | 5 mL |
| 1.2M $Na_2SO_4$ | 25 mL | 25 mL |
| Water | 17 mL | — |
| Gel Adsorbent (1:1 slurry) | 1 mL | 1 mL |

The solution was mixed for 30 min, transferred to an Econo-Column and the flow through (FT) collected. The adsorbent bed was washed with binding buffer (3×3 mL for a 1 mL bed volume and scale correspondingly for larger column volumes) and eluted (25 mM Hepes pH 7.0) (3×2 mL for a 1 mL bed volume and scale correspondingly for larger column volumes). Samples of the crude starting material, FT, washes and elutions were analysed by gradient 7.5-15% SDS-PAGE using silver staining.[42] Samples were adjusted to achieve a constant concentration of $Na_2SO_4$. The main elution fraction (E1) from each adsorbent was then run on a gradient 7.5-15% SDS-PAGE to compare purity using silver staining. The fractions for the 20 mg experiment were run without the addition of salt.

These E1 fractions and a concentration series of pure mAb (0.2, 0.5, 1.0 and 2.0 mg/mL) were run on a gradient (7.5-15%) SDS-PAGE and Coomassie-stained. The intensity of all the stained mAb bands (pure and E1 fractions) were measured on a Bio-Rad ChemiDoc in order to determine the amount of mAb eluted in the main elution fraction (E1).

6.10. Fast Protein Liquid Chromatography (FPLC) Purifications

6.10.1. Purification of Crude mAb at a concentration of 1.0 mg/mL

The crude mAb solution (1.0 mg/mL) was diluted (1 in 4) in the binding buffer. The adsorbent to be tested (0.5 mL) was packed into a glass Econo-Column and connected to the Bio-Rad BioLogic Duo Flow Chromatographic System. The following protocol was used at a flow rate of 1 mL/min.

- The column was equilibrated with Buffer A (600 mM $Na_2SO_4$, 25 mM Tris, pH 9.0) (2 mL),
- the crude mAb sample (40 mL) was injected onto the column,
- the column was washed with Buffer A (5 mL),
- bound protein was eluted with a gradient system (5 mL) (100% Buffer A–100% Buffer B (25 mM Tris pH 9.0)),
- the column was washed with Buffer B (5 mL),
- Buffer C (2 mL) (25 mM Hepes pH 7.0) was injected.

The protocol was setup to allow the fractions collected during the adsorption trials to be analysed with a fast turn round time as specified in Table N.

A sample of the flow through (FT), wash (W) and eluted fractions (E) were analysed on a gradient (7.5-15%) SDS-PAGE using silver staining.[42] Samples were adjusted to achieve a constant concentration of $Na_2SO_4$.

TABLE N

Fractions collected during purification of crude mAb (1.0 mg/mL)

|  | Fraction Number | Fraction Vol. |
|---|---|---|
| Flow through (FT) | 2-9 | 5 mL |
| Wash (W): Buffer A | 10-11 | 2.5 mL |
| Elution Gradient (E): Buffer A-Buffer B | 12-16 | 1 mL |
| Elution (E): Buffer B | 17-21 | 1 mL |
| Elution (E): Buffer C | 22-26 | 1 mL |

6.10.2. Purification of Crude mAb at a Concentration of 1.08 mg/mL

The crude mAb solution (1.08 mg/mL) was diluted into the binding buffer (600 mM $Na_2SO_4$, 25 mM Tris pH 9) to give various concentrations (ca. 5 mg, 10 mg, 15 mg, 20 mg and 30 mg in 50 mL).

The adsorbent to be tested was packed into glass Econo-Columns (for the small scale experiments column volumes of 1.0 mL were employed) and connected to the Bio-Rad BioLogic Duo Flow Chromatographic System and the following protocol executed at a flow rate of 1 mL/min.

- The column was equilibrated with Buffer A (600 mM $Na_2SO_4$, 25 mM Tris pH 9.0) (5 mL),
- the crude mAb solution (50 mL) was injected onto the column,
- the column was washed with Buffer A (15 mL),
- bound protein was eluted with Buffer B (10 mL) (25 mM Hepes pH 7.0),
- the column was regenerated with 0.5 M NaOH (5 mL),
- the column was washed with Buffer B (5 mL).

The protocol was setup to collect fractions as specified in Table O.

TABLE O

Fractions collected during purification of crude mAb (1.08 mg/mL)

|  | Fraction Number | Fraction Vol. |
|---|---|---|
| Flow through (FT) | 2-11 | 5 mL |
| Wash (W): Buffer A | 12-14 | 5 mL |
| Elution (E): Buffer B | 15-19 | 2 mL |
| Regeneration (Reg): 0.5M NaOH | 20-21 | 2.5 mL |
| Wash: Buffer B | 22 | 5 mL |

The above protocol was also carried out using depleted media (0 mg mAb) (10 mL or 15 mL in 50 mL) instead of crude monoclonal antibody. The samples collected were analysed on gradient (7.5-15%) SDS-PAGE gel with Coomassie staining. Again samples were adjusted to achieve a constant concentration of $Na_2SO_4$.

6.11. Purification of Crude IgM

A crude IgM solution (~375 mL) was diluted into the binding buffer by adding Tris pH 9.0 (20 mL) and adding water until the total volume was 400 mL before portion-wise addition of 1.2 M $Na_2SO_4$ (400 mL). The various adsorbents were washed with water (for a 1 mL column bed volume 20 mL were used for the wash) and incubated with the crude IgM solution (100 mL) for 30 min with continuous mixing. The mixture was then transferred to Econo-Columns and the flow through collected. The gel adsorbent was transferred into a glass Econo-Column with Binding Buffer A (600 mM $Na_2SO_4$, 25 mM Tris pH 9.0). The column was then connected to the Bio-Rad BioLogic Duo Flow Chromatographic System and the following protocol executed at a flow rate of 1 mL/min.

- The column was washed with Buffer A (2.5 mL),
- bound protein was eluted with Buffer B (25 mM Hepes pH 7.0) (7.5 mL).

Samples of the crude starting material, flow through (FT), wash (W), and eluted fractions (E) were analysed on a gradient (5-10%) SDS-PAGE using silver staining.[42]

The elution fractions were then pooled and concentrated (Vivaspin 6 mL concentrator membrane 50,000 MWCO[†]) by centrifugation at 3000 r.p.m. and 8° C. until the volume was 2 mL. A HiLoad 16/60 Superdex 200 column[††] was washed with water (150 mL) at a flow rate of 0.5 mL/min and then equilibrated with TBSt[†††] (150 mL at 0.5 mL/min). The concentrated antibody sample (2.0 mL) was injected onto the column and washed through with TBS (140 mL at 1 mL/min). Elution fractions were collected in 5 mL aliquots. The appropriate fractions were combined and concentrated to 2 mL as described above. Samples of the crude starting material and eluted fractions were analysed by 10% SDS-PAGE using silver staining.[42]

[†] Molecular weight cut-off
[††] 16/60 Superdex 200 column: 60 cm bed height in 16 mm diameter columns containing dextran covalently bonded to highly cross-linked agarose with separation range of ca. Mr 10,000-600,000.
[†††] Tris buffered saline (iii) Adsorbent Characterisation and Results

7. Ligand Immobilisation and Adsorbent Screening

7.1. Immobilisation of Ligands

Sepharose 6 Fast Flow® was the chosen solid support for this investigation in conjunction with epichlorohydrin as the activating agent. The matrix is now classified as "activated" (Scheme (a)).

Scheme (a): Activation of Sepharose with epichlorohydrin and immobilisation of ligand onto activated Sepharose.

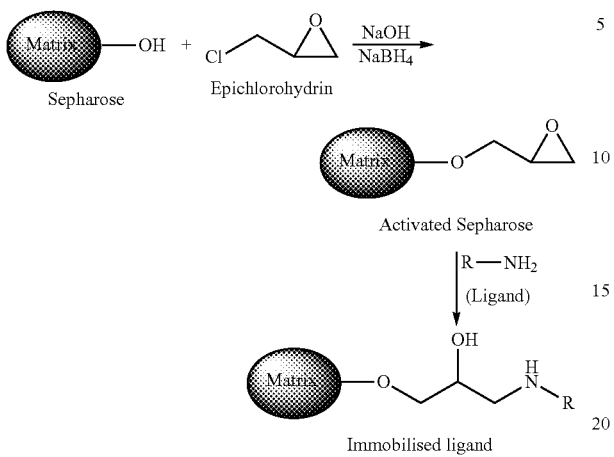

The desired ligands incorporate a nucleophilic group distal amine which facilitates immobilisation onto the epoxy-activated gel. The ligand is thus attached to the matrix via, for example, a 3-carbon spacer (Scheme (a)). For immobilisation of amine containing ligands, it is preferable that the pH is high enough that the amine group is not protonated. An example of ligand immobilisation is shown below (Scheme (b))

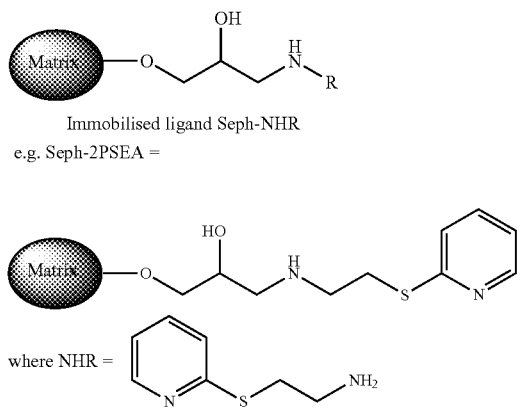

Ligand immobilisation was achieved by modifying methods described by Porath[43] and Hearn.[36-39] The conditions used for the immobilisation of each ligand are found in Section 6.3, Tables B and C.

7.2. Solvents Used for Coupling

A high aqueous component is desirable in the solvent for retaining the extent of matrix swelling. Generally, aqueous MeOH was used as the solvent in 25-50% (v/v) concentration. Sodium hydroxide (2 M aqueous) was also used to ensure that the ligand solution was basic. The pH of the amine ligand solutions in aqueous MeOH usually ranged between pH 7-9.

7.3. Immobilised Density

The extent of ligand immobilisation was determined using samples of the resin (dried in vacuo) by elemental analysis. As an illustrative test example, a sample of Seph-2-MP was dried and analysed with respect to both nitrogen and sulfur content. The nitrogen analysis gave a ligand density of 343 μmol/g dry gel while the sulfur analysis gave a ligand density of 312 μmol/g dry gel. Since the ligand contains a 1:1 ratio of nitrogen and sulfur, the results imply there is a correlation between the two independent types of analysis.

TABLE P

Ligand density derived from nitrogen analysis

| Entry | Ligand | Immobilised Density (μmol/ g dry gel)[#] | Solvent |
|---|---|---|---|
| 1 | 2-MP | 457 | 50% MeOH |
| 2 | | 429 | 50% MeOH (pH 8)[‡] |
| 3 | | 172 | 66% MeOH |
| 4 | | 307 | 0.2M Na$_2$CO$_3$/ NaHCO$_3$ (pH 9) |
| 5 | | 300 | 0.1M Na$_2$HPO$_4$/ NaH$_2$PO$_4$ (pH 7.5) |
| 6 | 4-MP | 414 | 50% MeOH |
| 7 | 2-PSEA | 307 | 25% MeOH |
| 8 | | 145 | 66% MeOH (pH 10)[‡] |
| 9* | | 314 | 25% MeOH (pH 10)[‡] |
| 10* | | 308 | 25% MeOH |
| 11* | 2-PSEA•2HCl | 300 | 25% MeOH[†] |
| 12 | 3-PSEA | 218 | 50% MeOH |
| 13 | 4-PSEA | 357 | 25% MeOH |
| 14 | | 325 | 50% MeOH |
| 15 | 2-PSPA | 282 | 50% MeOH |
| 16 | 4-PSPA | 270 | 60% MeOH |
| 17 | 2-PMSEA | 182 | 25% MeOH |
| 18 | 3-PMSEA | 189 | 25% MeOH |
| 19 | 4-PMSEA | 218 | 25% MeOH |
| 20 | | 318 | 25% MeOH |
| 21 | 2-PESEA | 200 | 25% MeOH |
| 22 | 4-PESEA | 225 | 25% MeOH |
| 23 | 4-Me-2-PSEA | 259 | 50% MeOH |
| 24 | 6-Me-2-PSEA | 265 | 50% MeOH |
| 25 | 6-Ph-2-PSEA | 232 | 90% EtOH |
| 26 | 2-Ph-4-PSEA | 196 | 100% EtOH |
| 27 | 6-OMe-2-PSEA | 223 | 80% MeOH |
| 28 | 4-NO$_2$-2-PSEA | 175 | 66% MeOH |
| 29 | | 307 | 50% MeOH |
| 30 | 2-QSEA | 255 | 80% MeOH |
| 31* | 2-QSEA•2HCl | 329 | 50% MeOH[†] |
| 32* | | 345 | 50% MeOH[†] |
| 33 | 4-QSEA | 565 | 25% MeOH |
| 34* | 4-QSEA•2HCl | 346 | 50% MeOH[†] |
| 35 | 1-IQSEA | 194 | 80% MeOH |
| 36 | 1-IQSEA•2HCl | 337 | 50% MeOH[†] |

NB: Specific ligand examples are referred to in the subsequent text with their ligand density value. e.g. entry 7, Seph-2-PSEA (307) is the 2-PSEA matrix at a density of 307 μmol/g gel.
[#]Immobilised density values presented in the above Table are associated with a maximum error of ±14 μmol/g dry gel.
[‡]Indicates adjusted to pH with 2M NaOH
[†]Indicates HCl salt neutralised with 2M NaOH in situ With the procedures employed, the nitrogen analysis is associated with an uncertainty of ±14 μmol/g dry gel while sulfur analysis is associated with an uncertainty of ±25 μmol/g dry gel. Subsequently, all other adsorbents were submitted for only the less expensive and more accurate nitrogen analysis. The results of these analyses are presented in Table P, which also includes a brief summary of the solvent used for each immobilisation.

In order to test the consistency of the nitrogen analysis results, a sample of the Seph-2-MP (entry 2) was re-analysed three months after the initial analysis. The analyses indicated the initial amount of ligand was 429 μmol/g dry gel and after three months, the amount was 400 μmol/g dry gel. These results suggest that the ligand remains stable with a reasonable shelf life (stored at 4° C. in 20% EtOH) and that the nitrogen analyses can be repeated with reasonable consistency. The adsorbents listed in Table Q were similarly prepared.

TABLE Q

Ligand density derived from nitrogen analysis

| Entry | Ligand | Immobilised Density (μmol/g dry gel) | Solvent |
|---|---|---|---|
| 1 | 2PSEA | 184 | 25% MeOH, 10 mL |
| 2 | | 283 | 25% MeOH, 20 mL |
| 3 | | 282 | 25% MeOH, 10 mL (incl. 2eq NaCl) |
| 4 | | 270 | 25% MeOH, 10 mL |
| 5 | | 261 | 50% MeOH, 10 mL |
| 6 | 2PSEA•2HCL | 281 | 25% MeOH, 10 mL (incl. 2 mL NaOH) |
| 7 | | 285 | 25% MeOH, 20 mL (incl. 4 mL NaOH) |
| 8 | | 159 | 50% MeOH, 10 mL (incl. 2 mL NaOH) |
| 9 | | 127 | 50% MeOH, 20 mL (incl. 4 mL NaOH) |
| 10 | 2PSEA•sulfate | 282 | 25% MeOH, 10 mL (incl. 2 mL NaOH) |
| 11 | | 277 | 50% MeOH, 10 mL (incl. 2 mL NaOH) |
| 12 | 3PSEA | 176 | 25% MeOH, 20 mL |
| 13 | 3PSEA•2HCl | 181 | 25% MeOH, 10 mL (incl. 2 mL NaOH) |
| 14 | 4PSEA | 195 | 25% MeOH, 10 mL |
| 15 | 4PSEA•2HCl | 219 | 25% MeOH, 15 mL (incl. 3 mL NaOH) |
| 16 | 5-Br-2PSEA•2HCl | 321 | 25% MeOH, 20 mL (incl. 4 mL NaOH) |
| 17 | 6-Br-2PSEA•2HCl | 293 | 25% MeOH, 20 mL (incl. 4 mL NaOH) |
| 18 | 4-Me-2PSEA•2HCl | 297 | 25% MeOH, 20 mL (incl. 4 mL NaOH) |
| 19 | BPSEA• | 264 | 50% MeOH, 10 mL |
| 20 | TerPSEA | 311 | 50% MeOH, 25 mL (incl. 5 mL NaOH) |

7.4. Screening of Binding Conditions

The conditions under which the target protein binds favourably to the immobilised ligand must firstly be determined before the adsorbent can be employed for protein purification. Several methods are available for the screening of binding conditions involving solid phase adsorbents such as frontal analysis and batch bath experiments. This investigation involved the use of both of these experimental procedures for rapid screening of various conditions with minimal consumption of pure mAb solution.

The batch experiments were based on a static binding method and involved the incubation of the protein (e.g. pure mAb), affinity resin and desired buffers in a closed system. After allowing sufficient time for the binding equilibrium to be established, the supernatant was analysed for remaining protein and hence the amount of protein bound calculated. The detection of protein within the supernatant can be achieved by colorimetric, fluorescence or radiolabelled assays, as well as UV-Vis analysis at certain wavelengths.

The detection and quantification methods employed in these studies include UV-Vis analysis and the BCA colorimetric assay. Based on previous work by some of the present inventors examining a range of lyotropic salts for antibody adsorption, sodium sulfate was primarily the salt of choice in these studies. Addition of lyotropic salts promotes binding by a salting out effect.

7.5. Monoclonal Antibody Batch Binding Studies

In order to identify a suitable monoclonal antibody binding condition with regard to lyotropic salts (e.g. $Na_2SO_4$) and pH, the immobilised ligands were evaluated in a batch (bath) adsorption-screening assay for their monoclonal antibody binding capacity. Non-specific mAb binding to the Sepharose matrix was also evaluated.

The pH values of the incubation buffers were accurately measured using a calibrated pH meter. As the mAb solution was diluted (1 part in 10) into the subsequent reaction mixtures, the effect of the mAb buffer solution on the pH of the incubation buffer was determined by preparing a model experiment corresponding to this dilution. The pH of the resulting solutions was found to be pH 3.78, 4.96, 6.7 and 8.8 respectively compared to the notional pH of the incubation buffers described above of pH 3.75, 5.0, 7.0 and 9.0 respectively. For simplicity in discussion, values of the relevant incubation buffer will be used, however, they will be quoted as pH 3.75, pH 5.0, pH 7.0 and pH 9.0 respectively.

Figure 2:
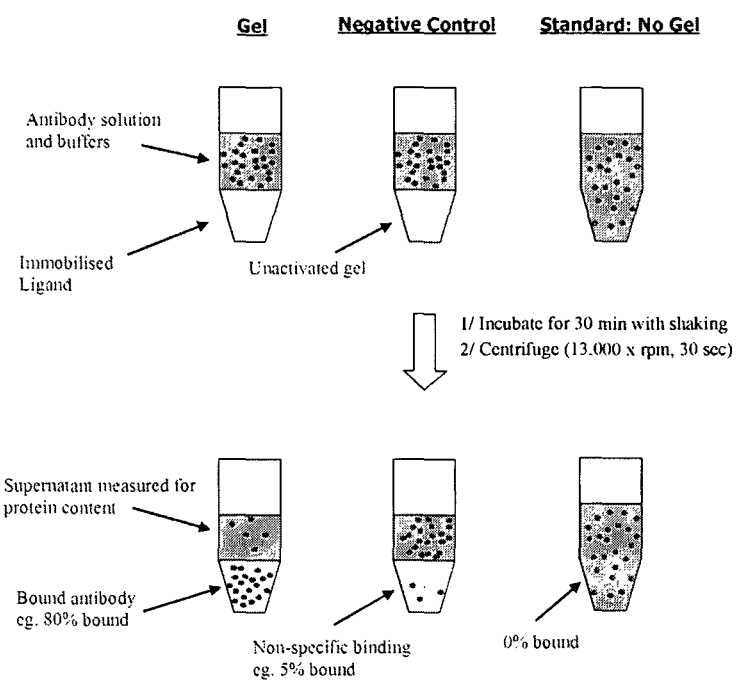
FIG. 2: Depiction of screening assay.

The amount of monoclonal antibody in the supernatant was measured by either a BCA assay (595 nm) or UV-Vis spectrometry (280 nm). A binding result of 100% indicates that no monoclonal antibody was detected by the screening assay (FIG. 2) in the supernatant after incubation with the gel. Depending on the molality of the salt used, this corresponded in the case of the sodium sulphate system with the optimised (selected group) of ligand affinity sorbents of between ~20 mg antibody/mL of gel and 60 mg antibody/mL of gel as assessed from these static adsorption experiments.

The percentage values obtained and documented in the Tables below relate to the normalised (but BCA uncorrected) amount of monoclonal antibody bound by these affinity adsorbents in these screening assays, and thus can be converted to actual amount of antibody bound per mL of affinity adsorbent using the above conversion factor. The BCA method was extensively utilised, due to its ease of use and the ability to assay large number of samples at once in a 96-well format, unlike the individual sample processing required for UV-Vis detection. However, as noted below, the BCA method routinely underestimated the amount of mAb bound by ca 10-15% when high salt concentrations were present in the samples and as such these data require adjustment by this conversion factor to determine the absolute amount of mAb bound to the new adsorbents.

7.5.1. Non-specific Binding

With the exception of the pH 7.0, no salt experiment and the pH 3.75, 300 mM $Na_2SO_4$, experiment where a very low level of interaction was evident, the Sepharose matrix showed minimal non-specific binding over all pH and salt concentrations screened (Table R). No binding occurred at pH 9, 600 mM $Na_2SO_4$, which was found to be the optimum condition for binding of monoclonal antibodies of class IgG to the affinity adsorbents prepared. Due to the nature of the assay procedures, the binding values were normalised with a "no binding" value set at zero. Furthermore, it was found that a combination of high salt concentration (600 mM $Na_2SO_4$) and low pH (3.75) caused the mAb to precipitate from solution and therefore no further testing under these conditions was carried out.

TABLE R

Monoclonal antibody binding results for the unactivated Sepharose matrix
Sepharose

| Salt mM | pH 3.75 | | pH 5 | | pH 7 | | pH 9 | |
|---|---|---|---|---|---|---|---|---|
| | Ab Bound | Std Dev | Ab Bound | Std Dev | Ab Bound | Std Dev | Ab Bound | Std Dev |
| 0 | 4.7% | 4.3% | 0.1% | 2.8% | 12.9% | 0.9% | 1.2% | 1.5% |
| 100 | 4.7% | 0.4% | 0.3% | 0.8% | 0.0% | 0.0% | 0.0% | 0.0% |
| 300 | 11.7% | 11.3% | 0.6% | 0.1% | 0.8% | 1.3% | 0.5% | 1.0% |
| 600 | | | 0.4% | 4.1% | 2.1% | 3.8% | 1.0% | 3.6% |

7.5.2. Specific Binding for Different Adsorbents Assessed from the Batch Adsorption Studies:

The various adsorbents were evaluated under static binding conditions at different pH and salt concentration conditions as described above with the amount bound normalised to an absolute percentage as detailed below.

7.5.2.1. Series II Adsorbents (see FIG. 1)

This series relates to the 2-, 3- and 4-PSEA ligand group, containing the ethylamine pendant arm. Because this series represents the core structures, it could be considered the parent group for all subsequent comparisons.

TABLE S

Monoclonal antibody binding results for Series II (PSEA) affinity adsorbents

| Salt mM | pH 3.75 | | pH 5 | | pH 7 | | pH 9 | |
|---|---|---|---|---|---|---|---|---|
| | Ab Bound | Std Dev | Ab Bound | Std Dev | Ab Bound | Std Dev | Ab Bound | Std Dev |
| Seph-2-PSEA (307) | | | | | | | | |
| 0 | 2.4% | 3.6% | 0.0% | 0.0% | 0.0% | 0.0% | 9.9% | 9.2% |
| 100 | 3.7% | 8.4% | 0.0% | 0.0% | 0.0% | 0.0% | 0.0% | 10.6% |
| 300 | 6.0% | 3.3% | 0.0% | 0.0% | 0.0% | 0.0% | 0.9% | 6.7% |
| 600 | | | 0.0% | 0.0% | 15.9% | 1.1% | 42.9% | 8.7% |
| Seph-2-PSEA (307) - after 18 months | | | | | | | | |
| 0 | 4.6% | 3.2% | 0.0% | 0.0% | 0.7% | 1.1% | 2.4% | 0.3% |
| 100 | 7.8% | 4.2% | 1.8% | 1.1% | 0.1% | 2.9% | 1.9% | 2.2% |
| 300 | 11.0% | 5.3% | 1.6% | 1.8% | 1.7% | 0.2% | 4.6% | 0.8% |
| 600 | | | 3.3% | 4.4% | 26.5% | 1.5% | 48.4% | 1.9% |
| Seph-3-PSEA (218) | | | | | | | | |
| 0 | 4.3% | 2.3% | 0.0% | 0.0% | 0.0% | 0.0% | 2.9% | 3.0% |
| 100 | 2.7% | 3.1% | 2.4% | 2.7% | 0.0% | 0.0% | 2.7% | 5.0% |
| 300 | 7.2% | 3.5% | 1.3% | 1.4% | 2.4% | 0.4% | 0.3% | 3.5% |
| 600 | | | 1.2% | 3.1% | 2.9% | 4.9% | 11.6% | 3.8% |
| Seph-4-PSEA (357) | | | | | | | | |
| 0 | 0.0% | 0.0% | 0.0% | 0.0% | 0.0% | 0.0% | 6.0% | 1.6% |
| 100 | 2.6% | 10.4% | 4.2% | 12.2% | 0.0% | 0.0% | 1.8% | 13.3% |
| 300 | 3.6% | 2.5% | 0.0% | 0.0% | 0.0% | 0.0% | 7.0% | 7.0% |
| 600 | | | 3.6% | 3.6% | 18.1% | 1.1% | 40.6% | 7.7% |

7.5.2.2. Series III Adsorbents (see FIG. 1)

This series relates to the 2- and 4-PSPA ligand group, containing the propylamine arm, and thus represent homologous compounds to the Series II of greater intrinsic hydrophobicity.

TABLE T

Monoclonal antibody binding results for Series III (PSPA) affinity adsorbents

| Salt mM | pH 3.75 | | pH 5 | | pH 7 | | pH 9 | |
|---|---|---|---|---|---|---|---|---|
| | Ab Bound | Std Dev | Ab Bound | Std Dev | Ab Bound | Std Dev | Ab Bound | Std Dev |
| Seph-2-PSPA (282) | | | | | | | | |
| 0 | 1.7% | 4.8% | 0.4% | 1.3% | 2.8% | 1.7% | 2.2% | 1.0% |
| 100 | 3.2% | 0.8% | 3.2% | 0.5% | 3.1% | 0.5% | 3.1% | 0.1% |
| 300 | 4.2% | 7.1% | 2.3% | 1.9% | 5.1% | 1.4% | 4.4% | 1.2% |
| 600 | | | 6.6% | 3.8% | 29.2% | 2.9% | 52.9% | 1.3% |

TABLE T-continued

Monoclonal antibody binding results for Series III (PSPA) affinity adsorbents

| Salt mM | pH 3.75 | | pH 5 | | pH 7 | | pH 9 | |
|---|---|---|---|---|---|---|---|---|
| | Ab Bound | Std Dev | Ab Bound | Std Dev | Ab Bound | Std Dev | Ab Bound | Std Dev |
| Seph-4-PSPA (270) | | | | | | | | |
| 0 | 2.1% | 5.3% | 1.0% | 0.8% | 3.9% | 3.9% | 5.1% | 1.0% |
| 100 | 2.5% | 2.1% | 3.4% | 1.0% | 2.6% | 0.7% | 2.9% | 0.6% |
| 300 | 3.3% | 5.5% | 2.7% | 1.9% | 5.6% | 0.4% | 5.4% | 1.2% |
| 600 | | | 4.4% | 3.6% | 20.2% | 1.7% | 45.3% | 1.3% |

7.5.2.3. Series IV Adsorbents (see FIG. 1)

This series relates to the 2-, 3- and 4-PMSEA ligand group, containing the methylthio-bridge prior to the ethylamine arm.

TABLE U

Monoclonal antibody binding results for Series IV (PMSEA) affinity adsorbents

| Salt mM | pH 3.75 | | pH 5 | | pH 7 | | pH 9 | |
|---|---|---|---|---|---|---|---|---|
| | Ab Bound | Std Dev | Ab Bound | Std Dev | Ab Bound | Std Dev | Ab Bound | Std Dev |
| Seph-2-PMSEA (182) | | | | | | | | |
| 0 | 0.0% | 0.0% | 0.0% | 0.0% | 0.0% | 0.0% | 0.0% | 0.0% |
| 100 | 0.0% | 0.0% | 0.0% | 0.0% | 0.0% | 0.0% | 0.0% | 0.0% |
| 300 | 18.4% | 4.9% | 0.0% | 0.0% | 0.0% | 0.0% | 0.0% | 0.0% |
| 600 | | | 0.0% | 0.0% | 3.4% | 1.8% | 12.7% | 8.2% |
| Seph-3-PMSEA (189) | | | | | | | | |
| 0 | 0.0% | 0.0% | 0.0% | 0.0% | 0.0% | 0.0% | 0.0% | 0.0% |
| 100 | 0.0% | 0.0% | 0.0% | 0.0% | 0.0% | 0.0% | 0.0% | 0.0% |
| 300 | 19.5% | 5.0% | 0.0% | 0.0% | 0.0% | 0.0% | 0.2% | 3.4% |
| 600 | | | 0.0% | 0.0% | 1.3% | 1.0% | 8.9% | 2.0% |
| Seph-4-PMSEA (218) | | | | | | | | |
| 0 | 0.0% | 0.0% | 0.0% | 0.0% | 0.0% | 0.0% | 0.0% | 0.0% |
| 100 | 1.9% | 1.6% | 2.3% | 3.6% | 1.5% | 1.5% | 2.1% | 0.5% |
| 300 | 16.8% | 5.6% | 2.5% | 7.7% | 2.4% | 0.4% | 1.8% | 2.6% |
| 600 | | | 8.9% | 19.2% | 3.3% | 2.8% | 9.5% | 0.7% |

7.5.2.4. Series V Adsorbents (see FIG. 1)

The compounds in this series contain the novel ethylamine moiety attached to the ethylthio-moiety. These compounds are thus more hydrophobic of Series II and may be more flexible in binding.

TABLE V

Monoclonal antibody binding results for Series V (PESEA) affinity adsorbents

| Salt mM | pH 3.75 | | pH 5 | | pH 7 | | pH 9 | |
|---|---|---|---|---|---|---|---|---|
| | Ab Bound | Std Dev | Ab Bound | Std Dev | Ab Bound | Std Dev | Ab Bound | Std Dev |
| Seph-2-PESEA (200) | | | | | | | | |
| 0 | 0.0% | 0.0% | 0.0% | 0.0% | 0.0% | 0.0% | 0.0% | 0.0% |
| 100 | 2.6% | 5.2% | 0.0% | 0.0% | 1.7% | 5.3% | 2.1% | 0.9% |
| 300 | 9.0% | 18.7% | 0.0% | 0.0% | 2.9% | 2.3% | 5.2% | 3.8% |
| 600 | | | 5.3% | 8.2% | 5.4% | 3.1% | 20.7% | 0.5% |
| Seph-4-PESEA (225) | | | | | | | | |
| 0 | 0.0% | 0.0% | 0.0% | 0.0% | 0.0% | 0.0% | 0.0% | 0.0% |
| 100 | 0.0% | 0.0% | 0.0% | 0.0% | 0.0% | 0.0% | 0.0% | 0.0% |
| 300 | 0.0% | 0.0% | 0.0% | 0.0% | 0.0% | 0.0% | 0.0% | 0.0% |
| 600 | | | 0.0% | 0.0% | 0.0% | 0.0% | 14.9% | 0.9% |

The results obtained in the above sections suggest that the sulfur atom is preferred to be directly attached to the pyridine ring for favourable binding interaction to occur.

7.5.2.5. Series VI Adsorbents (see FIG. 1)

Various substituents were attached to the PSEA core to observe their effects on binding. The PSEA core was chosen for the ease of its synthesis and the variety of substituents available from commercial starting materials, even though binding was slightly lower for PSEA adsorbents (2- and 4-derivatives, Series II) compared to adsorbents with the PSPA core (Series III).

TABLE W

Monoclonal antibody binding results for Series VI ((R) - PSEA) affinity adsorbents; R = Me or Ph

| Salt mM | pH 3.75 | | pH 5 | | pH 7 | | pH 9 | |
|---|---|---|---|---|---|---|---|---|
| | Ab Bound | Std Dev | Ab Bound | Std Dev | Ab Bound | Std Dev | Ab Bound | Std Dev |
| Seph-4-Me-2-PSEA (259) | | | | | | | | |
| 0 | 2.3% | 3.4% | 4.1% | 2.9% | 0.0% | 0.0% | 6.4% | 3.3% |
| 100 | 0.0% | 0.0% | 5.4% | 0.9% | 1.6% | 1.1% | 0.9% | 4.1% |
| 300 | 4.2% | 2.4% | 1.8% | 3.7% | 3.7% | 2.8% | 5.1% | 3.3% |
| 600 | | | 5.9% | 2.7% | 25.8% | 2.7% | 39.6% | 0.9% |
| Seph-6-Me-2-PSEA (265) | | | | | | | | |
| 0 | 0.0% | 0.0% | 0.5% | 1.5% | 0.6% | 3.9% | 3.1% | 1.6% |
| 100 | 0.0% | 0.0% | 3.5% | 2.4% | 0.0% | 0.0% | 0.0% | 0.0% |
| 300 | 0.0% | 0.0% | 1.7% | 4.6% | 2.7% | 2.3% | 4.2% | 2.3% |
| 600 | | | 3.7% | 2.6% | 27.1% | 2.6% | 40.1% | 0.9% |
| Seph-2-Ph-4-PSEA (196) | | | | | | | | |
| 0 | 2.6% | 6.9% | 0.0% | 0.0% | 1.0% | 1.9% | 21.6% | 2.0% |
| 100 | 5.6% | 0.8% | 1.1% | 0.1% | 2.8% | 4.0% | 8.4% | 0.6% |
| 300 | 10.5% | 14.6% | 4.0% | 0.1% | 18.5% | 1.1% | 26.2% | 2.1% |
| 600 | | | 28.0% | 2.5% | 63.3% | 0.9% | 65.5% | 3.5% |
| Seph-6-Ph-2-PSEA (232) | | | | | | | | |
| 0 | 0.0% | 0.0% | 0.0% | 0.0% | 0.0% | 0.0% | 27.6% | 1.3% |
| 100 | 1.8% | 0.4% | 0.3% | 0.5% | 6.6% | 4.0% | 21.5% | 0.8% |
| 300 | 18.3% | 10.8% | 5.6% | 0.5% | 30.8% | 1.8% | 45.6% | 0.8% |
| 600 | | | 47.9% | 2.3% | 69.5% | 0.9% | 68.1% | 3.5% |

TABLE X

Monoclonal antibody binding results for Series VI ((R) - PSEA) affinity adsorbents; R = OMe, NO$_2$, Br, and for BPSEA and TerPSEA

| Salt mM | pH 3.75 | | pH 5 | | pH 7 | | pH 9 | |
|---|---|---|---|---|---|---|---|---|
| | Ab Bound | Std Dev | Ab Bound | Std Dev | Ab Bound | Std Dev | Ab Bound | Std Dev |
| Seph-6-OMe-2-PSEA (223) | | | | | | | | |
| 0 | 0.0% | 0.0% | 0.0% | 0.0% | 0.0% | 0.0% | 2.2% | 1.6% |
| 100 | 0.0% | 0.0% | 1.5% | 1.0% | 2.0% | 1.3% | 1.0% | 0.7% |
| 300 | 0.0% | 0.0% | 3.3% | 1.4% | 4.4% | 0.5% | 5.8% | 0.9% |
| 600 | | | 5.9% | 3.9% | 32.7% | 0.3% | 49.3% | 1.5% |
| Seph-4-NO$_2$-2-PSEA (307) | | | | | | | | |
| 0 | | | | | 1.1% | 0.8% | 14.4% | 3.7% |
| 100 | | | | | 5.1% | 0.9% | 13.1% | 3.4% |
| 300 | | | | | 17.5% | 0.5% | 30.2% | 1.7% |
| 600 | | | | | 62.6% | 3.6% | 68.8% | 3.3% |

| Salt mM | pH 5 | | pH 8 | | pH 9 | |
|---|---|---|---|---|---|---|
| | Ab Bound | Std Dev | Ab Bound | Std Dev | Ab Bound | Std Dev |
| Seph-5-Br-2PSEA (321) | | | | | | |
| 0 | 0.60% | 0.90% | 5.50% | 1.80% | 4.40% | 4.20% |
| 300 | | | 17.40% | 1.80% | 14.10% | 2.30% |
| 600 | | | 78.50% | 0.80% | 69.60% | 1.40% |
| Seph-6-Br-2PSEA (293) | | | | | | |
| 0 | 1.2% | 1.6% | 5.0% | 2.3% | 7.0% | 2.5% |
| 300 | | | 13.5% | 3.6% | 6.3% | 2.0% |
| 600 | | | 54.5% | 3.6% | 52.2% | 1.9% |

TABLE X-continued

Monoclonal antibody binding results for Series VI ((R) - PSEA) affinity adsorbents; R = OMe, $NO_2$, Br, and for BPSEA and TerPSEA

| | pH 3.75 | | pH 5 | | pH 7 | | pH 9 | |
|---|---|---|---|---|---|---|---|---|
| Salt mM | Ab Bound | Std Dev | Ab Bound | Std Dev | Ab Bound | Std Dev | Ab Bound | Std Dev |
| Seph-3BPSEA (265) | | | | | | | | |
| 0 | 0.9% | 1.7% | 2.2% | 1.5% | 6.6% | 2.2% | | |
| 300 | | | | | 14.1% | 1.0% | 13.4% | 2.1% |
| 600 | | | | | 53.1% | 0.9% | 58.8% | 1.4% |
| Seph-4TerPSEA (311) | | | | | | | | |
| 0 | 1.5% | 2.2% | | | | | | |
| 500 | | | | | 70.2% | 4.6% | 68.8% | 3.8% |
| 600 | | | | | 73.1% | 4.1% | 71.6% | 5.2% |

The above results suggest that changes in electron densities on the ring nitrogen, e.g. with a 6-methoxy, 5-bromo, 6-bromo or a 4-nitro group (and a 5-thiomethoxy or 6-thiomethoxy), has a positive effect on increasing the mAb binding capacity when compared to the parent Seph-2-PSEA adsorbent. Since the proposed mechanism of binding involves electron-donating and electron-accepting effects between the ligand and monoclonal antibody, these induced changes in ligand structure appear to favourably alter the binding properties.

7.5.2.6. Series VII Adsorbents (see FIG. 1)

The compounds in this series relate to the 2- and 4-quinolinyl- and 1-isoquinolinyl compounds with the thiol group attached to the heterocyclic ring. The same route to immobilisation was used.

7.5.2.7. Series I Adsorbents

TABLE Z

Monoclonal antibody binding results for Series I (MP) affinity adsorbents

| | 25 mM Tris pH 9, 600 mM $Na_2SO_4$ | |
|---|---|---|
| Adsorbent | Ab Bound | Std Dev |
| Seph-2-MP (457) | 59.7% | 0.2% |
| Seph-4-MP (414) | 58.0% | 4.8% |

7.5.3. Binding Capacity Versus Ligand Density

TABLE Y

Monoclonal antibody binding results for Series VII ((I)QSEA) affinity adsorbents

| | pH 3.75 | | pH 5 | | pH 7 | | pH 9 | |
|---|---|---|---|---|---|---|---|---|
| Salt mM | Ab Bound | Std Dev | Ab Bound | Std Dev | Ab Bound | Std Dev | Ab Bound | Std Dev |
| Seph-4-QSEA (565) | | | | | | | | |
| 0 | 0.0% | 0.0% | 0.0% | 0.0% | 0.0% | 0.0% | 5.0% | 2.6% |
| 100 | 0.0% | 0.0% | 0.0% | 0.0% | 0.0% | 0.0% | 4.1% | 1.9% |
| 300 | 0.0% | 0.0% | 0.0% | 0.0% | 5.9% | 1.1% | 18.4% | 3.6% |
| 600 | | | 0.0% | 0.0% | 36.0% | 4.9% | 47.9% | 2.7% |
| Seph-2-QSEA (255) | | | | | | | | |
| 0 | 1.3% | 6.0% | 1.3% | 1.1% | 1.6% | 3.2% | 26.0% | 3.2% |
| 100 | 1.5% | 0.8% | 4.2% | 2.4% | 10.1% | 0.5% | 18.0% | 0.7% |
| 300 | 5.4% | 5.6% | 6.4% | 1.1% | 27.7% | 1.4% | 36.9% | 0.7% |
| 600 | | | 33.1% | 3.6% | 63.4% | 0.7% | 66.1% | 1.4% |
| Seph-1-IQSEA (194) | | | | | | | | |
| 0 | 0.0% | 0.0% | 0.0% | 0.0% | 0.0% | 0.0% | 0.0% | 0.0% |
| 100 | 0.0% | 0.0% | 0.0% | 0.0% | 0.0% | 0.0% | 0.0% | 0.0% |
| 300 | 0.0% | 0.0% | 0.0% | 0.0% | 0.0% | 0.0% | 0.0% | 0.0% |
| 600 | | | 0.0% | 0.0% | 10.3% | 6.5% | 26.6% | 3.6% |
| Seph-1-IQSEA (337) | | | | | | | | |
| 0 | | | | | 0.0% | 0.0% | 13.4% | 2.0% |
| 100 | | | | | 10.6% | 0.7% | 18.7% | 0.5% |
| 300 | | | | | 27.3% | 1.7% | 38.8% | 2.4% |
| 600 | | | | | 67.5% | 3.6% | 70.6% | 3.1% |

The batch binding results presented in the above tables show the effects that certain structural changes can induce in the binding capacity. An important observation that arose from this study was the beneficial preference for a ligand density at or above ca. 300 μmol/g dry gel in order to obtain optimal binding. Table AA shows a comparison of a range of ligands that have been immobilised on separate batches of activated Sepharose and indicates their mAb binding capacity, under the optimised conditions, in respect to the relevant immobilised density. Information about the required "minimum" ligand density factor was acquired throughout this study.

TABLE AA

Monoclonal antibody binding of selected adsorbents at various immobilised densities

| | | 25 mM Tris pH 9, 600 mM Na$_2$SO$_4$ | |
|---|---|---|---|
| Entry | Adsorbent | Ab Bound | Std Dev |
| 1 | Seph-2-PSEA (307) | 42.9% | 9.5% |
| 2 | Seph-2-PSEA (145) | 0.4% | 2.3% |
| 3 | Seph-2-PSEA (314) | 48.9% | 2.1% |
| 4 | Seph-2-PSEA (308) | 47.1% | 1.2% |
| 5 | Seph-2-PSEA (300) | 37.2% | 1.2% |
| 6 | Seph-4-PSEA (357) | 40.6% | 7.7% |
| 7 | Seph-4-PSEA (325) | 41.4% | 1.8% |
| 8 | Seph-2-MP (457) | 59.7% | 0.2% |
| 9 | Seph-2-MP (172) | 2.7% | 1.5% |
| 10 | Seph-2-MP (307) | 50.5% | 1.6% |
| 11 | Seph-2-MP (300) | 47.0% | 1.3% |
| 12 | Seph-2-QSEA (255) | 66.1% | 1.4% |
| 13 | Seph-2-QSEA (329) | 70.2% | 1.4% |
| 14 | Seph-4-QSEA (565) | 47.9% | 2.7% |
| 15 | Seph-4-QSEA (346) | 68.6% | 1.8% |
| 16 | Seph-4-PMSEA (218) | 9.5% | 70.0% |
| 17 | Seph-4-PMSEA (318) | 30.4% | 1.7% |

Figure 3:
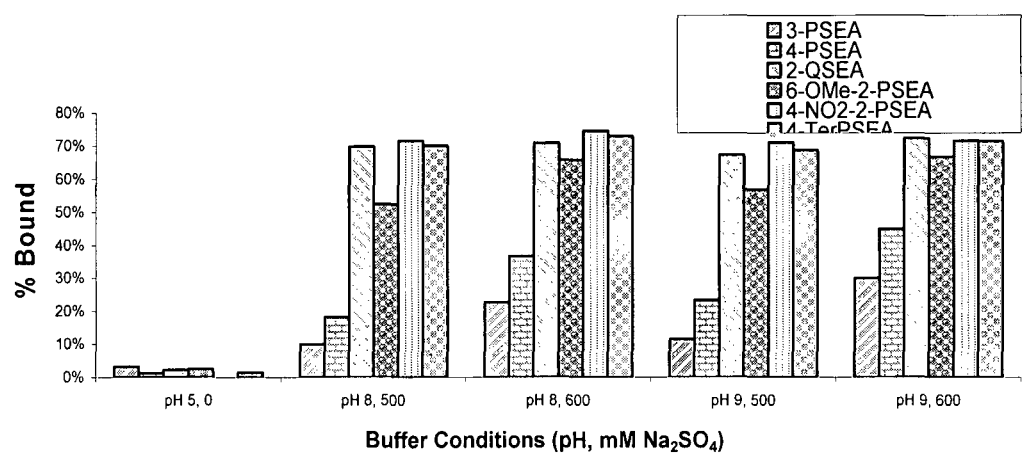
FIG. 3: Graph depicting relative binding of adsorbents for mAbs.

Relative binding results using five different combinations of pH and salt concentrations were used to evaluate the binding affinity of a few of the adsorbents are summarised in Table AB and FIG. 3 (mAb Batch Binding).

TABLE AB mAb percentage bound for best and worst binding conditions. Upper figures (bold) in each row signify the mean, lower figures give SD.

| | Ligand | % mAb Bound | | |
|---|---|---|---|---|
| Adsorbent | Density (mmol/g dry gel) | pH 5; 0 mM Na$_2$SO$_4$ | pH 8; 600 mM Na$_2$SO$_4$ | pH 9; 600 mM Na$_2$SO$_4$ |
| 4NO2-2PSEA | 339 | 0.0% | 74.6% | 71.7% |
| | | 2.5% | 1.0% | 5.8% |
| 5Br-2PSEA | 321 | 0.8% | 71.7% | 74.4% |
| | | 1.0% | 4.8% | 1.1% |
| 6Br-2PSEA | 293 | 1.2% | 51.4% | 52.2% |
| | | 1.6% | 4.5% | 1.9% |
| 6OMe-2PSEA | 324 | 2.6% | 65.9% | 66.8% |
| | | 4.3% | 0.6% | 5.2% |
| 2QSEA | 325 | 2.3% | 71.1% | 72.4% |
| | | 2.1% | 4.1% | 5.2% |
| 4TerPSEA | 311 | 1.5% | 73.1% | 71.6% |
| | | 2.2% | 4.1% | 5.2% |

7.5.4. Further Studies Involving the Effect of Sodium Sulfate Concentration

Figure 4:
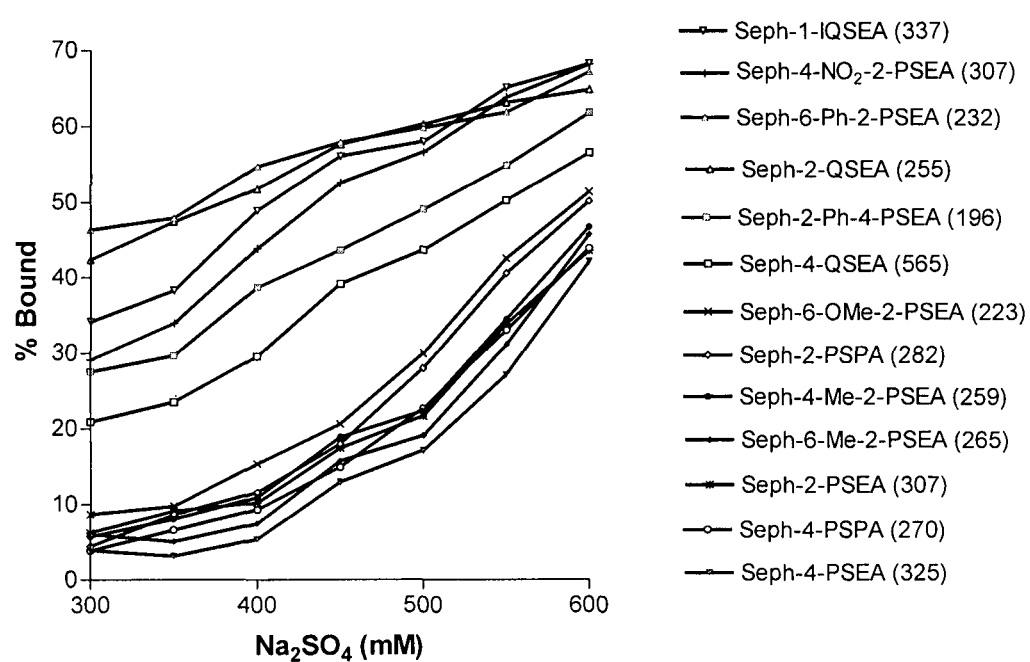
FIG. 4: Graph depicting monoclonal antibody binding at pH 9 and the effects of different $NaSO_4$ concentrations (mM).

As depicted in graph (see FIG. 4), a majority of the adsorbents show a steep incline in the percentage bound between 500-600 mM, although this is more apparent for the lower binding adsorbents (bottom 7 in list). The ligands associated with the top 6 adsorbents in the list are all considerably more hydrophobic in nature than those located in the bottom 7 adsorbents, with either a phenyl or a bicyclic structure present, except for the 4-NO$_2$-2-PSEA derivative. These adsorbents appear to bind a high amount of mAb over the lower salt concentration range. Overall, the decrease in binding that occurs as the salt concentration is lowered from the optimally determined value (600 mM in the case of the 1QSEA for example) suggests that this characteristic can be utilised (in conjunction with lowering of the pH) for the elution of monoclonal IgGs from these novel adsorbents.

7.5.5. Further Studies Involving the Effect of pH

The screening conditions investigated above showed that while a number of ligands (usually the more hydrophobic members) retained binding capacity when the pH was dropped from 9 to 7 at the same salt concentrations, other adsorbents showed a dramatic decrease in binding capacity. An experiment was therefore conducted to examine the effect on binding capacity at pH 8.

TABLE AC

Monoclonal antibody binding at high pH

| | pH 7 | | pH 8 | | pH 9 | |
|---|---|---|---|---|---|---|
| | % Bound | std dev % bound | % Bound | std dev % bound | % Bound | std dev % bound |
| Seph-2-PSEA (307) | 22.1% | 0.3% | 46.2% | 6.5% | 50.5% | 2.2% |
| Seph-2-PSPA (282) | 32.3% | 6.7% | 49.6% | 6.7% | 54.4% | 4.3% |

NB. Binding was conducted in the presence of 600 mM Na$_2$SO$_4$

This characteristic implies that capture and elution from a pH 8.0 condition is feasible and that decreasing the pH from the pH 9.0 or pH 8.0 condition can be used as a method to initiate elution of, for instance, monoclonal antibodies (in conjunction with decreasing the salt concentration).

7.5.6. Detection Methods

Due to the fact that the BCA assay method of analysis is based on colorimetric detection and requires the addition of external buffers and reagents to the sample to be analysed, a sample of the BCA assay solution and reaction buffers only (no mAb) was analysed (as previously discussed above). Table AD was prepared as a comparison of the adjusted (buffer only value normalised to 100%) and unadjusted values. The adjusted capacities showed an increase of between 7-15% over the unadjusted values, with a greater difference observed for adsorbents showing >60% binding in the BCA assay.

Analysis of the samples by UV-Vis spectrometry does not require the addition of external buffers or reagents and the absorbance can be measured directly in a disposable micro cuvette cell at 280 nm. The measured mAb binding capacities utilising this method (Table AD) produced results that were on average 16-21% higher than the unadjusted values measured by the BCA assay. Despite these shortcomings, the BCA assay is still useful for the screening of adsorbents and determining the binding condition conducive for maximum binding as samples can be assayed in a 96-well plate format. This configuration allows a large number of samples to be assayed in a shorter time compared to the UV-Vis method, which is more accurate but also time consuming. It can thus be noted that the BCA method underestimated the binding capacities by ~20% in these systems, and this will have a material bearing on the determination of system productivities if this factor is not taken into account. Procedures can however be readily put in place to compensate for this effect in absolute terms, whilst in terms of comparative evaluations this effect should not have a significant impact on the trends in terms of the rank order of the highest to lowest binders as shown in the above graph.

TABLE AD

Comparison of binding results obtained using different analysis methods

| Entry | Adsorbent | % Bound BCA | % Bound BCA (normalised) | % Bound UV |
|---|---|---|---|---|
| 1 | Seph-2-PSEA (300) | 43.4% | 52.2% | 62.2% |
| 2 | Seph-4-PSEA (325) | 33.8% | 40.6% | 50.0% |
| 3 | Seph-4-Me-2-PSEA (259) | 46.5% | 56.0% | 61.5% |
| 4 | Seph-6-Me-2-PSEA (265) | 41.7% | 50.1% | 52.9% |
| 5 | Seph-6-Ph-2-PSEA (232) | 70.2% | 84.4% | 86.4% |
| 6 | Seph-2-Ph-4-PSEA (196) | 61.9% | 74.5% | 82.7% |
| 7 | Seph-2-PSPA (282) | 50.8% | 61.1% | 70.0% |
| 8 | Seph-4-PSPA (270) | 43.7% | 52.6% | 58.4% |
| 9 | Seph-2-QSEA (329) | 70.4% | 84.7% | 90.8% |
| 10 | Seph-4-QSEA (346) | 67.3% | 80.9% | 87.6% |
| 11 | Seph-1-IQSEA (337) | 67.7% | 81.5% | 88.6% |
| 12 | Seph-2-PyzSEA (319) | 42.1% | 50.6% | 60.8% |
| 13 | Seph-6-OMe-2-PSEA (223) | 48.8% | 58.7% | 65.1% |
| 14 | Seph-4-NO$_2$-2-PSEA (307) | 69.2% | 83.2% | 86.9% |
| 15 | Buffer (pH 9, 600 mM Na$_2$SO$_4$) | 83.1% | 100.0% | |

* Refers to free solution amount

7.5.7. Varying Lyotropic Salts

The effectiveness of the lyotropic salt added to the protein solution for a salting out effect is mainly determined by the nature of the anion, with multicharged anions in conjunction with monovalent cations being the most effective.[44] The lyotropic salt used above (Na$_2$SO$_4$) was substituted by potassium chloride and the results are shown below.

TABLE AE

Monoclonal antibody binding in the presence of KCl

| | | pH 7 | | pH 9 | |
|---|---|---|---|---|---|
| | KCl (M) | Ab Bound | Std Dev | Ab Bound | Std Dev |
| Sepharose | 0.3 | 1.6% | 1.3% | 4.8% | 4.2% |
| | 0.6 | 2.1% | 0.7% | 3.0% | 2.4% |
| | 1.0 | 2.2% | 2.8% | 2.1% | 1.3% |
| | 2.0 | 52.4% | 4.1% | 0.0% | 0.0% |
| Seph-2-PSEA (307) | 0.3 | 1.7% | 0.3% | 1.2% | 1.3% |
| | 0.6 | 3.6% | 0.6% | 3.7% | 2.7% |
| | 1.0 | 3.4% | 2.0% | 4.6% | 1.4% |
| | 2.0 | 5.4% | 2.7% | 0.0% | 0.0% |

Similarly, Table AF shows an example of the results obtained from screening mAb binding in the presence of ammonium sulfate.

TABLE AF

Monoclonal antibody binding in the presence of (NH$_4$)$_2$SO$_4$

| | | pH 9 | |
|---|---|---|---|
| | (NH4)$_2$SO$_4$ (M) | Ab Bound | Std Dev |
| Sepharose | 0.3 | 0.0% | 0.0% |
| | 0.6 | 0.0% | 0.0% |
| | 1.0 | 3.1% | 4.1% |
| | 2.0 | 40.6% | 6.6% |
| Seph-2-PSEA (307) | 0.3 | 0.0% | 0.0% |
| | 0.6 | 0.0% | 0.0% |
| | 1.0 | 26.8% | 5.7% |
| | 2.0 | 44.0% | 3.6% |

7.6. Transferrin Static Binding Studies

Binding assays were carried out to study the static binding capacities of immobilised ligands under a range of conditions (Na$_2$SO$_4$ salt concentration and pH). To this end, 2PSEA, 3PSEA, 4PSEA, 2QSEA, 4QSEA, 4NO$_2$-2PSEA, 4Me-2PSEA, 5Br-2PSEA, 6Br-2PSEA, 6OMe-2PSEA, 3BPSEA and TerPSEA immobilised ligands were tested for evaluation of binding of bovine holo-transferrin and recombinant human transferrin. Conditions tested were:

25 mM NaOAc pH 5.0 with 0, 300, 600 mM Na$_2$SO$_4$
25 mM Hepes pH 7.0 with 0, 300, 600 mM Na$_2$SO$_4$
25 mM Tris pH 8.0 with 0, 300, 600 mM Na$_2$SO$_4$
25 mM Tris pH 9.0 with 0, 300, 600 mM Na$_2$SO$_4$ The combination of pH and salt concentrations conditions resulted in 12 different conditions. These conditions were used to test the binding affinities of selected immobilised ligands towards the recombinant human transferrin chimeric fusion protein-F by batch binding methods. The BCA assay was conducted in the same way as described above. The amount of recombinant human transferrin chimeric fusion protein-F present in the supernatant was evaluated and calculated for the selected adsorbents. Static binding results of the selected ligands are shown in the following Table AG.

TABLE AG

Recombinant human transferrin chimeric fusion protein-F percentage bound for the best and least binding conditions. Upper figures in each row signify the mean, lower figures give SD.

| | | % Tf Bound | | |
|---|---|---|---|---|
| Adsorbent | Ligand Density | pH 5.0; 0 mM Na$_2$SO$_4$ | pH 7.0; 0 mM Na$_2$SO$_4$ | pH 7.0; 300 mM Na$_2$SO$_4$ |
| 5-Br-2PSEA | 321 | 15.8% | 77.9% | 4.7% |
| | | 1.4% | 2.9% | 2.3% |
| 4-Me-2PSEA | 297 | 9.6% | 77.7% | 1.5% |
| | | 1.4% | 2.0% | 3.7% |
| 2PSEA | 325 | 4.0% | 79.0% | 1.9% |
| | | 1.4% | 2.9% | 2.2% |
| 4PSEA | 361 | 4.0% | 78.6% | 4.2% |
| | | 1.5% | 3.0% | 2.1% |

All of the above adsorbents demonstrated good binding for these transferring-related proteins at pH 7.0 in the absence of Na$_2$SO$_4$; however binding was effectively abolished at this pH by inclusion of 300 mM Na$_2$SO$_4$. Generally very little binding was observed for all adsorbents at pH 5.0 in the absence of Na$_2$SO$_4$, although 5Br-2PSEA demonstrated very weak binding. The optimal binding conditions (pH 7.0 and 0 mM Na$_2$SO$_4$) of the static binding studies were used in further studies to calculate dynamic binding capacities of these adsorbents using FPLC.

7.7. Recombinant Chimeric Fusion Protein Batch Binding Studies

Binding assays were carried out to study the static binding capacities of ligands under a range of conditions (Na$_2$SO$_4$ salt concentration and pH). 2PSEA, 3PSEA, 4PSEA, 2QSEA, 4QSEA, 4NO$_2$-2PSEA, 6OMe-2PSEA, 5Br-2PSEA, 6Br-2PSEA, 4Me-2PSEA, 3BPSEA and TerPSEA immobilised ligands were tested for evaluation of binding of the recombinant chimeric fusion protein-A, recombinant chimeric fusion protein-B and recombinant chimeric fusion protein-C and recombinant chimeric fusion protein-E. The conditions tested were 25 mM NaOAc pH 5
25 mM Hepes pH 7 with 0, 300, 600 mM Na$_2$SO$_4$
25 mM Tris pH 8 with 600 mM Na$_2$SO4
25 mM Tris pH 9 with 0, 300, 600 mM Na$_2$SO$_4$ The combination of pH and salt concentrations conditions resulted in eight different conditions. These conditions were used to test the binding affinities of selected immobilised ligands towards all samples of recombinant chimeric fusion proteins by using batch binding method. The BCA assay technique was conducted in the same way as described above. The amount of recombinant chimeric fusion proteins in the supernatant was evaluated and presented in following tables.

TABLE AH

Recombinant chimeric fusion protein-A percentage bound for the best and least binding conditions. Upper figures in each row signify the mean, lower figures give SD.

| | | % Rec. chimeric fusion protein-A bound | | |
|---|---|---|---|---|
| Adsorbent | Ligand Density | pH 5; 0 mM Na$_2$SO$_4$ | pH 7; 0 mM Na$_2$SO$_4$ | pH 7; 600 mM Na$_2$SO$_4$ |
| 5-Br-2PSEA | 321 | 1.3% | 63.4% | 57.8% |
| | | 0.8% | 2.8% | 5.3% |
| 6-Br-2PSEA | 293 | 0.5% | 57.3% | 53.4% |
| | | 2.0% | 4.3% | 3.7% |
| 3BPSEA | 325 | 0.3% | 65.4% | 28.1% |
| | | 0.7% | 2.9% | 3.5% |
| 4PSEA | 361 | 0.5% | 57.6% | 11.8% |
| | | 1.4% | 2.0% | 3.7% |
| 4-Me-2PSEA | 297 | 0.1% | 51.2% | 30.7% |
| | | 0.8% | 2.6% | 6.50% |
| 4-NO$_2$-2PSEA | 339 | 50.0% | 64.4% | 59.6% |
| | | 1.4% | 2.0% | 3.7% |
| 2QSEA | 325 | 0.0% | 60.8% | 68.4% |
| | | 1.4% | 2.0% | 3.7% |
| 6-OMe-2PSEA | 324 | 4.8% | 64.4% | 54.3% |
| | | 1.4% | 2.0% | 3.7% |
| TerPSEA | 311 | 0.0% | 64.0% | 60.6% |
| | | 1.4% | 2.0% | 0.7% |

7.7.1. Recombinant Chimeric Fusion Protein-A

All the above ligands displayed good binding for recombinant chimeric fusion protein-A at pH 7 with zero salt Na$_2$SO$_4$ concentration and also showed binding at pH 8, 9, 600 mM salt concentration. 4PSEA showed binding at the pH 7, 9 with zero salt, however there was very little binding at higher pH and salt concentration. The best ligand for binding this recombinant chimeric fusion protein-A was found to be 2QSEA at 600 mM salt concentration and especially at pH 7, 8 or 9 with values in the range of 67-69%. All adsorbents showed almost no binding at pH 5 for zero salt concentration, Therefore this set of elution conditions was used in the dynamic binding studies. Table AH shows percentage of protein bound for the best binding and elution conditions.

7.7.2. Recombinant Chimeric Fusion Protein-B:

The BCA assays for recombinant chimeric fusion protein-B showed all ligands have good binding affinity at pH7, 8 or 9 and salt concentration 600 mM, and also at pH 7 with zero salt concentration. However 4PSEA showed binding at pH 7 and 9 with no salt and expressed much less binding in the presence of salt concentration of 600 mM. Overall, pH 7 with zero salt was found to be the best binding condition for all adsorbents (Table AI).

TABLE AI

Percentage of recombinant chimeric fusion protein-B percentage bound for the best and least binding conditions. Upper figures in each row signify the mean, lower figures give SD.

| | | % Rec. chimeric fusion protein-B bound | | |
|---|---|---|---|---|
| Adsorbent | Ligand Density | pH 5; 0 mM Na$_2$SO$_4$ | pH 7; 0 mM Na$_2$SO$_4$ | pH 7; 600 mM Na$_2$SO$_4$ |
| 5-Br-2PSEA | 321 | 3.7% | 63.5% | 61.7% |
| | | 1.9% | 5.1% | 2.5% |
| 6-Br-2PSEA | 293 | 3.4% | 64.0% | 53.4% |
| | | 1.6% | 3.0% | 3.7% |
| 3BPSEA | 325 | 3.2% | 64.2% | 28.1% |
| | | 4.3% | 2.9% | 3.5% |
| 4PSEA | 361 | 3.7% | 70.8% | 18.2% |
| | | 1.4% | 2.0% | 3.7% |
| 4-Me-2PSEA | 297 | 2.0% | 63.7% | 30.7% |
| | | 2.1% | 2.8% | 6.50% |
| 4-NO$_2$-2PSEA | 339 | 8.5% | 68.7% | 54.8% |
| | | 1.4% | 2.0% | 3.7% |
| 2QSEA | 325 | 13.9% | 69.1% | 68.7% |
| | | 1.4% | 2.0% | 3.7% |
| 6-OMe-2PSEA | 324 | 8.7% | 73.3% | 56.8% |
| | | 1.4% | 2.0% | 3.7% |
| TerPSEA | 311 | 29.1% | 69.9% | 60.5% |
| | | 1.4% | 2.0% | 3.7% |

7.7.3. Recombinant Chimeric Fusion Protein-E:

BCA studies of the recombinant chimeric fusion protein-E showed pH 5 and 7 with zero salt as the best binding conditions for all ligands (Table AJ). However 2QSEA adsorbent again showed binding at higher salt concentration such as 600 mM as well.

7.7.4 Recombinant Chimeric Fusion Protein-C:

All immobilised ligands showed less binding for recombinant chimeric fusion protein-C as compared with the other recombinant chimeric fusion protein samples. Considering all conditions, the optimal condition is found to be pH 7 without Na$_2$SO$_4$ salt. 4-NO$_2$-2PSEA showed the best binding of nearly 51% (Table AK).

TABLE AJ

Percentage of the recombinant chimeric fusion protein-E bound for the best and least binding conditions. Upper figures in each row signify the mean, lower figures give SD.

| | | % recombinant chimeric fusion protein-E Bound | | | |
|---|---|---|---|---|---|
| Adsorbent | Ligand Density | pH 5; 0 mM Na$_2$SO$_4$ | pH 7; 0 mM Na$_2$SO$_4$ | pH 7; 600 mM Na$_2$SO$_4$ | pH 9; 300 mM Na$_2$SO$_4$ |
| 5-Br-2PSEA | 321 | 79.8% | 80.7% | 53.0% | 12% |
| | | 0.2% | 3.0% | 1.0% | 1.30% |
| 6-Br-2PSEA | 293 | 75.7% | 77.8% | 40.9% | 9.30% |
| | | 0.6% | 2.8% | 1.4% | 2.80% |
| 3BPSEA | 325 | 81.5% | 83.1% | 37.0% | 8.9% |
| | | 1.2% | 2.9% | 2.0% | 3% |
| 4PSEA | 361 | 67.7% | 72.6% | 11.9% | 8.7% |
| | | 1.4% | 2.0% | 3.7% | |
| 4-Me-2PSEA | 297 | 70.5% | 76.6% | 30.9% | 0.60% |
| | | 40.0% | 2.8% | 1.90% | 3.30% |
| 4-NO$_2$-2PSEA | 339 | 74.2% | 72.9% | 37.9% | 11.30% |
| | | 1.4% | 2.0% | 3.7% | |
| 2QSEA | 325 | 69.2% | 55.8% | 53.1% | 24.6% |
| | | 1.4% | 2.0% | 3.7% | |
| 6-OMe-2PSEA | 324 | 75.3% | 75.7% | 40.3% | 10.4% |
| | | 1.4% | 2.0% | 3.7% | |

TABLE AJ-continued

Percentage of the recombinant chimeric fusion protein-E bound for the best and least binding conditions. Upper figures in each row signify the mean, lower figures give SD.

| | | % recombinant chimeric fusion protein-E Bound | | | |
|---|---|---|---|---|---|
| Adsorbent | Ligand Density | pH 5; 0 mM Na$_2$SO$_4$ | pH 7; 0 mM Na$_2$SO$_4$ | pH 7; 600 mM Na$_2$SO$_4$ | pH 9; 300 mM Na$_2$SO$_4$ |
| TerPSEA | 311 | 76.3% 1.4% | 65.8% 2.0% | 48.7% 0.7% | 12.4% |

TABLE AK

Percentage of recombinant chimeric fusion protein-C percentage bound for the best and least binding conditions. Upper figures in each row signify the mean, lower figures give SD.
recombinant chimeric fusion protein-C bound

| pH | Salt Conc | Sepharose | sep-4PSEA | sep-2QSEA | sep-4-NO2-2PSEA | sep-6-OMe-2PSEA | sep-TerPSEA |
|---|---|---|---|---|---|---|---|
| pH 5 | 0 | 17.77% | 6.64% | 7.69% | 3.56% | 8.89% | 12.04% |
| pH 7 | 0 | 8.38% | 41.71% | 35.17% | 50.47% | 45.55% | 45.13% |
| pH 9 | 0 | −0.49% | 21.97% | 10.18% | 5.07% | 5.44% | 8.26% |
| pH 7 | 300 | 2.86% | 16.05% | 22.76% | 12.69% | 24.39% | 17.77% |
| pH 9 | 300 | 2.91% | 8.79% | 17.87% | 11.55% | 10.37% | 10.46% |
| pH 7 | 600 | −0.51% | 0.77% | 22.38% | 8.35% | 8.93% | 13.16% |
| pH 8 | 600 | −2.55% | −0.46% | 20.80% | 6.77% | 6.73% | 10.44% |
| pH 9 | 600 | 1.57% | 3.50% | 22.25% | 12.20% | 12.24% | 18.91% |

In conclusion, conditions were found which gave good binding and elution for all tested adsorbents for monoclonal antibodies (mAbs), recombinant chimeric fusion proteins A-E as well as for the holo-transferrin and the recombinant human transferrin chimeric fusion protein-F.

8. Adsorbent Binding Properties 8.1. Static Batch Binding Studies

The saturation binding experiments performed in this study measure specific binding at equilibrium at various concentrations of mAb. Analysis by non-linear regression in conjunction with various linear representations were used to calculate the mAb binding parameters such as equilibrium dissociation constant ($K_D$) and the maximum mAb binding capacity ($q_m$). A selection of affinity adsorbents (those that showed >40% binding in initial screening studies, Section 7.5.) were employed with various concentrations of mAb (see Section 6.5.) at pH 9, 600 mM Na$_2$SO$_4$ (in triplicate) and the amount of mAb bound was determined by a BCA assay. A plot of bound mAb (q) versus free mAb (C) for each initial mAb concentration was analysed by non-linear regression while various linear transformations were also completed using Prism 3 software (Graph Pad Inc.).

Figure 5:
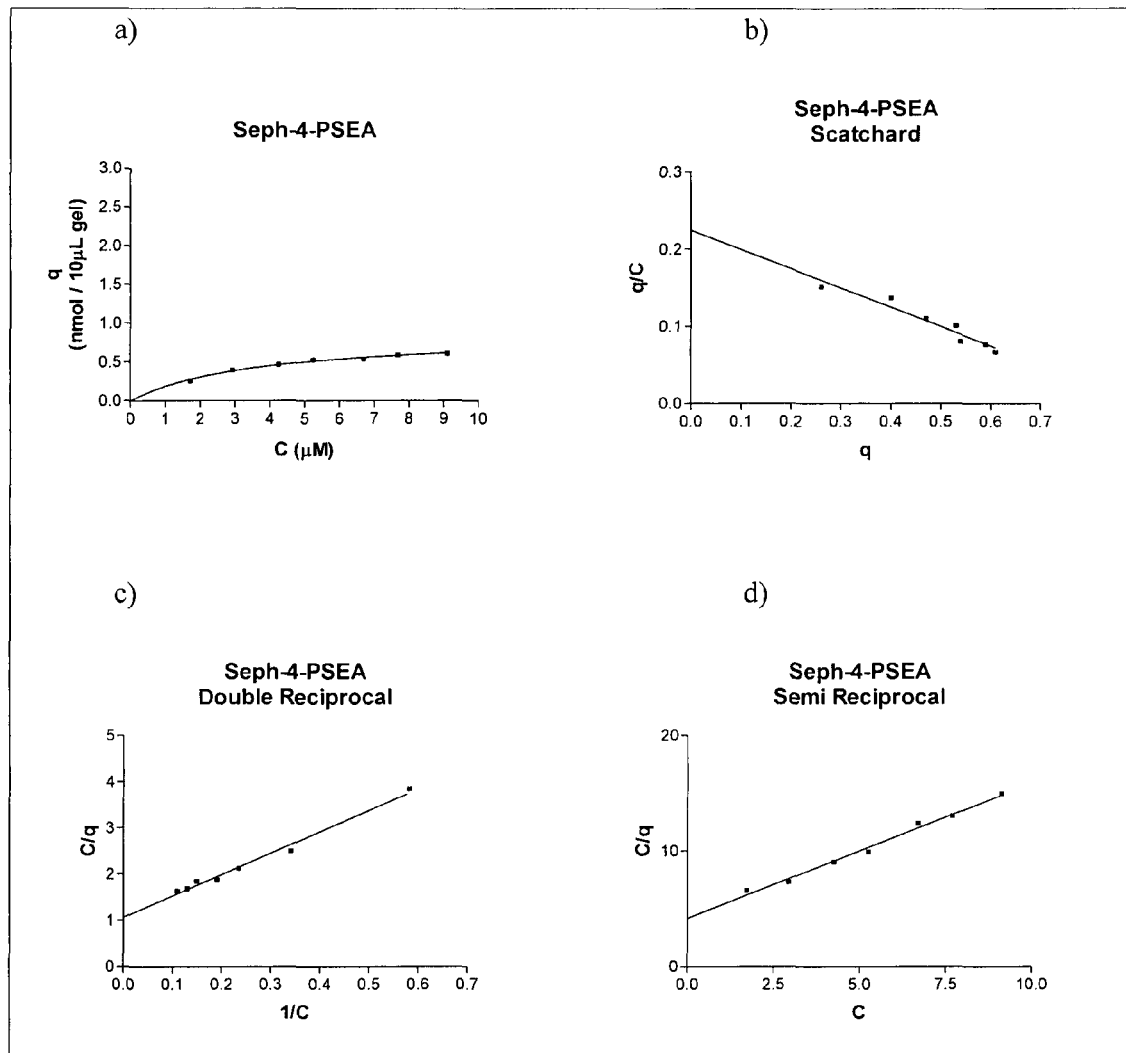
FIG. 5: Plots for determining $K_D$ and $q_m$ for Seph-4-PSEA. a) Adsorption Isotherm, b) Scatchard, c) Double Reciprocal, d) Semi Reciprocal Plots for monoclonal antibody binding.
Figure 6:
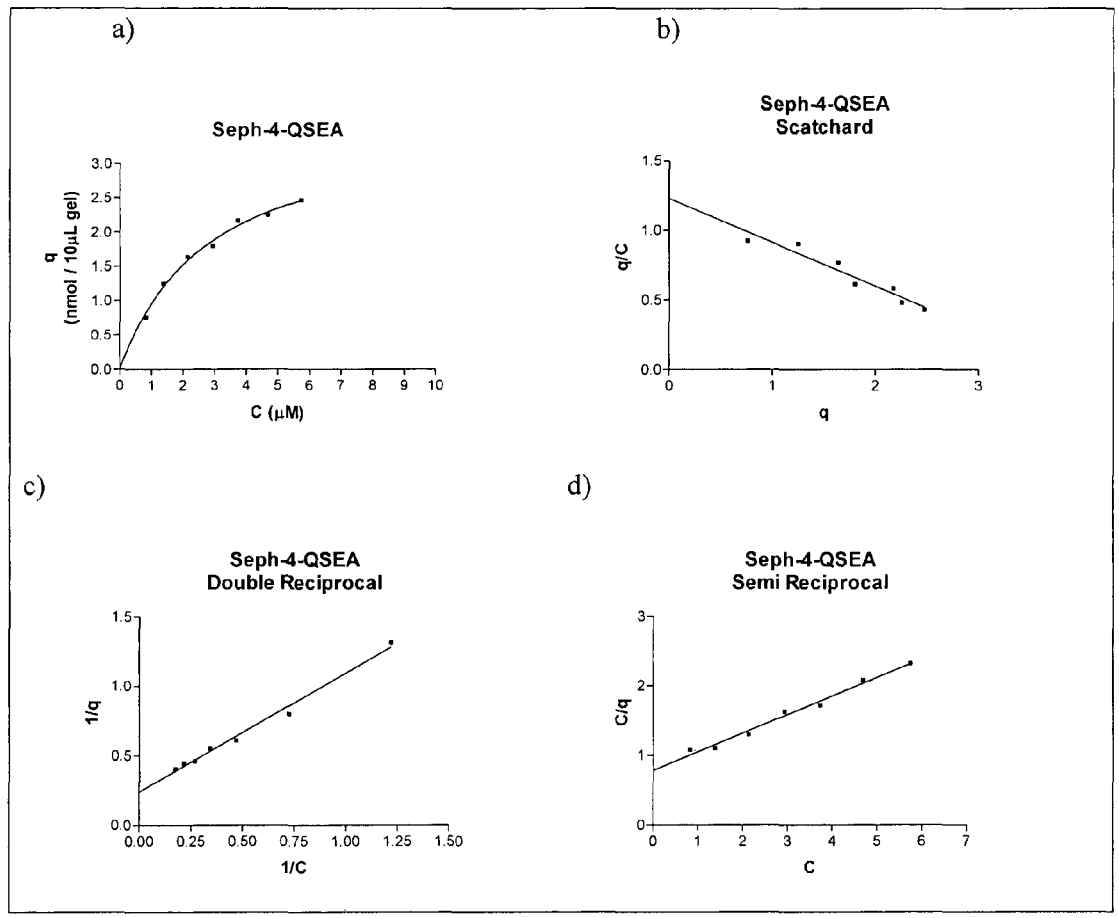
FIG. 6: Plots for determining $K_D$ and $q_m$ for Seph-4-QSEA: a) Adsorption Isotherm, b) Scatchard, c) Double Reciprocal, d) Semi Reciprocal Plots for monoclonal antibody binding.

The non-linear regression analysis (fitting the hyperbola to the graph) of the isotherms was based on the Langmuir model (one site binding), which allowed for the calculation of the equilibrium dissociation constant ($K_D$) in µM and also the maximum binding capacity ($B_{max}$), presented in the units entered (nmol/10µL gel). The $B_{max}$ values were converted into the standard binding capacity units of mg/mL ($q_m$), and presented in Table AM. The Scatchard, double-reciprocal and semi-reciprocal plots show linear relationship in the concentration ranges tested, which suggests single-site homogeneous interactions occur with these new ligand systems. Plots for a selection of the data are shown in FIG. 5 and FIG. 6.

Adsorption Isotherm: shows the concentration of protein bound by the desired adsorbent vs. the concentration of protein.

Scatchard Plot was used for studying protein adsorption onto the adsorbent surface. It is used to find maximum binding ($q_m$) without the need to reach saturation experimentally. A linear slope indicates a homogeneous interaction.

Reciprocal plots were used to provide alternate estimates for $q_m$ (maximum binding) and $K_D$ (dissociation constant) values and to ensure accuracy:

Semi reciprocal shows the effect of binding at higher concentration.

Double reciprocal shows the effect of binding at lower concentration.

The gradient of the Scatchard plot relates to the binding affinity, (dissociation constant, $K_D$), occurring between the monoclonal antibody and the adsorbent. A steeper gradient, FIG. 6b, (cf. FIG. 5b) correlates to a lower value of $K_D$ which in turn is associated with a stronger binding affinity. Table AL and the related plots (FIG. 5-FIG. 6), illustrate the affinity of the adsorbents tested towards the mAb. The results obtained in this study show that the binding affinity ($K_D$) of the mAb to the immobilised ligands facilitates successful monoclonal antibody purifications from crude mixtures. Binding was successfully achieved at various mAb concentrations and the calculated capacity of the novel adsorbents is significantly higher than other sorbents such as Protein A as described previously.

TABLE AL

Adsorbent binding properties calculated from various analysis methods.

| | | $K_D$ (µM) | $B_{max}$ nmol/10 µL gel | $R^2$ | $q_m$ (mg/mL) |
|---|---|---|---|---|---|
| Seph-2-PSEA (314) | Isotherm | 3.35 | 1.64 | 0.988 | 24.7 |
| | Scatchard | 3.65 | 1.70 | 0.967 | 25.6 |
| | Double Reciprocal | 3.66 | 1.71 | 0.997 | 25.7 |
| | Semi Reciprocal | 3.30 | 1.63 | 0.989 | 24.5 |
| Seph-4-PSEA (325) | Isotherm | 3.52 | 0.85 | 0.985 | 12.8 |
| | Scatchard | 4.01 | 0.90 | 0.932 | 13.6 |
| | Double Reciprocal | 4.30 | 0.93 | 0.987 | 14.0 |
| | Semi Reciprocal | 3.60 | 0.86 | 0.989 | 12.9 |
| Seph-2-PSPA (282) | Isotherm | 3.74 | 1.86 | 0.966 | 28.0 |
| | Scatchard | 4.69 | 2.07 | 0.891 | 31.1 |
| | Double Reciprocal | 4.78 | 2.09 | 0.992 | 31.4 |
| | Semi Reciprocal | 3.74 | 1.84 | 0.960 | 27.8 |

TABLE AL-continued

Adsorbent binding properties calculated from various analysis methods.

| | | $K_D$ (µM) | $B_{max}$ nmol/10 µL gel | $R^2$ | $q_m$ (mg/mL) |
|---|---|---|---|---|---|
| Seph-4-PSPA (270) | Isotherm | 4.13 | 1.32 | 0.966 | 19.9 |
| | Scatchard | 4.25 | 1.34 | 0.871 | 20.1 |
| | Double Reciprocal | 3.65 | 1.24 | 0.976 | 18.6 |
| | Semi Reciprocal | 4.02 | 1.30 | 0.968 | 19.5 |
| Seph-4-Me-2-PSEA (259) | Isotherm | 5.18 | 2.07 | 0.987 | 31.2 |
| | Scatchard | 5.29 | 2.09 | 0.954 | 31.5 |
| | Double Reciprocal | 5.18 | 2.07 | 0.997 | 31.2 |
| | Semi Reciprocal | 5.20 | 2.07 | 0.979 | 31.2 |
| Seph-6-Me-2-PSEA (265) | Isotherm | 4.11 | 1.36 | 0.989 | 20.5 |
| | Scatchard | 4.08 | 1.36 | 0.960 | 20.5 |
| | Double Reciprocal | 3.92 | 1.33 | 0.994 | 20.0 |
| | Semi Reciprocal | 4.07 | 1.36 | 0.990 | 20.4 |
| Seph-6-Ph-2-PSEA (232) | Isotherm | 2.19 | 2.86 | 0.995 | 43.1 |
| | Scatchard | 2.18 | 2.86 | 0.985 | 43.1 |
| | Double Reciprocal | 2.15 | 2.84 | 0.998 | 42.8 |
| | Semi Reciprocal | 2.21 | 2.88 | 0.997 | 43.3 |
| Seph-2-Ph-4-PSEA (196) | Isotherm | 4.02 | 3.13 | 0.996 | 47.2 |
| | Scatchard | 3.87 | 3.08 | 0.980 | 46.3 |
| | Double Reciprocal | 3.65 | 2.97 | 0.998 | 44.7 |
| | Semi Reciprocal | 3.94 | 3.10 | 0.993 | 46.7 |
| Seph-6-OMe-2-PSEA (223) | Isotherm | 6.74 | 2.97 | 0.977 | 44.8 |
| | Scatchard | 8.30 | 3.38 | 0.830 | 51.0 |
| | Double Reciprocal | 8.83 | 3.53 | 0.991 | 53.2 |
| | Semi Reciprocal | 7.26 | 3.09 | 0.929 | 46.6 |
| Seph-4-NO$_2$-2-PSEA (307) | Isotherm | 2.97 | 3.51 | 0.981 | 52.8 |
| | Scatchard | 3.03 | 3.55 | 0.931 | 53.4 |
| | Double Reciprocal | 2.87 | 3.44 | 0.994 | 51.8 |
| | Semi Reciprocal | 2.95 | 3.49 | 0.978 | 52.6 |
| Seph-2-QSEA (329) | Isotherm | 2.60 | 3.76 | 0.990 | 56.6 |
| | Scatchard | 2.98 | 4.01 | 0.924 | 60.4 |
| | Double Reciprocal | 3.36 | 4.30 | 0.989 | 64.8 |
| | Semi Reciprocal | 2.73 | 3.82 | 0.986 | 57.6 |
| Seph-4-QSEA (346) | Isotherm | 2.81 | 3.67 | 0.990 | 55.3 |
| | Scatchard | 3.17 | 3.90 | 0.925 | 58.7 |
| | Double Reciprocal | 3.55 | 4.16 | 0.989 | 62.6 |
| | Semi Reciprocal | 2.94 | 3.74 | 0.985 | 56.3 |
| Seph-1-IQSEA (337) | Isotherm | 2.44 | 3.24 | 0.986 | 48.7 |
| | Scatchard | 2.54 | 3.30 | 0.952 | 49.7 |
| | Double Reciprocal | 2.53 | 3.29 | 0.995 | 49.6 |
| | Semi Reciprocal | 2.46 | 3.24 | 0.987 | 48.8 |

Comparison of maximum binding capacity ($q_m$) and dissociation constants ($K_D$) obtained using Adsorption Isotherm, Scatchard, Double Reciprocal and Semi Reciprocal Plots for monoclonal antibody binding. The $R^2$ value is a measure of the "goodness of fit" with 1.0 showing no deviation in the line of best-fit from the acquired data.

TABLE AM

Maximum binding capacity ($B_{max}$ and $q_m$) and dissociation constant ($K_D$) of some further selected adsorbents for monoclonal antibodies.

| Adsorbent | | Bmax (nmole/10 µl gel) | KD (µM) | $R^2$ | $q_m$ (mg/mL) |
|---|---|---|---|---|---|
| 2PSEA (285) | Isotherm | 2.52 | 3.63 | 0.9729 | 38.0 |
| | Scatchard | 2.76 | 4.42 | 0.9572 | 41.6 |
| | Double Reciprocal | 3.30 | 5.94 | 0.9490 | 49.6 |
| | Semi Reciprocal | 2.63 | 3.99 | 0.9863 | 39.5 |
| 6OMe-2PSEA (324) | Isotherm | 3.46 | 2.03 | 0.9981 | 52.1 |
| | Scatchard | 3.51 | 2.10 | 0.9981 | 52.9 |
| | Double Reciprocal | 3.52 | 2.11 | 0.9996 | 53.0 |
| | Semi Reciprocal | 3.45 | 2.07 | 1.0000 | 51.9 |
| 4Me-2PSEA (297) | Isotherm | 2.77 | 6.99 | 0.9826 | 41.7 |
| | Scatchard | 2.71 | 6.72 | 0.9265 | 40.8 |
| | Double Reciprocal | 2.60 | 6.31 | 0.9929 | 39.1 |
| | Semi Reciprocal | 2.71 | 6.86 | 0.9800 | 40.8 |
| 5Br-2PSEA (321) | Isotherm | 3.96 | 3.67 | 0.9818 | 59.6 |
| | Scatchard | 4.15 | 4.75 | 0.9164 | 62.5 |
| | Double Reciprocal | 4.44 | 5.20 | 0.9929 | 62.5 |
| | Semi Reciprocal | 3.85 | 4.18 | 0.9800 | 57.9 |
| 6Br-2PSEA (293) | Isotherm | 2.21 | 2.86 | 0.9643 | 33.3 |
| | Scatchard | 2.33 | 3.37 | 0.9767 | 35.1 |
| | Double Reciprocal | 2.32 | 3.33 | 0.9905 | 35.0 |
| | Semi Reciprocal | 2.28 | 3.26 | 0.9800 | 34.4 |
| 3BPSEA (265) | Isotherm | 3.80 | 5.73 | 0.9935 | 57.2 |
| | Scatchard | 2.33 | 3.37 | 0.9767 | 35.1 |
| | Double Reciprocal | 2.32 | 3.33 | 0.9905 | 35.0 |
| | Semi Reciprocal | 2.28 | 3.26 | 0.9800 | 34.4 |
| 4TerPSEA (311) | Isotherm | 4.09 | 3.86 | 0.9795 | 61.4 |
| | Scatchard | 5.03 | 5.53 | 0.7842 | 75.8 |
| | Double Reciprocal | 6.19 | 7.41 | 0.9805 | 92.9 |
| | Semi Reciprocal | 4.38 | 4.46 | 0.9356 | 65.7 |
| 2QSEA (325) | Isotherm | 2.30 | 3.65 | 0.9656 | 55.0 |
| | Scatchard | 2.40 | 3.73 | 0.8660 | 56.2 |
| | Double Reciprocal | 2.29 | 3.64 | 0.9794 | 54.8 |
| | Semi Reciprocal | 2.27 | 3.62 | 0.9685 | 54.5 |
| 4NO$_2$-2PSEA (339) | Isotherm | 2.97 | 3.51 | 0.9807 | 52.8 |
| | Scatchard | 3.03 | 3.55 | 0.9308 | 53.4 |
| | Double Reciprocal | 2.87 | 3.44 | 0.9937 | 51.8 |
| | Semi Reciprocal | 2.95 | 3.49 | 0.9782 | 52.6 |

8.1.1. Varying Analysis Methods

The adsorption isotherm experiments were repeated with two ligands and the amount of non-bound mAb was determined by direct BCA, BCA (normalised with subtraction of background values) and UV-Vis (Table AN).

TABLE AN

Comparison of binding properties calculated by different detection methods

| | | BCA | | | BCA (normalised) | | | UV-Vis | | |
|---|---|---|---|---|---|---|---|---|---|---|
| | | $K_D$ (mM) | $B_{max}$ | $q_m$ (mg/mL) | $K_D$ (mM) | $B_{max}$ | $q_m$ (mg/mL) | $K_D$ (mM) | $B_{max}$ | $q_m$ (mg/mL) |
| Seph-2-QSEA (329) | | | | | | | | | | |
| Isotherm | | 2.30 | 3.65 | 55.0 | 0.64 | 3.14 | 47.3 | 0.33 | 3.40 | 51.2 |
| Scatchard | | 2.40 | 3.73 | 56.2 | 0.54 | 3.04 | 45.7 | 0.26 | 3.28 | 49.5 |
| Double Reciprocal | | 2.29 | 3.64 | 54.8 | 0.44 | 2.86 | 43.1 | 0.19 | 3.04 | 45.8 |
| Semi Reciprocal | | 2.27 | 3.62 | 54.5 | 0.67 | 3.19 | 48.0 | 0.34 | 3.44 | 51.9 |
| Seph-6-OMe-2-PSEA (223) | | | | | | | | | | |
| Isotherm | | 4.67 | 2.78 | 41.9 | 2.30 | 2.49 | 37.5 | 1.57 | 2.81 | 42.3 |
| Scatchard | | 5.05 | 2.91 | 43.8 | 2.35 | 2.52 | 38.0 | 1.32 | 2.68 | 40.4 |
| Double Reciprocal | | 4.58 | 2.74 | 41.3 | 2.03 | 2.36 | 35.6 | 1.00 | 2.42 | 36.5 |
| Semi Reciprocal | | 4.56 | 2.74 | 41.3 | 2.15 | 2.43 | 36.6 | 1.50 | 2.78 | 41.9 |

Figure 7:
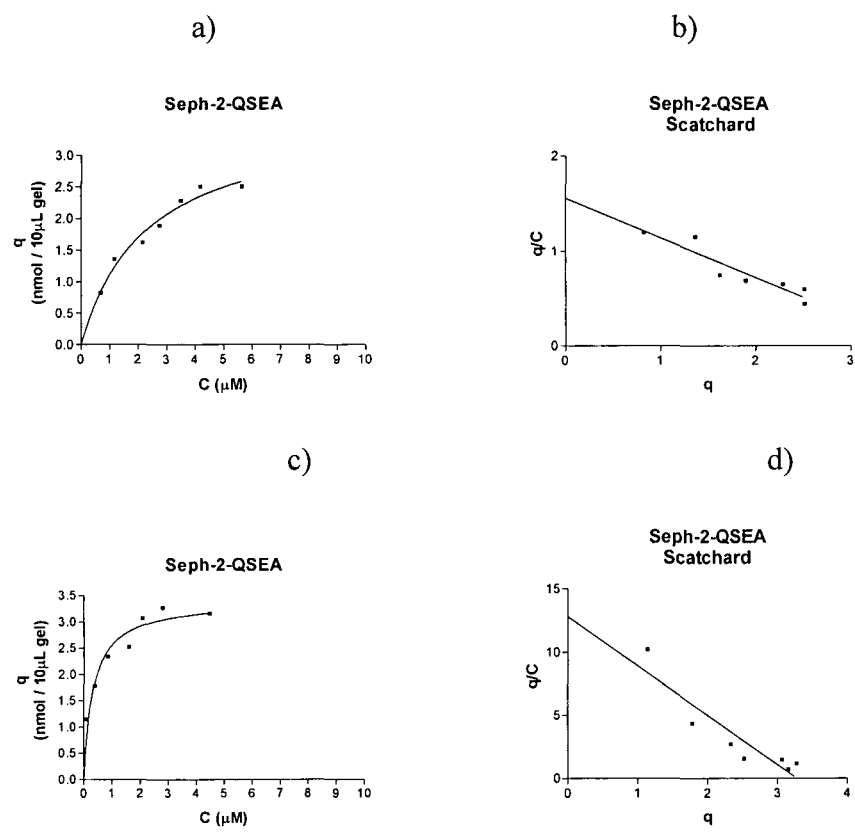
FIG. 7: a) Adsorption Isotherm and b) Scatchard Plots obtained for Seph-2-QSEA using BCA assay; c) Adsorption Isotherm and d) Scatchard Plots obtained for Seph-2-QSEA using UV-Vis analysis.

Maximum binding capacity ($q_m$) and dissociation constants ($K_D$) using different detection methods: Adsorption Isotherm, Scatchard, Double Reciprocal and Semi Reciprocal Plots for mAb binding (see FIGS. 7 and 8). All $R^2$ values were >0.84, with the majority >0.95.

The $K_D$ values obtained in these studies compare very well to other antibody affinity sorbents. For example, Protein A has a dissociation constant of $10^{-7}$M for IgG.

8.2. Transferrin Dynamic Binding

The following table gives adsorbent binding properties of selected adsorbents for the binding of the recombinant human transferrin chimeric fusion protein-F calculated from various analysis methods.

TABLE AO

Maximum binding capacity (Bmax and $q_m$) and dissociation constant ($K_D$) of the selected adsorbents for recombinant human transferrin chimeric fusion protein-F recombinant human transferrin chimeric fusion protein-F.

| Adsorbent | | Bmax (nmole/10 µl gel) | $K_D$ (µM) | $R^2$ | $q_m$ (mg/mL) |
|---|---|---|---|---|---|
| 4PSEA | Isotherm | 6.61 | 5.75 | 0.98 | 51.54 |
| | Scatchard | 6.99 | 6.41 | 0.90 | 54.53 |
| | Double Reciprocal | 6.94 | 6.54 | 0.99 | 54.13 |
| | Semi Reciprocal | 6.70 | 5.73 | 0.98 | 52.28 |
| 4NO$_2$-2PSEA | Isotherm | 6.93 | 8.54 | 1.00 | 54.02 |
| | Scatchard | 7.08 | 8.87 | 0.96 | 55.19 |
| | Double Reciprocal | 7.05 | 8.82 | 1.00 | 54.97 |
| | Semi Reciprocal | 6.98 | 8.69 | 0.99 | 54.47 |
| 6OMe-2PSEA | Isotherm | 6.68 | 5.79 | 0.96 | 52.10 |
| | Scatchard | 7.00 | 7.28 | 0.96 | 54.63 |
| | Double Reciprocal | 7.15 | 7.96 | 0.98 | 55.79 |
| | Semi Reciprocal | 6.99 | 6.44 | 0.94 | 54.55 |
| 4Me-2PSEA | Isotherm | 10.68 | 17.43 | 0.99 | 83.30 |
| | Scatchard | 10.68 | 18.52 | 0.93 | 83.29 |
| | Double Reciprocal | 11.27 | 18.67 | 1.00 | 87.93 |
| | Semi Reciprocal | 11.11 | 18.89 | 0.96 | 86.67 |
| 5Br-2PSEA | Isotherm | 11.12 | 9.60 | 0.99 | 86.74 |
| | Scatchard | 11.00 | 14.29 | 0.82 | 85.80 |
| | Double Reciprocal | 10.52 | 14.02 | 0.99 | 82.06 |
| | Semi Reciprocal | 10.52 | 13.12 | 0.93 | 82.06 |
| 6Br-2PSEA | Isotherm | 6.15 | 7.79 | 0.98 | 47.97 |
| | Scatchard | 6.11 | 7.65 | 0.95 | 47.68 |
| | Double Reciprocal | 6.17 | 7.37 | 0.99 | 48.12 |
| | Semi Reciprocal | 6.10 | 7.67 | 0.99 | 47.59 |
| 3BPSEA | Isotherm | 11.09 | 7.90 | 0.96 | 86.50 |
| | Double Reciprocal | 11.11 | 12.00 | 0.95 | 86.67 |

Comparison of maximum binding capacity ($q_m$) and dissociation constants ($K_D$) are obtained using Adsorption Isotherm, Scatchard, Double Reciprocal and Semi Reciprocal Plots. The $R^2$ value is a measure of the "goodness of fit" with 1.0 showing no deviation in the line of best-fit from the acquired data.

8.3. Dynamic Binding Studies

Dynamic binding capacities (frontal analysis) for selected immobilised ligands were determined by affinity chromatography using Fast Flow Protein Liquid Chromatography (FPLC). The optimal binding conditions derived from static binding studies were selected and tested for binding of pure mAb, recombinant chimeric fusion proteins and transferrin-related protein samples at ambient temperature. The protein sample was injected at a constant flow rate into the adsorbent column. The column was washed with binding buffer to remove unbound protein, followed by elution to recover bound protein. The AKTA purifier (GE Healthcare) was used to run a 1 mL column for the selected adsorbents to assess the maximum kinetic binding capacity for protein samples such as the mAbs, recombinant chimeric fusion protein samples and transferrins (bovine holo-protein as well as the recombinant human transferrin chimeric fusion protein-F).

Typical FPLC Protocol

Procedure used to evaluate antibody binding using flow rate 1 mL/min:

Equilibrate column with 5 CV: binding buffer, 25 mM Tris pH 8.0, 600 mM Na$_2$SO$_4$, Inject sample: 20 mL, 50 mL or 75 mL (2 mg/mL of IgG 8.5, 11 mAb A or mAb B prepared in binding buffer), Wash out unbound protein with 5, 10, 20 or 30 CV: binding buffer, Elute bound protein with 10 CV: 25 mM NaOAc pH 5.0, Regenerate with 5 CV: 0.5 M NaOH, Wash with 5 CV: 25 mM NaOAc pH 5.0.

The collected fractions were analysed at 280 nm using UV-Vis spectrometry. The amount of protein obtained in the elution fractions was calculated by measuring their UV absorbance and also by freeze drying the samples. A standard curve of absorbance vs concentration was prepared to allow determination of the total amount of mAb recovered and the amount in the elution fractions. The total recovery calculated from the UV results.

8.3.1. Monoclonal Antibody Studies

Figure 9:
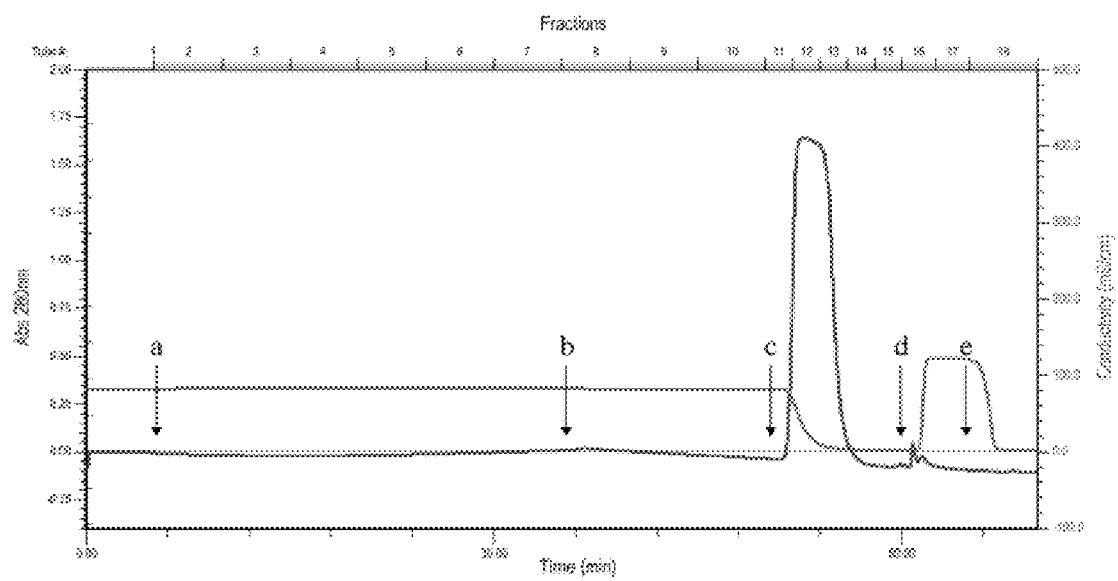
FIG. 9: FPLC chromatogram of Seph-4-QSEA (13.5 mg mAb in 30 mL) a) sample injection, b) wash, c) elution, d) regeneration (1M NaOH), e) regeneration b) at pH 5.

The mAb results are summarised in Table AP. The amount of mAb captured and eluted was dependent on both the original amount loaded and the flow rate. As evident from Table AP for Seph-2-QSEA and Seph-4-NO$_2$-2-PSEA, the elution and regeneration process did not affect the binding capacity of the adsorbents (compare entries 1 vs 2 and 4 vs 5). Re-use of these adsorbents with very similar loading conditions and concentrations (i.e. ca. 14 mg mAb at 1 mL/min) consistently led to very similar capture and eluted amounts of recovered mAb. The success of this procedure to limit the loss of mAb in the breakthrough and allow relatively dilute feedstocks to be employed was illustrated in the experiments with the 4-QSEA ligand (e.g. FIG. 9) where a reasonably flat baseline obtained throughout the entire loading of the sample.

TABLE AP

Dynamic Binding Capacity of Adsorbents

| Adsorbent | Entry | Amount mAb (mg) Loaded in 30 mL | Eluted mAb (mg) | Elution % | Recovery mAb (mg) | Recovery % |
|---|---|---|---|---|---|---|
| Seph-2-QSEA (329) | 1 | 14.2 | 9.8 | 69 | 11.1 | 78 |
| | 2 | 14.5 | 11.2 | 77 | 12.0 | 82 |
| | 3 | 30.9 | 18.8 | 61 | 26.9 | 87 |
| Seph-4-NO$_2$-2-PSEA (307) | 4 | 14.4 | 12.3 | 85 | 14.2 | 99 |
| | 5 | 14.0 | 11.9 | 85 | 13.7 | 97 |
| | 6 | 30.1 | 18.2 | 61 | 27.3 | 91 |
| Seph-2-PSEA (307) | 7 | 3.6 | 3.1 | 84 | 3.5 | 96 |
| | 8 | 9.4 | 5.5 | 59 | 8.0 | 85 |
| | 9 | 19.9 | 9.0 | 45 | 17.9 | 90 |
| Seph-2-PSPA (282) | 10 | 9.8 | 7.3 | 74 | 8.3 | 84 |
| | 11 | 15.3 | 10.7 | 70 | 13.8 | 91 |
| | 12 | 19.2 | 12.1 | 63 | 17.5 | 91 |
| | 13 | 19.9* | 14.1 | 71 | 18.0 | 91 |
| Seph-4-QSEA (346) | 14 | 13.5 | 11.8 | 87 | 11.9 | 88 |
| | 15 | 28.2 | 19.0 | 67 | 25.4 | 90 |
| | 16 | 28.6* | 23.4 | 82 | 26.6 | 93 |
| MEP HyperCel | 17 | 13.5 | 6.6 | 49 | 12.9 | 95 |

Antibody adsorption by the MEP HyperCel® adsorbent usually occurs in a buffer consisting of 50 mM Tris pH 8 (as specified by the manufacturer[45]). However, this condition is unfavourable for the novel adsorbents developed in this work. Although the MEP HyperCel® consists of a pyridine head group and exocyclic sulfur atom (FIG. 8.6), the side chain and spacer arm immobilised to the resin impose a significantly different effect, leading towards the hydrophobic nature of interaction.

It is suggested, therefore, that the mechanism of binding to the novel adsorbents studied here does not predominantly involve hydrophobic interaction.

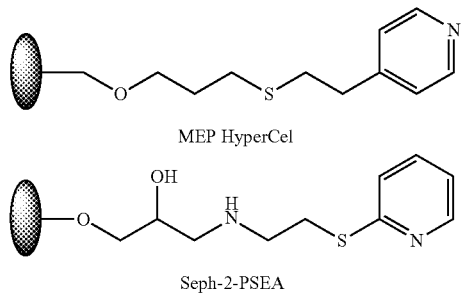

Figure 8:
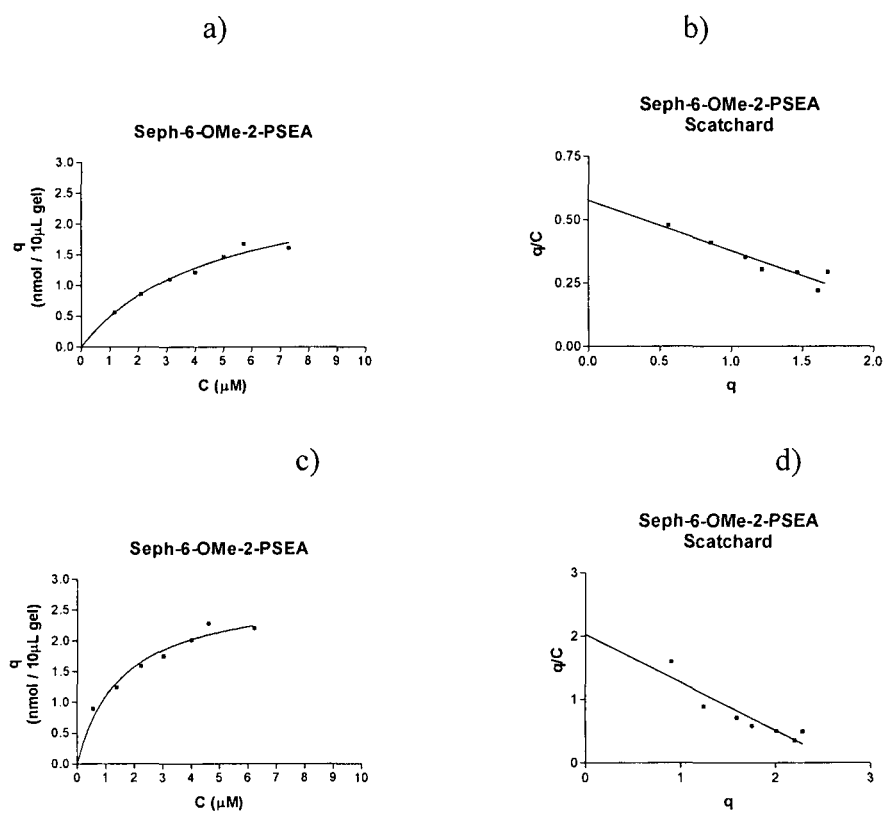
FIG. 8: a) Adsorption Isotherm and b) Scatchard Plots obtained for Seph-6-OMe-2-PSEA using BCA assay; c) Adsorption Isotherm and d) Scatchard Plots obtained for Seph-6-OMe-2-PSEA using UV-Vis analysis.

Figure 8.6: Structures of MEP HyperCel® and the novel Seph-2-PSEA

Figure 10:
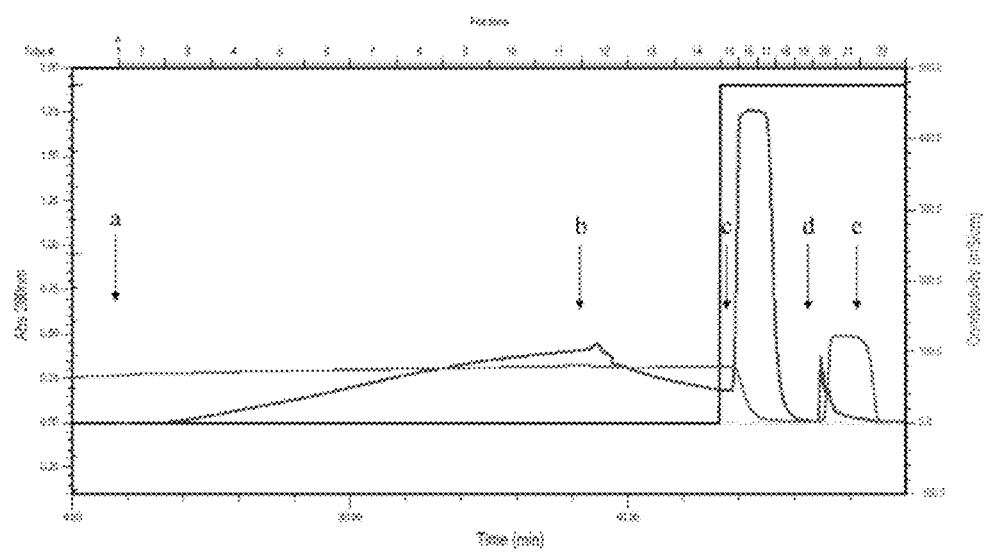
FIG. 10: Chromatogramic profiles for mAb elution from Seph-4-QSEA using two different loading regimes. a) sample injection, b) wash, c) elution, d) regen. (NaOH), e) regen. (pH 5).
Figure 10:
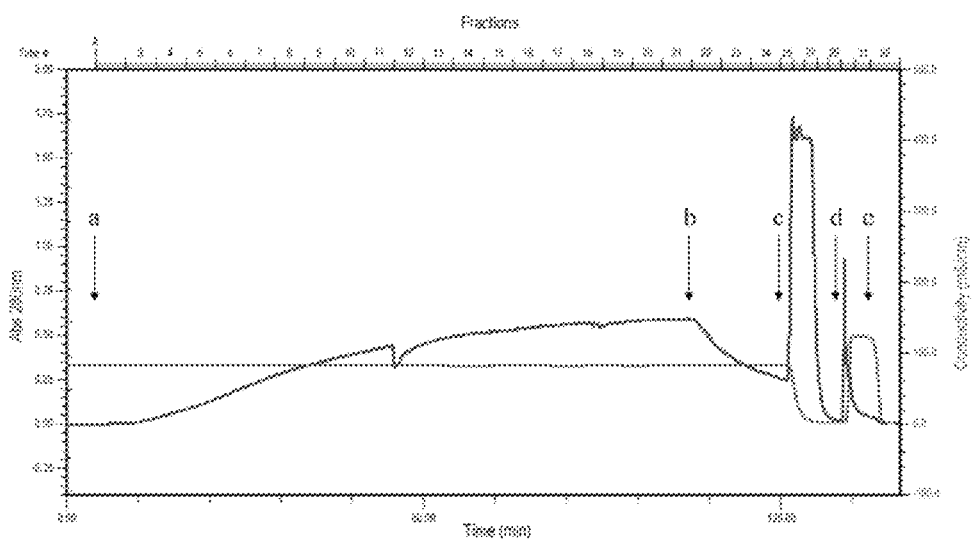

For the purpose of comparative experiments, saturation of the adsorbents with mAb could be achieved at higher mAb loadings, either by increasing the volume of the injected sample, or its concentration, whilst maintaining constant linear flow velocities. The Seph-4-QSEA adsorbent was chosen for this study, using a 1 mL column bed and the results are shown in FIG. 10 and Table AQ. From the corresponding chromatograms for these two experiments it is evident that dynamic capacities for mAb binding in the range of 28-34 mg/mL can be realised depending on the feedstock concentrations and other chosen conditions.

TABLE AQ

Dynamic Binding Capacities for Seph-4-QSEA

| Adsorbent | Entry | Amount mAb (mg) Loaded | Eluted mAb (mg) | Elution % | Recovery mAb (mg) |
|---|---|---|---|---|---|
| Seph-4-QSEA (346) | 1 | 50.9 (in 50 mL) | 27.8 | 55 | 48.4 |
| | 2 | 100.11 (in 100 mL) | 33.6 | 34 | 96.6 |

Static binding studies of selected immobilised ligands for each monoclonal antibody sample showed adsorbents 4NO$_2$-2PSEA 2QSEA, 4QSEA, 6OMe-2PSEA, 4TerPSEA and 5Br-2PSEA have better antibody binding than the other ligands. To calculate dynamic binding capacities two samples of antibody were selected (8.5 mg/mL and mAb A).

Figure 11:
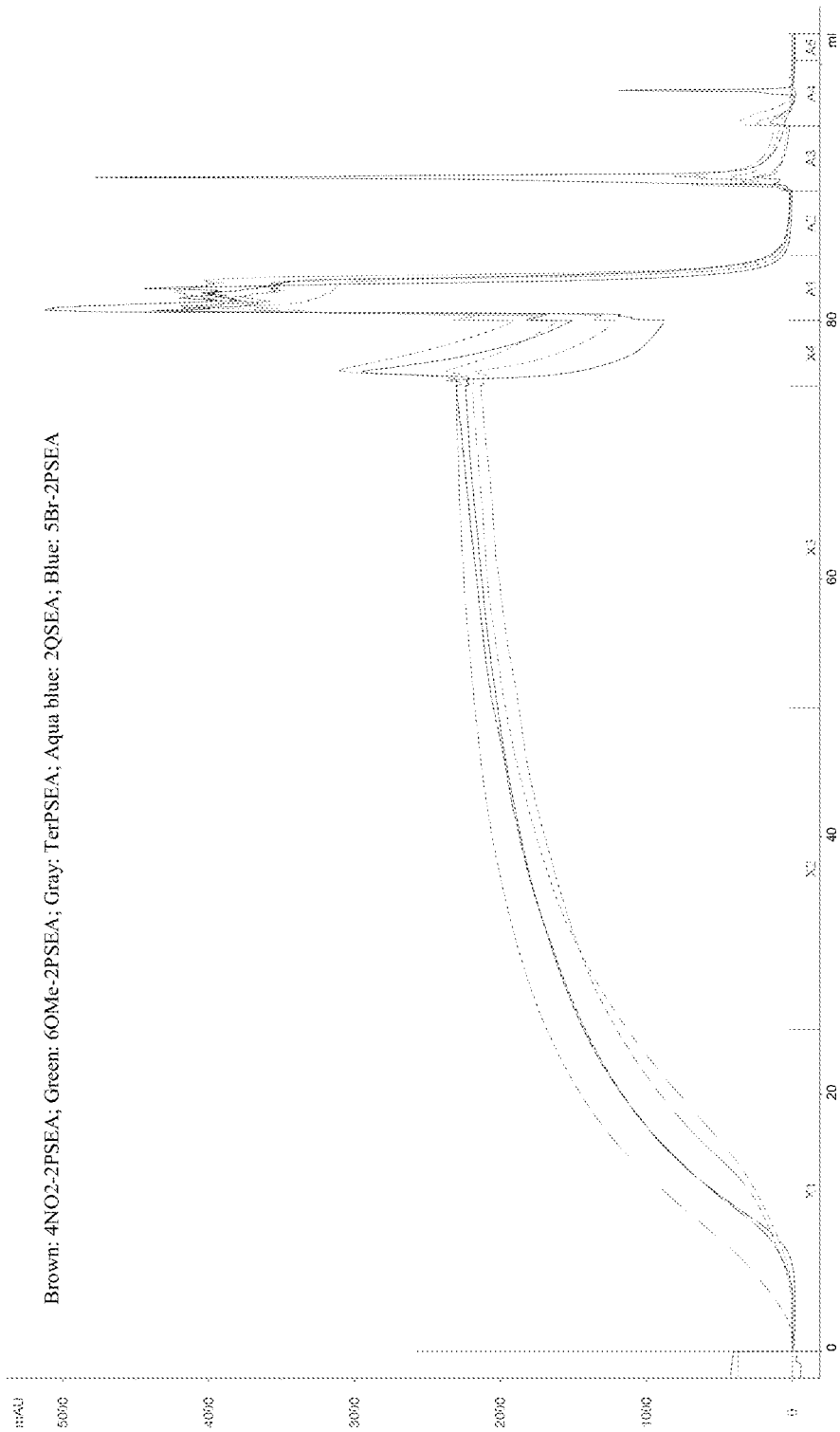
FIG. 11: Relative binding of adsorbents for mAb B. Chromatograms show relative dynamic binding affinities of 5 ligands (−) 5Br-2PSEA, (−) 4NO$_2$-2PSEA, (−) 6OMe-2PSEA, (−) 2QSEA and (−) 4TerPSEA. (Curve Compare of selected ligands for mAb 75 mL Injection of ~2 mg/mL mAb; 5CV Wash (unbound mAb Wash))
Figure 12:
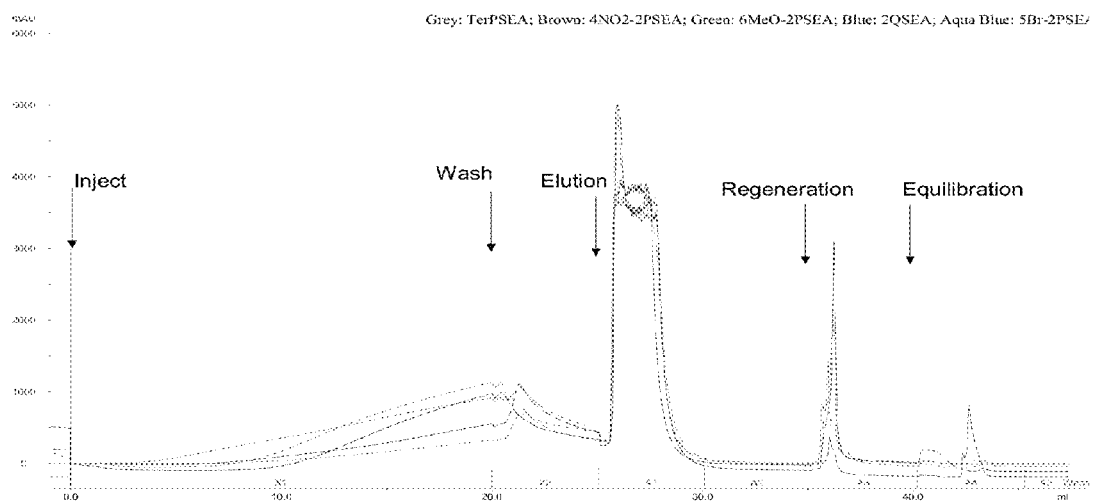
FIG. 12: Relative binding of adsorbents for mAb B. Chromatograms show relative dynamic binding affinities of 5 ligands (−) 2QSEA, (−) 4NO$_2$-2PSEA, (−) 6OMe-2PSEA, (−) 5Br-2PSEA and (−) 4TerPSEA.

Initially 50 mL of 2 mg/mL mAb solution was injected at the rate of 1 mL/min (60 CV/h) to reach the dynamic equilibrium of the 1 mL adsorbent. However, we observed that the column was not saturated. Therefore, the amount of mAb solution (2 mg/mL) injected was increased to 75 mL at a flow rate of 1 mL/min (60 CV/h) in order to calculate the maximum binding capacities of the adsorbents after saturation. IgG 8.5, mAb B and mAb A antibodies were tested (see table AR and FIG. 11). Amounts of mAb bound were summarised in table AT. All these 5 ligand were further tested by injecting 20 mL mAb B solution (2 mg/mL) to calculate the binding capacity of 1 mL adsorbent (see table AS and FIG. 12).

Figure 13:
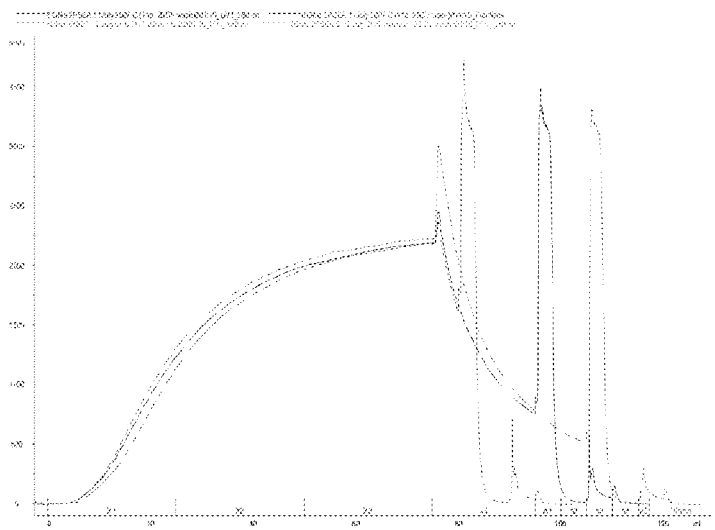
FIG. 13: Comparative elution under different conditions (CV) for removal of unbound antibodies: (a) 6OMe-2PSEa, (b) TerPSEA.
Figure 13:
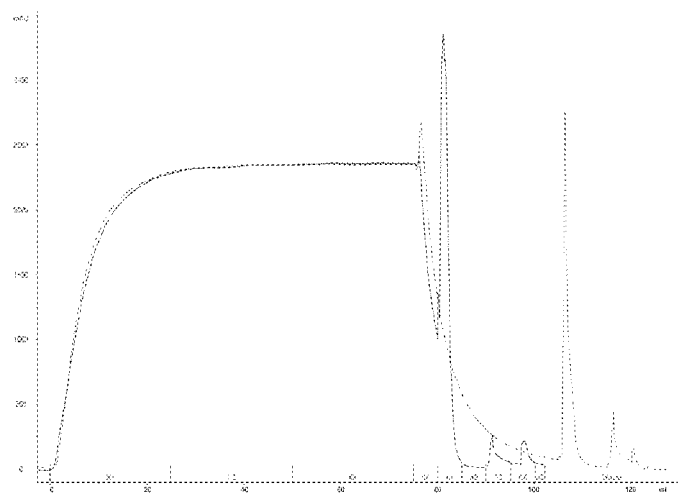

Initially a 5 CV wash of binding buffer was used to remove unbound antibodies from the column, which was further extended to 10 CV, 20 CV and 30 CV wash for comparative studies shown in FIGS. 13 (a) and (b) for 6OMe-2PSEA and 4TerPSEA respectively.

The elution fractions were collected and analysed using a UV spectrometer (280 nm). The amount obtained in the elution fractions and the total recovery was determined by using a standard concentration curve which was prepared by measuring the absorbance of pure IgG (7.7 mg/mL). Total amounts of antibodies injected, eluted and recovered were calculated (Table AS and AT). Repeat evaluation of adsorbents such as 2QSEA, 6OMe-2PSEA under the same conditions was carried out as a reproducibility check. More than 96% of mAb was recovered and 35-66 mg of antibody/mL gel (25 mM NaOAc, pH 5.0 buffer was used for elution) recovery was obtained for the various adsorbents.

TABLE AR

Relative dynamic binding of the selected adsorbents for 75 mL sample injection of 2 mg/mL mAb solutions. 75 ml injection of ~2 mg/ml mAb sample; Flow rate 60 CV

| Entry | Adsorbent | mAb Id (mg/mL) | Injected Ab (mg) | Eluted Ab (mg) | Elution % | Recovered Ab (mg) | Recovery % | Status | Wash for unbound (CV) |
|---|---|---|---|---|---|---|---|---|---|
| 1 | 2QSEA | 8.5 | 161 | 54 | 33 | 159 | 98 | Fresh | 5 |
| 2 | | 8.5 | 157 | 54 | 34 | 151 | 96 | Reuse 1 | 5 |
| 3 | | mAbA 11 | 140 | 32 | 23 | 136 | 96 | Reuse 2 | 5 |
| 4 | | mAbA 11 | 137 | 37 | 27 | 136 | 99 | Fresh | 5 |
| 6 | 4NO$_2$-2PSEA | mAbA 11 | 143 | 58 | 40 | 140 | 98 | Fresh | 5 |
| 5 | | 8.5 | 153 | 63 | 41 | 153 | 99 | Reuse 1 | 5 |
| 7 | 6OMe-2PSEA | mAbA 11 | 121 | 36 | 30 | 121 | 100 | Fresh | 5 |
| 8 | | 8.5 | 129 | 41 | 32 | 128 | 99 | Reuse 1 | 5 |
| 9 | | 8.5 | 129 | 35 | 27 | 128 | 100 | Reuse 2 | 10 |
| 10 | | mAbA 11 | 139 | 30 | 22 | 138 | 99 | Reuse 3 | 20 |
| 11 | 6OMe-2PSEA | 8.5 | 144 | 48 | 33 | 142 | 99 | Fresh | 5 |
| 12 | | mAbA 11 | 146 | 46 | 32 | 142 | 98 | Reuse 1 | 5 |
| 13 | | mAbA 11 | 143 | 34 | 24 | 140 | 98 | Reuse 2 | 20 |
| 14 | | mAbA 11 | 144 | 20 | 14 | 144 | 100 | Reuse 3 | 30 |
| 15 | TerPSEA | mAbA 11 | 155 | 17 | 11 | 155 | 99 | Fresh | 5 |
| 16 | | mAbA 11 | 155 | 7 | 5 | 154 | 100 | Reuse 1 | 30 |
| 17 | | 8.5 | 159 | 37 | 23 | 158 | 99 | Reuse 2 | 5 |
| 18 | | mAbB 11 | 163 | 30 | 18 | 163 | 100 | Reuse 3 | 5 |

TABLE AR-continued

Relative dynamic binding of the selected adsorbents for 75 mL sample injection of 2 mg/mL mAb solutions.
75 ml injection of ~2 mg/ml mAb sample; Flow rate 60 CV

| Entry | Adsorbent | mAb Id (mg/mL) | Injected Ab (mg) | Eluted Ab (mg) | Elution % | Recovered Ab (mg) | Recovery % | Status | Wash for unbound (CV) |
|---|---|---|---|---|---|---|---|---|---|
| 19 | 5Br-2PSEA | 6.7 | 156 | 66 | 42 | 156 | 99 | Fresh | 5 |
| 20 | | 8.5 | 156 | 65 | 42 | 154 | 98 | Reuse 1 | 5 |

TABLE AS

Relative dynamic binding results of the selected adsorbents for 20 mL sample injection of 2 mg/mL mAb solutions.
20 ml injection of ~2 mg/ml mAb B new sample; Flow rate 60 CV; Wash for unbound mAb 5 CV

| Entry | Adsorbent | Injected Ab (mg) | Eluted Ab (mg) | Elution % | Recovered Ab (mg) | Recovery % | Status | mAb used (mg/ml) |
|---|---|---|---|---|---|---|---|---|
| 1 | 4NO$_2$-2PSEA | 42 | 36 | 86 | 41 | 99 | Fresh | mAbB (6.7) new sample |
| 2 | | 41 | 33 | 80 | 39 | 97 | Reuse 1 | IgG 8.5 |
| 3 | | 39 | 33 | 85 | 39 | 99 | Reuse 2 | mAbB old sample |
| 4 | 2QSEA | 35 | 27 | 77 | 34 | 99 | Fresh | mAbB (6.7) new sample |
| 5 | 6-OMe-2PSEA | 35 | 31 | 89 | 33 | 97 | Fresh | mAbB (6.7) new sample |
| 6 | TerPSEA | 39 | 26 | 67 | 37 | 97 | Fresh | mAbB (6.7) new sample |
| 7 | 5Br-2PSEA | 41 | 33 | 80 | 41 | 100 | Fresh | mAbB (6.7) new sample |
| 8 | | 39 | 29 | 74 | 38 | 97 | Reuse 2 | mAbB old sample |

TerPSEA showed very high affinity, particularly for mAb A antibodies where dynamic equilibrium was achieved in a shorter time compared to the other immobilised ligands. However, the elution process was also very fast. These effects may be explained by the static binding results. Also, the $K_D$ value indicates that TerPSEA is a fast binder but also showed weak binding resulting in low antibody elution. However other immobilised ligands are slow binders but eluted more antibody amount.

TABLE AT

Amount of mAb bound using selected adsorbents.

| | 75 ml injection | |
|---|---|---|
| Adsorbents | % Ab Bound | Ab amount bound (mg) |
| Seph-5Br-2PSEA | 42 | 66 |
| Seph-4NO2-2PSEA | 41 | 63 |
| Seph-2QSEA | 34 | 54 |
| Seph-6OMe-2PSEA | 33 | 48 |
| Seph-TerPSEA | 23 | 37 |

8.4. Dynamic Binding Studies with Transferrin-related Proteins

The transferrin sample ((~1 mg/mL) was prepared in a binding buffer and loaded onto a column at constant flow rate (1 mL/min). The column was then washed with 5 column volumes before elution with a salt free buffer. The elution examined isocratic and gradient elution conditions (see FIG. 14 and FIG. 15).

While evaluating the binding affinities (static binding studies) for the transferrin-related proteins it was found that all adsorbents have better binding at low pH and low or zero salt concentrations and very poor binding in the presence of salt. Therefore, the following conditions were tested for elution.

25 mM NaOAc pH 5.0 or
25 mM Hepes pH 7.0, gradient 0-300 mM Na$_2$SO$_4$ (length of gradient 3 mL)

While testing 2PSEA, 4PSEA, 4Me-2PSEA and 5Br-2PSEA adsorbents for their dynamic binding capacities it was observed that all these ligands have good binding affinity. However 5Br-2PSEA showed higher static binding for various binding conditions (referring to static binding results). It may suggest this adsorbent bound transferrin-related biomolecules faster and stronger and reached equilibrium more quickly but then eluted lower amounts. This could be due to strong interaction between the adsorbent and transferring-related proteins, which therefore makes dissociation difficult. The eluted fraction samples were collected and analysed at 280 nm using a UV spectrophotometer to calculate the amount of eluted protein. The original sample of transferrin for every column was also analysed to calculate the total amount of protein injected on the column, the total percentage recovery of protein and the percentage in the eluted fractions.

TABLE AU

Relative dynamic binding for the selected adsorbents for 5 mL sample injection of 1 mg/mL Tf solution. (* is for bovine holo transferrin and rest of the results are for recombinant human transferrin chimeric fusion protein-F).
5 ml injection of ~1 mg/ml Tf sample; Flow rate 60 CV; 5 CV wash for unbound Tf.

| Adsorbent | Injected Tf (mg) | Eluted Tf (mg) | Elution % | Recovery % | Status | Elution method |
|---|---|---|---|---|---|---|
| 5Br-2PSEA | 3.9 | 2.0 | 49.6 | 91.9 | Fresh | Step |
| | 4.2 | 3.1 | 74.7 | 91.8 | Reuse 1 | Gradient |
| | 4.7 * | 4.2 | 90 | 99 | Fresh | Step |
| | 4.7 * | 3.3 | 71.0 | 98.1 | Fresh | Gradient |
| 2PSEA | 4.1 | 3.9 | 95.8 | 95.7 | Fresh | Gradient |
| | 4.1 | 3.7 | 92.0 | 91.5 | Reuse 1 | Step |
| 4PSEA | 4.1 | 3.8 | 95.0 | 94.2 | Fresh | Step |
| | 4.1 | 3.7 | 92.0 | 90.0 | Reuse 1 | Gradient |
| 4Me-2PSEA | 4.7 | 3.8 | 75.0 | 81.2 | Fresh | Step |
| | 3.7 | 3.6 | 92.0 | 99.0 | Reuse 1 | Gradient |
| | 4.7 | 3.8 | 81.0 | 88.0 | Fresh | Gradient |
| | 3.7 | 3.5 | 94.5 | 99.4 | Reuse 1 | Gradient |

Figure 16:
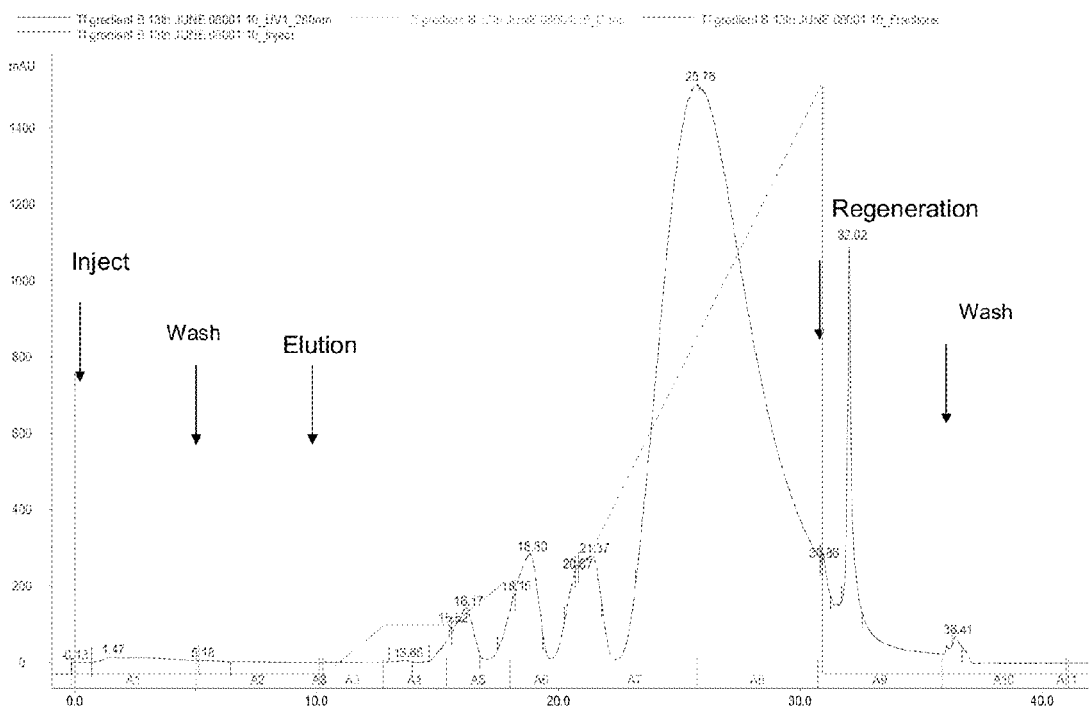
FIG. 16: Dynamic binding of 4Me-2PSEA for the recombinant human transferrin chimeric fusion protein-F (gradient and step elution combination)

The chromatogram obtained by combining steps and gradients for elution showed 3 samples of transferrin-related proteins were eluted prior to recovery of the bulk of the protein (see FIG. 16). The fractions were analysed by SDS-PAGE.

Figure 14:
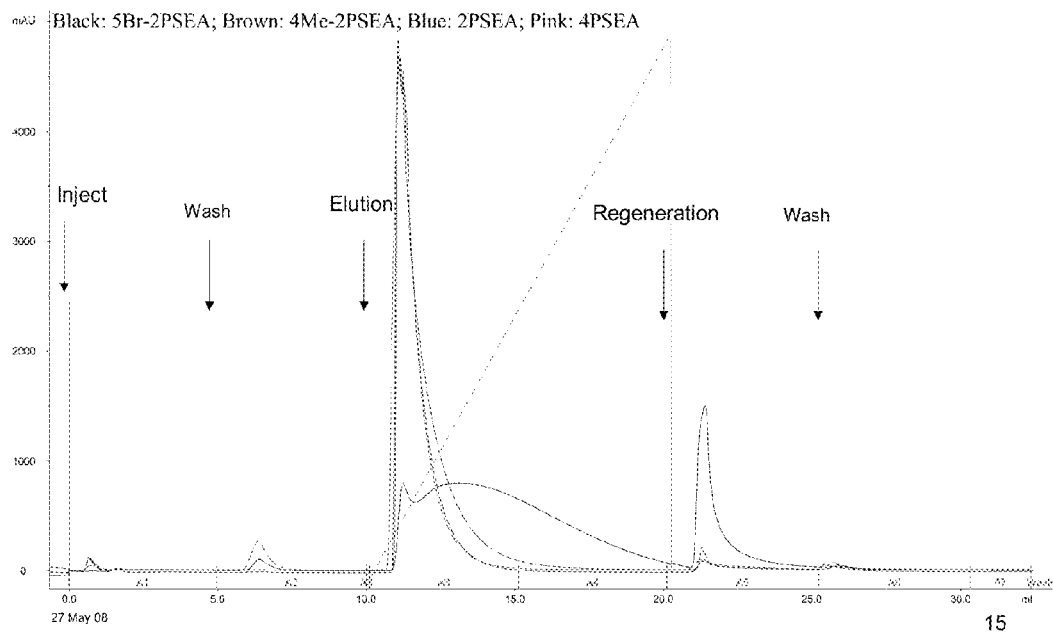
FIG. 14: Relative dynamic binding of adsorbents for transferrin (gradient elution) Chromatograms show relative dynamic binding affinities of 5 ligands (–) 5Br-2PSEA, (–) 4Me-2PSEA, (–) 2PSEA and (–) 2PSEA.
Figure 15:
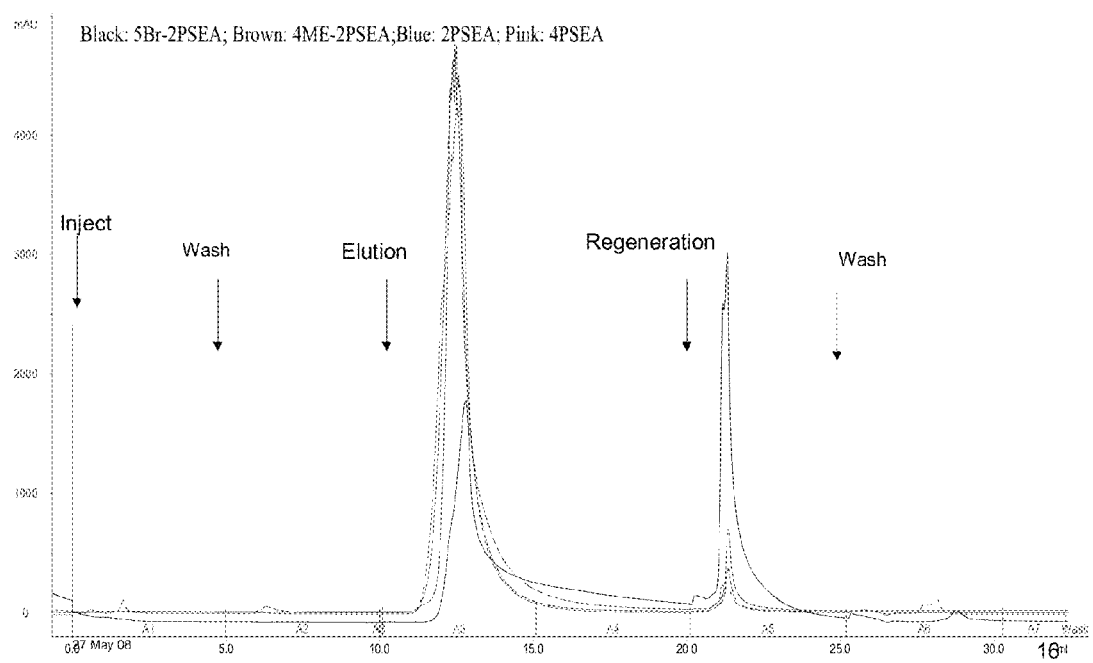
FIG. 15: Relative dynamic binding of adsorbents for recombinant human transferrin chimeric fusion protein-F (Step elution condition) Chromatograms show relative dynamic binding affinities of five ligands (–) 5Br-2PSEA, (–) 4Me-2PSEA, (–) 2PSEA and (–) 2PSEA.

Comparative chromatograms for both gradient and step elution conditions are presented in FIGS. 14 and 15, respectively.

8.4.1. SDS-PAGE

Figure 17:
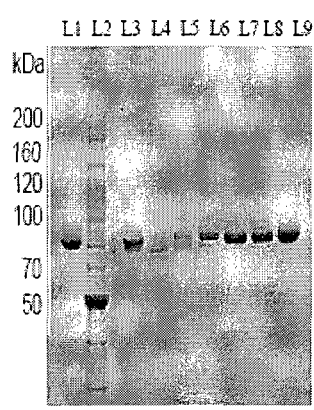
FIG. 17: SDS-PAGE of the fractionated Tf species from the 2PSEA column using a 5-segment gradient elution protocol. Stained with Coomassie Brilliant Blue; L1-Tf; L2-Standards; L3-Tf; L4-A6 ($1^{st}$ fraction); L5-A8 (2" fraction); L6-A12 ($3^{rd}$ fraction); L7-B11 ($4^{th}$ th fraction); L8-B10 ($5^{th}$ th fraction).
Figure 18:
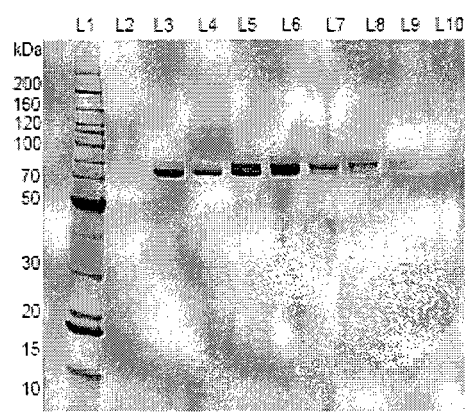
FIG. 18: SDS-PAGE of the fractionated Tf species from the 2PSEA column using a 7-segment gradient elution protocol. Stained with Coomassie Brilliant Blue; L1-Standards; L2-A6 ($1^{st}$ fraction); L3-A8 ($2^{nd}$ fraction); L4-A11 ($3^{rd}$ fraction); L5-B11 ($4^{th}$ fraction); L6-B10 ($4^{th}$ fraction); L7-B8 ($5^{th}$ th fraction); L8-B7 ($6^{th}$ th fraction); L10-B3 ($7^{th}$ fraction).

Protein purity was evaluated by SDS-PAGE analysis following visualization by Coomassie blue and/or silver staining. The representatives SDS-PAGE of the collected fractions are given above in FIGS. 17 and 18.

8.5. Dynamic Binding Studies of the Recombinant Chimeric Fusion Proteins

Dynamic binding capacities of selected adsorbents (4PSEA, 2QSEA and 4NO$_2$-2PSEA) were evaluated using 1 mL FPLC columns. The experiments were performed using various concentrations (dilution of 1:2 and 1:10), volumes (1 mL, 5 mL) and flow rates (60 CV and 20 CV) for samples of pure recombinant chimeric fusion protein-A. This was followed by running a column for recombinant chimeric fusion protein-A, recombinant chimeric fusion protein-B and recombinant chimeric fusion protein-E.

8.5.1. FPLC of Recombinant Chimeric Fusion Protein-A

The recombinant chimeric fusion protein-A sample was prepared in a binding buffer and injected onto a column at constant flow rate 1 mL/min. The column was then washed with 5 column volumes before elution with a salt free buffer to remove unbound protein. Samples were eluted by isocratic or gradient elution conditions.

Figure 19:
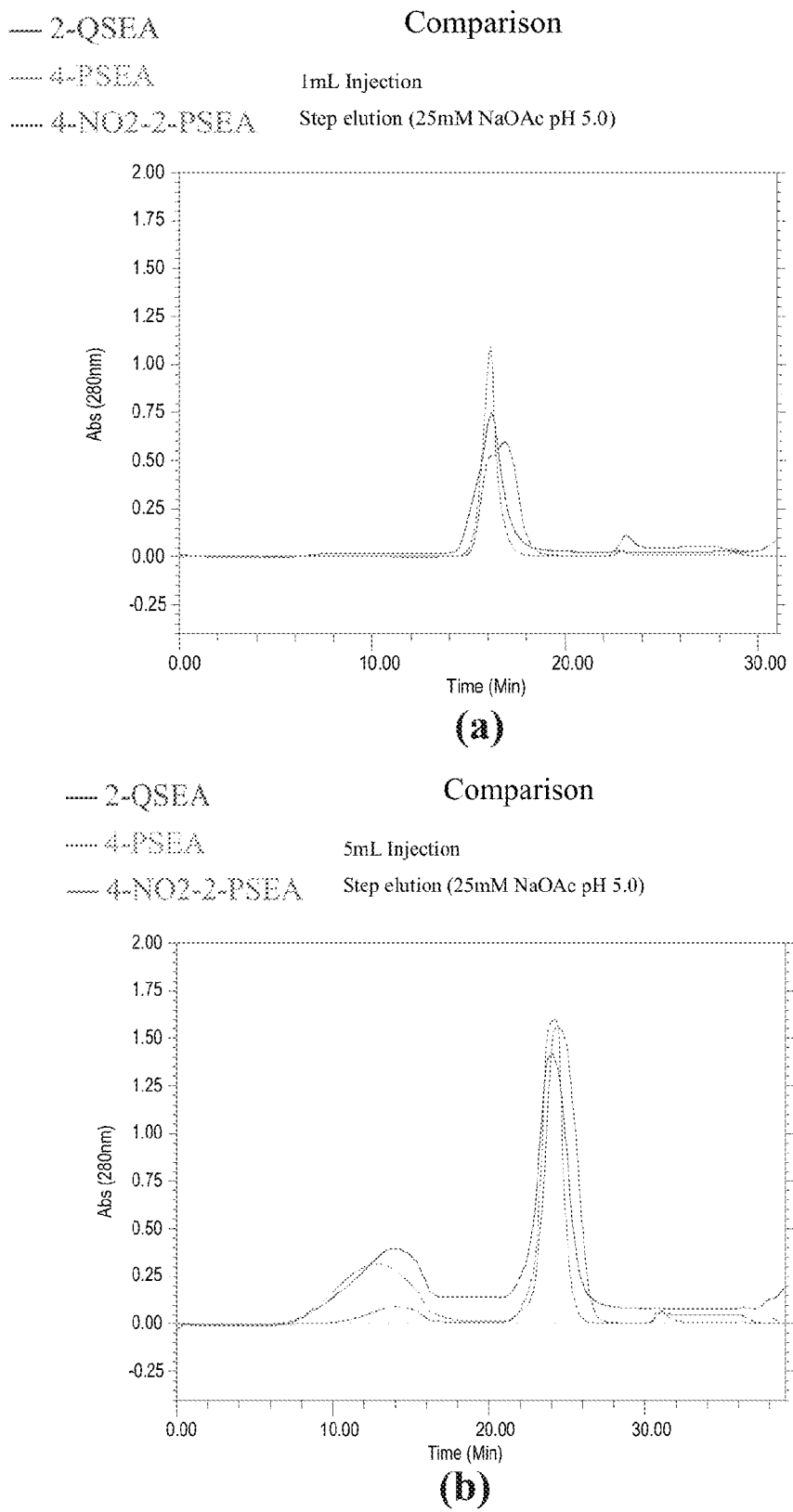
FIG. 19: Chromatograms of elution comparison for different conditions using adsorbents 2QSEA, 4PSEA and 4NO2-2PSEA. a) 1 mL injection, b) 5 mL injection, c) 1 mL injection 0-1M NaCl, gradient elution, d) 1 mL injection 0-600 mM $Na_2SO_4$, gradient elution.
Figure 19:
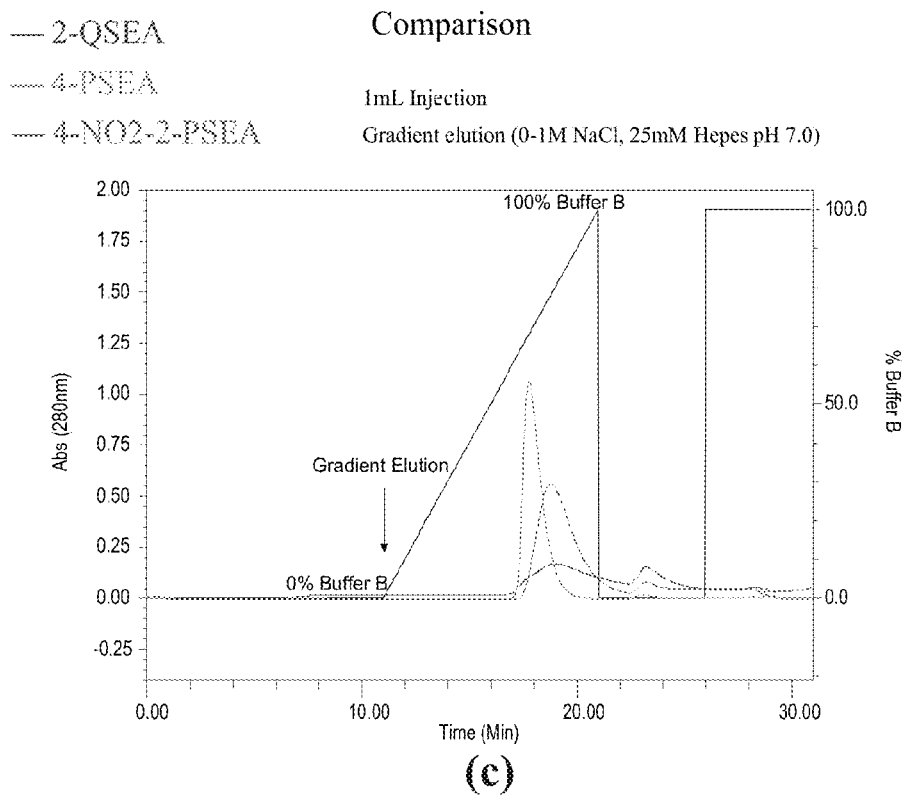
Figure 19:
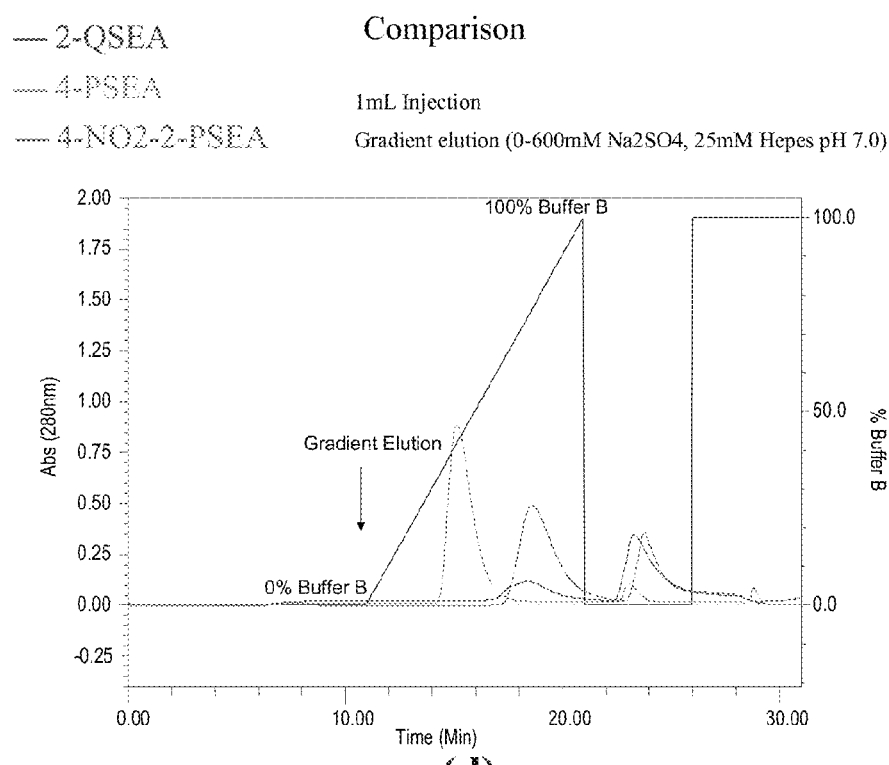
Figure 21:
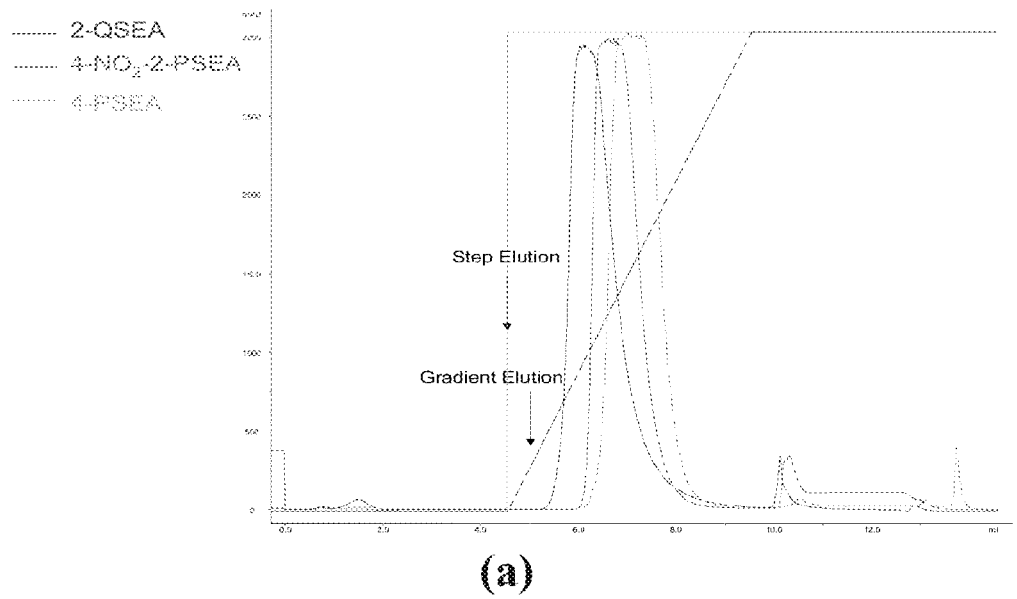
FIG. 21: Chromatograms of elution comparison for different conditions using adsorbents 2QSEA, 4PSEA and $4NO_2$-2PSEA. a) 1 mL injection and b) 5 mL injection of recombinant chimeric fusion protein-E
Figure 21:
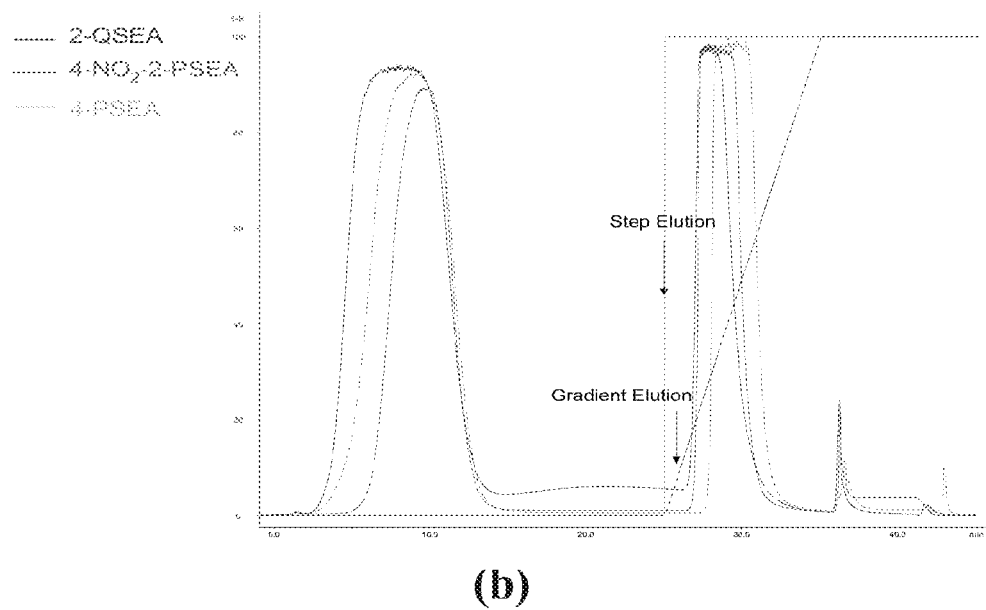

While evaluating the binding affinities (static binding studies) for the recombinant chimeric fusion proteins it was found that all adsorbents have better binding at low pH and low or zero salt concentrations and poor binding in the presence of salt. Therefore, the following conditions were tested for elution of the recombinant chimeric fusion proteins 1. 25 mM NaOAc pH 5.0 (5 mL) or
2. 25 mM Hepes pH 7.0 Gradient 0-1 M NaCl or
3. 25 mM Hepes pH 7.0 Gradient 0-600 mM Na$_2$SO$_4$ Testing of the 4PSEA, 2QSEA and 4NO$_2$-2PSEA adsorbents for their dynamic binding capacities confirmed that all these ligands have good binding affinity. However, 4PSEA showed not only good binding, but eluted higher amount of recombinant chimeric fusion proteins under all elution conditions. This indicates that 4PSEA binds under specific binding condition (FIG. 19). Comparative chromatograms for all elution condition are given below. FIGS. 21 (*a*), (*b*) represent elution for 1 mL and 5 mL sample injection respectively under isocratic elution conditions; (*c*), (*d*) represent gradient elution for 1 mL and 5 mL sample injection respectively. Under all conditions high recovery occurred with the sep-4PSEA for the recombinant chimeric fusion proteins.

TABLE AV

Recombinant chimeric fusion protein-A elution % and recovery % under various elution conditions for 4PSEA fractional collections.

| Entry | Conditons | Amount loaded Ab (mg) | Flow rate CV/hr | Eluted Ab (mg) | Elution % |
|---|---|---|---|---|---|
| 1 | 1 mL Protein 1:2 dil. 25 mM Hepes pH 6.87 | 1.87 | 60 | 1.035 | 55 |
| 2 | 1 mL Protein 1:2 dil. 50 mM Hepes pH 7.2 | 1.6 | 60 | 1.0175 | 64 |
| 3 | 1 mL Protein 1:2 dil. 25 mM Hepes pH 6.87 gradient elution 0-1M NaCl | 1.61 | 60 | 0.122 | 76 |
| 4 | 1 mL Protein 1:2 dil. 25 mM Hepes pH 6.87 gradient elution 0-600 mM Na$_2$SO$_4$ | 1.577 | 60 | 1.17 | 74 |

TABLE AV-continued

Recombinant chimeric fusion protein-A elution % and recovery % under various elution conditions for 4PSEA fractional collections.

| Entry | Conditons | Amount loaded Ab (mg) | Flow rate CV/hr | Eluted Ab (mg) | Elution % |
|---|---|---|---|---|---|
| 5 | 1 mL Protein 1:10 dil. 25 mM Hepes pH 6.88 | 1.6 | 60 | 1.18 | 74 |
| 6 | 5 mL Protein 1:2 dil. 25 mM Hepes pH 6.87 | 8.425 | 60 | 4.36 | 52 |
| 7 | 5 mL Protein 1:2 dil. 25 mM Hepes pH 6.87 | 8.015 | 20 | 4.8 | 60 |

The eluted fractional samples were collected and then analysed at 280 nm using a UV spectrophotometer to calculate the percentage of eluted protein. The original sample of protein for every column was also analysed to calculate the total amount of protein injected on the column and the total amount of eluted protein (Table AV).

8.5.2. FPLC of Recombinant Chimeric Fusion Protein-B

Figure 20:
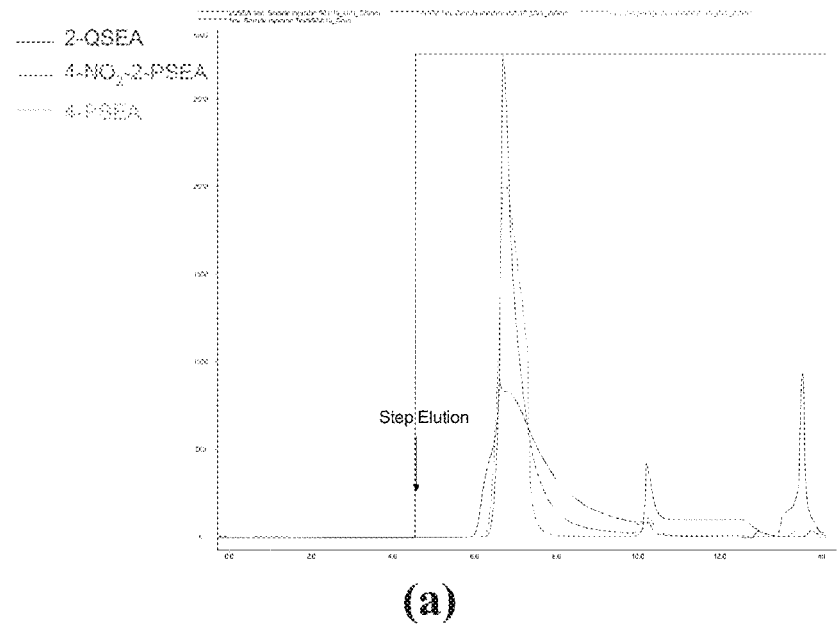
FIG. 20: Elution comparison under various conditions for adsorbents 2QSEA, 4PSEA and $4NO_2$-2PSEA. a) 1 mL injection and b) 5 mL injection of recombinant chimeric fusion protein-B.
Figure 20:
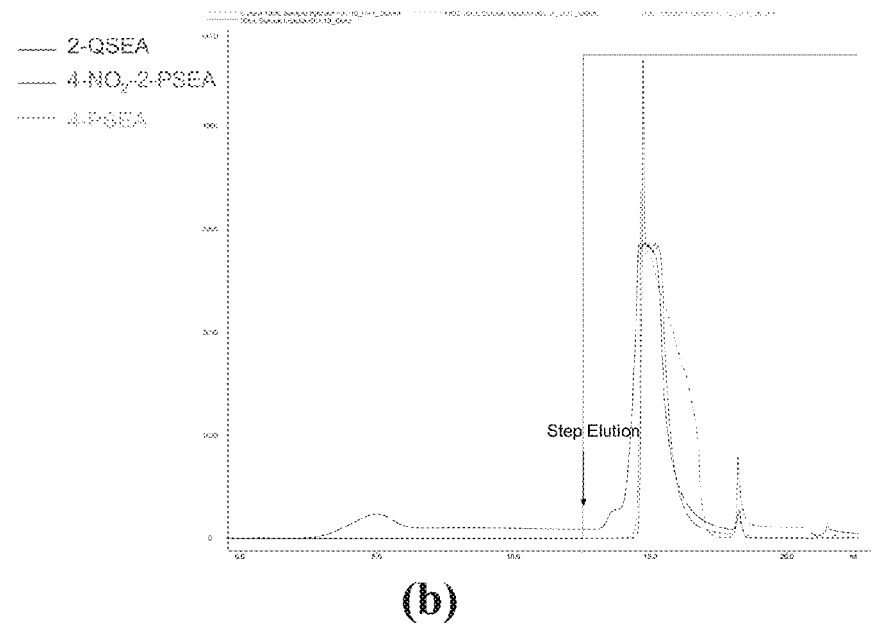

A 1 mL FPLC column was used to test the adsorbents 4PSEA, 2QSEA and 4NO$_2$-2PSEA for their dynamic binding capacities towards recombinant chimeric fusion protein-B. During static binding studies, 4PSEA showed good binding affinity at pH 7 with zero Na$_2$SO$_4$ salt. A dynamic binding study of these three immobilised ligands was performed on 1 mL column by injecting 1 mL and 5 mL of the recombinant chimeric fusion protein-B samples. Elution was carried out under isocratic conditions. The elution buffer used was 25 mM NaOAc pH 5.0, (5 mL). It was found that 4PSEA has good binding affinity and can elute a higher concentration of recombinant chimeric fusion protein-B than either of the 4NO$_2$-2PSEA and 2QSEA ligands. (FIG. 20: a, b).

8.5.3. FPLC of the Recombinant Chimeric Fusion Protein-E.

While studying dynamic binding capacities for this recombinant chimeric fusion protein, successful protein elution could not be achieved under isocratic conditions using 25 mM Tris buffer, at pH 9 for 4PSEA. However, elution was achieved using a salt gradient (0-1 M NaCl Gradient, 25 mM Hepes pH 7.0, 5 mL). 2-QSEA and 4-NO$_2$-2PSEA adsorbents eluted the recombinant chimeric fusion protein-E successfully using 25 mM Tris pH 9.0, step elution.

Comparisons of the 1 mL sample injection-elution and 5 mL sample injection-elution, by using gradient elution from buffer A (25 mM Hepes pH 7.0) to buffer C (1 M NaCl, 25 mM Tris pH 7.0), are shown in FIG. 8.18, a and b. For the recombinant chimeric fusion protein binding, adsorbents TerPSEA, 6OMe-2PSEA, 4NO$_2$-2PSEA showed good static binding capacities. 2QSEA showed the highest binding affinity of all ligands and retained the majority of the recombinant chimeric fusion proteins. 4PSEA showed lower binding capacity but appeared to have the best selectivity under binding conditions. The static binding study also showed that 4PSEA was very specific for binding conditions and eluted the maximum amount of recombinant chimeric fusion proteins. This may suggest that the adsorbent has reached equilibrium and has become saturated with recombinant chimeric fusion proteins therefore leading to elution of higher purity. Consequently larger amount of recombinant chimeric fusion proteins were eluted in 4PSEA fractions, compared to those of 4NO$_2$-2PSEA and 2QSEA possibly due to faster adsorption rate for desired protein molecule. These ligands except 4PSEA showed higher binding for various binding conditions. It can be suggested that these adsorbents bind recombinant chimeric fusion proteins and other proteins faster and stronger and reached equilibrium more quickly. This could be due to strong interaction between the adsorbent and recombinant proteins.

9. Purification of Crude mAb

Figure 22:
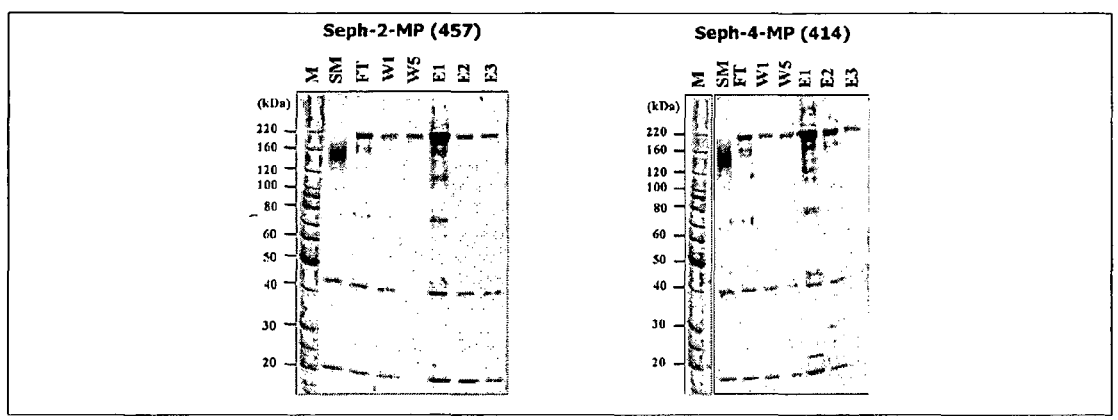
FIG. 22: 7.5-15% SDS-PAGE of mAb fractions collected by MP adsorbents.
Figure 23:
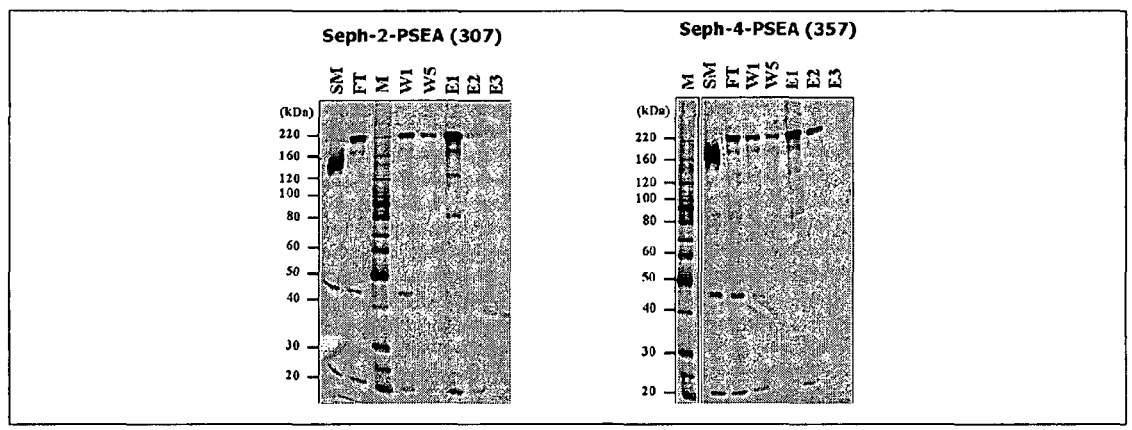
FIG. 23: 7.5-15% SDS-PAGE of mAb fractions collected by PSEA adsorbents.

Open column studies: The ability of the novel adsorbents to bind mAb in crude cell lysates was investigated. The desired affinity adsorbent was equilibrated with binding buffer, the crude mAb sample loaded, the column washed with binding buffer and bound mAb eluted under the influence of 25 mM NaAc pH 5 (i.e. low pH, no salt). Eluted fractions were analysed by gradient (7.5-15%) SDS-PAGE and silver stained according to the method of Swain.[42] Silver staining was the method of choice for analysis of purifications with crude material due to its increased sensitivity over Coomassie staining methods.[46] The results for four of the adsorbents tested are shown below, FIGS. 22 and 23.

In this experiment (see FIG. 22) a 0.2 mL bed volume of the adsorbent was equilibrated with binding buffer (25 mM Tris pH 9, 600 mM $Na_2SO_4$) and then the mAb sample (5.0 mg of crude mAb in 25 mM Tris pH 9, 600 mM $Na_2SO_4$) (20 mL) was loaded. SM=starting material, M=markers, FT=flow through, W1-W5=wash (25 mM Tris pH 9, 600 mM $Na_2SO_4$), E1-E3=elution (25 mM NaAc pH 5).

In this experiment a 0.2 mL bed volume of the adsorbent was equilibrated with binding buffer (25 mM Tris pH 9, 600 mM $Na_2SO_4$) and then the mAb sample (5.0 mg of crude mAb in 25 mM Tris pH 9, 600 mM $Na_2SO_4$) (20 mL) was loaded. SM=starting material, M=markers, FT=flow through, W1-W5=wash (25 mM Tris pH 9, 600 mM $Na_2SO_4$), E1-E3=elution (25 mM NaAc pH 5).

All adsorbents tested in this experiment were found to bind the test monoclonal antibodies under typical chromatographic conditions although with varying affinity. By comparing the starting material (SM) to the elution fractions (E1-E3), the specificity/selectivity of the adsorbents can be observed, as well as any concentration of the sample. These silver stained SDS-PAGE gradient gels (7.5-15%) (FIG. 22 and FIG. 23) show that, besides the mAb at ca. 150 kDa, there are four other species within the crude sample (ca. 120, 80, 45, 20 kDa). Since these specific mAbs have been prepared via a cell culture system using chemical defined media (no foetal calf serum present), the presence of only a few contaminating proteins is not unexpected.

9.1. Evaluation of Contamination Bands

In order to determine what the low molecular weight (MW) bands bound to the adsorbents might represent, these proteins were isolated and analysed by mass spectroscopy. In order to prepare the samples, electrophoresis of the crude sample was carried out on a gradient (7.5-15%) SDS-PAGE and the resulting gel stained with Coomassie dye. The lower MW bands from the gel (120, 80, 45, 20 kDa) were subjected to a trypsin digestion[†].[47] The samples were then submitted for MALDI-TOF[††] mass spectral analysis. The results of the mass spectra, were entered into the Swiss Protein Database[48] using MS-Fit software (peptide mass fingerprinting tool developed by Peter Baker and Karl Clauser at UCSF) which showed a good fit (MOWSE score[†††] of 199) for the presence of Ig kappa chain V-III regions (Swiss Protein accession numbers P01620 and P01623) for three out of the four lower MW bands (80, 45, 20 kDa). It is therefore probable that the lower MW bands represent proteolytic cleavage products of monoclonal IgG and would therefore show similar affinity to the adsorbents as the intact mAb (150 kDa).

[†] Typsin digestion was performed using the optimised detergent-mediated conditions developed in the Hearn Laboratory.
[††] Matrix assisted laser desorption/ionisation—time of flight (MALDI-TOF) mass spectral analysis was performed on a Voyager DE-STR (Applied Biosystems) in the Hearn Laboratory.
[†††] Based on scoring system described in Pappin et al., Current Biology, 1993, 3, 327.

9.1.1. Loading Conditions Experiments

Figure 24:
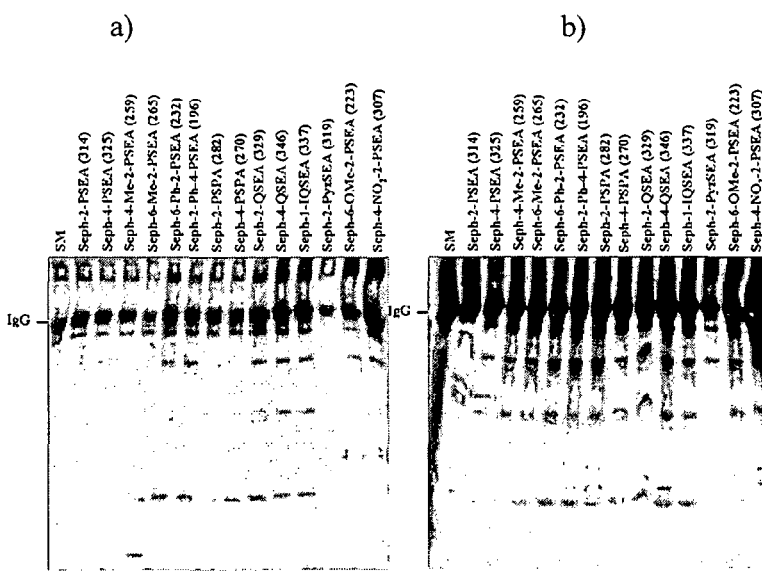
FIG. 24: 7.5-15% SDS-PAGE of first elution fraction (E1) collected by various adsorbents.

The ability of the adsorbents to selectively bind to intact mAb over other species present in the crude sample was studied by varying the concentration of the mAb loaded. All adsorbents, with >15 mg/mL gel capacity as assessed by the procedures outlined previously, were investigated. FIG. 24 shows the elution fractions (E1) obtained using two different concentrations of mAb. For these experiments, the adsorbents were loaded with the crude mAb sample in the presence of the binding buffer, and the flow through, washes and elutions (25 mM Hepes pH 7) collected. The samples were analysed by gradient 7.5-15% SDS-PAGE and silver staining. The main elution fraction (E1) from each adsorbent was then run on a gradient 7.5-15% SDS-PAGE and silver stained to compare purity.

Application of a low concentration of monoclonal antibody determined whether the adsorbents had the ability to capture mAbs under dilute conditions. By adding a low concentration of mAb, the column should be 'underloaded' with respect to its binding sites and would therefore highlight the selectivity of the particular adsorbent by putatively allowing other cellular proteins with potentially lower affinities to bind. To further analyse the selectivity of the adsorbent and determine if a certain loading concentration was required for maximum purification, the loading of the mAbs at low and higher concentrations was used.

In these experiments (see FIG. 24) the adsorbent (1 mL slurry) was incubated with the crude mAb (IgG) sample at a) low concentration (2.2 mg of mAb) and b) high concentration (20.5 mg of mAb) in 25 mM Tris pH 9, 600 mM $Na_2SO_4$ (50 mL total). The adsorbent was collected, then washed (25 mM Tris pH 9, 600 mM $Na_2SO_4$) and the bound mAb eluted (25 mM Hepes pH 7). SM=starting material.

Figure 25:
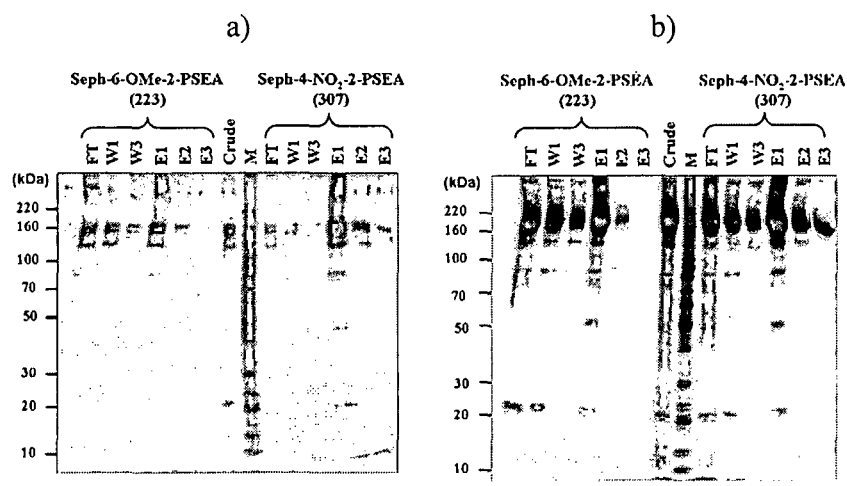
FIG. 25: 7.5-15% SDS-PAGE of chromatographic fractions collected by Seph-6-OMe-2-PSEA and Seph-4-$NO_2$-2-PSEA adsorbents. The adsorbent (1 mL) was incubated with the crude mAb (IgG) sample at a) low concentration (2.2 mg of mAb) and b) high concentration (20.5 mg of mAb) in 25 mM Tris pH 9, 600 mM $Na_2SO_4$ (50 mL total). The adsorbent was collected, then washed (25 mM Tris pH 9, 600 mM $Na_2SO_4$) and the bound mAb eluted (25 mM Hepes pH 7). SM=starting material, M=markers, FT=flow through, W1-W3=washes, E1-E3=elutions.

The higher loading concentration of mAb would illustrate the adsorbent's selectivity based on its ability to either bind the mAb preferentially or, once all of the binding sites are occupied, the intact mAb's ability to displace other species that may have already bound. In order to quantify the amount of protein recovered following purification with these affinity resins, the intensity of the Coomassie-stained SDS-PAGE protein bands in the E1 fractions of the higher concentration experiment were compared to a 10-fold concentration range of pure monoclonal antibody (FIG. 25). Most of the adsorbents evaluated in this preliminary study gave similar recoveries as determined from measurements with the Bio-Rad ChemiDoc scans of the corresponding SDS-PAGE gels.

Figure 26:
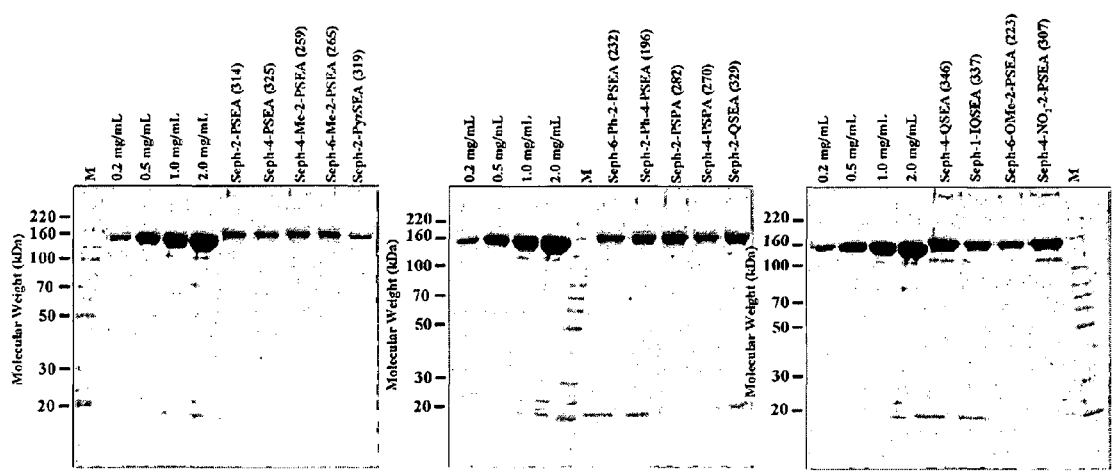
FIG. 26: 7.5-15% SDS-PAGE of first elution fraction (E1) collected by various adsorbents and referenced against different concentrations (0.2-2.0 mg/mL) of pure mAb.

In this experiment (see FIG. 26) the adsorbent (1 mL slurry) was incubated with the crude mAb sample (20.5 mg of mAb in 25 mM Tris pH 9, 600 mM $Na_2SO_4$) (50 mL total). The adsorbent was collected, then washed (25 mM Tris pH 9, 600 mM $Na_2SO_4$) and the bound mAb eluted (25 mM Hepes pH 7). M=markers.

9.1.2. Comparison of MEP HyperCel® and the Novel Adsorbents

Figure 27:
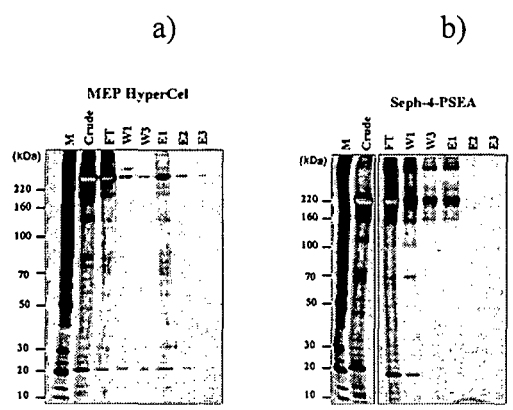
FIG. 27: 7.5-15% SDS-PAGE of chromatographic fractions a) collected by MEP HyperCel®; b) collected by Seph-4-PSEA; The adsorbent (1 mL slurry) was incubated with the crude mAb sample (10.8 mg of mAb in 25 mM Tris pH 9, 600 mM $Na_2SO_4$) (50 mL total). The adsorbent was collected, then washed (25 mM Tris pH 9, 600 mM $Na_2SO_4$) and bound mAb eluted (25 mM Hepes pH 7). Crude=crude mAb starting material, Pure=pure mAb sample, M=markers, FT=flow through, W1-W3=washes, E1-E3=elutions.

The novel adsorbents were compared to MEP HyperCel® by evaluating the ability of these adsorbents to bind mAbs from a crude sample under i) the conditions developed in these studies and ii) the conditions specified by the manufacturer of MEP HyperCel®. The outcome demonstrated greater purification with the new adsorbents and significantly lower levels of contaminants (FIGS. 27 (a) and (b)).

9.1.3. Purification of Crude mAb—by Gradient Elution Fast Protein Liquid Chromatography (FPLC)

FPLC gradient analysis was used to analyse the binding of the mAb to selected novel adsorbents and more accurately determine the optimal buffer conditions for elution of the proteins. Overall, gradient elution showed promise in the ability to selectively remove different bound species from the adsorbents, although under these conditions the results suggest that the intact mAb (150 kDa) and lower MW species have similar affinities for the adsorbents.

Figure 28:
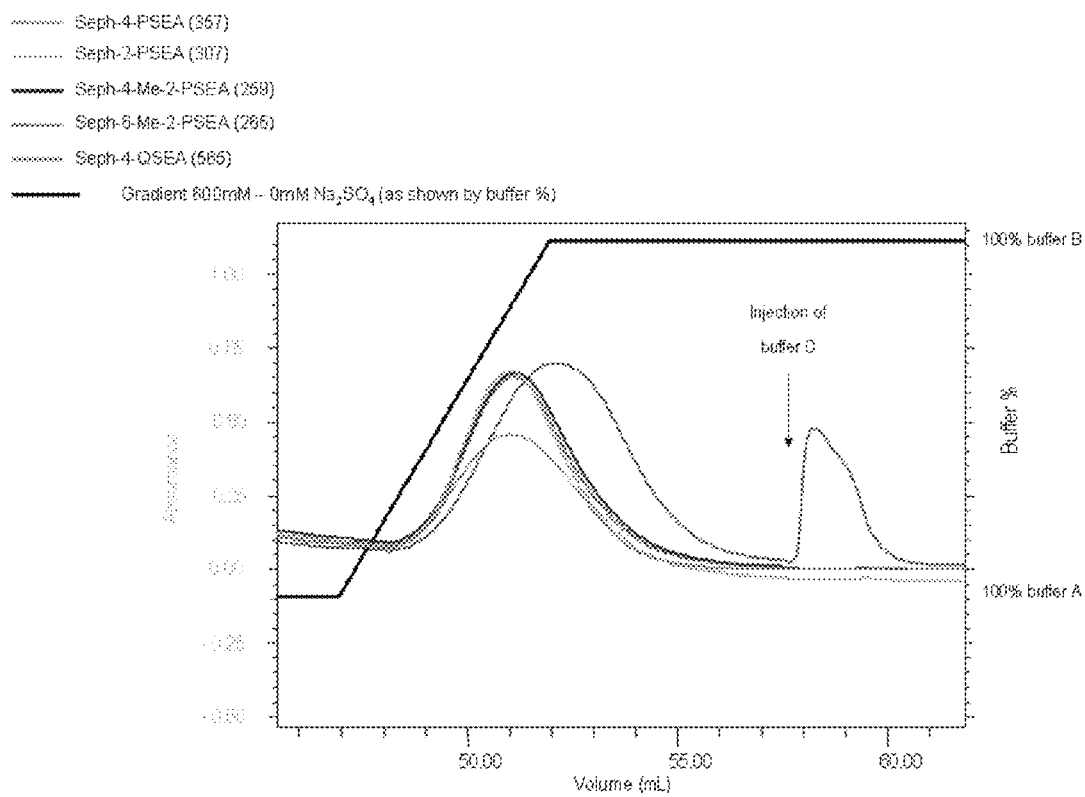
FIG. 28: Overlay of FPLC traces for gradient elution.

In this experiment (see FIG. 28) a 0.5 mL bed volume of the adsorbent was equilibrated with binding buffer (25 mM Tris pH 9, 600 mM $Na_2SO_4$) and then the crude mAb sample (10 mg of mAb in Buffer A–25 mM Tris pH 9, 600 mM $Na_2SO_4$) (40 mL) was loaded. The column was then washed (Buffer A–25 mM Tris pH 9, 600 mM $Na_2SO_4$) and bound mAb eluted using i) a salt gradient (100% Buffer A–100% Buffer B (25 mM Tris pH 9), ii) elution Buffer B (25 mM Tris pH 9), and iii) elution Buffer C (25 mM Hepes pH 7).

Figure 29:
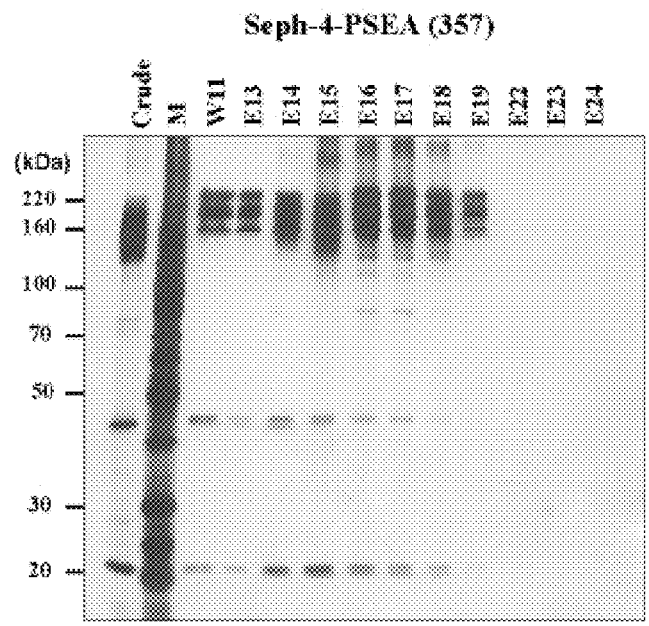
FIG. 29: 7.5-15% SDS-PAGE of chromatographic fractions collected by various adsorbents.
Figure 29:
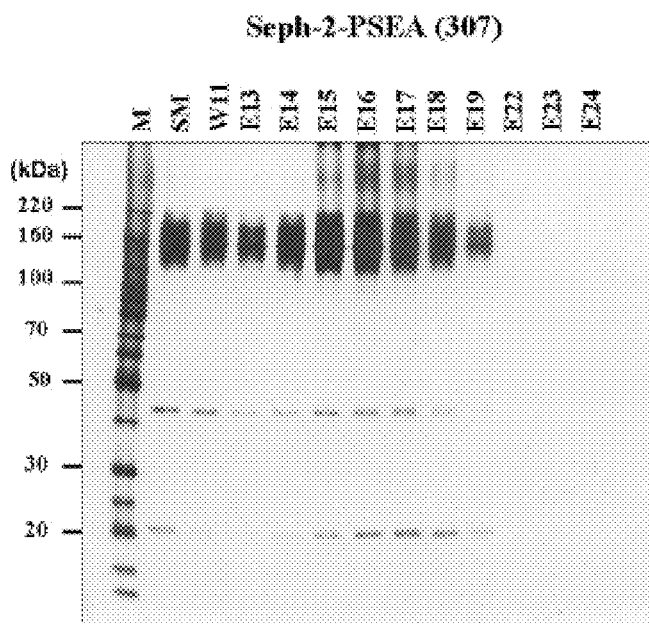
Figure 29:
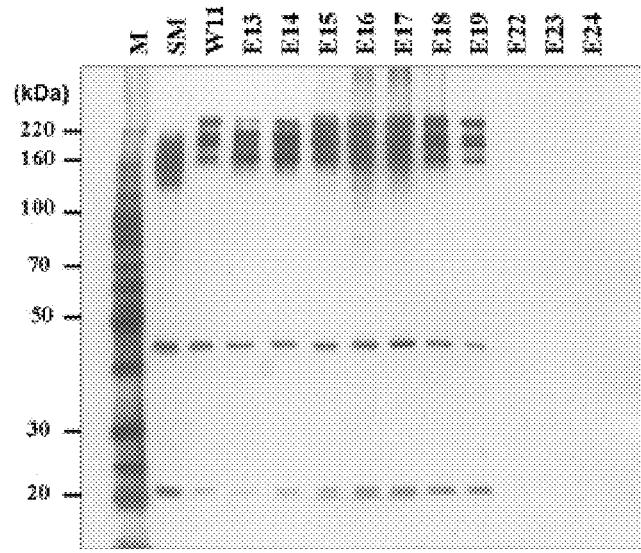
Figure 29:
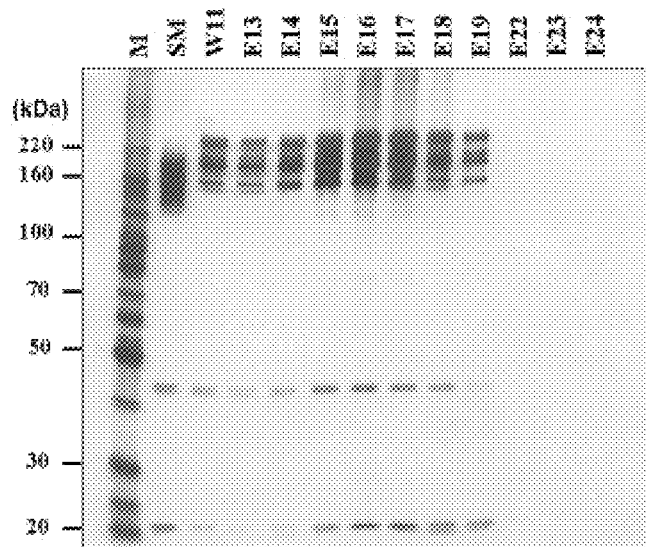
Figure 29:
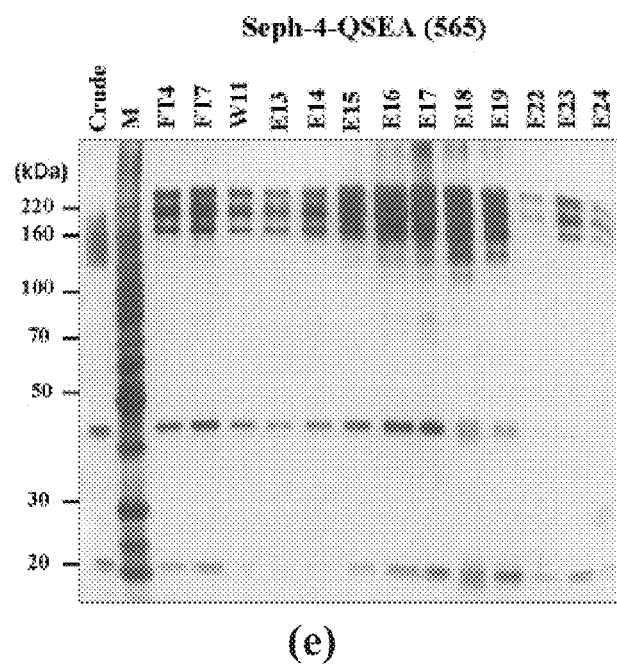

In this experiment (see FIG. 29) a 0.5 mL bed volume of the adsorbent was equilibrated with binding buffer (25 mM Tris pH 9, 600 mM $Na_2SO_4$) and then the crude mAb sample (10 mg of mAb in Buffer A–25 mM Tris pH 9, 600 mM $Na_2SO_4$) (40 mL) was loaded. The column was then washed (Buffer A–25 mM Tris pH 9, 600 mM $Na_2SO_4$) and bound mAb eluted using i) a salt gradient (100% Buffer A–100% Buffer B (25 mM Tris pH 9), ii) elution Buffer B (25 mM Tris pH 9), and iii) elution Buffer C (25 mM Hepes pH 7). Crude=crude mAb starting material, M=markers, FT2-FT9=flow through, W10-W11=washes, E12-E16=gradient elution, E17-E21=elution Buffer B, E22-E26=elution Buffer C.

9.1.4 Purification of mAb from MAb Broth

Figure 30:
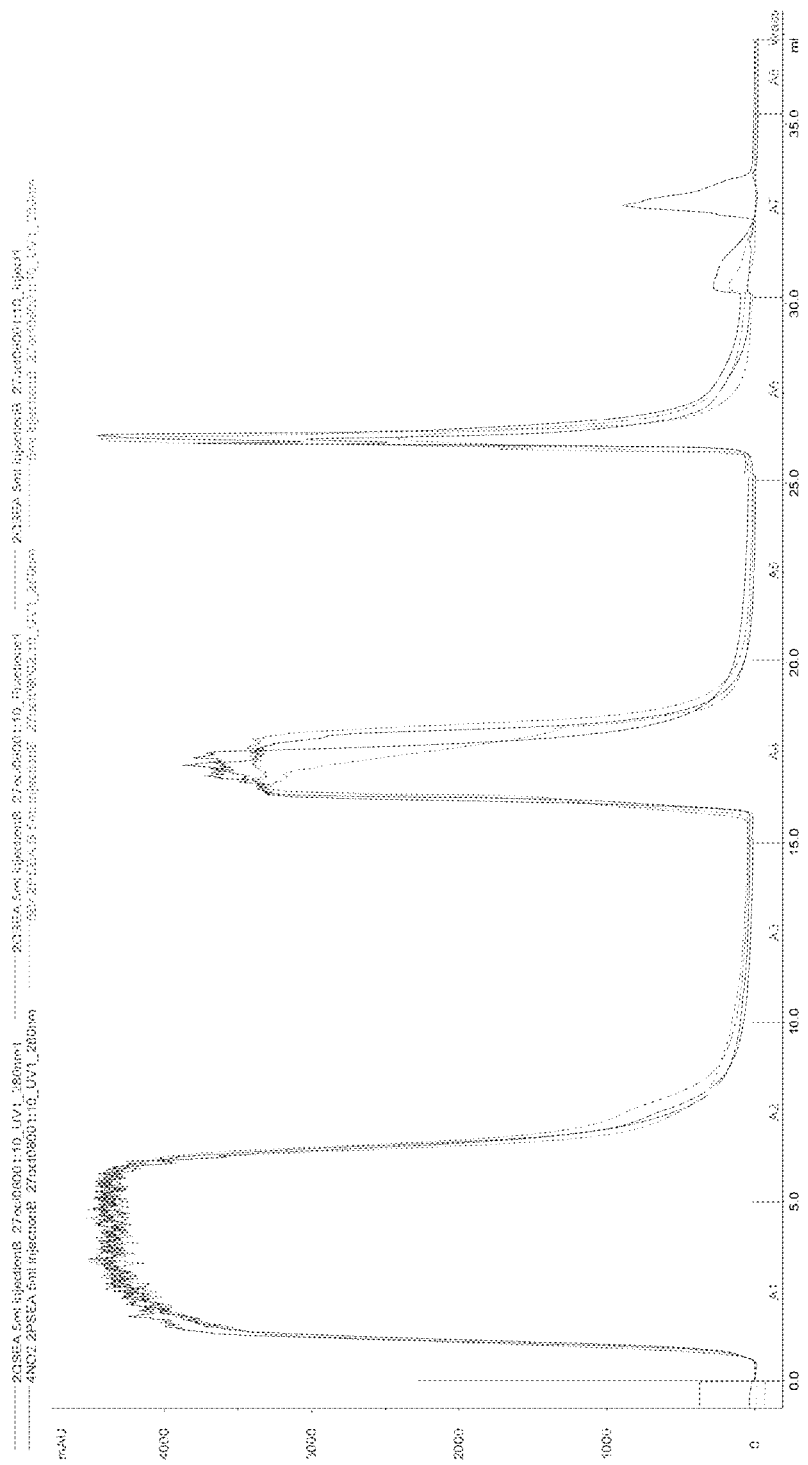
FIG. 30: Relative binding of 4 adsorbents for mAb broth. Chrom-atograms showed the separation/elution of pure mAb, (–) 2QSEA, (–) $4NO_2$-2PSEA, (–) 6OMe-2PSEA and (–) 5Br-2PSEA.

The binding affinity of selected adsorbents towards mAb was then further investigated using mAb broth. The desired affinity adsorbent on 1 mL scale was equilibrated with binding buffer (25 mM Tris pH 9, 600 mM $Na_2SO_4$), the mAb broth sample was loaded, the unbound protein was washed with binding buffer and bound mAb eluted by changing the buffer conditions (25 mM NaAc, pH 5, no salt). All four selected adsorbents were found to bind mAb with similar affinity. The method was validated for mAb separation from broth using 5Br-2PSEA, 4NO$_2$-2PSEA, 2QSEA and 6OMe-2PSEA shown in the following FIG. 30.

Figure 31:
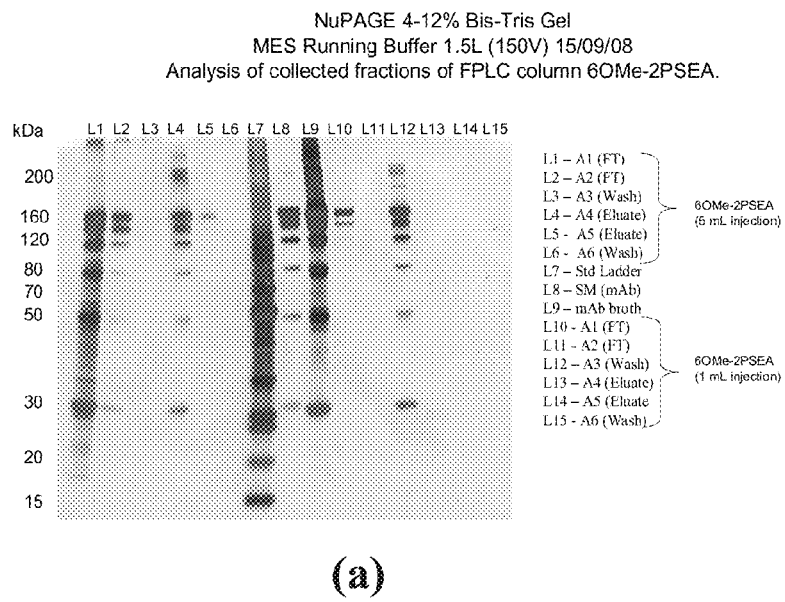
FIG. 31: SDS-PAGE of fractions collected from various adsorbents.
Figure 31:
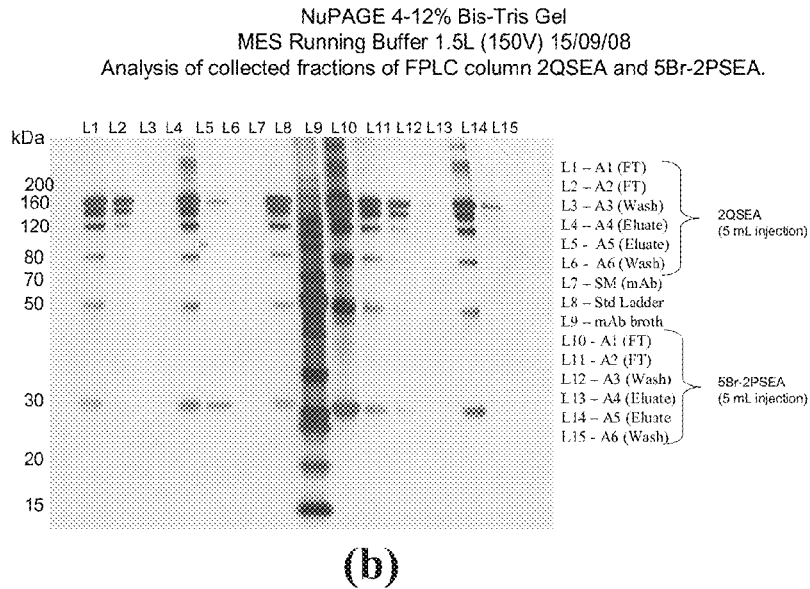
Figure 31:
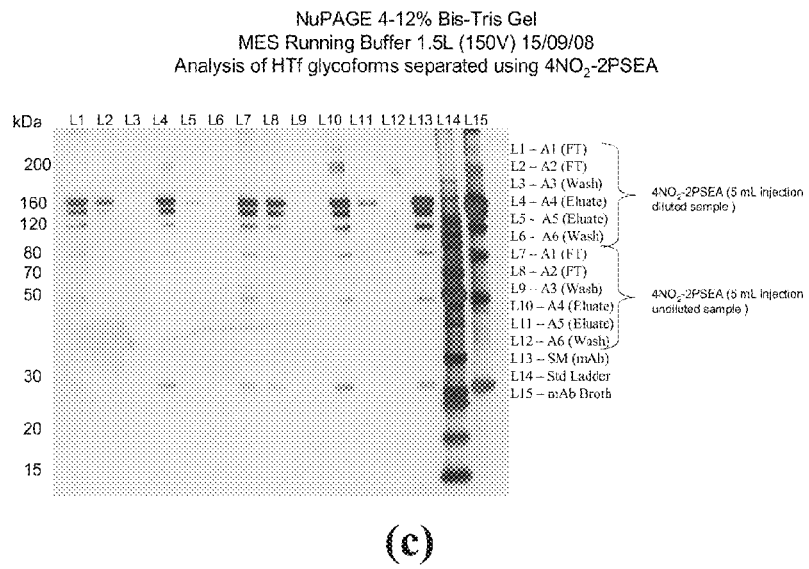

The collected fractions were analysed by electrophoresis using gradient SDS-PAGE, shown below in FIG. 31. The majority of adsorbed proteins eluted within the first elution fraction. A small amount of mAb was detected in the FT fractions of these adsorbents suggesting incomplete adsorption of total loaded mAb or saturation of binding sites on the adsorbent by the total mAb population initially loaded to the adsorbents. The wash fraction also contains traces of protein. The analysis of collected fraction is shown in FIG. 31 and Table AW.

TABLE AW

Amount of mAb separated (11.5 mg mAb were loaded) using selected adsorbents.

| Sample | Ligand | Ab amount bound (mg) |
|---|---|---|
| mAb Broth (2.3 mg/mL) | 4-NO2-2PSEA | 9.9 |
| | 5Br-2PSEA | 10.8 |
| | 6-OMe-2PSEA | 7.4 |
| | 2QSEA | 5.7 |

Figure 32:
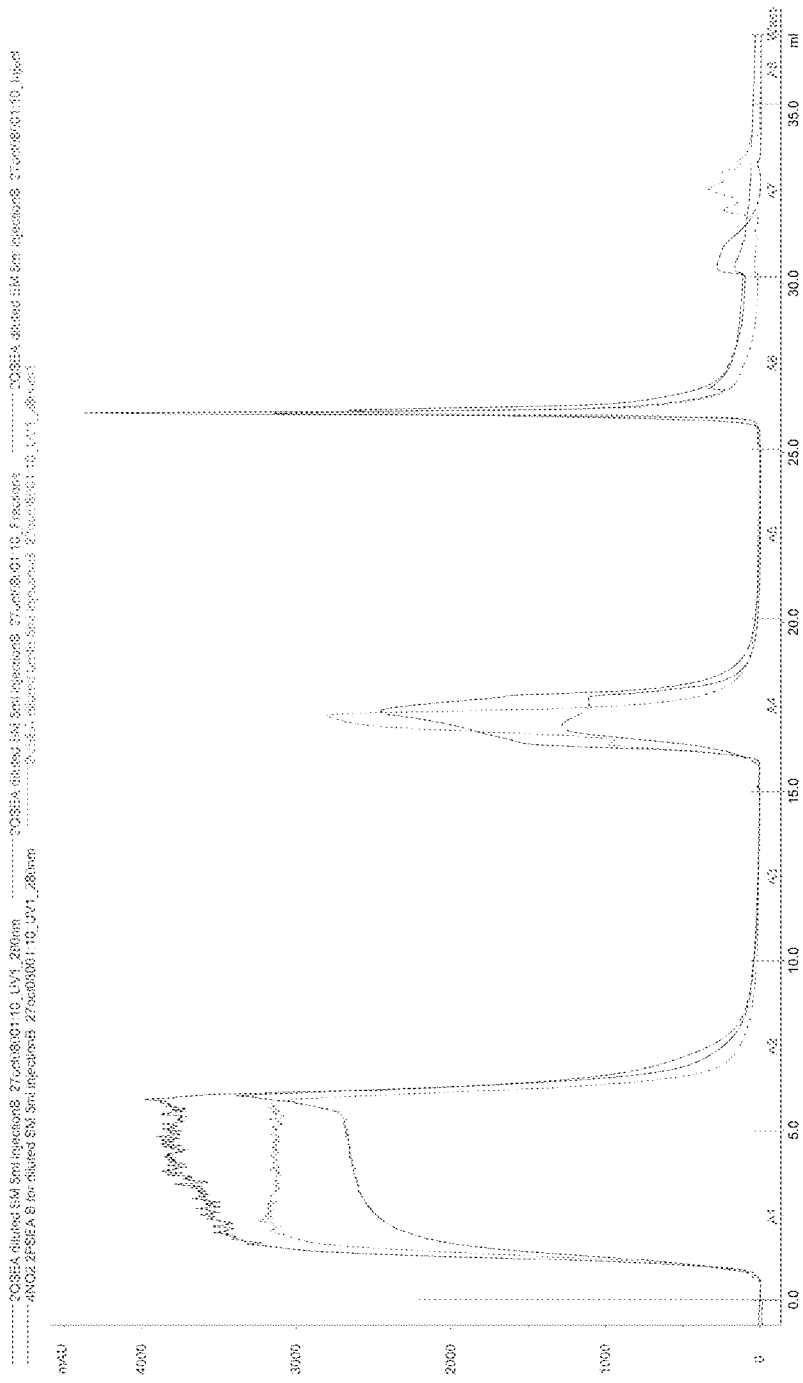
FIG. 32: Relative binding of 3 adsorbents for diluted mAb broth. Chromatograms the separation/elution of pure mAb, (–) 2QSEA, (–) $4NO_2$-2PSEA and (–) 5Br-2PSEA.
Figure 33:
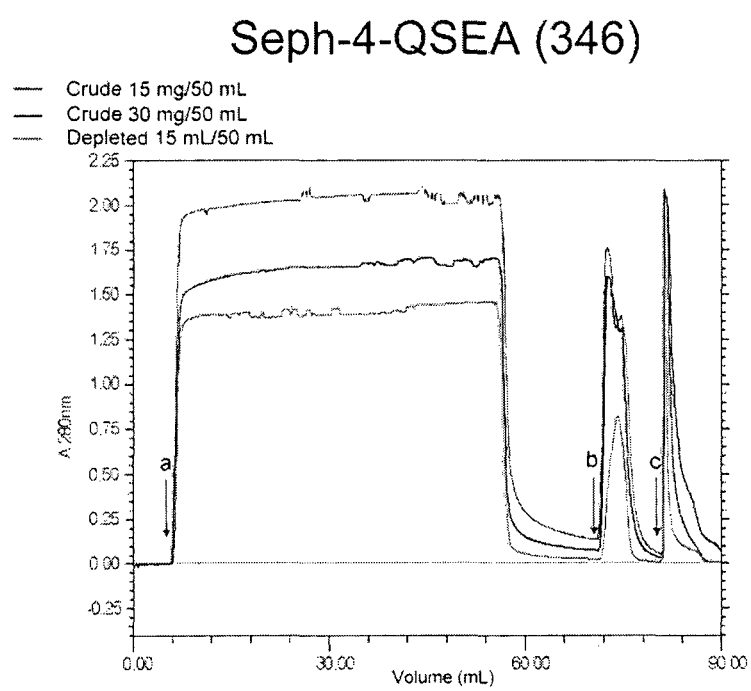
FIG. 33: FPLC absorbance chromatogram for Seph-4-QSEA (1.0 mL bed volume). a) sample loading, 15 or 30 mg crude mAb or 15 mL depleted media in 25 mM Tris pH 9, 600 mM $Na_2SO_4$ (50 mL); b) injection of elution buffer, 25 mM Hepes pH 7; c) regeneration of the column, 0.5 M NaOH.

The method was further tested using diluted mAb broth, showed the similar results as shown in FIG. 32.

9.1.5. Adsorption of mAb vs Media Components

The ability of cell culture derived contaminants, including IgG proteolysis products, to bind to the affinity resins was investigated using antibody depleted harvest medium. The experiments were performed under binding conditions that were determined to be optimal for the binding of the mAb. These conditions would also show whether bound contaminants would elute under the conditions that are employed to promote monoclonal antibody elution. As a control, these experiments were also carried out using media containing the desired mAb.

Figure 34:
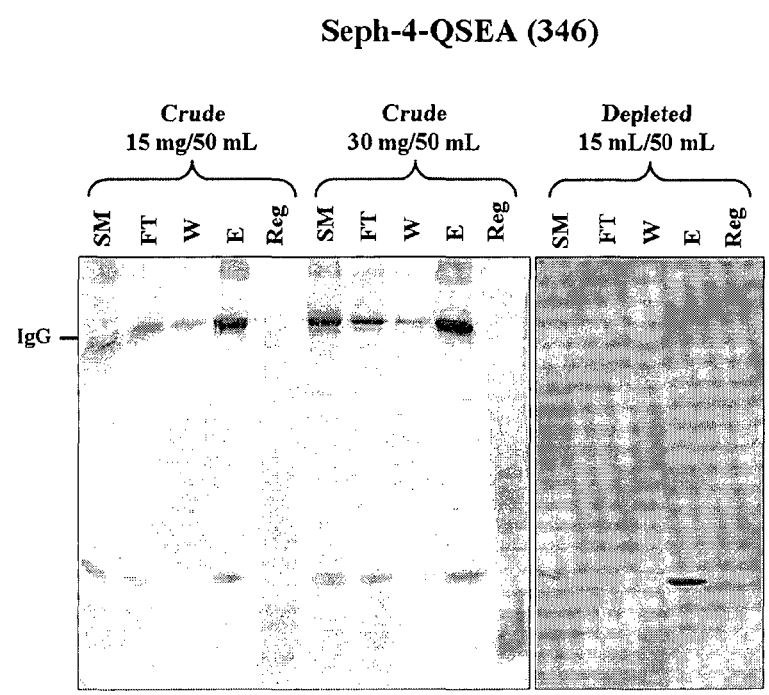
FIG. 34: 7.5-15% SDS-PAGE of chromatographic fractions collected from Seph-4-QSEA.
Figure 35:
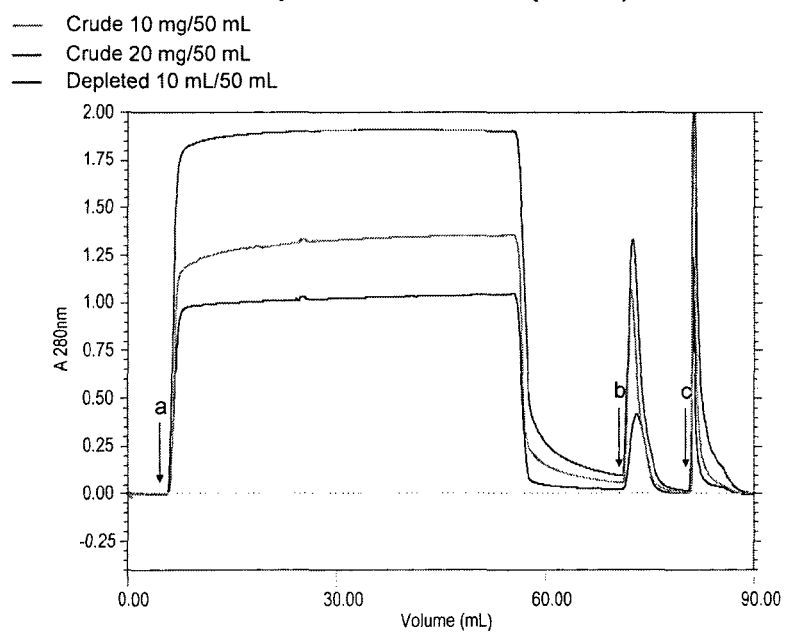
FIG. 35: FPLC absorbance chromatogram for Seph-2-PSPA (1.0 mL bed volume). a) sample loading, 10 or 20 mg crude mAb or 10 mL depleted media in 25 mM Tris pH 9, 600 mM $Na_2SO_4$ (50 mL); b) injection of elution buffer, 25 mM Hepes pH 7; c) regeneration of the column, 0.5 M NaOH.
Figure 36:
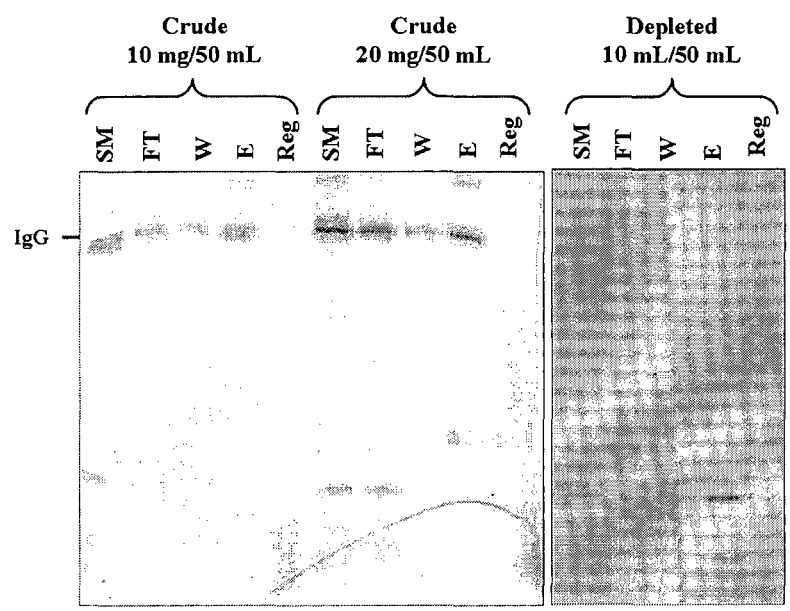
FIG. 36: 7.5-15% SDS-PAGE of chromatographic fractions collected from Seph-2-PSPA.

In this experiment (see FIG. 34) a 1.0 mL bed volume of the adsorbent was equilibrated with binding buffer (25 mM Tris pH 9, 600 mM $Na_2SO_4$) and then the sample (15 or 30 mg crude mAb or 15 mL depleted media in 25 mM Tris pH 9, 600 mM $Na_2SO_4$) (50 mL) was loaded. The adsorbent bed was then washed (25 mM Tris pH 9, 600 mM $Na_2SO_4$) and bound mAb eluted (25 mM Hepes pH 7). SM=starting material, FT=flow through, W=wash, E=elution, Reg=regeneration of the column (0.5 M NaOH). In this experiment (see FIG. 36) a 1.0 mL bed volume of the adsorbent was equilibrated with binding buffer (25 mM Tris pH 9, 600 mM $Na_2SO_4$) and then the sample (10 or 20 mg crude mAb or 10 mL depleted media in 25 mM Tris pH 9, 600 mM $Na_2SO_4$) (50 mL) was loaded. The adsorbent bed was then washed (25 mM Tris pH 9, 600 mM $Na_2SO_4$) and bound mAb eluted (25 mM Hepes pH 7). SM=starting material, FT=flow through, W=wash, E=elution, Reg=regeneration of the column (0.5 M NaOH).

Overall, these comparisons document that the mode of interaction, the type of elution conditions, and the extent of selectivity for host cell proteins, are different to the MEP HyperCel® type of adsorbent with the new ligand systems performing significantly better as a consequence.

9.1.6. Purification of IgM

A two-step purification procedure, involving firstly affinity chromatography using the novel adsorbents prepared here as the capture step, and secondly size exclusion chromatography (SEC) for the intermediate/polishing step was implemented for the isolation of IgM from a crude sample derived from cell culture using DMEM medium containing 10% foetal calf serum. The corresponding SDS-PAGE results are shown below.

Figure 37:
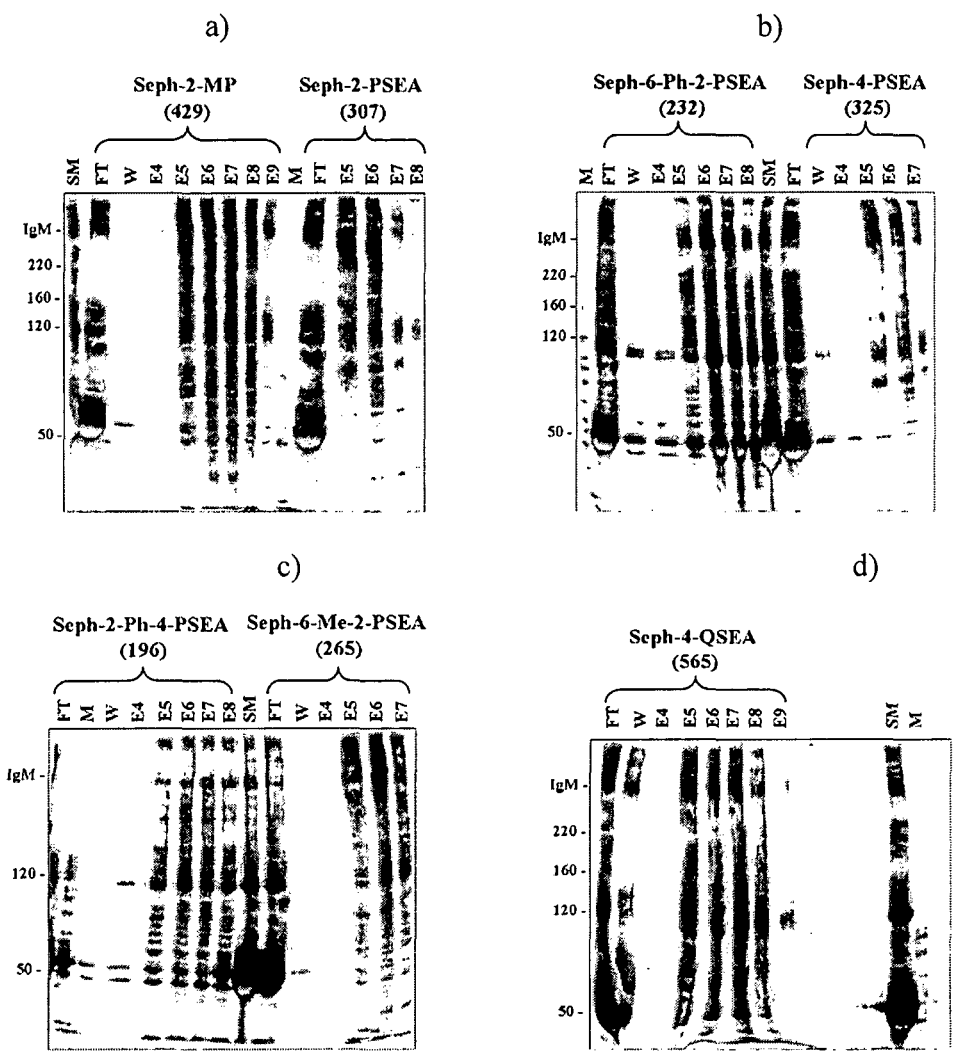
FIG. 37: 5-10% SDS-PAGE of chromatographic fractions collected from various adsorbents.

In this experiment (see FIG. 37), 0.5 mL of the adsorbent was incubated with the crude IgM sample in 25 mM Tris pH 9, 600 mM $Na_2SO_4$ (100 mL). The adsorbent was collected, then washed (25 mM Tris pH 9, 600 mM $Na_2SO_4$) and bound protein eluted (25 mM Hepes pH 7). M=markers, SM=crude IgM starting material, FT=flow through, W=wash, E4-E9=elutions.

In this experiment (see FIG. 38) the column was equilibrated with buffer (TBS), the captured and concentrated IgM sample (2.0 mL) was loaded, and the sample eluted using TBS buffer. SM=original starting material (from before first purification (capture) step). M=markers, E9-E11=elutions collected in 5 mL fractions: IgM fraction (diluted 1 in 5 cf. all other fractions), E12-E25=elutions collected in 5 mL fractions: lower molecular weight contaminants.

Figure 38:
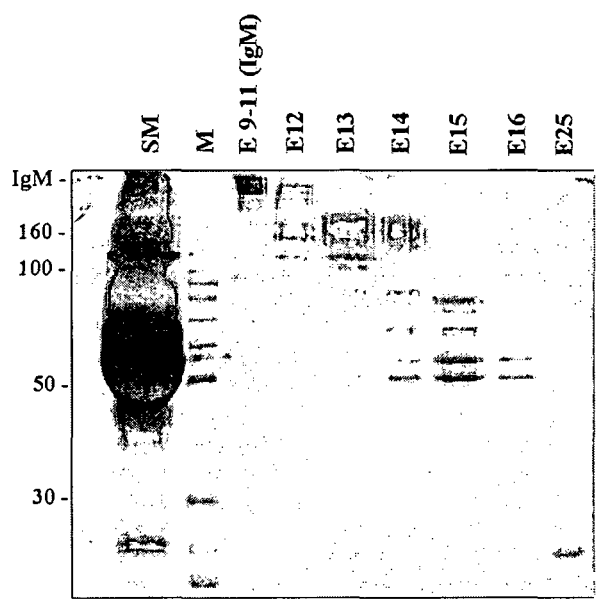
FIG. 38: 10% SDS-PAGE of the gel filtration fractions collected from the HiLoad 16/60 Superdex 200 column.

Size exclusion chromatography was used to further purify the elution fractions obtained from the affinity adsorbents in the above capture step. The two-step purification procedure that incorporated affinity chromatography and SEC showed that IgM can be isolated from DMEM media (10% foetal calf serum) efficiently, with good recovery and with significant purification (FIG. 38).

The invention claimed is:

1. An affinity ligand-matrix conjugate comprising a ligand of general formula (I):

$$\text{(I)}$$

wherein:
m represents an integer from 0-2;
n represents an integer from 0-6;
p represents an integer from 0-4;
$R^1$ represents hydrogen or $C_{1-3}$ alkyl; and
each $R^2$, when present, may be selected independently from carboxyl, cyano, halogen, hydroxy, nitro, phosphono, phosphorylamino, phosphinyl, sulfo, trihalomethanethio, optionally substituted acyl, optionally substituted acylamino, optionally substituted acylimino, optionally substituted acyliminoxy, optionally substituted acyloxy, optionally substituted arylalkyl, optionally substituted arylalkoxy, optionally substituted alkenyl, optionally substituted alkenyloxy, optionally substituted alkoxy, optionally substituted alkyl, optionally substituted alkynyl, optionally substituted alkynyloxy, optionally substituted amino, optionally substituted aminoacyl, optionally substituted aminoacyloxy, optionally substituted aminosulfonyl, optionally substituted aminothioacyl, optionally substituted aryl, optionally substituted arylamino, optionally substituted aryloxy, optionally substituted cycloalkenyl, optionally substituted cycloalkyl, optionally substituted heteroaryl, optionally substituted heterocyclyl, optionally substituted oxyacyl, optionally substituted oxyacylamino, optionally substituted oxyacyloxy, optionally substituted oxyacylimino, optionally substituted oxysulfinylamino, optionally substituted oxysulfonylamino, optionally substituted oxythioacyl, optionally substituted oxythioacyloxy, optionally substituted sulfinyl, optionally substituted sulfinylamino, optionally substituted sulfonyl, optionally substituted sulphonylamino, optionally substituted thio, optionally substituted thioacyl, and optionally substituted thioacylamino, or any two adjacent $R^2$ may together form an optionally substituted aryl, optionally substituted heteroaryl, or optionally substituted heterocyclyl and said ligand is immobilised unto a support matrix in position (X), optionally through a linker group (L) interposed between the matrix and ligand.

2. An affinity ligand-matrix conjugate according to claim 1, wherein $R^1$ is H; m is 0 or 1; n is 2 or 3; and p is 0, 1, or 2.

3. An affinity ligand-matrix conjugate according to claim 1, wherein p is 0; or p is 1 and $R^2$ is selected from halogen, nitro, thio, optionally substituted $C_{1-3}$ alkyl, optionally substituted $C_{1-3}$ alkoxy, optionally substituted heteroaryl, optionally substituted heterocyclyl, or optionally substituted aryl; or p is 2 and each $R^2$ is independently selected from halogen, optionally substituted $C_{1-3}$ alkyl, optionally substituted $C_{1-3}$ alkoxy, thio, optionally substituted heteroaryl, optionally substituted heterocyclyl, or optionally substituted aryl; or the $R^2$ groups are adjacent and represent an optionally substituted aryl, optionally substituted heteroaryl or optionally substituted heterocyclyl group.

4. An affinity ligand-matrix conjugate according to claim 1, wherein the group is selected from -continued

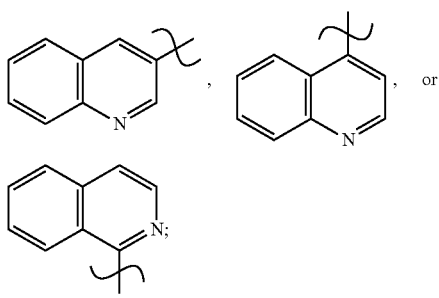

wherein each R² , when present, independently represents halogen, nitro, thio, $C_{1-3}$alkyl, halo-$C_{1-3}$alkyl, $C_{1-3}$alkoxy, halo-$C_{1-3}$alkoxy, optionally substituted heteroaryl, optionally substituted heterocyclyl, or optionally substituted aryl.

5. An affinity ligand-matrix conjugate according to claim 4, wherein the

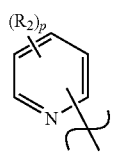

group is selected from

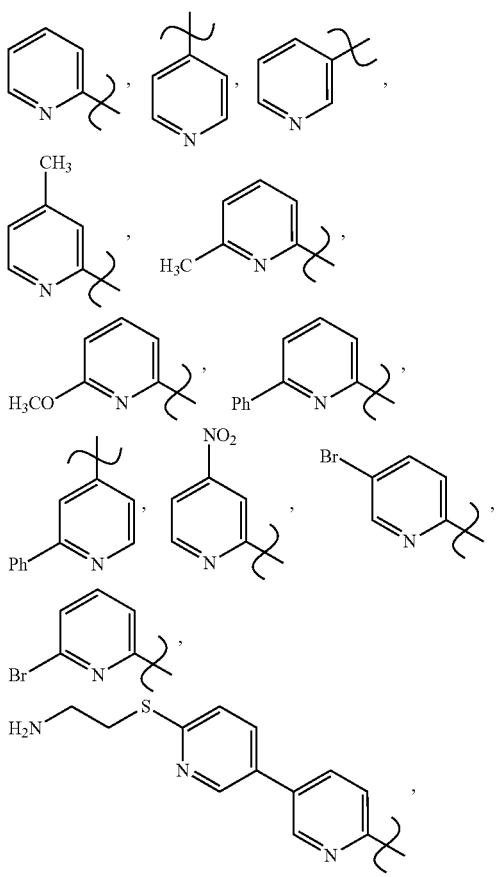

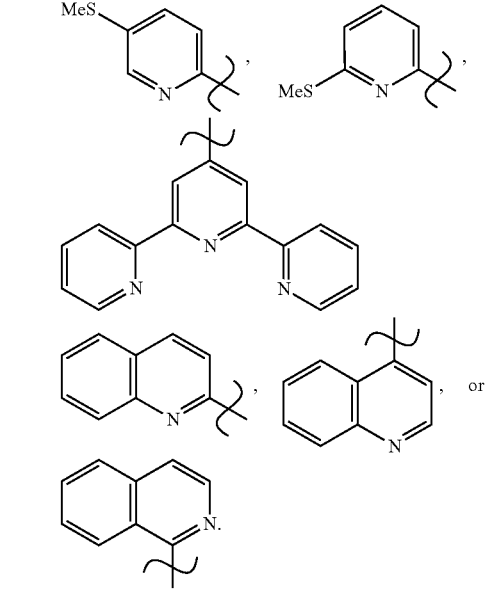

6. An affinity ligand-matrix conjugate according to claim 1, wherein the linker group L is an optionally substituted $C_{1-20}$ alkylene group.

7. An affinity ligand-matrix conjugate according to claim 6, wherein the linker group L is

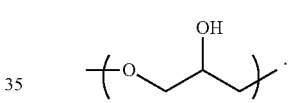

8. A compound of formula

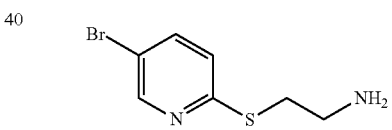

or an amino protected form, or a salt thereof.

9. A compound of formula

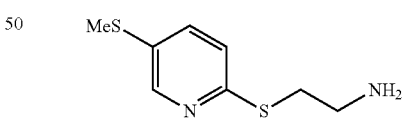

or an amino protected form, or a salt thereof.

10. A compound of formula

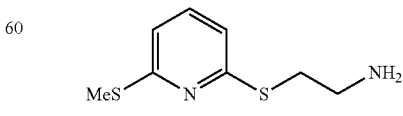

or an amino protected form, or a salt thereof.

11. An affinity ligand-matrix conjugate according to claim 1 comprising a ligand of the general formula

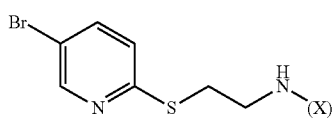

wherein said ligand is immobilised unto a support matrix in position (X), optionally through a linker group (L) interposed between the matrix and ligand.

12. An affinity ligand-matrix conjugate according to claim 1 comprising a ligand of the general formula

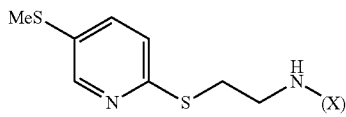

wherein said ligand is immobilised unto a support matrix in position (X), optionally through a linker group (L) interposed between the matrix and ligand.

13. An affinity ligand-matrix conjugate according to claim 1 comprising a ligand of the general formula

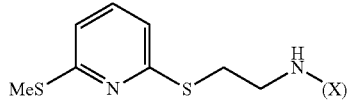

wherein said ligand is immobilised unto a support matrix in position (X), optionally through a linker group (L) interposed between the matrix and ligand.

14. An affinity ligand-matrix conjugate according to claim 6, wherein the linker group L is a hydroxy substituted $C_{1-20}$ alkylene group.

15. An affinity ligand-matrix conjugate according to claim 4, wherein each $R^2$, when present, independently represents bromo, chloro, nitro, thio, $C_{1-3}$alkyl, halo-$C_{1-3}$alkyl, $C_{1-3}$alkoxy, halo-$C_{1-3}$alkoxy, optionally substituted heteroaryl, optionally substituted heterocyclyl, or optionally substituted aryl.

* * * * *